US010920241B2

(12) United States Patent
Vermunt

(10) Patent No.: US 10,920,241 B2
(45) Date of Patent: Feb. 16, 2021

(54) BIOLOGICAL CONTROL OF PLANT VIRUSES

(71) Applicant: Looije Applications B.V., De Lier (NL)

(72) Inventor: Adrianus Marinus Wilhelmus Vermunt, De Lier (NL)

(73) Assignee: LOOIJE APPLICATIONS B.V., De Lier (NL)

( * ) Notice: Subject to any disclaimer, the term of this patent is extended or adjusted under 35 U.S.C. 154(b) by 62 days.

(21) Appl. No.: 15/765,684

(22) PCT Filed: Oct. 4, 2016

(86) PCT No.: PCT/NL2016/050684
§ 371 (c)(1),
(2) Date: Apr. 3, 2018

(87) PCT Pub. No.: WO2017/061859
PCT Pub. Date: Apr. 13, 2017

(65) Prior Publication Data
US 2019/0048323 A1     Feb. 14, 2019

(30) Foreign Application Priority Data
Oct. 5, 2015 (EP) .................................... 15188418

(51) Int. Cl.
| | | |
|---|---|---|
| *C12N 15/82* | (2006.01) | |
| *A01N 63/00* | (2020.01) | |
| *C12N 7/00* | (2006.01) | |
| *C12Q 1/04* | (2006.01) | |

(52) U.S. Cl.
CPC ......... *C12N 15/8283* (2013.01); *A01N 63/00* (2013.01); *C12N 7/00* (2013.01); *C12Q 1/04* (2013.01); *C12N 2770/26011* (2013.01); *C12N 2770/26021* (2013.01); *C12N 2770/26031* (2013.01); *C12N 2770/26062* (2013.01)

(58) Field of Classification Search
None
See application file for complete search history.

(56) References Cited

PUBLICATIONS

Schenk et al, Europ J Plant Pathol 127: 249-261, 2010 (Year: 2010).*
International Search Report and Written Opinion in corresponding PCT Application No. PCT/NL2016/050684, dated Oct. 3, 2017.
Beata Hasiw-Jaroszewska et al:, Single 1.2.4-13 mutation converts mild pathotype of the Pepino mosaic virus into necrotic one, Virus Research. Amsterdam. NL., vol. 159. No. 1., Apr. 22, 2011 (Apr. 22, 2011). pp. 57-61.
I. M. Hanssen et al: "Pepino mosaic virus isolates and differential symptomatology in tomato", Plant Pathology. vol. 58, No. 3, Feb. 18, 2009 (Feb. 19, 2009). pp. 450-460.
Godwill Mih Chewachong: "Engineering Plant Virus "Vaccines" Using Pepino Mosaic Virus as a Model", Ph. D. thesis, 2013. pp. i-xviii, 1-102.
Martijn F Schenk et al: "The use of attenuated isolates of Pepino mosaic virus for cross-protection", European Journal of Plant Pathology Kluwer Academic Publishers. DO, vol. 127m No. 2, Mar. 1, 2010 (Mar. 1, 2010), pp. 249-261.
Godwi LL M. Chewachong et al: "Generation of an Attenuated. Cross-Protective Pepino mosaic virus Variant Through Alignment-Guided Mutagenesis of the Viral Capsid Protein", Phytopathology, vol. 105, No. 1, Jan. 2015 (Jan. 2015), pp. 126-134.
Beata Hasiow-Jaroszewska et al:, "Ratio of mutated versus wild-type coat protein sequences in Pepino mosaic virus determines the nature and severity of yellowing symptoms on tomato plants", Molecular Plant Pathology, vol. 14, No. 9, Jul. 15, 2013 (Jul. 15, 2013), pp. 923-933.
Beata Hasiow-Jaroszewska et al:, "A method for detection and discrimination of Pepino mosaic virus isolates using high resolution melting analysis of the triple gene block 3", Journal of Virological Methods, vol. 193, No. 1, May 13, 2013 (May 13, 2013), pp. 1-5.
Inge M. Hanssen et al, "Pepino mosaic virus : a successful pathogen that rapidly evolved from emerging to endemic in tomato crops", Molecular Plant Pathology, vol. 11, No. 2, Nov. 12, 2009 (Nov. 12, 2009). pp. 179-189.

* cited by examiner

*Primary Examiner* — Elizabeth F McElwain
(74) *Attorney, Agent, or Firm* — Leason Ellis LLP

(57) ABSTRACT

The present disclosure provides new attenuated Pepino mosaic viruses useful in the control of plant disease. Compositions for biological control of plant disease are also provided as well as methods for producing Pepino mosaic virus resistant plants.

Figures 1A, 1B:

8 Claims, 58 Drawing Sheets
(38 of 58 Drawing Sheet(s) Filed in Color)
Specification includes a Sequence Listing.

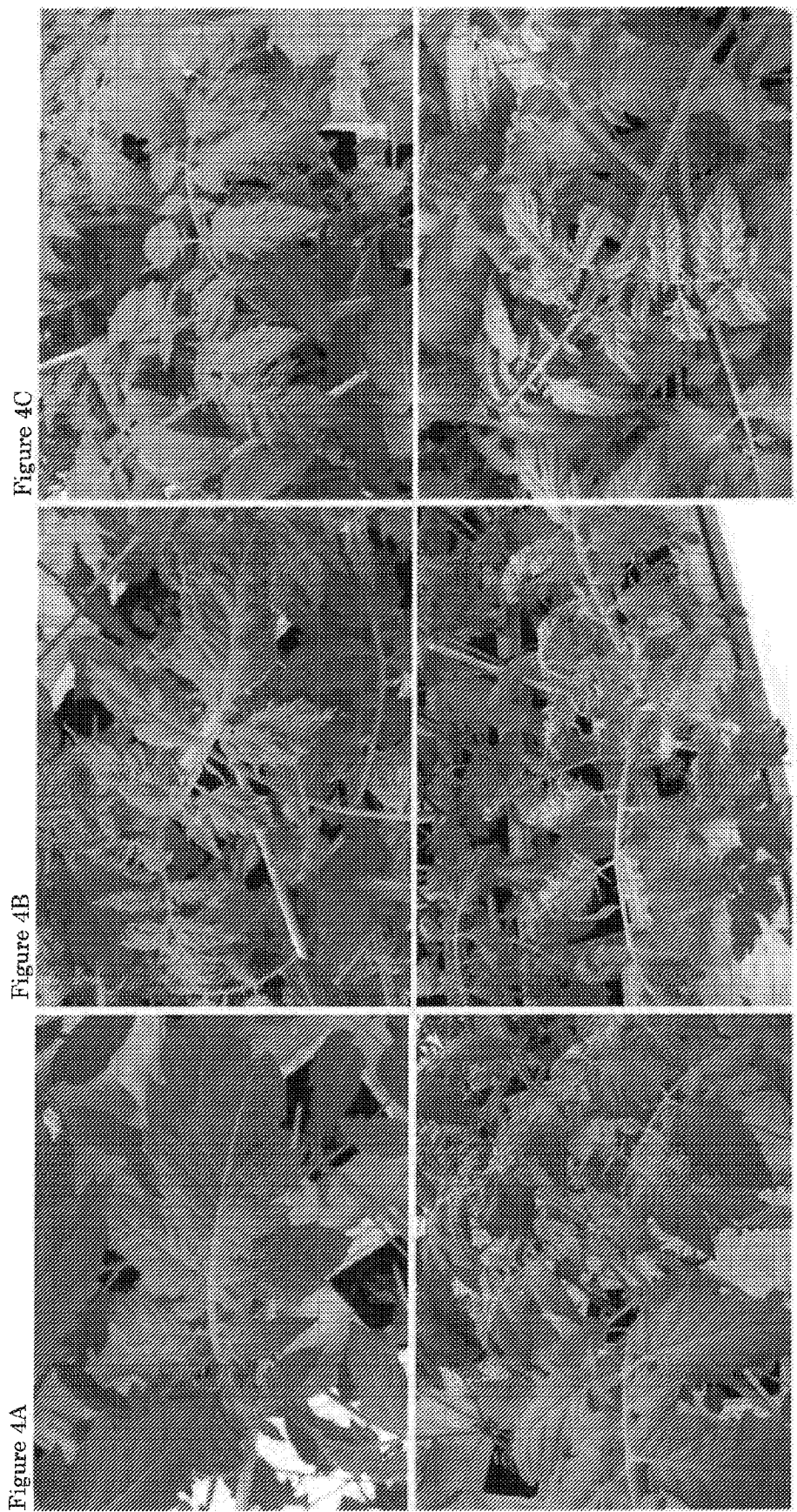

```
SEQ ID NO:1
CTAGCATTTGTGAAGCCGCTTACCAACATGTTAGACCTGTGCTCAAGGAATCCCTAATCAACTGTCCTTATGCGC
TTAATGACTATGAAGCAGACACCCTTGAGAATTTAGGTGTGCACAATAAACCCCCATGCAATCCAAACACATACTC
ATGCGGCAGCTAAAGTTGTGGAAAATAGAATGCTCGAAATCGTTGGACACCACTTGCCCAAGGACGAGAAAGTTA
CCTTCATTTTCCTCAAAAGAAGCAAACTGAGATACATGCGAAGAGCTGCTGTACATAAAGATGTTTTTGTTAATC
ACAATATAGAACCCAAGGATTTCTTCAGGTATGATGAGGAATCTACATCTACTAGTTTCTCCGTGAACACCAGGA
TCGCTTACATCTCCGATTCTCTACATTTCATGGAACCAGCTGATGTGACCCACCTCTTTGACCGTTGCCACAATC
TTAAAACACTGATGGCAACTGTCGTTTTACCTGTTGAAGCCATCCACAAACAAACATCTTTATTTCCAGCGATAT
ACTCCATTAATTACAATGAAGAAGGTTTTGAGTATATCCCTGGTTCTCATGGTGGAGGGGCATACTTTCATAAGT
ATGAAACATTAGACTGGCTCAAATACTCTAGATTCATTGGCCAGGACCCCTTAACTGGACTCCGATACACCATAA
CCATTCAAATGGTAGAGAGTTTAGGAGCCAACCATCTTTTCCTCTTCCAAAGAGGAAATTTTGAAACACCTTTAT
ACAGGACGTTTCAAAAAAATAGCTTTGTGACCTTTCCTAACATCTTCCATCCCCAACATGTTAATGCCACAAAGC
CCATGCCAAGATCCAGGGCAATTCAGCTGTATTTATATGTCAAATCTGTCAATAAGGTGACACAAAGAGATATCT
TTGCGAAAGTAAGGCAACTTATATCTACAGCTGAACTTGAATTGTATGACCCTGATGAACTTACACATATTGTCA
ATTATTTCGCATATGTCTCAGAACTAAGCTCAATCAACGACTATGACAATATGCTCAAATCAAGTTTTTTCAAAA
AACTTGTTGCACCCATGCAACATGACTGGAGGTGCATGATTGAATTCTTTCGGGGAAAAAGTGATTTCAATCAAC
TTTTAACTGCTCTTCAATGGAAAGACTTCTCTTACACCATTAAAACTGAAGAGTTAGTTGTTGCTACACACACTG
AAATTGGCCAGGCAATCTGTGAAGCTGCGACCACATACAAAGAAAGAAGACAATTGACCAATTTAGTCAAACAAG
GCGCAGTAACATTAGCTGATTTCAAAGAAGCGGACCAGCATGTGGAGTACACTCACTTTGATCCTGAGTTTAAAT
CCACTGTTGACCCCACCGGAGCTATGAAAATGCCATCAACAATCTTGGCATTGAGATTAATGAGGATGTACCTG
AAAGTTCCGGCACTAATAAAACATTGCTTAACAATGAAATATCTTTAGCAATGTCAY₁CTGCTGAACATGTGCAA
GCCGTTCAAGAAATTGAGTCTTTACTCTCTAACCCCGAAGCGGCACCAATATTGCCCCCTGCACATGTTAAAACA
TGGGCTAGCCTTGCATCTGACAY₂TTCCAGCACTAAAAACCGTGAAATCGAAGATATAGTGGCTAAGCTGGAAAT
ACAAAGAAATGAAGCTAGTTGCAGCTACCTTCAACCAAATAAGGAATTGTCAAAACCCAAGGCTGCTGATAACAA
TCTCCCCTGGAATGCTTGGATCCCATTGCTTAATGCACACGGCTTCAAAGGAGATCAATTACAATACGGCCCAGA
TGGTAACTTGATACAGCCCATCCAAGACATTAACAATTCACAGCCTAGATCTGACTATCCGTCTTCTCTGCCATG
TGAACTTGTGGAAACTTTGAGGAAAATTAAGCGTGCTGTCTATGCCATCCCAATAAGCCACAGGAGAGCTAGTGC
TTACAGTTCTGACATCAAAAATAACAGAACTGGCAAACTTCTCTGCAACCAAAGCAAAGAATGGAAAGAAAGCTT
TGCTTTCAAAATGCAACATGAAGACATCGTCAAATCAGGTGTTGTCATACATGGTTGCGGAGGTTCTGGCAAATC
CCAGGCATTACAAAACTTCTTGAGAACATTGGGTGATTCAAATGATTGCTGTACTGTTGTAGTACCCACTGTTGA
ACTTAGAAATGACTGGGTAAACAAACTCCATAAATTGCCCATGGAGCATATCAAAACATTTGAGAAAGCAATGAT
TCAACCTGGCTTTCCAATTGTTATATTTGATGATTACACCAAGTTGCCACCTGGCTACATTGAAGCATACCTATT
TCACCATGCCAACACTGAGCTTTTCATACTCACTGGTGATTCTAGGCAAAGCGTGTACCATGAATCTAACAATGA
AGCGTACATTGCCTCATTAGATGAAGCTGTTGCATACTACGCTAATTACTGCGGTTTTTATTTAAATGCTACTCA
TAGAAATGTCCGTAGTTTAGCCAACAAACTTGGTGTTTACAGTGAGAAAGAAGGACACTTGAAAATCACTTTTGC
TTCACATGCCTTACAAAAGTGCAAAGTGCCAATTTTAGTTCCTTCTCAAATGAAAAGGAGTGCTATGTY₃AGACA
TTGGACATAAATCCATGACCTATGCTGGTTGCCAAGGGTTTAACAGCACCCAAGGTACAAATTCTCCTTGATAACC
ACACGCAACATTGCTCTGACAGAGTTCTGTACACCTGTCTGTCTCGTGCAGTTGATTCCATCCACTTCATTAATA
CTGGTCCCAACAATTCAGAATTTTGGGATAAGCTTGAAGCAACACCATATCTCAAAGCCTTCATTGATGTCTATA
GAGATGAAAAAACTGAAATGTTCAATTCTAAGCCTGCTGATGACAGTCCAACTGAGCCTGAAGCACCTGTTACAC
ATTTCCCAATAGCAAATGGAAATAACTTAGAGAAATTAGCTTCTGCTTTGCCTGAAAAATTGCTAGGGAGATTT
ATGACAAGCATCATGGCCACTCCAACACAATCCAAACTGAGAACCCTGTGGTCCAACTTTTCCAACATCAACAAG
CGAAAGACGAGACACTCTTTTGGGCTACAATTGAAGCTAGATTGTCCATAACAACTCCTGAAGCAAACCTCAGAG
AATTTTTGTTTAAGAAAGATGTTGGAGACATTCTCTTCTTCAATTACCATAATGCGATGTGCTTGCCTGCCGACC
CTGTTGACTTTGAAGAAAGACCTGGGAGATCTGTGCTGCTGAAGTGAAAAACACTTATCTTGCCAAACCCATGG
CCAATCTTATCAATGCGGCAAGTAGACAATCACCCGACTTTGACTCTAATAAGATCTCATTATTCCTAAAGTCTC
AATGGGTGAAAAAGTGGAAAAACTTGGAGCTATCAAATCAAAACCTGGGCAGACCATAGCTGCTTTTATGCAAC
AAACAGTCATGTTGTATGGTACTATGGCCAGGTACTTAAGGAAAATGCGGCAAAGATTCCAGCCAAAACACATAT
TCATCAATTGTGAAACCACAACTGATGATCTCAATAAATTTGTCAAAGAY₄GGCTGGAACTTTAACAGAACCGCC
CAAACAAATGACTTCACTGCTTTTGATCAGTCACAAGATGGAGCAATGCTTCAATTTGAAGTCATGAAAGCAAAA
TTTTTTAACATTCCAGCTGATGTCATTGAAGGCTACATCAACATCAAGCTGAATGCTAAAATTTTCCTTGGAACA
CTCTCAATAATGAGACTTTCTGGTGAAGGTCCCACATTTGACGCTAACACTGAGTGTTCGATTGCATACACTGCC
ACAAGATTCCATATTGACAATACTGTTAAGCAAGTGTATGCCGGTGACGACATGGCATTAGATGGAGTTGTGAGT
GAAAAGAAATCATTCAGGAAGTTACAAAATCTACTAAAACTCACTTCAAAAACGCTGTACCCAAAACAGGTTAAA
GGGAATTACGCTGAATTTTGTGGTTGGACTTTCACACCAGGGGGTATAATTAAAAATCCACTTAAAATGCATGCC
TCAATTATGCTGCAAGAAGCCATTGGCAATCTGCACACAGCAGCCAGATCTTATGCAATTGACATGAAGCATTCA
TACCAAATGGGTGACCAACTGCATGACTACCTAACCCCCGATGAAGCTGAACAACATTCCTAGCTGTGAGAAAG
CTTCACAAACTCCATCAAGGCGAGGCCATGCGTCTTGGGGAGAAAAGTCCACCAAGATCAACCCATTAAGGGGTT
AAGTTTTCCCCAGTTTGAAATGGAAAGATCAACTTTGATCAATTTACTTCTGTTACACAAATTTGAACACAAGAT
TAACACTGAAGGAATCATTGTTGTGCACGGAATTGCTGGAACTGGGAAAACCACATTGCTTAGGACTTTATTTTC
```

FIG. 7A-2

```
TGCATACCCTAGCTTAGTTATAGGTTCACCTAGGCCTTGTTACTTAGATAAAGCTAATAAAATTTCACAAGTTTG
CCTTTCTTGTTTTCCAAATACCTTGTGTGACATTGTTGACGAGTATCATCTCTTAGAAAGTTTTCCTGAACCAAA
ACTAGCCATTTTTGGTGACCCCTGTCAGTGCACTTACATTGAAAGGTTGAGAACACCCAACTACACATCCTTCAG
AACACACCGATTTGGCAAATCCACTGCTGCTCTACTAAACCAGTTATTTGATCTTAACATTGAGTCAGTCAAAGC
ACAAGACGACACAGTAGAATACTTTGATCCTTTCGCAGTGGACCCCTCTGAACACATTTCTGCTTCAGAAAAAGA
AGTTTGGAATTTGTAGGTGATCAAGTTGAGACTACAAGCTCTGAAGAACTAGCTGGTCTCGAGTTTAGTGAAGT
TACTTTCTACTGTACCACACTTGCTGGTGCTGTTCAAGAAAATCCTGCTAAAACCTTCATTTCACTCACTAGACA
CACTTCAAAGCTCACAATTGGTGAACTAAATGCCAGGTCTGACTCCAGAGCTGATCTTACTGACACGTATAAAA
TCATTGCTATAGCCTTTCTACTGTCAGCTTGCATTTACTTCCAAAACAGTCATATCAACCAGTTGCAGGTGATA
ATTTGCACAGACTACCCTTTGGTGGTCAGTATCAAGACGGAACTAAGAAGATTCTTACTTTCCGCAGCAACAAT
CCTACTTCACTCAGGAAACAAGCTTAATGTCCTCATACTTATCTTCATTCTTACACTGGGTATTGTCCTCACCA
ATAAATTTAGTTTTAGCATTAGCCGTAATACTCACCAGCATCATTGCTACAACACACATTCTGCAACCCAAACAG
GTCAATCAGTGCCAGGTCATCATTGACGGTGCAGCCATAGTTATAACAAATTGTCCAAAACACACCCGAAGTTCTT
AAAGCAATCAACTTCTCCCCTTGGAACGGGTTAAGTTTTCCTCAATTGTGAAATTATATTTGTTATCTAGTTAAA
TTCAAACAATTTAACTCACTATGGAAAACCAACCTACAGCTTCTAACCCATCAGATGCACCACCAACTGCTGCT
CAAGCTGGTGCCCAGAGCCCAGCSGACTTCTCAAATCCTAATACAGCTCCTTCCCTAAGTGATTTGAAGAAGATC
AAATACGTGTCAACTGTCACTTCAGTTGCCACGCCTGCTGAAATTGAGGCCCTTGGCAAGATCTTTACTGCCATG
GGTTTAGCAGCCAATGAGACCGGACCTGCCATGTGGGACCTCGCTCGTGCTTATGCTGATGTGCAAAGTTCAAAA
TCTGCACAACTTAY₆AGGTGCCACACCATCCAACCCTGCTTTGTCTAGACGTGCACTTGCTGCACAGTTTGATCG
TATCAATATCACACCCAGACAATTCTGCATGTATTTTGCAAAAATTGTTTGGAACATACTGTTAGACAGCAATGT
GCCACCTGCCAACTGGGCAAAATTGGGCTATCAGGAAGATACCAAGTTTGCTGCTTTTGACTTCTTTGATGGAGT
CACAAATCCAGCTAGTCTACAGCCY₆GCAGATGGCCTAATCAGGCAGCCCAATGAAAAAGAGCTTGCTGCTCACT
CGGTTGCTAAATATGGTGCCCTTGCCCGCCAGAAAATATCCACTGGTAACTACATCACCACCCTTGGTGAAGTTA
CACGTGGTCACATGGGCGGCGCCAACACTATGTACGCAATTGATGCACCTCCTGAACTTTAAACACTCGAAACTT
AATCAGAGTGGG
```

SEQ ID NO:2
```
SICEAAYQHVRFVLKESLINCFYALNDYEADTLEHLGVTINFHAIQTHTHAAAKVVENRMLEIVGHELPKDEKVT
FIFLKRSKLRYMRKAAVHKDVFVNHNIEFKDFFRYDEESTSISFSVNTRIAYISDSLHFMEPADVTHLFDRCHNL
KTLMATVVLFVEAIHKQTSLFPAIYSINYNEEGFEYIFGSRGGGAYFHKYETLDWLKYSRFIGQDPLTGLRYTIT
IQMVESLGANRLFLFQRGNFETPLYRTFQKNSFVIFPNIFHFQHVNATKPMPRSFAIQLYLYVKSVNKVTQRDIF
AKVRQLISTAELELYDPDELTHIVNYFAYVSELSSINDYDNMLKSSFFAKLVAPMQHDWRCMIEFFRGKSDFNQL
LIALQWKDFSYIIKTEELVVAIHTEIGQAICEAATTYKERRQLTNLVKQGAVTLADFKEADQHVEYTHFDPEFKS
IVDPHRSYEMAINNLGIEINEDVPESSGTNXTLLNNEISLAMSNAERVQAVQEIESLLGNFEAAPILPPAHVKIW
ASLASDXSSTKNREIEDIVAKLEIQRNEASCSYLQPNKELSKPKAADNNLPWNAWIPLLNAHGFKGDQLQYGPDG
NLIQPIQDINNSQPRSDYPSSLFCELVETLRKIKRAVYAIPISRRRASAYSSDIKNNFTGKLLCNQSKEWKESFA
FRMQHEDIVKSGVVIRGCGGSGKSQALQNFLRTLGDSNDCCTVVVPTVELPNDWVRKLHKLPMEHIKTFEKAMIQ
FGFPIVIFDDYTKLPPGYIEAYLFHHANFELFILTGDSRQSVYHESNNEAYIASLDEAVAYYANYCGFYLNATHF
NVRSLANKLGVYSEKEGHLKITFASHALQKCKVFILVFSQMKESAMYDIGHKSMTYAGCQGLTAPKVQILLDNRT
QHCSDRVLYTCLSRAVDSIHFINTGPRNSEFWDKLEATPYLKAFIDVYRDEKTEMFNSKFADDSPTEPEAPVTHF
PIANGNRLEKLASALPEKFAPEIYDKRHGHSNTIQTENPVVQLFQRQQAKDETLFWATIEARLSITTPEANLREF
LFKKDVGDILFFMYRNAMCLPADPVDFEEKTWEICAAEVKNTYLAKFMANLINAACRQSPDFDSNKISLFLKSQW
VKKVEKLGAIKSKFGQTIAAFMQQTVMLYGTMARYLRKMRQRFQFKHIFINCETTIDDLNKFVKDGWNFNRIAQT
NDFTAFDQSQDGAMLQFEVMKAKFFNIPADVIEGYINIKLNAKIFLGTLSIMRLSGEGFIFDANTECSIAYTATF
FHIDNTVKQVYAGDDMALDGVVSEKKSFRKLQNLLKLTSKTLYFKQVKGNYAEFCGRTFIFGGIIKNPLKMRASI
MLQEAIGNLRTAARSYAIDMKHSYQMGDQLHDYLTPDEASQHFLAVRKLRKLRQGEAMRLGEKSPPRSTH
```

SEQ ID NO:3 EU AJ438767
```
GAAAACAAAACAAATAAACAAATATACAAAGTTAAACTAACACAACATAACCACGTGGAAAAACAGCGAA
AGCACTTACCCACATTATGTCTCGTGTCAGAAATACTTTGGAAAGATCAGAGACCCACAAGTACAGTCC
AGCATTTGTGAAGCTGCCTATCAACATGTTCGACCTGTACTTAAAGAATCTCTAATCAATTGTCCTTACG
CGCTTAATGATTATGAAGCAGACACCCTTGAGAATCTTGGTGTCACAATTAACCCCCATGCAATCCAAAC
ACACACACATGCCGCAGCCAAAGTAGTCGAAAATCGTATGCTTGAAATTGTTGGACATCACTTGCCTAAA
GATGAAAAAGTAACTTTCATCTTCCTCAAACGTAGCAAGCTGCGTTACATGAGAAGAGCTGCTGTGCATA
AAGATGTCTTTGTCAATCATAACATTGAACCAAAAGACTTCTTCAGGTATGATGAAGAGTCTACATCAAC
CAGCTTTTCCGTTGATACGAGAATCGCATACATTTCAGATTCTCTACACTTTATGGAACCTGCTGATGTG
ACTCACTTGTTTGACCGTTGCCAAAACCTTAAAACATTGATGGCAACTGTTGTACTACCTGTGGAAGCTA
TACACAGACAGACATCTCTATTCCCTGCGATTTACTCCATTAACTACAATGAAGAAGGCTTTGAGTATAT
CCCAGGATCACACGGTGGTGGGGCATATTTCCACAAATATGAAACCCTAGAATGGCTCAAATACTCTAGA
TTCATTGGACATGATCCATTGACTGGTTTAAAATACACCATTACGATTCAAATGGTGGAGAGTCTTGGTG
CCAACCACCTTTTCCTCTTCCAAAGAGGAAACTTTGAGACGCCGCTATACAGGACGTTTCAAAAGAATAG
```

FIG. 7A-3

```
TTTTGTGACATTCCCAAATATATTCCATCCCCGACACGTCAATGCCACAAAACCTATGCCTAGATCAAGG
GCCATACAGCTGTACTTATATGTGAAATCAGTAAATAAAGTTACGCAAAGAGATATATTTGCCAAGGTTA
GACAACTGATTTCCACTGCTGAGCTAGAATTGTATGACCCTGATGAACTCACGCATGTTGTAAATTATTT
CACATATGTGTCACAACTGTCATCTATCAATGATTATGACAACATGCTCAAATCCAGTTTCTTCAAAAAA
CTGGTTGCACCCATGCAACACGACTGGAGGTGCATGATTGAATTCTTCCGGGGAAAGAGTGACTTCAATC
AACTGCTCACAGCTCTTCAATGGAAAGATTTTTCCTATACTATTAAGACTGAAGAGCTTGTAATTACTAC
ACACACTGCTATAGGACAAGCAATAAGCAATGCAGCTGCCACATATAAAGAAAGAAAGCAGCTGACTCAA
TTGGTCAAAAAAGGTACAATATCCTTAGCAGATTTTGAACAGAGAGAGCCTGAAATAACTTACACTGAGT
TTGAGCCTGAAACTAGGCCCCAAGTGGACTGCGTTACTAATTATAATAATGCAGTTAAAAATTTAGGTCT
TTCTGCACTTGATGAACAGCCCCAATGTTCATCTTCTAACAGTCATCTACCCTGCAATGAAATATCCTTA
GCAATGACTGATGACGACAATGTGCGGCCATTCATGAAATTGAATCTCTATTGTCTGAACCGATAATAG
CTCCTCAACTCCCAGCATTGCCACACAAGACATGGGCCAGTTATGCTTCAGACACTTCATCCATGAAGAA
CCGTGAGATTGAGAACATAATTGCTGAGCTTGAAATCTCACGGAAGGAAAATAATGTGCAGCAAACTACT
CATGATTACCATGCAGTTTCTGACACAGCTCAGAGCTCCGGAGATCTCCCATGGAAAGCATGGATTCCAC
TTCTGAATGCACACGGCTTCAAGGGAGACCAACTTCAATACAGTCCGGATGGCAAAGTGATTCAGCCAAT
CCAGGACATCAACAACAAAACACCAAGATCTGAGTACCCATCCAGCATTCCTGCAGATCTTGTGGATACA
CTGCGAAACATTAAAAGAGCAGTGTATGCCATTCCTATTAGCCATCGAAGGGCAAGTGCTTACAGCTCTG
ATATCAAAAACAATAGGACCGGCAAATTACTCTGTTCCCAATCAAAAGAATGGAAGGAAAGTTTTGCTTT
CAAAATGCAACATGAAGACATCGTTAAATCTGGAGTAGTCATTCATGGCTGTGGCGGCTCTGGAAAATCA
CAAGCATTACAAAACTTTCTCAGAACTCCTGGCGACTCTAATGACTGCTGCACAGTGGTTGTGCCAACTG
TTGAACTCAGAAATGATTGGGTGAACAAATTGTGTAAGCTACCCATGAACACATTAAAACATTTGAAAA
AGCAATGATTCAACCAGGATTCCCAGTTGTATCTTGATGACTACACTAAATTGCCACCTGGTTACATT
GAAGCCTATTTGTTCCACCATGCCAACACTGAACTTTTCATTCTTACTGGGGACTCGCGGCAAAGTGTAT
ATCATGAGTCCAACAATGAAGCATACATTGCCTCATTAGATGAAGCCGTCGCTTATTATGCTAACTACTG
TGGATTTTACCTAAATGCTACACACAGAAATGTTCGCAGTTTGGCCAATAAGCTAGGTGTTTACAGTGAG
AAAGAAGGTCACCTCAAAATTACCTTTGCCTCAAATGCTCTACAAAAGTGCAAAGTGCCAATTTTGGTGC
CCTCTCAAATGAAGAAGAGTGCTATGCAAGACATAGGGCACAAAGCCATGACCTACGCTGGGTGTCAAGG
GCTTACTGCACCGAGAGTCCAAATTTGCTTGACAACCACACACAACACTGCTCAGACAGGGTGCTGTAC
ACTTGTCTCTCCAGAGCTGTGGATTCCATCCACTTTATCAATACAGGCCCAAACAATTCTGAATTTTGGG
ACAAGCTTGAGGCAACACCATACCTCAAAGCATTATTGATACTTACAGAGATGAGAAAACAGAAATGCT
CAATTCTAAGCCTGCTGATGACAGTCCCGCTGAGCCTGAAGCTCCATTGACTCACTTTCCAGTGTCAAAC
GGCAATAACTTGGAAAAGTTAGCTTCAGCGCTTCCTGAAAAATTTGCAAGAGAGTTATATGATAAACACC
ATGGATATTCTAATACAATCCAAACTGAAAATCCAGTGGTGCAACTTTTCCAGCATCAACAAGCCAAAGA
TGAAACACTTTTCTGGGCAACAATAGAAGCTAGACTTTCTATTACAACTCCGGAAGCCAACTTACGAGAA
TTTGTGCTAAAGAAAGATGTTGGAGATATCTTGTTTTTCAATTACCACAATGTCATGTGCTTACCTGCCG
ACCCAGTGGATTTCGAGCCAAGAACATGGGAAATATGTGCTGCTGAAGTTAAAAATACATACTTAGCCAA
ACCAATGGCTAACTTGATCAATGCTGCTAGCAGACAATCTCCTGATTTCGACGCTAACAAAATTTCCCTG
TTCCTAAAATCTCAATGGGTCAAGAAAGTGGAAAAATTAGGTGCTGTCAAGTCAAAGCCTGGCCAGACCA
TTGCAGCTTTCATGCAACAAACAGTGATGTTGTATGGACCATGGCCAGATACCTCAGAAAGATGAGACA
AAGATTTCAACCAAAACATATTTTCATCAATTGTGAAACAACAACTGATAATCTGAACCAATTTGTTAAA
CAAGGTTGGAATTTTAACAGAACAGCTCAGACAAATGATTTCACAGCTTTTGACCAATCACAAGATGGTG
CAATGCTTCAATTTGAAGTCATGAAGGCAAAATTCTTCAATATCCCTGCCGACATCATTGAAGGATACAT
CAACATCAAATTGAACGCCAAAATTTTCCTTGGCACATTGTCCATTATGAGGTTGTCTGGTGAAGGTCCA
ACTTTTGATGCCAACACAGAATGTTCAATAGCATATACTGCTACAAGATACCATCTTGATTCTACAGTCA
AGCAGGTTTATGCTGGAGATGATATGGCATTAGATGGAGTTGTCCAAGAAAAACCCTCTTTTAAAAAACT
ACAGAACAAGCTTAAACTCACCTCAAAGACACTATTTCCAAAACAGGTTAAAGGTGATTATGCTGAATTC
TGTGGTTGGACTTTCACTCCTGGTGGTATCATTAAAAACCCTTTGAAAATGCATGCTTCCATTATGTTGC
AAGAGGCAATCGGCAATTTACACACTGCTGCCAGATCATATGCCATTGACATGAAGCATTCATACCAAAT
GGGTGATGAGCTGCACAATTACTTAACACCAGATGAAGCTGAACAACACTTCCTTGCTGTTCGGAAGTTG
CACAAGTTACACCAAGGAGAAGCAATGAGACTTGGTGAAAAGAGCCCTCCAAAAGCAACACATTGAGGGG
TTAAGTTTTCCCAGTTCGAAATGGAAAGATCAACTCTGATTAATTTACTTCAATTGCACCACTTCGAGC
CAAAACTCAGTGTTGAAGGAATCATAGTTGTGCACGGAATTGCAGGCACTGGGAAAACCACTTTACTTAG
GACTTTATTTCTGCTTACCCTAGCTTAGTTATAGGTTCACCTAGGCCTTGCTATTTAGATAAACAAAAC
AAAATTCACAAGTTTGCTTATCTTGCTTTCCCAATACCCATTGTGATATTGTCGATGAGTATCATTGC
TAGAAAGTTTTCCAGAACCAAAATTGGCTATCTTTGGTGACCCCTGTCAATGCACATACATTGAGAGACT
TAGAGTCCACATTACACTTCCTTCAGAACTCATAGATTTGGAAAGTCAACTGCTGAGATTTTGAACAAA
CTGTTTGACCTTAATATAGTCTCAGTTAAGAAAGAAGACGACATCGTTGAATTCTTTAACCCTTTCGAAG
TTGACCCCACTGAGCATATCTCTGCCTCTGAAGAAGAAGTCTTGGACTTTGTTTCTGACCAAGTGGTGAC
CACTAGCTCAGAGGAACTAGCAGGACTTGAGTTTGCAGAAACAACTTTCTACTGCACAACATTGGCCGCA
GCTGTTGCTGAAAATCCTGCTAAGACTTTCATCTCTCTGACTAGACACACCCACAAACTCACCATTGGGG
AACTAAATGCCAGGTCTAACTCCTAGAGCTGACCTCACTGACACATACAAAATCATTGCCATTGCTTTCT
```

FIG. 7A-4

```
TGTTGTCAGCTTGCATTTACTTCCAAAATAGCCACTACCAACCTGTTGCTGGAGACAACTTGCACCGTTT
GCCTTTTGGTGGCCAATATCAAGACGGCACCAAAAAGATATCTTATTTTCCACAACAGCAGTCATACTTT
CATTCTGGAAACAAATTAAATGTCCTCATACTTATCTTCATTCTCACATTGGGTATTGTCCTCACCAATA
AATTTAGTTTTAGCTTTAGTCGTACTACTCACCAGCATTCTTGCTATAACACACATTCAGCAACCAACAA
TACACAACCATTGTCAGGTCATCATTGACGGTGCTGCAATAGTCATAACAAATTGTGAGAACACACCAGA
AGTGCTTAAAGCAATCAACTTCTCCCCTTGGAACGGGTTAAGTTTTCCTAAATTTGAAAATTAATATTGA
GTGTTCACAAAAATCAACTTCAATAAACAATCATGCCTGACACAACACCTGTTGCTGCCACTTCAAGTGC
ACCACCCACAGCCAAAGATGCTGGTGCCAAAGCTCCTTCTGACTTCTCAAATCCCAATACAGCTCCTAGT
CTCAGTGATTTGAAGAAAGTCAAGTATGTCTCCACCGTGACCTCCGTGGCCACACCAGCTGAAATTGAAG
CCCTAGGCAAAATCTTCACCGCTATGGGCCTTGCCGCCAATGAGACTGGTCCGGCCATGTGGGATCTAGC
TCGTGCATATGCTGATGTGCAGAGTTCTAAATCGGCACAGCTGATTGGAGCTACCCCTTCCAACCCTGCA
CTATCACGCCGAGCCCTTGCTGCTCAGTTTGATCGAATCAATATAACCCCCAGGCAATTTGCATGTACT
TTGCCAAAGTTGTTTGGAACATACTTCTCGACAGCAACATTCCACCAGCAAATTGGGCCAAACTTGGTTA
CCAAGAAGATACAAAATTTGCTGCATTTGACTTCTTCGATGGAGTCACCAACCCTGCCAGCCTGCAGCCT
GCTGATGGTCTTATCAGGCAGCCAAATGAGAAAGAACTAGCTGCTCACTCCGTAGCTAAGTACGGCGCCT
TGGCTAGGCAAAAGATCTCCACAGGTAATTATATTACCACACTTGGAGAAGTCACACGTGGACACATGGG
AGGAGCTAACACCATGTACGCGATAGACGCACCCCCTGAACTTTAAACACTCGAAACTTAATCAGAGTGG
GGTTTCTACAGTTTATCTTCCTAATTATTTCTTTGAAAT
```

SEQ ID NO: 4 EU Sp-13

```
GAAAACAAAATAAATAAATAAATATACAAAGTTAAACTAACACAACATAACCACGTGGAAAAACAGCGAA
AGCACTTTACCACATTATGTCTCGTGTTAGAAATACTTTGGAAAAGATCAGAGACCCACAAGTACAGTCC
AGCATTTGTGAAGCTGCCTATCAACATGTTCGACCTGTACTTAAAGAATCTCTAATCAATTGTCCTTACG
CGCTTAATGATTATGAAGCAGACACCCTTGAGAATCTTGGTGTCACAATTAACCCCCATGCAATCCAAAC
ACACACACATGCCGCAGCCAAAGTAGTCGAAAATCGTATGCTTGAAATTGTTGGACATCACTTGCCTAAA
GATGAAAAGTAACTTTCATCTTCCTCAAACGTAGCAAGCTGCGTTACATGAGAAGAGCTGCTGTGCATA
AAGATGTCTTTGTCAATCATAACATTGAACCAAAAGACTTCTTCAGGTATGATGAAGAGTCTACATCAAC
CAGCTTTTCCGTTGATACGAGAATCGCATACATTTCAGATTCTCTACACTTTATGGAACCTGCTGATGTG
ACTCACTTGTTTGACCGTTGCCAAAACCTTAAAACATTGATGGCAACTGTTGTACTACCTGTGGAAGCTA
TACACAGACAGACATCTCTATTCCCTGCGATTTACTCCATTAACTACAATGAAGAAGGCTTTGAGTATAT
CCCAGGATCACACGGTGGTGGGGCATATTTCCACAAATATGAAACCCTAGAATGGCTCAAATACTCTAGA
TTCATTGGACATGATCCATTGACTGGTTTAAAATACACCATTACGATTCAAATGGTGGAGAGTCTTGGTG
CCAACCACCTTTTCCTCTTCCAAAGAGGAAACTTTGAGACGCCGCTATACAGGACGTTTCAAAAGAATAG
TTTTGTGACATTCCCAAATATATTCCATCCCCGACACGTCAATGCCACAAAACCTATGCCTAGATCAAGG
GCCATACAGCTGTACTTATATGTGAAATCAGTAAATAAAGTTACGCAAAGAGATATATTTGCCAAGGTTA
GACAACTGATTCCACTGCTGAGCTAGAATTGTATGACCCTGATGAACTCACGCACGTTGTAAATTATTT
CACATATGTGTCACAACTGTCATCTATCAATGATTATGACAACATGCTCAAATCCAGTTCTTCAAAAAA
CTGGTTGCACCCATGCAACACGACTGGAGGTGCATGATTGAATTCTTCCGGGGAAAGAGTGACTTCAATC
AACTGCTCACAGCTCTTCAATGGAAAGATTTTTCCTATACTATTAAGACTGAAGAGCTTGTAATTACTAC
ACACACTGCTATAGGACAAGCAATAAGCAATGCAGCTACCACATATAAAGAAAGAAGGCAGCTGACTCAA
TTGGTCAAAAAGGTACAATATCCTTAGCAGATTTTGAACAGAGAGAACCTGAAATAACTTACACTGAGT
TTGAGCCTGAAACTAGGCCCCAAGTGGACTGCGTTACTAATTATAATAATGCAGTAAAAAATTTAGGTCT
TTCTGCACTTGATGAACAGCCTCAATGTTCATCTTCTAGCAGTCATATACCCTGCAATGAAATATCCTTA
GCAATGACTGATGACGACAATGCTGCGGCCATTCATGAAATTGAATCTCTATTGTCTGAACCGATAATAG
CTCCTCAACTCCCAGCATTGCCACACAAGACATGGGCCAGTTATGCTTCAGACACTTCATCCATGAAGAA
CCGTGAGATTGAGAACATAATTGCTGAGCTTGAAATCTCACGGAAGGAAAATAATGTGCAGCAAACTACT
CATGATTACCATGCAGTTTTTGACACAGCTCAGAGCTCCGGAGATCTCCCATGGAAAGCATGGATTCCAC
TTCTGAATGCACACGGCTTCAAGGGAGACCAACTTCAATACAGTCCGGATGGCAAAGTGATTCAGCCAAT
CCAGGACATCAATAACAAAACACCAAGATCTGAGTACCCATCCAGCATTCCTGCAGATCTTGTGAATACA
CTGCGAAACATTAAAAGAGCAGTGTATGCCATTCCTATTAGCCATCGAAGGGCAAGTGCTTACAGCTCTG
ATATCAAAACAATAGGACCGGCAAATTACTCTGTTCCCAATCAAAAGAATGGAGGGAAAGTTTTGCTTT
CAAAATGCAACATGAAGACATCGTTAAATCTGGAGTAGTCATTCATGGCTGTGGCGGCTCTGGAAAATCA
CAAGCATTACAAACTTTCTCAGAACTCTTGGCGACTCTAATGACTGCTGCACAGTGGTTGTGCCAACTG
TTGAACTCAGAAATGATTGGGTGAACAAATTGTGTAAGCTACCCATGGAACACATTAAAACATTTGAAAA
AGCAATGATTCAACCAGGATTCCCAGTTGTTATCTTGATGACTACACTAAATTGCCACCTGGTTACATT
GAAGCCTATTTGTTCCACCATGCCAACACTGAACTTTTCATTCTTACTGGAGACTCGCGGCAAAGTGTAT
ATCATGAGTCCAACAATGAAGCATACATTGCCTCATTAGATGAAGCCGTCGCTTATTATGCTAACTACTG
TGGATTTTACCTAAATGCTACACACAGAAATGTTCGCAGTTTGGCCAATAAGCTAGGTGTTTACAGTGAG
AAAGAAGGTCACCTCAAAATTACCTTGCCTCAAATGCTCTACAAAAGTGCAAAGTGCCAATTTTGGTGC
CCTCTCAAATGAAGAAGAGTGCTATGCAAGACATAGGGCACAAAGCCATGACCTACGCTGGGTGTCAAGG
GCTTACTGCACCGAGAGTCCAAATTTTGCTTGACAACCACACACAACACTGCTCAGACAGGGTGCTGTAC
```

FIG. 7A-5

```
ACTTGTCTCTCCAGAGCTGTGGATTCCATCCACTTTATCAATACAGGCCCAAACAATTCTGAATTTTGGG
ACAAGCTTGAGGCAACACCATACCTCAAAGCATTTATTGATACTTACAGAGATGAGAAAACAGAAATGCT
CAATTCTAAGCCTGCTGATGACAGTCCCGCTGAGCCTGAAGCTCCATTGACTCACTTTCCAGTGTCAAAC
GGCAATAACTTGGAAAAGTTAGCTTCAGCGCTTCCTGAAAAATTTGCAAGAGAGTTATATGATAAACACC
ATGGATATTCTAATACAATCCAAACTGAAAATCCAGTGGTGCAACTTTTCCAGCATCAACAAGCCAAAGA
TGAAACACTTTTCTGGGCAACAATAGAAGCTAGACTTTCTATTACAACTCCGGAAGCCAACTTACGAGAA
TTTGTGCTAAAGAAAGATGTTGGAGATATCTTGTTTTTCAATTACCACAATGTCATGTGCTTACCTGCCG
ACCCAGTGGATTCGAGCCAAGAACATGGGAAATATGTGCTGCTGAAGTTAAAAATACATACTTAGCCAA
ACCAATGGCTAACTTGATCAATGCTGCTAGCAGACAATCTCCTGATTTCGACGCTAACAAAATTTCCCTG
TTCCTAAAATCTCAATGGGTCAAGAAAGTGGAAAAATTAGGTGCTGTCAAGTCAAAGCCTGGCCAGACCA
TTGCAGCTTTCATGCAACAAACAGTGATGTTGTATGGGACCATGGCCAGATACCTCAGAAAGATGAGACA
AAGATTTCAACCAAAACATATTTTCATCAATTGTGAAACAACAACTGATAATCTGAACCAATTTGTTAAA
CAAGGTTGGAACTTTAACAGAACAGCTCAGACAAATGATTTCACAGCTTTTGACCAATCACAAGATGGTG
CAATGCTTCAATTTGAAGTCATGAAGGCAAAATTCTTCAATATCCCTGCCGACATCATTGAAGGATACAT
CAACATCAAATTGAACGCCAAAATTTTTCTTGGCACATTGTCCATTATGAGGTTGTCTGGTGAAGGTCCA
ACTTTTGATGCCAACACAGAATGTTCAATAGCATATACTGCTACAAGATACCATCTTGATTCTACAGTCA
AGCAGGTTTATGCTGGAGATGATATGGCATTAGATGGAGTTGTCCAAGAAAAACCCTCTTTTAAAAAACT
ACAGAACAAGCTTAAACTCACCTCAAAGACACTATTTCCAAAACAGGTTAAAGGTGATTATGCTGAATTC
TGTGGTTGGACTTTCACTCCTGGTGGTATCATTAAAAACCCTTTGAAAATGCATGCTTCCATTATGTTGC
AAGAGGCAATCGGCAATTTACACACTGCTGCCAGATCATATGCCATTGACATGAACATTCATACCAAAT
GGGTGATGAGCTGCACAATTACTTAACACCAGATGAAGCTGAACAACACTTCCTTGCTGTTCGGAAGTTG
CACAAGTTACACCAAGGAGAAGCAATGAGACTTGGTGAAAAGAGCCCTCCAAAAGCAACACATTGAGGGG
TTAAGTTTTCCCCAGTTCGAAATGGAAAGATCAACTCTGATTAATTTACTTCAATTGCACCACTTCGAGC
CAAAACTCAGTGTTGAAGGAACCATAGTTGTGCACGGAATTGCAGGCACTGGGAAAACCACTTTACTTAG
GACTTTATTTTCTGCTTACCCTAGCTTAGTTATAGGTTCACCTAGGCCTTGCTATTTAGATAAACAAAAC
AAAATTTCACAAGTTTGCTTATCTTGCTTTCCCAATACCCATTGTGATATTGTCGATGAGTATCATTTGC
TAGAAAGTTTTCTAGAACCAAAATTGGCTATCTTTGGTGACCCCTGTCAATGCACATACATTGAGAGACT
TAGAGTCCCACATTACACTTCCTTCAGAACTCATAGATTTGGAAAGTCAACTGCTGAGATTTTGAACAAA
CTGTTTGACCTTAATATAGTCTCAGTTAAGAAAGAAGACGACATCGTTGAATTCTTTAACCCTTTTGAAG
TTGACCCCACTGAGCATATCTCTGCCTCTGAAGAAGAAGTCTTGGACTTTGTTTCTGACCAAGTGGTGAC
CACTAGCTCAGAGGAACTAGCAGGACTTGAGTTTGCAGAAACAACTTTCTACTGCACAACATTGGCCGCA
GCTGTTGCTGAAAATCCTGCTAAGACTTTCATCTCTCTGACTAGACACACCCACAAACTCACCATTGGGG
AACTAAATGCCAGGTCTAACTCCTAGAGCTGACCTCACTGACACATACAAAATCATTGCCATTGCTTTCT
TGTTGTCAGCTTGCATTTACTTCCAAAATAGCCACTACCAACCTGTTGCTGGAGACAACTTGCACCGTTT
GCCTTTTGGTGGCCAATATCAAGACGGCACCAAAAAGATATCCTATTTTCCACAACAGCAGTCATACTTT
CATTCTGGAAACAAATTAAATGTCCTCATACTTATCTTCATTCTCACGTTGGGTATTGTCCTCACCAATA
AATTTAGTTTTAGCTTTAGTCGTACTACTCACCAGCATTCTTGCTATAACACACATTCAGCAACCAACAA
TACACAACCATTGTCAGGCCATCATTGACAGTGCTGCAATAGTCATAACAAATTGTGAGAACACACCAGA
AGTGCTTAAAGCAATAAAACTTCTCCCCTTGGAACGGGTTAAGTTTTCCTAAATTTGAAAATTAGTATTGA
GTGTTCACAAAAATCAACTTCAATAAACAATCATGCCTGACACAACACCTGTTGCTGCCACTTCAAGTGC
ACCACCCACAGCCAAAGATGCTGGTGCCAAAGCTCCTTCTGACTTCTCAAATCCCAATACAGCTCCTAGT
CTCAGTGATTTGAAGAAAGTCAAGTATGTCTCCACCGTGACCTCCGTGGCCACACCAGCTGAAATTGAAG
CCCTAGGCAAAATCTTCACCGCTATGGGCCTTGCCGCCAATGAGACTGGTCCGGCCATGTGGGATCTAGC
TCGTGCATATGCTGATGTGCAGAGTTCTAAATCGGCACAGCTGATTGGAGCTACCCCTTCCAACCCTGCA
CTATCACGCCGAGCCCTTGCTGCTCAGTTTGATCGAATCAATATAACCCCCAGGCAATTTTGCATGTACT
TTGCCAAAGTTGTTTGGAACATACTTCTCGACAGCAACATTCCACCAGCAAATTGGGCCAAACTTGGTTA
CCAAGAAGATACAAAATTTGCTGCATTTGACTTCTTCGATGGAGTCACCAACCCTGCCAGCCTGCAGCCT
GCTGATGGTCTTATCAGGCAGCCAAATGAAAAGAACTAGCTGCTCACTCCGTAGCTAAGTACGGCGCCT
TGGCTAGGCAAAAGATCTCCACAGGTAATTATATTACCACACTTGGAGAAGTCACACGTGGACACATGGG
AGGAGCTAACACCATGTACGCGATAGACGCACCCCCTGAACTTTAAACACTCGAAACTTAATCAGAGTGG
GGTTTTCTACAGTTTATTTTCCTAATTATTCTTGAAATAAAAAAAAAAAAAAAAAAAAAAAAAAAAAAAA
AAAAAAAAA

SEQ ID NO:5 LE-2002
GAAAACAAAATAAATAAACAATTATACAAAGTTAAACTAACACAACATAACCACGTGGAAAAACAGCGAA
AGCACTTTACCGCATTATGTCTCGTGTCAGAAATACTTTGGAAAAGATCAGAGACCCACAAGTACAGTCC
AGCATTTGTGAAGCTGCCTATCAACATGTTCGACCTGTACTTAAAGAATCTCTAATCAATTGTCCTTACG
CGCTTAATGATTATGAAGCAGACACCCTTGAGAATCTTGGTGTCACAATTAACCCCCATGCAATCCAAAC
ACACACACATGCCGCAGCCAAAGTAGTCGAAAATCGTATGCTTGAAATTGTTGGACATCACTTGCCTAAA
GATGAAAAGTAACTTTCATCTTCCTCAAACGTAGCAAGCTGCGTTACATGAGAAGAGCTGCTGTGCATA
AAGATGTCTTTGTCAATCATAACATTGAACCAAAAGACTTCTTCAGGTATGATGAAGAGTCCACATCAAC
```

FIG. 7A-6

```
CAGCTTTTCCGTTGATACGAGAATCGCATACATTTCAGATTCTCTACACTTTATGGAACCTGCTGATGTG
ACTCACTTGTTTGACCGTTGCCAAAACCTTAAAACATTGATGGCAACTGTTGTACTACCTGTGGAAGCTA
TACACAGACAGACATCTCTATTCCCTGCGATTTACTCCATTAACTACAATGAAGAAGGCTTTGAGTATAT
CCCAGGATCACACGGTGGTGGGGCATATTTCCACAAATATGAAACTCTAGAATGGCTCAAATACTCTAGA
TTCATTGGACATGATCCATTGACTGGTTTAAAATACACCATTACGATTCAAATGGTGGAGAGTCTTGGTG
CCAACCACCTTTTCCTCTTCCAAAGAGGAAACTTTGAGACGCCGCTATACAGGACGTTTCAAAAGAATAG
TTTTGTGACATTCCCAAATATATTCCATCCCCGACACGTCAATGCCACAAAACCTATGCCTAGATCAAGG
GCCATACAGCTGTACTTATATGTGAAATCAGTAAATAAAGTTACGCAAAGAGATATATTTGCCAAGGTTA
GACAACTGATTTCCACTGCTGAGCTAGAATTGTATGACCCTGATGAACTCACGCATGTTGTAAATTATTT
CACATATGTGTCACAACTGTCATCTATCAATGATTATGACAACATGCTCAAATCCAGTTTCTTCAAAAAA
CTGGTTGCACCCATGCAACACGACTGGAGGTGCATGATTGAATTCTTCCGGGGAAGAGTGACTTCAATC
AACTGCTCACAGCTCTTCAATGGAAAGATTTTTCCTATACTATTAAGACTGAAGAGCTTGTAATTACTAC
ACACACTGCTATAGGACAAGCAATAAGCAATGCAGCTACCACATATAAAGAAAGAAAGCAGCTGACTCAA
TTGGTCAAAAAAGGTACAATATCCTTAGCAGATTTTGAACAGAGAGAACCTGAAATAACTTACACTGAGT
TTGAGCCTGAAACTAGGCCCAAGTGGACTGCGTTACTAATTATAATAATGCAGTTAAAAATTTAGGTCT
TTCTGCACTTGATGAACAGCCTCAATGTTCATCTTCTAGCAGTCATCTACCCTGCAATGAAATATCCTTA
GCAATGACTGATGACGACAATGCTGCGGCCATTCATGAAATTGAATCTCTATTGTCTGAACCGATAATAG
CTCCTCAACTTCCAGCATTGCCACACAAGACATGGGCCAGTTATGCTTCAGACACTTCATCCATGAAGAA
CCGTGAGATTGAGAACATAATTGCTGAGCTTGAAATCTCACGGAAGGAAAATAATGTGCAGCAAACTACT
CATGATTACCATGCAGTTTCTGACACAGCTCAGAGCTCCGGAGATCTCCCATGGAAAGCATGGATTCCAC
TTCTGAATGCACACGGCTTCAAGGGAGACCAACTTCAATACAGTCCGGATGGCAAAGTGATTCAGCCAAT
CCAGGACATCAACAACAAAACACCAAGATCTGAGTACCCATCCAGCATTCCTGCAGATCTTGTGAATACA
CTGCGAAACATTAAAAGAGCAGTGATGCCATTCCTATTAGCCATCGAAGGGCAAGTGCTTACAGCTCTG
ATATCAAAAACAATAGGACCGGCAAATTACTCTGTTCCCAATCAAAAGAATGGAAGGAAAGTTTTGCTTT
CAAAATGCAACATGAAGACATCGTTAAATCTGGAGTAGTCATTCACGGCTGTGGCGGCTCTGGAAAATCA
CAAGCATTACAAAACTTTCTCAGAACTCTTGGCGACTCTAATGACTGCTGCACAGTGGTTGTGCCAACTG
TTGAACTCAGAAATGATTGGGTGAACAAATTGTGTAAGCTACCCATGGAACACATTAAAACATTTGAAAA
AGCTATGATTCAACCAGGATTCCCAGTTGTTATATTGATGACTACACTAAATTGCCACCTGGTTACATT
GAAGCCTATTTGTTCCACCATGCCAACACTGAACTTTTCATTCTTACTGGAGACTCGCGGCAAAGTGTAT
ATCATGAGTCCAACAATGAAGCATACATTGCCTCATTAGATGAAGCCGTCGCTTATTATGCTAACTACTG
TGGATTTTACCTAAATGCTACACACAGAAATGTTCGCAGTTTGGCCAATAAGCTAGGTGTTTACAGTGAG
AAAGAAGGTCACCTCAAAATTACCTTTGCCTCAAATGCTCTACAAAAGTGCAAAGTGCCAATTTTGGTGC
CCTCTCAAATGAAGAAGAGTGCTATGCAAGACATAGGGCACAAAGCCATGACCTACGCTGGGTGTCAAGG
GCTTACTGCACCGAGAGTCCAAATTTTGCTTGACAACCACACACAACACTGCTCAGACAGGGTGCTGTAC
ACTTGTCTCTCCAGAGCTGTGGATTCCATCCACTTTATCAATACAGGCCCAAACAATTCTGAATTTTGGG
ACAAGCTTGAGGCAACACCATACCTCAAAGGCATTTATTGATACTTACAGAGATGAGAAAACAGAAATGCT
CAATTCTAAGCCTGCTGATGACAGTCCCGCTGAGCTCCGTGAAGCTCCATTGACTCACTTTCCAGTGTCAAAC
GGCAATAACTTGGAAAAGTTAGCTTCAGCGCTTCCTGAAAAATTTGCAAGAGAGTTATATGATAAACACC
ATGGATATTCTAATACAATCCAAACTGAAAATCCAGTGGTGCAACTTTTCCAGCATCAACAAGCCAAAGA
TGAAACACTTTTCTGGGCAACAATAGAAGCTAGACTTTCTATTACAACTCCGGAAGCCAACTTACGAGAA
TTTGTTCTAAAGAAAGATGTTGGAGATATCTTGTTTTTCAATTACCACAATGTCATGTGCTTACCTGCCG
ACCCAGTGGATTTCGAGCCAAGAACATGGGAAATATGTGCTGCTGAAGTTAAAAATACATACTTAGCCAA
ACCAATGGCTAACTTGATCAATGCTGCTAGCAGACAATCTCCTGATTCGACGCTAACAAAATTCCCTG
TTCCTAAAATCTCAATGGGTCAAGAAAGTGGAAAAATTAGGTGCTGTCAAGTCAAAGCCTGGCCAAACCA
TTGCAGCTTTCATGCAACAAACAGTGATGTTGTATGGGACCATGGCCAGATACCTCAGAAAGATGAGACA
AAGATTTCAACCAAAACATATTTTCATCAATTGTGAAACAACAACTGATAATCTGAACCAATTTGTTAAA
CAAGGTTGGAACTTTAACAGAACAGCTCAGACAAATGATTTCACAGCTTTTGACCAATCACAAGATGGTG
CAATGCTTCAATTTGAAGTCATGAAGGCAAAATTCTTCAATATCCCTGCCGACATCATTGAAGGATACAT
CAACATCAAATTGAACGCCAAAATTTTTCTTGGCACATTGTCCATTATGAGGTTGTCTGGTGAAGGTCCA
ACTTTTGATGCCAACACAGAATGTTCAATAGCATATACCGCTACAAGATACCATCTTGATTCTACAGTCA
AGCAGGTTTATGCTGGAGATGATATGGCATTAGATGGAGTTGTCCAAGAAAAACCCTCTTTTAAAAAACT
ACAGAACAAGCTTAAACTCACCTCAAAGACACTATTTCCAAAACAGGTTAAAGGTGATTATGCTGAATTC
TGTGGTTGGACTTTCACTCCTGGTGGTATCATTAAAAACCCTTTGAAAATGCATGCTTCCATTATGTTGC
AAGAGGCAATCGGCAATTTACACACTGCTGCCAGATCATATGCCATTGACATGAAGCATTCATACCAAAT
GGGTGATGAGCTGCACAATTACTTAACACCAGATGAAGCTGAACAACACTTCCTTGCTGTTCGGAAGTTG
CACAAGTTACACCAAGGAGAAGCAATGAGACTTGGTGAAAAGAGCCCTCCAAAAGCAACACATTGAGGGG
TTAAGTTTTCCCCAGTTCGAAATGGAAAGATCAACTCTGATTAATTTACTTCAATTGCACCACTTCGAGC
CAAAACTCAGTGTTGAAGGAATCATAGTTGTGCACGGAATTGCAGGCACTGGGAAAACCACTTTACTTAG
GACTTATTTTCTGCTTACCCTAGCTTAGTTATAGGTTCACCTAGGCCTTGCTATTTAGATAAACAAAAC
AAAATTTCACAAGTTTGCTTATCTTGCTTTCCCAATACCCATTGTGATATTGTCGATGAGTATCATTTGC
TAGAAAGTTTTCTAGAACCAAAATTGGCTATCTTTGGTGACCCCTGTCAATGCACATACATTGAGAGACT
```

FIG. 7A-7

TAGAGTCCCACATTACACTTCCTTCAGAACTCATAGATTTGGAAAGTCAACTGCTGAGATTTTGAACAAA
CTGTTTGACCTCAATATAGTCTCAGTCAAGAAGAAGACGACATCGTTGAATTCTTTAACCCTTTTGAAG
TTGACCCCACTGAGCATATCTCTGCCTCTGAAGAAGAAGTCTTGGGCTTTGTTTCTGACCAAGTGGTGAC
CACTAGCTCAGAGGAACTAGCAGGACTTGAGTTGCAGAAACAACTTTCTACTGCACAACATTGGCCGCA
GCTGTTGCTAAAAATCCTGCTAAGACTTTCATCTCTCTGACTAGACACACCCACAAACTCACCATTGGGG
AACTAAATGCCAGGTCTAACTCCTAGAGCTGACCTCACTGACACATACAAAATCATTGCCATTGCTTCT
TGTTGTCAGCTTGCATTTACTTCCAAAATAGCCACTACCAACCTGTTGCTGGAGACAACTTGCACCGTTT
GCCTTTTGGTGGCCAATATCAAGACGGCACCAAAAAGATATCTTATTTTCCACAACAGCAGTCATACTTT
CACTCTGGAAACAAATTAAATGTCCTCATACTTATCTTCATTCTCACATTGGGTATTGTCCTCACCAATA
AATTTAGTTTTAGCTTTAGTCGTACTACTCACCACGCATTCTTGCTATAACACACATTCAGCAACCAACAA
TACACAACCATTGTCAGGTCATCATTGACGGTGCTGCAATAGTCATAACAAATTGTGAGAACACACCAGA
AGTGCTTAAAGCAATCAACTTCTCCCCTTGGAACGGGTTAAGTTTTCCTAAATTTGAAAATTAATATTGA
GTGTTCACAAAATCAACTTCAATAAACAATCATGCCTGACACAACACCTGTTGCTGCCACTTCAAGTGCA
CCACCCACAGCCAAAGATGCTGGTGCCAAAGCTCCTTCTGACTTCTCAAATCCCAATACAGCTCCTAGTC
TCAGTGATTTGAAGAAAGTCAAGTATGTCTCCACCGTGACCTCCGTGGCCACACCAGCTGAAATTGAAGC
CCTAGGCAAAATCTTCACCGCTATGGGCCTTGCCGCCAATGAGACTGGTCCGGCCATGTGGGATCTAGCT
CGTGCATATGCTGATGTGCAGAGTTCTAAATCGGCACAGCTGATTGGAGCTACCCCTTCCAACCCTGCAC
TATCACGCCGAGCCCTTGCTGCTCAGTTTGATCGAATCAATATAACCCCCAGGCAATTTTGCATGTACTT
TGCCAAAGTTGTTTGGAACATACTTCTCGACAGCAACATTCCACCAGCAAATTGGGCCAAACTTGGCTAC
CAAGAAGATACAAAATTTGCTGCATTTGACTTCTTCGATGGAGTCACCAACCCTGCCAGCCTGCAGCCTG
CTGATGGTCTTATCAGGCAGCCAAATGAGAAAGAACTAGCTGCTCACTCCGTAGCTAAGTACGGCGCCTT
GGCTAGGCAAAAGATCTCCACAGGTAATTATATTACCACACTTGGAGAAGTCACACGTGGACACATGGGA
GGAGCTAACACCATGTACGCGATAGACGCGCCCCCTGAACTTTAAACACTCGAAACTTAATCAGAGTGGG
GTTTTCTACAGTTTATTTTCCTAATTATTTCTTTGAAACAAAAAAAAAAAAAAAAAAAAAAAAAAAAAA
AAAAAAAAA

SEQ ID NO:6 US1
GAAAACAAAACATAACACATAATATCAAAAGTGACCAAACACAACATAACCACGTGGAAAAACAGCGAAA
GCACTTTACCACATTATGTCTCGTGTTAGAAACACTTTAGAAAAGATCAGGGACCCACAAGTACAGTCAA
GCATATGCGAAGCAGCATACCAACATGTTCGACCAGTTTGAAGGAATCTCTAATCAATTGTCCCTATGC
GCTCAATGATTATGAAGCCGACACCCTTGAGAATTTAGGTGTCACAATTAACCCTCATGCAATTCAAACC
CATACACACGCAGCAGCTAAAGTGGTTGAAAACCGAATGCTAGAGATTGTTGGTCACCATCTACCAAAAG
ATGAGAAGGTTACCTTCATTTTCCTAAAACGTAGTAAATTGCGTTACATGAGAAGAGCTGCTGTTCATAA
AGATGTTTTTGTCAACCATAACGTAGAGCCCAAAGATTTTTTAGGTATGACGAGGAGTCCACATCAACA
AGCTTCTCCGTGAATACTAGAATCGCATACATTTCAGACTCCTTACATTTCATGGAGCCAGCTGATGTTA
CACACCTTTTCGACCGTTGCCAAAATCTTAAAACATTAATGGCAACCGTTGTCCTACCTGTGAAGCAAT
TCATAGACAAACATCTTTATTTCCTGCGATATACTCCATTAACTACAATGAAGAAGGCTTTGAGTATATC
CCTGGTTCCCATGGTGGTGGGGCATACTTTCACAAGTATGAGACCTTAGACTGGCTTAAATATTCCAGAT
TCATAGGACATGATCCATTGACTGGCCTCAAATATACCATTACAATTCAAATGGTTGAAAGTCTAGGCGC
CAACCACCTTTTCCTTTTCCAAAGAGGAAATTTTGAAACGCCCTTATATAGGACCTTTCAAAAAAATAGT
TTTGTGACATTCCCTAATATATTTCATCCCCGACATGTCAATGCCACAAAACCTATGCCACGCTCCAGGG
CAATTCAATTGTACTTATATGTTAAGTCTGTCAACAAAGTCACACAAAGAGACATCTTTGCAAAAGTTAG
ACAGCTTATATCCACAGCTGAGCTGGAACTGTATGACCCTGATGAGCTTACTCATGTTGTCAATTACTTT
TCATATGTTTCACAATTGTCATCTATAAATGATTATGACAACATGCTAAAATCCAGTTTCTTCAAGAAAT
TGGTTGCACCCATGCAACAAGACTGGAGGTGCATGATTGAAYTCTTCCGGGGAAAGAGTGATTTCAATCA
ACTTCTCACCGCTCTTCAATGGAAAGATTTTTCCTATACTATCAAAACTGAAGAGCTAATAATTACTACA
CACACTGCCATTGGGCAAGCTATAAGTGGAGCAGCTAATACTTATAAGGAAAGAAGGCAATTGACACAAC
TGGTCAAGCAAGGAGTGATTTCACTCGCTGATTTTCAATCTGAAGAGCCCAAAATAGAATACACCGAATT
CGAGCGAGAAACAAAACCACCAGTTGATTGTGTGACTAATTACAACAATGCTGTTAAGAACCTTGGCCTG
TCTGAACCAGTGGATCTGCCAGAATGCTCATACGCTAGAAACTCTGTTCCTAACAATGAGATATCTATGG
CTATGACTGATGCTGACAACTTCGCTGTTATAAATGAAATTGAATCTCTCTTGTCTGAAGAAATCGCAGC
ACCAACACTTCCAGCATTGAAAAATAAAACATGGGCTAGTTATGCATCTGACACTTCATCAAAGAAGAAT
GAAGAAATTGAAAATATAATTGCTGAGCTAGAAGCTTCACGTAAGGTCTCCAATGTCCAGCAAACACAGC
ACAACTACCATATCTCACAATGCCCCACTTCCTTAACTGCTGATCTTCCATGGAAAGCCTGGCTCCCACT
TCTCAATGCCCATGGTTTCAAAGGAGATCAGATCCAACATAGTCCCGACGGCCAAATAATCCAACCAATT
CAGGACATCAACAATAAAACACCAAGATCTGAATACCCATCTAGCATCCCTGCAGATCTTGTTTCAACCT
TGCGCAATATTAAAGAGCAGTTTATGCTATTCCTATCAGCCACAGAAGGGCCAGCGCTTATAGCTCAGA
TGTTAAAAATAACAGAACTGGAAAACTGCTCTGTGCTCAATCCAAAGAATGGAAAGAGAGTTTTGCTTTC
AAAATGCAACATGAAGACATAGTCAAATCTGGTGTTGTCATACATGGTTGTGGCGGCTCCGGAAAATCAC
AAGCATTGCAAAACTTCCTTAGAACTTTGGGTGACAATAATGACTGCTGTACAGTTGTTGTCCCCACAGT
AGAGCTCAGGAATGACTGGGTTAACAAATTGTGCAAGTTGCCTATGGAACACATCAAAACATTTGAAAAA

FIG. 7A-8

```
GCAATGATTCAACCAGGCTTTCCTGTTGTCATTTTTGACGACTATACTAAGCTGCCACCCGGTTACATTG
AAGCTTATCTGTTCCATCATGCCAACACTGAACTCTTCATCCTCACTGGTGACTCTAGACAAAGTGTATA
TCATGAGTCCAACAATGAAGCTTACATTGCCTCTCTTGATGAAGCTGTTGCCTACTATTCCAACTACTGT
GGTTTCTATTTGAACGCTACGCACAGAAATGTACGTAGTTTAGCTAACAAGTTGGGAGTGTACAGTGAAA
AAGAAGGACACCTCAAAATTACTTTTGCATCCAATGCTCTACAAAAATGCAAAGTACCCATCTTGGTGCC
CTCTCAGATGAAGAAAAATGCAATGCAAGACATTGGCCATAAAGCAATGACTTATGCAGGATGTCAAGGA
CTTACTGCTCCAAGAGTTCAAATTTTGCTTGACAACCACACACAGCATTGCTCGGACAGAGTTCTTTACA
CATGTCTTTCACGAGCTGTGGATTCTATCCATTTTATCAATACTGGCCCCAACAATTCCGAATTTTGGGA
TAAGCTTGAAGCTACACCATACCTCAAAGCCTTTATTGATACATACCGGGATGAAAAGACTGAGATGTTG
AATTCAAAACCTGCAGATGACAGCCCTGTGGAACCTAGAGCTCCTGCTACTCATTTCCCCGTCTCTAACG
GCAACAACTTAGAGAAATTAGCTTCAACACTACCTGAAAAGTTTGCTCGGGAGATCTATGATAAACATCA
TGGTTATTCCAACACCATACAAACAGAGAACCCCATAGTACAACTTTTCCAACATCAGCAGGCAAAAGAT
GAAACTCTCTTTTGGGCAACAATTGAGGCAAGACTTTCTATAACCACACCAGATGCTAACCTCAGAGAAT
TTACTTTGAAGAAAGACGTTGGAGATATTCTGTTCTTTAACTATCACTCAGCAATGTGTCTGCCAGCTGA
CCCTGTCGACTTCGAGCCAAGAACTTGGGAAATATGTGCAGCTGAAGTCAAGAATACATACCTAGCAAAA
CCAATGGCTAATTTGATAAATGCCGCTAGTCGACAATCTCCTGACTTCGAGCCTAACAAGATCTCACTGT
TTTTGAAGTCACAATGGGTTAAGAAAGTAGAGAAATTGGGAGCAATCAAATCAAAGCCTGGGCAAACAAT
TGCCGGCTTTTATGCAGCAAACCGTCATGCTGTACGGAACTATGGCTAGATACTTAAGAAAAATGAGACAA
AGATTTCAACCAAAACACATTTCATCAATTGTGAAACTACAACTGATGATCTGAATAATTTTGTTCTCA
ATGGTTGGAACTTTAATCGAACTGCTCAGACTAATGATTTCACTGCATTTGATCAATCCCAAGATGGAGC
TATGTTACAATTTGAAGTCATGAAGGCTAAATTCTTCAACATTCCTGCAGACGTGATTGAAGGGTATATC
AACATTAAGCTTAACGCTAAAATTTTCCTAGGTACCCTTTCAATTATGAGGTTATCAGGTGAAGGTCCCA
CATTTGATGCAAACACTGAATGCTCTATTGCTTACACAGCAACAAGATACCATCTAAGTTCAGCAGTGAA
ACAAGTTTACGCTGGTGATGACATGGCTCTTGACGGAGTGGTCATGGAAAAACCCTCCTTTAAGAAACTA
CAGAGCAAGCTTAAATTGACATCAAAAACATTGTTTCCAAAACAAGTTAAGGGTGATTATGCCGAATTTT
GTGGGTGGACTTTTACCCCAGGTGGGATTATTAAAAATCCTTTGAAAATGCATGCATCCATCATGTTACA
AGAAGCAATAGGTAACCTCCACACTGCTGCTAGGTCGTATGCAATAGACATGAAGCATTCATACCAAATG
GGAGATAAATTGCATGAATACCTTACTCCTGATGAAGCTGAGCAACATTTCTTGGCTGTTCGCAAATTGC
ACAAACTCCACCAAGGTGAAGCCATGAGACTTGGGGAGAAGAGCCCCCAAAAGCAACACATTGACGGGT
TAAGTTTCCCCTGTTCGAAATGGAAAGATCCACTCTAATAAATTTACTTCAACTGCACCACTTTGAACCT
AAACTCAGCGTTGAAGGAGTTATTGTTGTACACGGAATCGCTGGAACAGGGAAAACTACCCTACTTAGAA
CTTTATTTTCCGCTTACCCGAACTTAGTTATAGGATCACCTAGGCCTTGTTATTTAGATAAAGCTAATAA
AATTTCACAAGTTTGTTTATCTTGCTTTCCAAACACCCTTTGTGATATTGTCGATGAGTACCATCTTCTA
GAAAGTTACCAAGAACCTACTTTGGCTTTGTTTGGAGACCCTTGTCAGTGTACTTTCATTGAAAGACTTA
GAATTCCACACTACACTTCCTTCAGAACACATAGATTTGGCAAGTCTACTGCAGAGCTTTAAACAAGTT
GTTTCAACTTCAAATTGTATCTGTAAAACAAGAAGACGACATAGTTGAATTCTTCGACCCATTTCAAGTA
GACCCAACTGAAAATATTTCAGCATCTGAGGAAGAAGTTTTGGAATTTGTCTCTGATCAAGTAGTGACAA
CCAGCTCTGAAGAATTAGCAGGATTGGAGTTCACTGAAACCACTTTCTACTGCACTACACTAGCTGCAGC
AGTCACTGAAAATCCTGCCAGAACTTTCATCTCCTTAACCAGACACACTCAGAGACTCACCATTGGCGAA
CTAAATGCCAGGATTGACTCCTAGAGCTGACCTCACTGACACCTACAAGATAATTGCTATTGCTTTTTTG
TTGTCAGCTTGCATTACTTCCAAAACAGCCATTACCAACCTGTTGCTGGAGATAATCTGCATAGATTGC
CATTTGGTGGCCAGTATCAAGACGGCACCAAGAAGATATCATATTTTCCTCAGCAACAATCATACTTTCA
CTCTGGTAACAAATTAAATGTCCTCATACTCATCTTCATTCTTACATTGGGTATCGTCCTCACCAATAAA
TTTAGTTTTAGCGTTAGCCGTACTACTCACCAGCATTCTTGCTACAATACACATTCTGCAGCCAACACAA
CACCACCATTGTCAGGTCATCATTGACGGAGCTGCCATAGTTGTTACTAATTGTGAAAACACGCCTGAAG
TTCTAAAAGCAATCAACTTCTCCCCTTGGAACGGGTTAAGTTTTCCTAGTGTTTGAAAATTAACTTTGAG
CACTTCACAATTAAGCTAACAATTCACTAATCATGGCTGACAATACCCCAGTTGCTGCTACTTCTGGTTC
CCCTCCAACTGCTCAAGATGCTGGTGCCAAAGCCCCTGCTGACTTTCAAATCCTAATACAGCTCCTAGC
CTCAGTGATTTGAAGAAAGTCAAGTATGTGTCCACAGTCACTTCAGTGGCAACACCAACTGAAATAGAAG
CCCTTGGAAAGATCTTCACCGCCATGGGACTGCTGCTAATGAAACTGGACCCGCTATGTGGGATCTAGC
GCGTGCTTATGCTGATGTCCAAAGTTCAAAATCCGCACAACTCATAGGTGCCACCCCTTCAAATCCAGCA
CTCTCACGCCGCGCACTTGCTGCCCAATTTGATCGTATTAACATCACACCCAGGCAGTTCTGCATGTATT
TTGCTAAAGTTGTCTGGAACATTCTGCTAGACAGCAATATCCCACCAGCAAACTGGGCAAGCTTGGTTA
CCAAGAAGACACAAAATTTGCTGCTTTCGATTTCTTCGATGGAGTCACCAATCCAGCAAGTTTGCAACCA
GCTGACGGCCTCATCCGACAACCCAATGAAAAGGAGCTTGCTGCTCACTCAGTTGCTAAGTATGGTGCAC
TAGCCAGGCAGAAAATTTCCACTGGCAACTACATAACCACACTTGGAGAGGTCACACGTGGACACATGGG
TGGAGCTAACACCATGTACGCAATTGATGCACCCCCAGAACTTTAAAACACTCGAAACTTAATTAGAGTG
GGGTTTTCTATAGTTTATTTTCCCAATAAATTGCTTTTGTAAT
```

FIG. 7A-9

```
SEQ ID NO: 7 LP-2001
GAAAACAAAATATAAACAAATATACAAAGTTAAACTAACACAACATAACCACGTGGAAAAACAGCGAAAG
CACTTTACCACATTATGTCTCGTGTCAGGAATACTTTGGAAAAGATCAGAGACCCACAAGTACAGTCCAG
CATTTGCGAAGCCGCATATCAACATGTTCGACCCGTACTTAAAGAATCTCTAATCAATTGTCCTTATGCG
CTTAATGATTATGAAGCAGACACCCTTGAGAATCTTGGTGTCACAATTAATCCCCACGCAATCCAAACAC
ACACACATGCCGCAGCTAAAGTAGTTGAAAATCGTATGCTTGAAATCGTTGGACATCACTTGCCAAAAGA
TGAAAAGGTAACTTTTATCTTCCTCAAACGTAGCAAGCTGCGTTACATGAGAAGAGCTGCTGTGCATAAA
GATGTCTTTGTCAATCATAACATTGAACCAAAAGACTTCTTCAGGTATGATGAAGAGTCTACATCAACTA
GCTTTTCCGTTAATACGAGAATCGCATACATTTCAGATTCTCTACACTTTATGGAACCTGCTGATGTGAC
TCACTTGTTTGACCGTTGCCAAAACCTTAAAACATTAATGGCAACTGTTGTACTACCTGTTGAAGCTATA
CACAGACAGACATCCCTATTCCCTGCCATTTACTCCATTAACTACAATGAAGAAGGCTTTGAGTACATCC
CAGGATCACACGGTGGTGGGGCATATTTCCACAAATATGAAACCCTAGAATGGCTCAAATACTCTAGATT
CATTGGACATGATCCATTGACTGGTTTAAAATACACCATTACAATTCAAATGGTAGAGAGTCTTGGTGCC
AACCACCTTTTCCTTTTCCAAAGAGGAAACTTTGAGACGCCGTTATACCGGACGTTTCAAAAGAATAGTT
TTGTGACATTCCCAAATATATTTCATCCCCGACATGTCAATGCCACAAAACCTATGCCTAGATCAAGGGC
CATACAGCTGTACCTATATGTGAAATCAGTAAATAAAGTTACGCAAAGAGACATATTTGCTAAACTTAGA
CAACTGATTTCCACTGCTGAACTAGAATTGTATGACCCTGATGAACTCACGCATGTTGTAAATTATTCA
CATATGTGTCACAACTGTCATCTATCAATGATTATGACAACATGCTCAAATCCAGTTTCTTTAAAAAACT
GGTGGCACCCATGCAACACGACTGGAGGTGCATGATTGAATTCTTCCGGGGAAAGAGTGACTTCAATCAA
CTGCTAACAGCTCTTCAATGGAAAGATTTTTCATACACTATTAAGACTGATGAGCTTGTAATCACTACAC
ACACTGCTATAGGACAAGCAATATGCAATGCAGCTGCTACATATAAAGAAAGAAGGCAGCTGACTCAATT
GGTCAAAAATGGTACAATATCCTTAGCAGATTTTGAACAGAAAGAACCTGAAATAACCTACACTGAATTT
GAGCCTGAAACTAGGCCCCAGGTGGACTGCGTTACTAATTACAATAATGCAGTCAGAAATTTAGGTCTTT
CTGCACTCGATGAACAGCCTCAATGTTCATCTTCTAACAGTCATATACCCTGCAATGAAATATCTCTAGC
AATGACTGATGATGATAATGCTGCGGCCATTCATGAAATTGAATCTCTATTGTCTGAACCGATAATAGCT
CCTCAACTCCCAGCATTGCCACACAAGACATGGGCTAGTTATGCTTCCGACACATCATCTATGAAGAACC
GTGAAATTGAGAACATAATTGCTGAGCTTGAAATCTCACGGAAGGAAAACAATGTGCAGCAAACTACTCA
TGATTACCATGCTGTTTCTGATACTGCTCAAAACTCTGGAGGTCTCCCATGGAAAGCATGGATTCCACTT
CTGAATGCACACGGCTTTAAGGGAGACCAACTTCAATACAGTCCTGATGGCAAAGTGATTCAGCCAATTC
AGGACATCAATAACAAAACACCAAGATCTGAGTACCCATCCAGTATTCCTGCAGATCTTGTAACTACACT
GCGAAACATTAAAAGAGCAGTGTATGCCATTCCTATTAGCCATCGAAGGGCAAGTGCTTACAGCTCTGAT
ATCAAGAACAATAGGACTGGCAAATTGCTTTGCTCCCAATCAAAAGAATGGAAGGAAAGTTTTGCTTTCA
AAATGCGACATGAAGCATCGTTAAATCTGGAGTGGTCATTCATGGCTGTGGTGGCTCTGGAAAATCACA
AGCATTACAAAACTTTCTCAGAACTCTTGGCGACACCAACGACTGTTGCACAGTGGTGGTGCCAACTGTT
GAGCTCAGAAATGATTGGGTGAACAAATTGTGCAAACTACCCATGGAACACATTAAAACATTTGAAAAAG
CAATGATTCAACCAGGATTCCCAGTCGTTATCTTTGATGACTACACCAAATTGCCACCTGGTTACATTGA
AGCCTATTTGTTCCACCATGCCAACACCGAACTTTTCATTCTCACTGGAGACTCGCGGCAAAGTGTATAT
CATGAGTCCAACAATGAAGCATACATTGCCTCCTTAGATGAAGCCGTTGCTTACTATGCTAACTACTGCG
GATTTTACCTAAATGCTACACATAGAAATGTTCGCAGTTTAGCCAATAAGCTAGGTGTTTACAGTGAGAA
AGAAGGCCACCTCAAAATTACCTTTGCCTCAAATGCTCTACAAAAGTGCAAAGTGCCAATTTTAGTGCCT
TCTAAAATGAAGAAAGGTGCCATGCAAGACATAGGGCACAAAGCCATGACCTACGCTGGTTGTCAAGGGC
TTACTGCTCCAAGAGTCCAAATTTTGCTTGACAACCACACAACACTGCTCAGACAGGGTGCTGTACAC
ATGTCTCTCTAGAGCTGTTGATTCCATCCATTTTATCAATACAGGTCCAAACAATTCTGAATTTTGGGAC
AAGCTCGAGGCAACACCATACCTCAAAGCATTTATTGATACTTACAGAGATGAGAAAACAGAAATGCTCA
ATTCTAAACCTGCTGACGACAGTCCTACTGAGCCTGAAGCTCCATTGACTCACTTTCCAGTGTCCAACGG
CAACAACTTGGAAAAGTTAGCTTCAGCACTTCCTGAAAAATTTGCAAGGGAGTTGTATGACAAACACCAT
GGGTATTCTAACACAATCCAAACTGAAAATCCAGTGGTACAACTTTTCCAGCATCAACAAGCCAAAGATG
AAACGCTTTTCTGGGCAACAATAGAAGCTAGACTTTCTATTACAACTCCGGAAGCCAATTTACGAGAATT
TGTGCTGAAGAAGATGTTGGAGACATCTTGTTTTTCAACTACCACAATGCGATGTGCTTACCCGCTGAT
CCAGTGGACTTTGAGCCAAGAACATGGGAAATATGTGCTGCTGAAGTTAAAAATACTTACTTAGCCAAAC
CAATGGCTAACCTGATCAATGCTGCTAGCAGACAATCTCCTGATTTTGATACTAATAAAATTTCCCTGTT
CTTAAAATCTCAATGGGTCAAAAAAGTGGAAAAATTAGGTGCTGTCAAATCAAAGCCTGGCCAGACCATC
GCAGCTTTCATGCAACAAACAGTGATGTTGTATGGGACCATGGCCAGATACCTCAGAAAGATGAGACAAA
GATTCCAACCAAAGCATATTTTCATTAATTGTGAGACAACAACGGATGATCTGAACCAATTGTTAAACA
AGGTTGGAACTTTAACAGAACTGCTCAGACAAATGATTTCACAGCTTTTGACCAATCACAAGATGGTGCA
ATGCTTCAATTTGAAGTCATGAAGGCAAAATTCTTCAATATCCCTGCTGACATTATTGAAGGATACATCA
ATATCAAATTGAACGCCAAAATTTCCTTGGTACATTGTCCATTATGAGGTTGTCTGGTGAAGGTCCAAC
TTTTGATGCTAACACAGAATGTTCAATAGCATATACTGCTACAAGATACCATCTCGATTCCACAGTCAAG
CAGGTTTATGCTGGAGATGACATGGCATTAGATGGAGTTGTCCAAGAAAAACCCTCTTTCAAAAATTTAC
AGAACAAGCTTAAACTCACCTCAAAGACACTATTTCCAAAGCAGGTCAAAGGTGATTACGCTGAATTCTG
TGGTTGGACTTTCACTCCTGGTGGCATCATTAAAAACCCTTTGAAAATGCATGCTTCAATCATGTTGCAA
```

FIG. 7A-10

```
GAGGCAATTGGCAATTTGCACACTGCTGCCAGATCATATGCCATTGACATGAAGCATTCATACCAAATGG
GTGATGAGCTGCATGATTACTTAACACCAGATGAAGCTGAACAACATTTCCTTGCTGTTCGGAAATTGCA
CAAGCTACACCAAGGAGAAGCAATGAGACTTGGTGAAAAGAGCCCTCCAAAATCAACACATTGAGGGGTT
AAGTTTTTCCCAGTTTGAAATGGAAAGATCAACTCTGATTAATTTACTTCAATTGCACCACTTCGAGCCA
AAACTCAGTGTTGAAGGAATCATAGTTGTGCACGGAATTGCAGGAACTGGGAAAACCACTTTACTTAGGA
CTTTATTTTCTGCTTACCCTAGCTTAGTTATAGGTTCACCTAGGCCTTGTTATTTAGACAAACAAATAA
AATTTCACAAGTTTGCTTATCTTGCTTTCCCAATACCCATTGTGACATTGTTGATGAGTATCATTTGCTA
GAAAGTTTCCCAGAACCAAAATTGGCTATCTTGGTGACCCCTGTCAATGCACATACGTTGAAAGACTTA
GAGTCCCACATTACACTTCCTTCAGAACTCATAGATTTGGAAAGTCAACTGCTGAGATTTTGAACAAACT
GTTTGATCTTAATATAATCTCAGTTAAGAAAGAAGACGACATTGTTGAATTCTTTAACCCTTTCGAAGTT
GACCCCACTGAACATATCTCAGCCTCTGAAGAAGAAGTCTTAGACTTTGTTTCTGACCAAGTGGTGACCA
CCAGCTCAGAAGAACTAGCAGGACTTGAATTTGCTGAAACAACTTTCTACTGCACCACACTGGCAGCAGC
CGTTGCTGAAAATCCTGCTAAGACTTTCATCTCTCTGACCAGACACACTCACAAACTCACCATTGGGGAA
CTAAATGCCAGGTCTAACTCCTAGAGCTGACCTCACTGACACATACAAAATCATTGCCATTGCCTTCTTG
TTGTCAGCCTGCATTACTTCCAAAATAGCCACTACCAACCTGTTGCTGGAGACAATTTGCACCGTTTGC
CTTTTGGTGGCCAATATCAAGACGGCACTAAAAGGATTTCTTATTTTCCACAACAGCAGTCATACTTTCA
TTCTGGAAACAAATTAAATGTCCTCATACTTATCTTCATTCTCACATTGGGTATTGTCCTCACCAATAAA
TTTAGTTTTAGCTTTAGTCGTACTACTCACCAGCATTCTTGCTATAACACACATTCAGCAACCAACAACA
CACAACCATTGTCAGGTCATCATTGACGGTGCTGCAATAGTCATAACAAATTGTGAGAACACACCAGAAG
TACTTAAGGCAATCAACTTCTCCCCCTGGAACGGGTTAAGTTTTCCTAAGTTTGAAAATCAATATTGAGT
GTTCACAACAATCAACTTCAACAAACAATCATGCCTGACACAACACCTGTTGCTGCCACTTCAAGTGCAC
CACCTACAGCCAAAGATGCTGGTGCCAAAGCTCCTTCTGACTTCTCAAATCCCAATACAGCTCCTAGTCT
CAGTGATTTGAAGAAAGTCAAGTATGTCTCCACAGTGACTTCCGTGGCCACACCAGCTGAAATTGAAGCC
CTAGGCAAAATCTTCACCGCTATGGGCCTTGCCGCCAATGAGACTGGTCCGGCGATGTGGGATCTAGCTC
GTGCGTATGCTGATGTGCAGAGCTCTAAATCCGCACAGCTGATTGGTGCTACCCCTTCCAACCCTGCATT
ATCACGCCGAGCCCTTGCTGCTCAGTTTGATCGAATCAATATAACACCCAGGCAATTTTGCATGTACTTT
GCTAAAGTTGTTTGGAACATCCTTCTCGACAGCAATATTCCACCAGCAAATTGGGCTAAACTTGGTTACC
AAGAAGATACAAAATTTGCTGCATTTGACTTCTTCGATGGAGTCACCAACCCTGCCAGCCTGCAGCCTGC
TGATGGTCTCATCAGGCAACCAAATGAGAAAGAACTAGCTGCTCACTCAGTAGCTAAATATGGCGCCTTG
GCTAGGCAAAAGATCTCCACAGGTAATTATATTACCACACTTGGAGAAGTCACACGTGGACACATGGGTG
GAGCTAACACCATGTACGCGATCGACGCACCCCCTGAACTTTAAACACTCGAAACTTAATCAGAGTGGGG
TTTTCTACAGTTTATTTTCCTAATTATTTCTTTGAAACAAAAAAAAAAAAAAAAAAAAAAAAAAAAAAAA
AAAAAAAA
```

FIG. 8A-1

SEQ ID NO: 8

AAAGCACTTTACCACATTATGTCTCGTGTTAGAAACACTTTAGAAAAGATCAGGGAC
CCACAAGTACAATCTAGCATTTGTGAAGCCGCTTACCAACATGTTAGACCTGTGCTC
AAGGAATCCCTAATCAACTGTCCTTATGCGCTTAATGACTATGAAGCAGACACCCTT
GAGAATTTAGGTGTCACAATAAACCCCATGCAATCCAAACACATACTCATGCGGCA
GCTAAAGTTGTGGAAAATAGAATGCTCGAAATCGTTGGACACCACTTGCCCAAGGA
CGAGAAAGTTACCTTCATTTTCCTCAAAAGAAGCAAACTGAGATACATGCGAAGAGC
TGCTGTACATAAAGATGTTTTTGTTAATCACAATATAGAACCCAAGGATTTCTTCAG
GTATGATGAGGAATCTACATCTACTAGTTTCTCCGTGAACACCAGGATCGCTTACAT
CTCCGATTCTCTACATTTCATGGAACCAGCTGATGTGACCCACCTCTTTGACCGTTG
CCACAATCTTAAAACACTGATGGCAACTGTCGTTTTACCTGTTGAAGCCATCCACAA
ACAAACATCTTTATTTCCAGCGATATACTCCATTAATTACAATGAAGAAGGTTTTGA
GTATATCCCTGGTTCTCATGGTGGAGGGGCATACTTTCATAAGTATGAAACATTAGA
CTGGCTCAAATACTCTAGATTCATTGGCCAGGACCCCTTAACTGGACTCCGATACAC
CATAACCATTCAAATGGTAGAGAGTTTAGGAGCCAACCATCTTTTCCTCTTCCAAAG
AGGAAATTTTGAAACACCTTTATACAGGACGTTTCAAAAAAATAGCTTTGTGACCTT
TCCTAACATCTTCCATCCCCAACATGTTAATGCCACAAAGCCCATGCCAAGATCCAG
GGCAATTCAGCTGTATTTATATGTCAAATCTGTCAATAAGGTGACACAAAGAGATAT
CTTTGCGAAAGTAAGGCAACTTATATCTACAGCTGAACTTGAATTGTATGACCCTGA
TGAACTTACACATATTGTCAATTATTTCGCATATGTCTCAGAACTAAGCTCAATCAAC
GACTATGACAATATGCTCAAATCAAGTTTTTTCAAAAAACTTGTTGCACCCATGCAA
CATGACTGGAGGTGCATGATTGAATTCTTTCGGGGAAAAGTGATTTCAATCAACTT
TTAACTGCTCTTCAATGGAAAGACTTCTCTTACACCATTAAAACTGAAGAGTTAGTT
GTTGCTACACACTGAAATTGGCCAGGCAATCTGTGAAGCTGCGACCACATACAAA
GAAAGAAGACAATTGACCAATTTAGTCAAACAAGGCGCAGTAACATTAGCTGATTTC
AAAGAAGCGGACCAGCATGTGGAGTACACTCACTTTGATCCTGAGTTTAAATCCACT
GTTGACCCCCACCGGAGCTATGAAAATGCCATCAACAATCTTGGCATTGAGATTAAT
GAGGATGTACCTGAAAGTTCCGGCACTAATRAAACATTGCTTAACAATGAAATATCT
TTAGCAATGTCAY$_1$CTGCTGAACATGTGCAAGCCGTTCAAGAAATTGAGTCTTTACTC
TCTAACCCCGAAGCGGCACCAATATTGCCCCTGCACATGTTAAAACATGGGCTAGC
CTTGCATCTGACAY$_2$TTCCAGCACTAAAAACCGTGAAATCGAAGATATAGTGGCTAA
GCTGGAAATACAAAGAAATGAAGCTAGTTGCAGCTACCTTCAACCAAATAAGGAATT
GTCAAAACCCAAGGCTGCTGATAACAATCTCCCCTGGAATGCTTGGATCCCATTGCT

FIG. 8A-2

TAATGCACACGGCTTCAAAGGAGATCAATTACAATACGGCCCAGATGGTAACTTGAT
ACAGCCCATCCAAGACATTAACAATTCACAGCCTAGATCTGACTATCCGTCTTCTCT
GCCATGTGAACTTGTGGAAACTTTGAGGAAAATTAAGCGTGCTGTCTATGCCATCCC
AATAAGCCACAGGAGAGCTAGTGCTTACAGTTCTGACATCAAAAATAACAGAACTGG
CAAACTTCTCTGCAACCAAAGCAAAGAATGGAAAGAAAGCTTTGCTTTCAAAATGCA
ACATGAAGACATCGTCAAATCAGGTGTTGTCATACATGGTTGCGGAGGTTCTGGCAA
ATCCCAGGCATTACAAACTTCTTGAGAACATTGGGTGATTCAAATGATTGCTGTAC
TGTTGTAGTACCCACTGTTGAACTTAGAAATGACTGGGTAAACAAACTCCATAAATT
GCCCATGGAGCATATCAAAACATTTGAGAAAGCAATGATTCAACCTGGCTTTCCAAT
TGTTATATTTGATGATTACACCAAGTTGCCACCTGGCTACATTGAAGCATACCTATTT
CACCATGCCAACACTGAGCTTTTCATACTCACTGGTGATTCTAGGCAAAGCGTGTAC
CATGAATCTAACAATGAAGCGTACATTGCCTCATTAGATGAAGCTGTTGCATACTAC
GCTAATTACTGCGGTTTTTATTTAAATGCTACTCATAGAAATGTCCGTAGTTTAGCCA
ACAAACTTGGTGTTTACAGTGAGAAAGAAGGACACTTGAAAATCACTTTTGCTTCAC
ATGCCTTACAAAGTGCAAAGTGCCAATTTTAGTTCCTTCTCAAATGAAAAGGAGTG
CTATGTY$_3$AGACATTGGACATAAATCCATGACCTATGCTGGTTGCCAAGGTTTAACA
GCACCCAAGGTACAAATTCTCCTTGATAACCACACGCAACATTGCTCTGACAGAGTT
CTGTACACCTGTCTGTCTCGTGCAGTTGATTCCATCCACTTCATTAATACTGGTCCC
AACAATTCAGAATTTTGGGATAAGCTTGAAGCAACACCATATCTCAAAGCCTTCATT
GATGTCTATAGAGATGAAAAAACTGAAATGTTCAATTCTAAGCCTGCTGATGACAGT
CCAACTGAGCCTGAAGCACCTGTTACACATTTCCCAATAGCAAATGGAAATAACTTA
GAGAAATTAGCTTCTGCTTTGCCTGAAAAATTTGCTAGGGAGATTTATGACAAGCAT
CATGGCCACTCCAACACAATCCAAACTGAGAACCCTGTGGTCCAACTTTTCCAACAT
CAACAAGCGAAAGACGAGACACTCTTTTGGGCTACAATTGAAGCTAGATTGTCCATA
ACAACTCCTGAAGCAAACCTCAGAGAATTTTTGTTTAAGAAAGATGTTGGAGACATT
CTCTTCTTCAATTACCATAATGCGATGTGCTTGCCTGCCGACCCTGTTGACTTTGAA
GAAAAGACCTGGGAGATCTGTGCTGCTGAAGTGAAAAACACTTATCTTGCCAAACCC
ATGGCCAATCTTATCAATGCGGCAAGTAGACAATCACCCGACTTTGACTCTAATAAG
ATCTCATTATTCCTAAAGTCTCAATGGGTGAAAAAAGTGGAAAAACTTGGAGCTATC
AAATCAAAACCTGGGCAGACCATAGCTGCTTTTATGCAACAAACAGTCATGTTGTAT
GGTACTATGGCCAGGTACTTAAGGAAAATGCGGCAAAGATTCCAGCCAAAACACAT
ATTCATCAATTGTGAAACCACAACTGATGATCTCAATAAATTTGTCAAAGAY$_4$GGCTG
GAACTTTAACAGAACCGCCCAAACAAATGACTTCACTGCTTTTGATCAGTCACAAGA
TGGAGCAATGCTTCAATTTGAAGTCATGAAAGCAAAATTTTTTAACATTCCAGCTGA
TGTCATTGAAGGCTACATCAACATCAAGCTGAATGCTAAAATTTTCCTTGGAACACT

FIG. 8A-3

```
CTCAATAATGAGACTTTCTGGTGAAGGTCCCACATTTGACGCTAACACTGAGTGTTC
GATTGCATACACTGCCACAAGATTCCATATTGACAATACTGTTAAGCAAGTGTATGC
CGGTGACGACATGGCATTAGATGGAGTTGTGAGTGAAAAGAAATCATTCAGGAAGT
TACAAAATCTACTAAAACTCACTTCAAAAACGCTGTACCCAAAACAGGTTAAAGGGA
ATTACGCTGAATTTGTGGTTGGACTTTCACACCAGGGGGTATAATTAAAAATCCAC
TTAAAATGCATGCCTCAATTATGCTGCAAGAAGCCATTGGCAATCTGCACACAGCAG
CCAGATCTTATGCAATTGACATGAAGCATTCATACCAAATGGGTGACCAACTGCATG
ACTACCTAACCCCCGATGAAGCTGAACAACATTTCCTAGCTGTGAGAAAGCTTCACA
AACTCCATCAAGGCGAGGCCATGCGTCTTGGGGAGAAAAGTCCACCAAGATCAACC
CATTAAGGGGTTAAGTTTTCCCCAGTTTGAAATGGAAAGATCAACTTTGATCAATTT
ACTTCTGTTACACAAATTTGAACACAAGATTAACACTGAAGGAATCATTGTTGTGCA
CGGAATTGCTGGAACTGGGAAAACCACATTGCTTAGGACTTTATTTTCTGCATACCC
TAGCTTAGTTATAGGTTCACCTAGGCCTTGTTACTTAGATAAAGCTAATAAAATTTCA
CAAGTTTGCCTTTCTTGTTTTCCAAATACCTTGTGTGACATTGTTGACGAGTATCATC
TCTTAGAAAGTTTTCCTGAACCAAAACTAGCCATTTTTGGTGACCCTGTCAGTGCA
CTTACATTGAAAGGTTGAGAACACCCAACTACACATCCTTCAGAACACACCGATTTG
GCAAATCCACTGCTGCTCTACTAAACCAGTTATTTGATCTTAACATTGAGTCAGTCA
AAGCACAAGACGACACAGTAGAATACTTTGATCCTTTCGCAGTGGACCCCTCTGAAC
ACATTTCTGCTTCAGAAAAAGAAGTTTTGGAATTTGTAGGTGATCAAGTTGAGACTA
CAAGCTCTGAAGAACTAGCTGGTCTCGAGTTTAGTGAAGTTACTTTCTACTGTACCA
CACTTGCTGGTGCTGTTCAAGAAAATCCTGCTAAAACCTTCATTTCACTCACTAGAC
ACACTTCAAAGCTCACAATTGGTGAACTAAATGCCAGGTCTGACTCCTAGAGCTGAT
CTTACTGACACGTATAAAATCATTGCTATAGCCTTTCTACTGTCAGCTTGCATTTACT
TCCAAAACAGTCATTATCAACCAGTTGCAGGTGATAATTTGCACAGACTACCCTTTG
GTGGTCAGTATCAAGACGGAACTAAGAAGATTTCTTACTTTCCGCAGCAACAATCCT
ACTTTCACTCAGGAAACAAGCTTAATGTCCTCATACTTATCTTCATTCTTACACTGGG
TATTGTCCTCACCAATAAATTTAGTTTTAGCATTAGCCGTAATACTCACCAGCATCAT
TGCTACAACACACATTCTGCAACCCAAACAGGTCAATCAGTGCCAGGTCATCATTGA
CGGTGCAGCCATAGTTATAACAAATTGTCCAAACACACCCGAAGTTCTTAAAGCAAT
CAACTTCTCCCCTTGGAACGGGTTAAGTTTTCCTCAATTGTGAAATTATATTTGTTAT
CTAGTTAAATTCAAACAATTTAACTCAACTATGGAAAACCAACCTACAGCTTCTAAC
CCATCAGATGCACCACCAACTGCTGCTCAAGCTGGTGCCCAGAGCCCAGCSGACTT
CTCAAATCCTAATACAGCTCCTTCCCTAAGTGATTTGAAGAAGATCAAATACGTGTC
AACTGTCACTTCAGTTGCCACGCCTGCTGAAATTGAGGCCCTTGGCAAGATCTTTAC
TGCCATGGGTTTAGCAGCCAATGAGACCGGACCTGCCATGTGGGACCTCGCTCGTG
```

FIG. 8A-4

CTTATGCTGATGTGCAAAGTTCAAAATCTGCACAACTTAY₅AGGTGCCACACCATCCA
ACCCTGCTTTGTCTAGACGTGCACTTGCTGCACAGTTTGATCGTATCAATATCACAC
CCAGACAATTCTGCATGTATTTTGCAAAAATTGTTTGGAACATACTGTTAGACAGCA
ATGTGCCACCTGCCAACTGGGCAAAATTGGGCTATCAGGAAGATACCAAGTTTGCT
GCTTTTGACTTCTTTGATGGAGTCACAAATCCAGCTAGTCTACAGCCY₆GCAGATGG
CCTAATCAGGCAGCCCAATGAAAAGAGCTTGCTGCTCACTCGGTTGCTAAATATGG
TGCCCTTGCCCGCCAGAAAATATCCACTGGTAACTACATCACCACCCTTGGTGAAGT
TACACGTGGTCACATGGGCGGCGCCAACACTATGTACGCAATTGATGCACCTCCTG
AACTTTAAACACTCGAAACTTAACCAGAGTGGGGTTTTCTATAGTTTATTTTCCCTTA

SEQ ID NO: 9
MSRVRNTLEKIRDPQVQSSICEAAYQHVRPVLKESLINCPYALNDYEADTLENLGVTI
NPHAIQTHTHAAAKVVENRMLEIVGHHLPKDEKVTFIFLKRSKLRYMRRAAVHKDV
FVNHNIEPKDFFRYDEESTSTSFSVNTRIAYISDSLHFMEPADVTHLFDRCHNLKTLM
ATVVLPVEAIHKQTSLFPAIYSINYNEEGFEYIPGSHGGGAYFHKYETLDWLKYSRFIG
QDPLTGLRYTITIQMVESLGANHLFLFQRGNFETPLYRTFQKNSFVTFPNIFHPQHVN
ATKPMPRSRAIQLYLYVKSVNKVTQRDIFAKVRQLISTAELELYDPDELTHIVNYFAYV
SELSSINDYDNMLKSSFFKKLVAPMQHDWRCMIEFFRGKSDFNQLLTALQWKDFSY
TIKTEELVVATHTEIGQAICEAATTYKERRQLTNLVKQGAVTLADFKEADQHVEYTHF
DPEFKSTVDPHRSYENAINNLGIEINEDVPESSGTNXTLLNNEISLAMSXAEHVQAVQ
EIESLLSNPEAAPILPPAHVKTWASLASDXSSTKNREIEDIVAKLEIQRNEASCSYLQP
NKELSKPKAADNNLPWNAWIPLLNAHGFKGDQLQYGPDGNLIQPIQDINNSQPRSD
YPSSLPCELVETLRKIKRAVYAIPISHRRASAYSSDIKNNRTGKLLCNQSKEWKESFAF
KMQHEDIVKSGVVIHGCGGSGKSQALQNFLRTLGDSNDCCTVVVPTVELRNDVVNK
LHKLPMEHIKTFEKAMIQPGFPIVIFDDYTKLPPGYIEAYLFHHANTELFILTGDSRQS
VYHESNNEAYIASLDEAVAYYANYCGFYLNATHRNVRSLANKLGVYSEKEGHLKITF
ASHALQKCKVPILVPSQMKRSAMXDIGHKSMTYAGCQGLTAPKVQILLDNHTQHCSD
RVLYTCLSRAVDSIHFINTGPNNSEFWDKLEATPYLKAFIDVYRDEKTEMFNSKPAD
DSPTEPEAPVTHFPIANGNNLEKLASALPEKFAREIYDKHHGHSNTIQTENPVVQLFQ
HQQAKDETLFWATIEARLSITTPEANLREFLFKKDVGDILFFNYHNAMCLPADPVDF
EEKTWEICAAEVKNTYLAKPMANLINAASRQSPDFDSNKISLFLKSQWVKKVEKLGA
IKSKPGQTIAAFMQQTVMLYGTMARYLRKMRQRFQPKHIFINCETTTDDLNKFVKXG
WNFNRTAQTNDFTAFDSQDGAMLQFEVMKAKFFNIPADVIEGYINIKLNAKIFLGT
LSIMRLSGEGPTFDANTECSIAYTATRFHIDNTVKQVYAGDDMALDGVVSEKKSFRK
LQNLLKLTSKTLYPKQVKGNYAEFCGWTFTPGGIIKNPLKMHASIMLQEAIGNLHTA

FIG.8A-5

ARSYAIDMKHSYQMGDQLHDYLTPDEAEQHFLAVRKLHKLHQGEAMRLGEKSPPRSTH

BIOLOGICAL CONTROL OF PLANT VIRUSES

CROSS-REFERENCE TO RELATED PATENT APPLICATIONS

This application is a U.S. National Phase Application under 35 U.S.C. § 371 of International Patent Application No. PCT/NL2016/050684, filed Oct. 4, 2016 and claims the priority of EP 15188418.6, filed Oct. 5, 2015, all of which are incorporated by reference in their entireties. The International Application was published on Apr. 13, 2017 as International Publication No. WO 2017/061859 A1.

INCORPORATION BY REFERENCE OF SEQUENCE LISTING

A sequence listing created on Apr. 3, 2018 as the ASCII text file "Seq1st_10114_006653_US0" having a file size of 261.9 bytes, is incorporated herein by reference in its entirety.

FIELD OF THE INVENTION

The present disclosure provides new attenuated Pepino mosaic viruses useful in the control of plant disease. Compositions for biological control of plant disease are also provided as well as methods for the induction of cross-protection and increased resistance against Pepino mosaic virus in plants.

BACKGROUND OF THE INVENTION

The present invention concerns the field of biological control in agriculture and horticulture, in particular, the control of plant pathogens.

Tomato is susceptible to various viral diseases, and one of the causal agents, Pepino mosaic virus (PepMV), has recently become a major limiting factor with regard to tomato production. PepMV belongs to the *Potexvirus* genus of the Alphaflexiviridae family PepMV has rapidly spread throughout commercial tomato cropping and is currently found throughout Europe and North-America (Jorda et al., 2001; Cotillon et al., 2002; Verhoeven et al., 2003; Ling et al., 2008). The RNA genome of PepMV encompasses approximately 6.4 kb and contains five open reading frames that encode a RNA-dependent polymerase (RdRp), a triple gene block (TGB), a coat protein (CP), and two short untranslated sequences flanking the coding regions (Aguilar et al., 2002; Cotillon et al., 2002). Isolates of PepMV group into four separate strains (genotypes) based on sequence similarity, namely the Peruvian (LP)-strain to which the original PepMV isolate belongs, the European (EU)-strain that was found in Europe in 1999 (Van der Vlugt et al., 2000), the CH2-strain that was discovered in infected tomato seeds in Chile, and the US1-strain that was discovered in diseased tomato plants in the USA (Ling, 2007). Symptom severity varies between different isolates of PepMV (Van der Vlugt et al., 2000) and differences in severity do not necessarily coincide with differences in genotype (Hanssen et al., 2008).

PepMV induces a wide range of symptoms on tomato (Van der Vlugt et al., 2000; Jorda et al., 2001), such as mosaic, leaf distortion, nettle-like heads, single yellow spots, interveinal chlorosis and fruit discoloration. Tomato plants display symptoms shortly after infection with PepMV and, in general, subsequently recover (Van der Vlugt & Stijger, 2008). Symptoms may, however, return later during the growing season. Expression of symptoms may also depend on environmental conditions, such as temperature and light intensity (Jorda et al., 2001; Van der Vlugt & Stijger, 2008). PepMV is sometimes suggested to cause yield losses in tomato, but the highest economic losses are attributed to symptoms that affect the commercial value of tomato fruits, such as flaming, marbling, blotchy ripening and fruit size reduction (Soler et al., 2000; Spence et al., 2006).

PepMV is transmitted efficiently by contaminated hands, clothing or tools (Van der Vlugt & Stijger, 2008). Direct contact between healthy and infected plants during routine crop handling also suffices to spread PepMV infection. The incidence of PepMV on tomato is very high in some tomato cultivation areas, where the virus may affect up to 90% of the greenhouses (Soler-Aleixandre et al., 2005). To stay free of virus is challenging under such circumstances.

There exists a need in the art to protect plants from PepMV infection and to prevent or reduce plant diseases associated with PepMV infection.

SUMMARY OF THE INVENTION

In one aspect, the disclosure provides an attenuated Pepino mosaic virus comprising a nucleic acid molecule comprising a nucleic acid sequence, wherein the nucleotide at the position corresponding to 2605 of SEQ ID NO:1 is G, the nucleotide at the position corresponding to 3156 of SEQ ID NO:1 is T, and/or the nucleotide at the position corresponding to 3422 SEQ ID NO: 1 is G. Preferably, the nucleic acid sequence is at least 80% identical to SEQ ID NO: 1.

In one aspect, the disclosure provides an attenuated Pepino mosaic virus comprising a nucleic acid molecule comprising a nucleic acid sequence encoding arginine at the position according to 868 of SEQ ID NO:2 and/or encodes phenylalanine at the position according to 1052 of SEQ ID NO:2. Preferably, the nucleic acid sequence is at least 80% identical to SEQ ID NO: 1, SEQ ID NO: 3, SEQ ID NO:4, SEQ ID NO:5, SEQ ID NO:6, or SEQ ID NO: 7. More preferably, the nucleic acid sequence is at least 80% identical to SEQ ID NO: 1.

In one aspect, the disclosure provides an isolated nucleic acid molecule comprising a nucleic acid sequence having at least 95% identity to a nucleic acid sequence selected from SEQ ID NO:1, SEQ ID NO: 3, SEQ ID NO:4, SEQ ID NO:5, SEQ ID NO:6, or SEQ ID NO: 7, wherein the nucleic acid sequence encodes arginine at the position according to 868 of SEQ ID NO:2 and/or encodes phenylalanine at the position according to 1052 of SEQ ID NO:2. In preferred embodiments, the isolated nucleic acid molecule encodes an amino acid sequence having at least 95% identity to any one of the amino acid sequences depicted in FIG. 6, wherein the nucleic acid sequence encodes arginine at position 887 of FIG. 6 and/or the nucleic acid sequence encodes phenylalanine at position 1071 of FIG. 6.

In one aspect, the disclosure provides an RNA-dependent RNA polymerase wherein the polymerase has an arginine at the position according to 868 of SEQ ID NO:2, a phenylalanine at the position according to 1052 of SEQ ID NO:2, a phenylalanine at the position corresponding to 956 of SEQ ID NO:2, and/or an asparagine at the position corresponding to 1325 of SEQ ID NO:2. Preferably said polymerase has an arginine at the position according to 868 of SEQ ID NO:2 and a phenylalanine at the position according to 1052 of SEQ ID NO:2. Preferably said polymerase has a phenylalanine at the position corresponding to 956 of SEQ ID NO:2 and an asparagine at the position corresponding to 1325 of SEQ ID NO:2. Preferably said polymerase has an arginine at the position according to 868 of SEQ ID NO:2 and a phenylalanine at the position corresponding to 956 of SEQ ID NO:2. In some embodiments the RNA-dependent RNA polymerases has at least 50%, at least 70%, at least 80%, or at least 90% identity to any one of the amino acid sequences depicted in FIG. 6. The invention also provides a nucleic acid molecule encoding a polymerase as indicated in this paragraph.

In one aspect, the disclosure provides an attenuated Pepino mosaic virus comprising a nucleic acid molecule comprising a nucleic acid sequence, wherein the nucleotide at the position corresponding to 2675 of SEQ ID NO:8 is G, the nucleotide at the position corresponding to 3226 of SEQ ID NO:8 is T, and/or the nucleotide at the position corresponding to 3492 SEQ ID NO: 8 is G. Preferably, the nucleic acid sequence is at least 80% identical to SEQ ID NO: 8.

Figure 2B:
Figure 2A:
Figures 1, 5A:
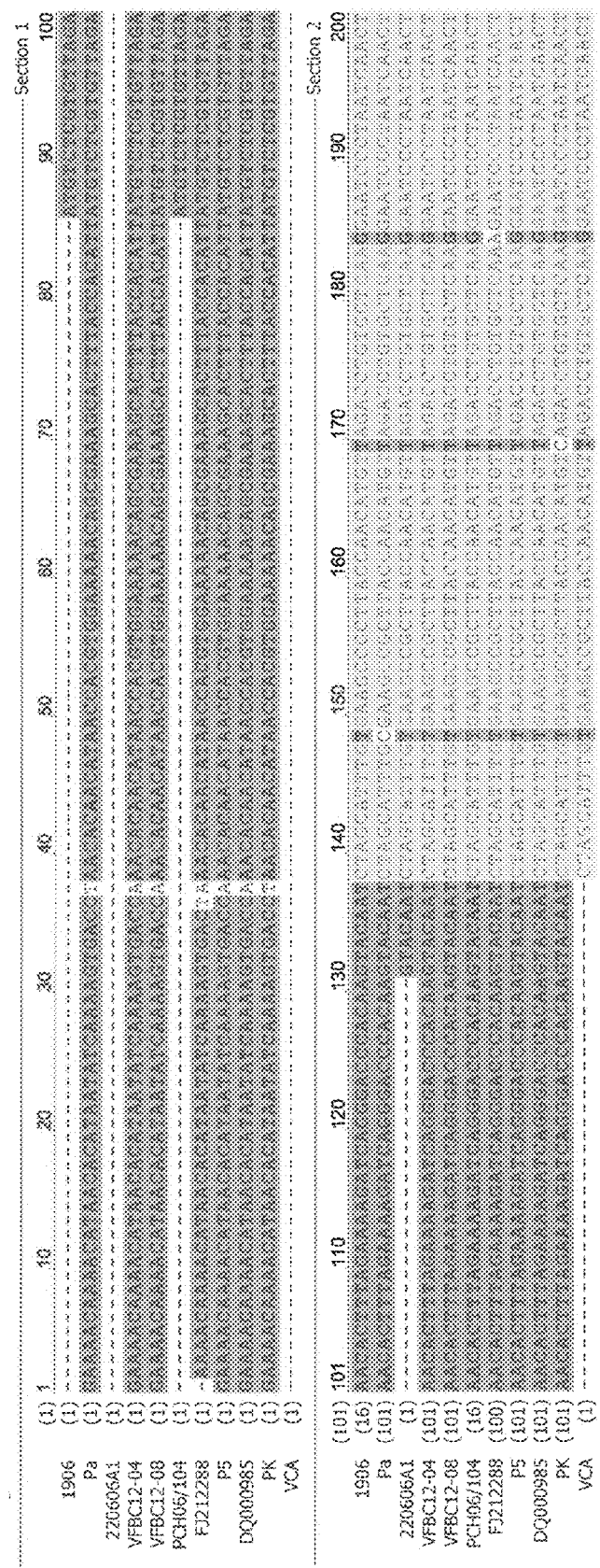
Figures 2, 5A:
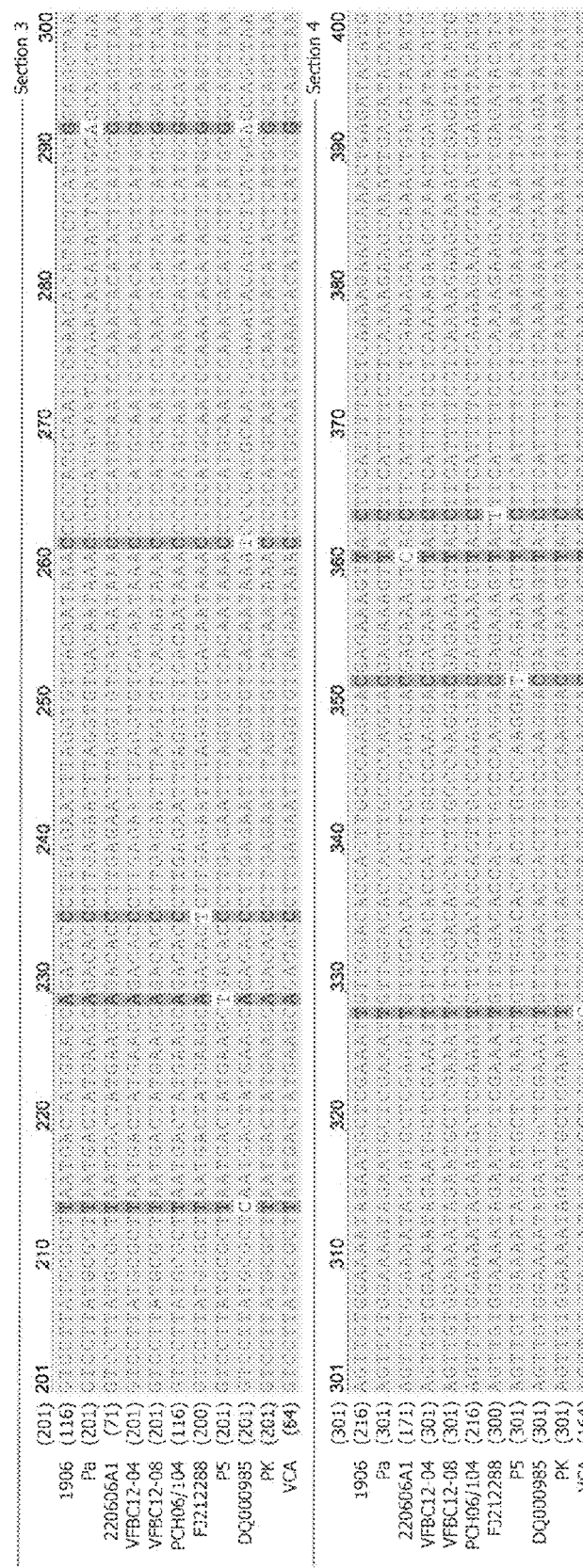

In one aspect, the disclosure provides an attenuated Pepino mosaic virus comprising a nucleic acid molecule comprising a nucleic acid sequence encoding arginine at the position according to 886 of SEQ ID NO:9 and/or encodes phenylalanine at the position according to 1070 of SEQ ID NO:9. Preferably, the nucleic acid sequence is at least 80% identical to SEQ ID NO: 1, SEQ ID NO: 3, SEQ ID NO:4, SEQ ID NO:5, SEQ ID NO:6, or SEQ ID NO: 7. More preferably, the nucleic acid sequence has at least 95%, at least 99%, or 100% identity to. SEQ ID NO: 8.

In one aspect, the disclosure provides an RNA-dependent RNA polymerase having at least 50%, at least 70%, at least 80%, least 90%, at least 99% or at least 100% identity to SEQ ID NO:9, wherein the polymerase has an arginine at the position according to 886 of SEQ ID NO:9 and/or a phenylalanine at the position according to 1070 of SEQ ID NO:9. Preferably said polymerase has an arginine at the position according to 886 of SEQ ID NO: 9 and a phenylalanine at the position according to 1070 of SEQ ID NO:9. Preferably said polymerase has a phenylalanine at the position corresponding to 974 of SEQ ID NO:2 and an asparagine at the position corresponding to 1343 of SEQ ID NO:2. Preferably said polymerase has an arginine at the position according to 886 of SEQ ID NO:2 and a phenylalanine at the position corresponding to 974 of SEQ ID NO:2. The invention also provides a nucleic acid molecule encoding a polymerase as indicated in this paragraph.

In one aspect the disclosure provides a vector, preferably an expression vector, comprising a nucleic acid molecule as disclosed herein. In one aspect the disclosure provides an isolated polypeptide encoded by a nucleic acid molecule disclosed herein. In one aspect the disclosure provides an antibody specific for the polypeptide encoded by a nucleic acid molecule as disclosed herein.

In one aspect the disclosure provides a composition for biological control of plant disease comprising an attenuated Pepino mosaic virus as disclosed herein, a nucleic acid molecule as disclosed herein or a vector as disclosed herein; and an agriculturally acceptable carrier.

In one aspect the disclosure provides a method for identifying a pepino mosaic virus (PepMV)-resistant plant, comprising a) exposing a plant or plant part to an attenuated Pepino mosaic virus as disclosed herein, a nucleic acid molecule as disclosed herein, a vector as disclosed herein, or the compositions as disclosed herein;

b) exposing the plant or plant part to an infective dosage of PepMV, and c) identifying said plant as PepMV-resistant plant when, after said exposure, disease-symptoms in said plant or plant part are reduced or delayed and/or PepMV accumulation in said plant or plant parts is reduced or delayed in comparison to a control PepMV infected plant.

In one aspect the disclosure provides a method for the detection of a pepino mosaic virus (PepMV) comprising providing a sample suspected of containing PepMV and detecting a PepMV virus as disclosed herein, a nucleic acid molecule as disclosed herein or a vector as disclosed herein. The method is useful among others to determine whether an application of the attenuated virus to a plant has been successful. The method is also useful to determine the extent of infection of a particular patch of crop. Particularly with a PepMV as disclosed herein. The sample is typically prepared from a plant or a part thereof that is susceptible to PepMV infection and/or replication. A sample is suspected of containing PepMV when there is reason to believe that the PepMV is present in the sample. A sample is also suspected of containing PepMV when the sample is from plant of which it needs to be verified that it does or does not contain a PepMV of the invention. Such a sample can be for instance from a plant in a greenhouse in the situation when in a nearby greenhouse a PepMV infection has been reported. It can also be from a plant with one or more symptoms that point towards a PepMV infection and one wants to confirm this. The invention also provides method for the detection of PepMV as described herein wherein the term "sample suspected of containing PepMV" is replaced by the term "sample of a plant susceptible to PepMV infection".

In one aspect the disclosure provides a method for producing a pepino mosaic virus (PepMV)-resistant plant, comprising exposing a plant or plant part to an attenuated Pepino mosaic virus as disclosed herein, a nucleic acid molecule as disclosed herein, a vector as disclosed herein, or the compositions as disclosed herein.

In one aspect the disclosure provides a PepMV-resistant plant comprising an attenuated Pepino mosaic virus as disclosed herein or a nucleic acid molecule as disclosed herein.

In one aspect the disclosure provides a method for controlling infection or disease in a plant comprising applying an effective amount of an attenuated Pepino mosaic virus as disclosed herein, a nucleic acid molecule as disclosed herein, a vector as disclosed herein, or the compositions as disclosed herein to said plant.

In one aspect the disclosure provides an attenuated Pepino mosaic virus as disclosed herein, a nucleic acid molecule as disclosed herein, a vector as disclosed herein, or the compositions as disclosed herein for use in controlling infection or disease in a plant. In particular, the use is for inducing resistance to PepMV.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 1. Inoculation of tomato plants with CHD alone resulted in strong necrosis of the leaves and stems, from 3 weeks after inoculation of CHD (FIG. 1A). Inoculation of tomato plants with VCA, followed by CHD, protected plants from necrosis (FIG. 1B).

FIG. 2. Thirty-nine days after inoculation of tomato plants with VC1 (FIG. 2A) or VCA (FIG. 2B).

Figure 3A:
Figure 3C:
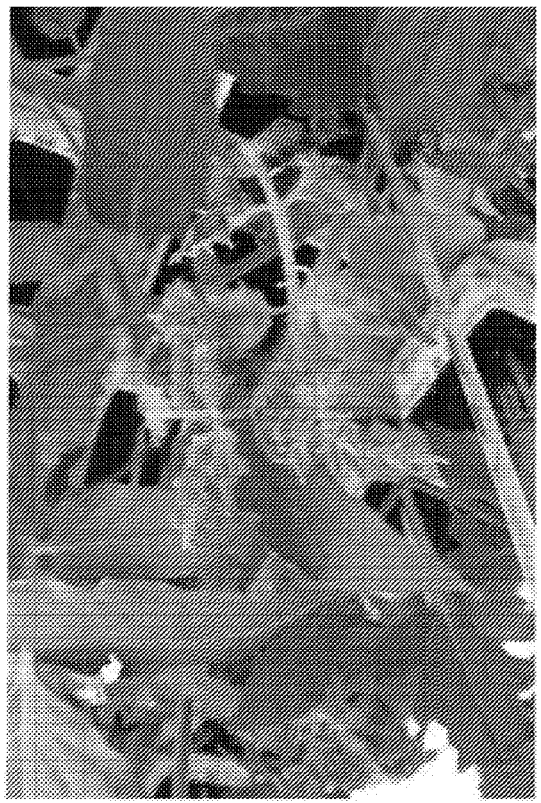
Figure 3B:
Figures 3, 5A:
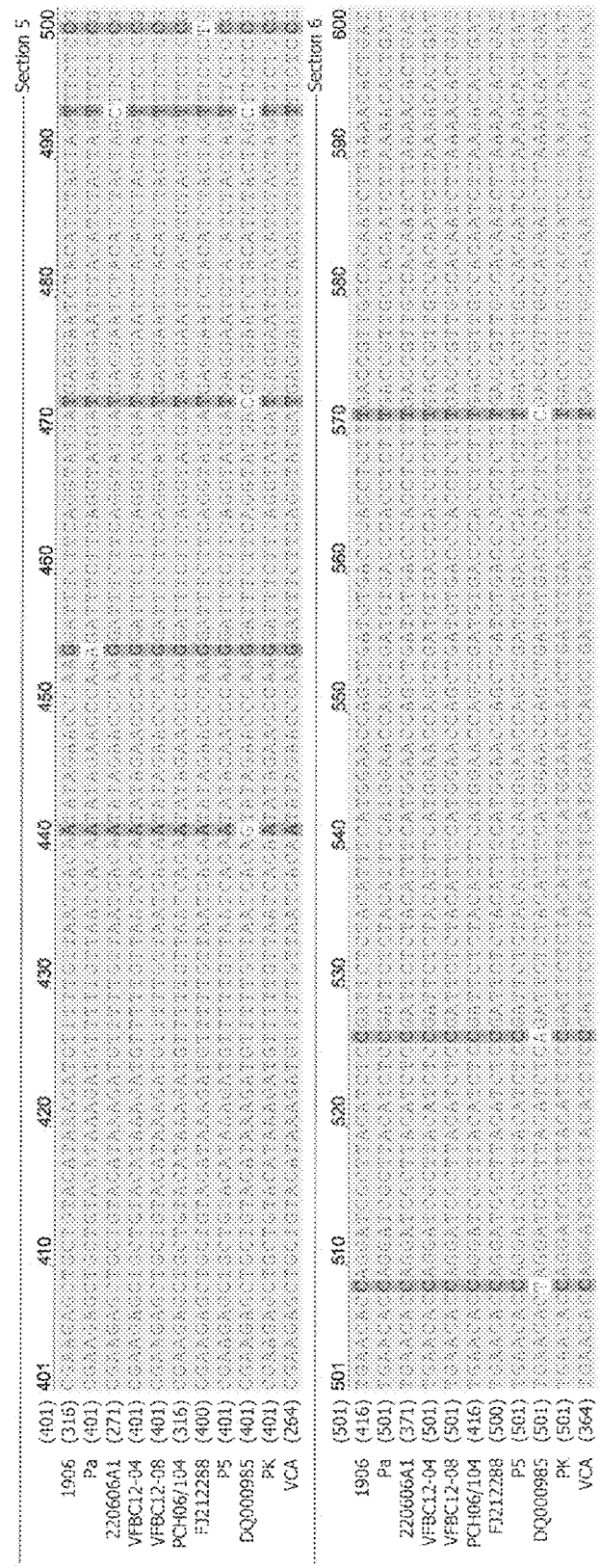

FIG. 3. Development of mild symptoms in infected plants; no treatment (FIG. 3A); VCA treatment (FIG. 3B); VC1 treatment (FIG. 3C).

FIG. 4. Comparison of symptoms in plants grown under optimal conditions (top row) versus sub-optimal conditions (bottom row); no treatment (FIG. 4A); VC1 treatment (FIG. 4B); VCA treatment (FIG. 4C).

FIGS. 5A-1-5A-33. An alignment of the sequence of VCA with closely related sequences identified from BLAST (Basic local alignment search tool) from NCBI. The sequence with the highest identity in the BLAST search was "1906", having 99.6% identity. The nomenclature listed in FIG. 5 corresponds to the annotations of NCBI as follows:
1906: Pepino mosaic virus isolate 1906 replicase, triple gene block protein 1 (TGBp1), triple geneblock protein 2 (TGBp2), triple gene block protein 3 (TGBp3), and coat protein genes, complete cds.
DQ000985: Pepino mosaic virus isolate Ch2, complete genome.
FJ212288: Pepino mosaic virus, complete genome.
Pa: Pepino mosaic virus isolate PepMV-Pa, complete genome.
PK: Pepino mosaic virus isolate PepMV-PK, complete genome.
220606A1: Pepino mosaic virus isolate 220606A1.
VFBC12-04: Pepino mosaic virus isolate VFBC12-04.
VFBC12-08: Pepino mosaic virus isolate VFBC12-08.
P5: Pepino mosaic virus isolate PepMV-P5, complete genome.
PCH06/104: Pepino mosaic virus isolate PCH 06/104 replicase, triple gene block protein 1 (TGBp1), triple gene block protein 2 (TGBp2), triple gene block protein 3 (TGBp3), and coat protein genes, complete cds FIGS. 6A-1-6A-5. An alignment of the amino acid sequence of RNA-dependent RNA polymerase from VCA and other PepMV viruses.
LE-2002, AJ438767, and Sp-13 are EU isolates. LP-2001 is an LP isolate. US1 is a US isolate.

Figures 5, 5A, 6, 7:
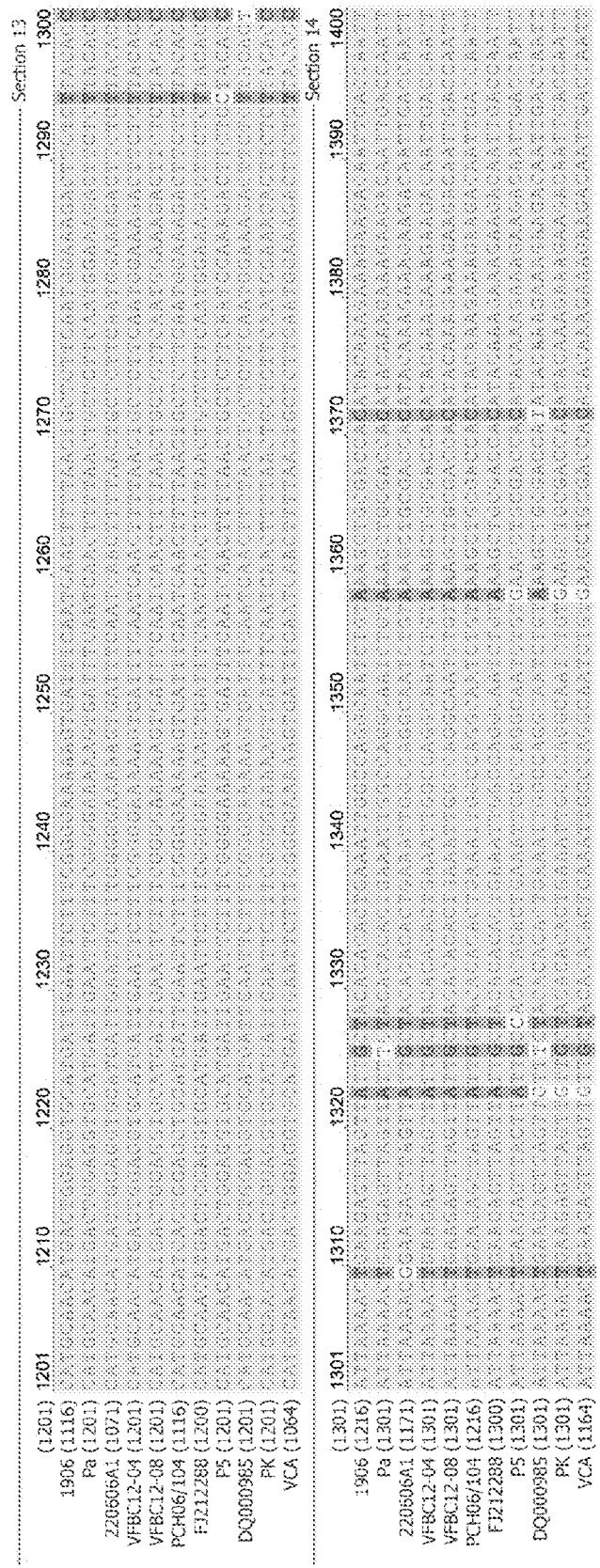
Figures 5, 5A, 6, 7, 8:
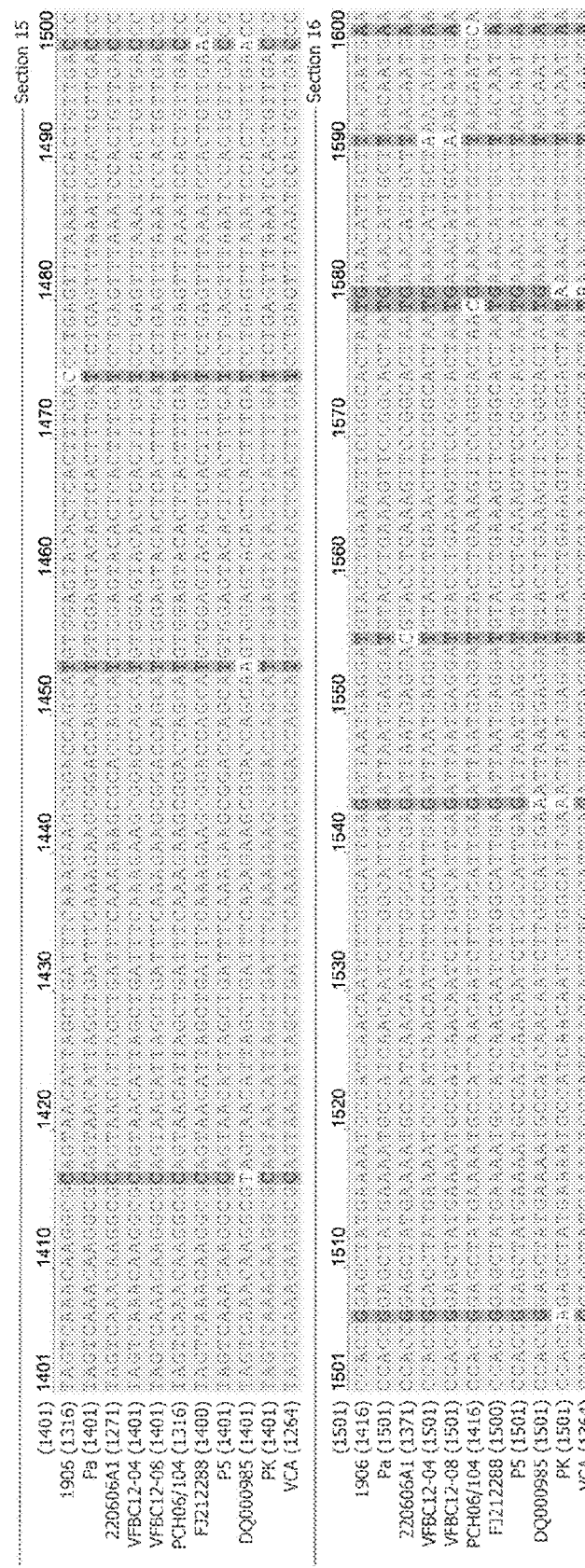
Figures 5, 5A, 6, 7, 8, 9:
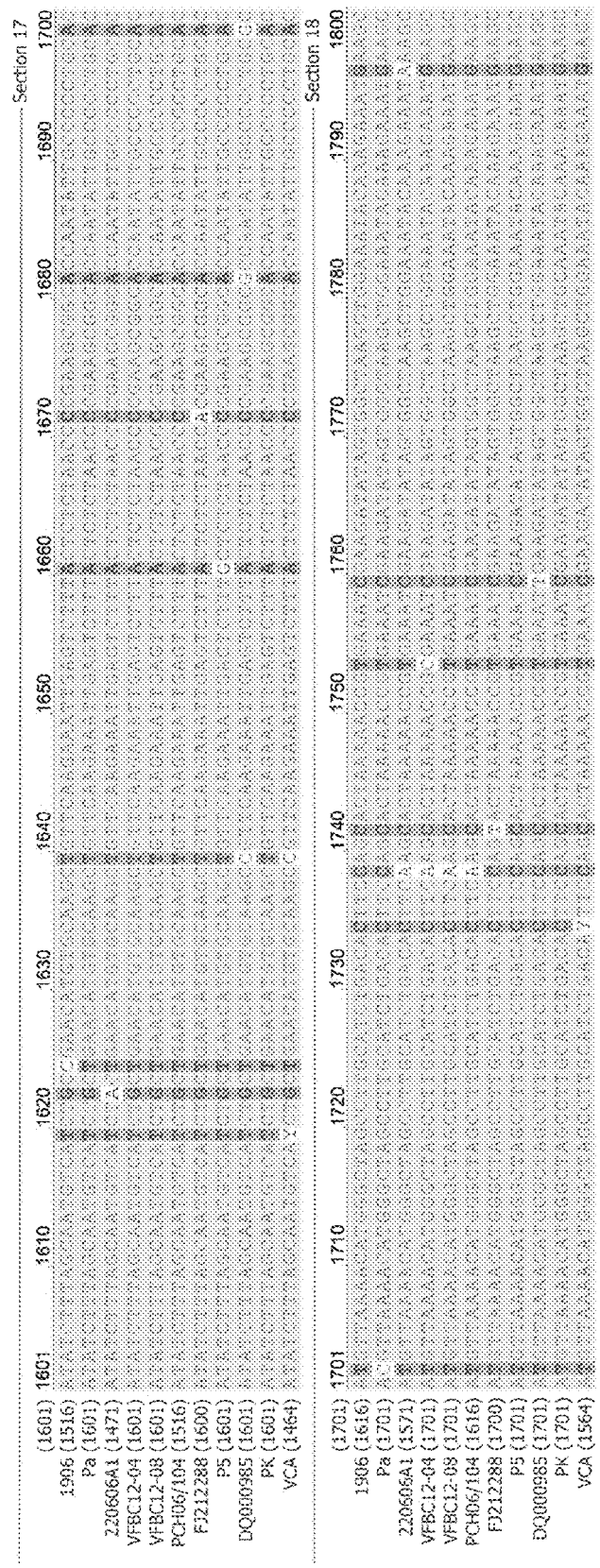
Figures 5, 5A, 6, 7, 8, 9, 10, 11, 12, 13, 14:
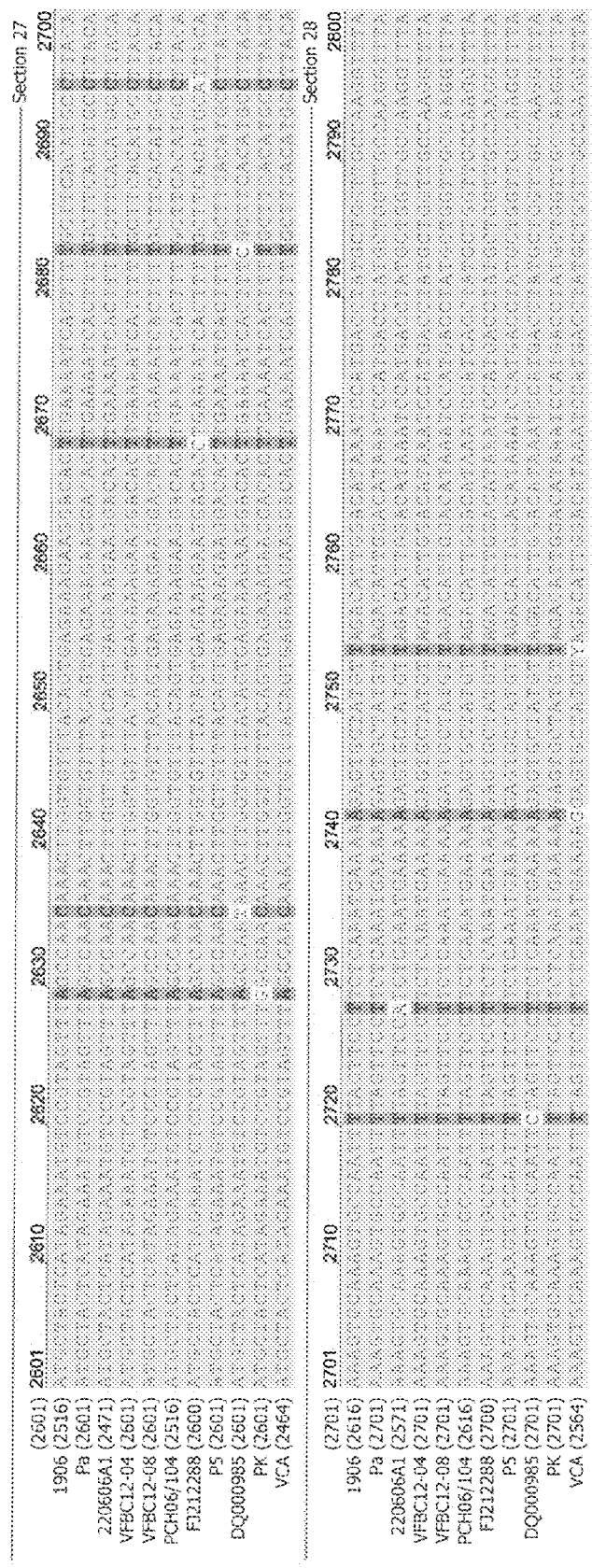
Figures 5, 5A, 6, 7, 8, 9, 10, 11, 12, 13, 14, 15, 16, 17, 18, 19, 20:
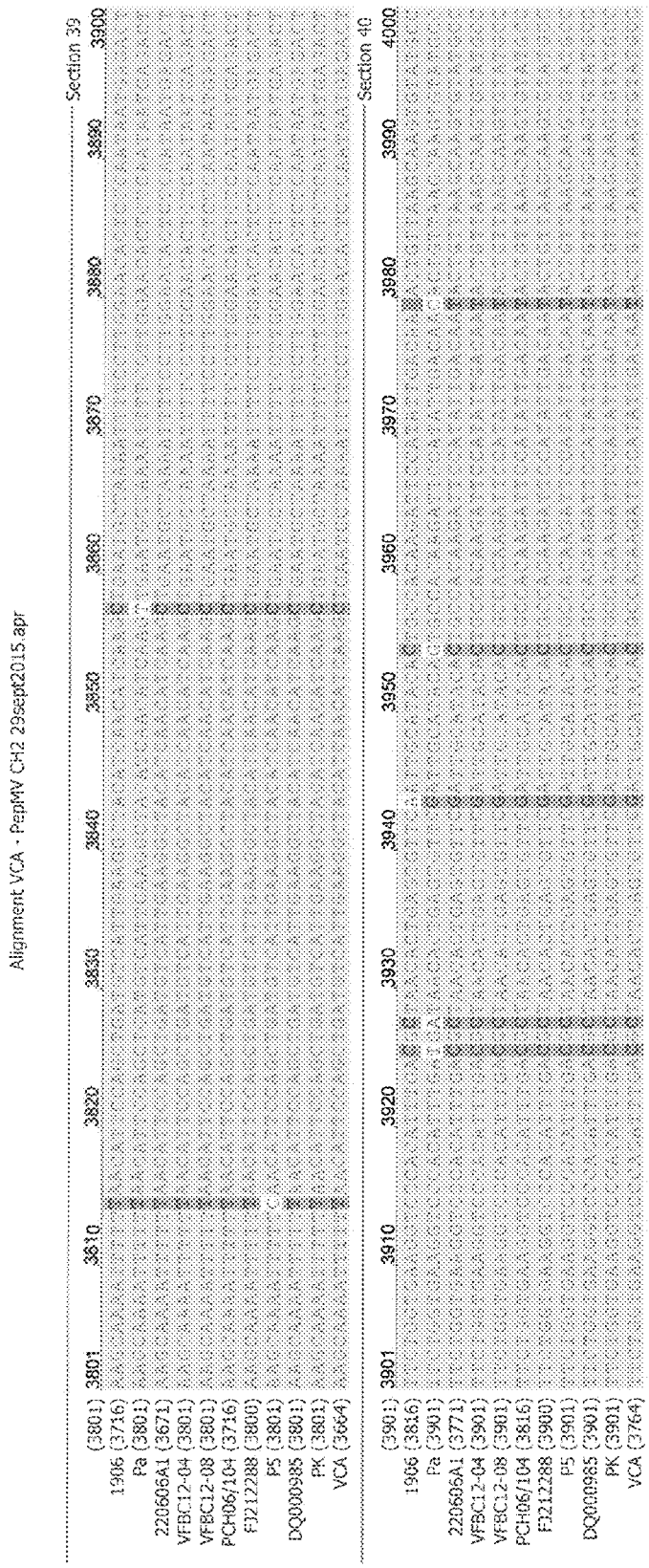
Figures 5, 5A, 6, 7, 8, 9, 10, 11, 12, 13, 14, 15, 16, 17, 18, 19, 20, 21, 22, 23, 24, 25:
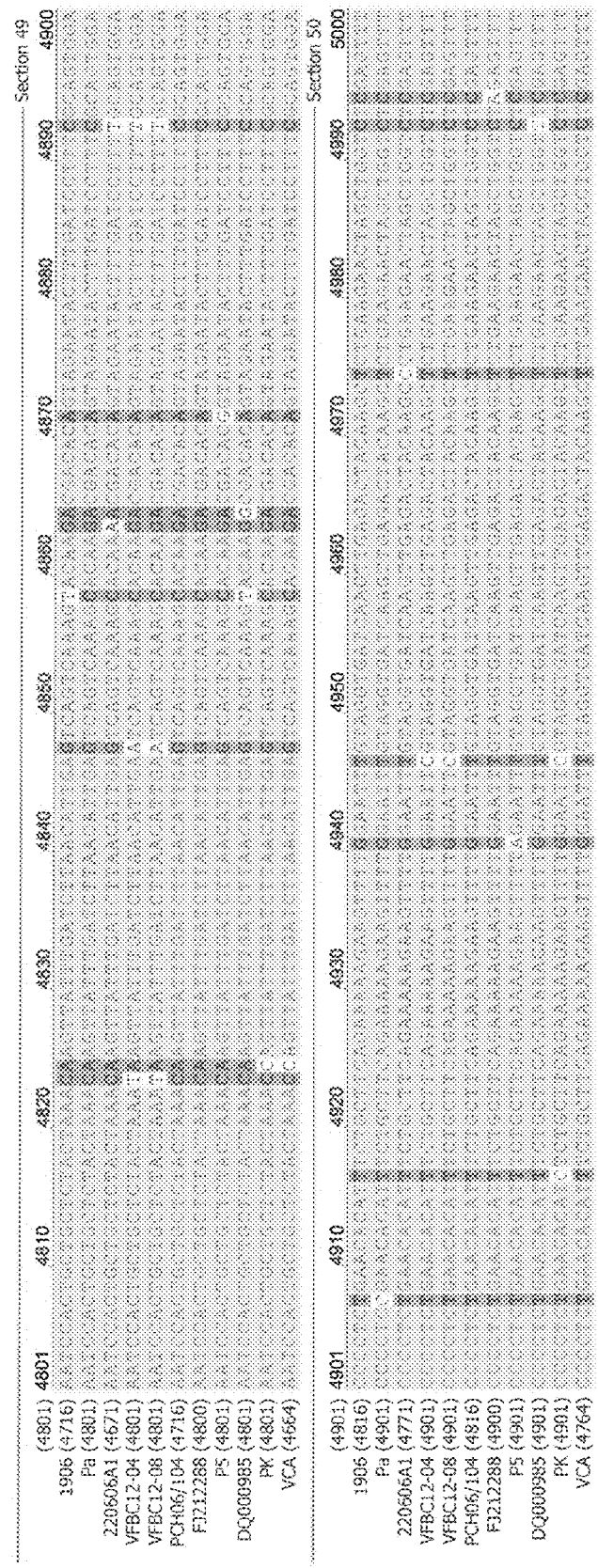
Figures 1, 6A:
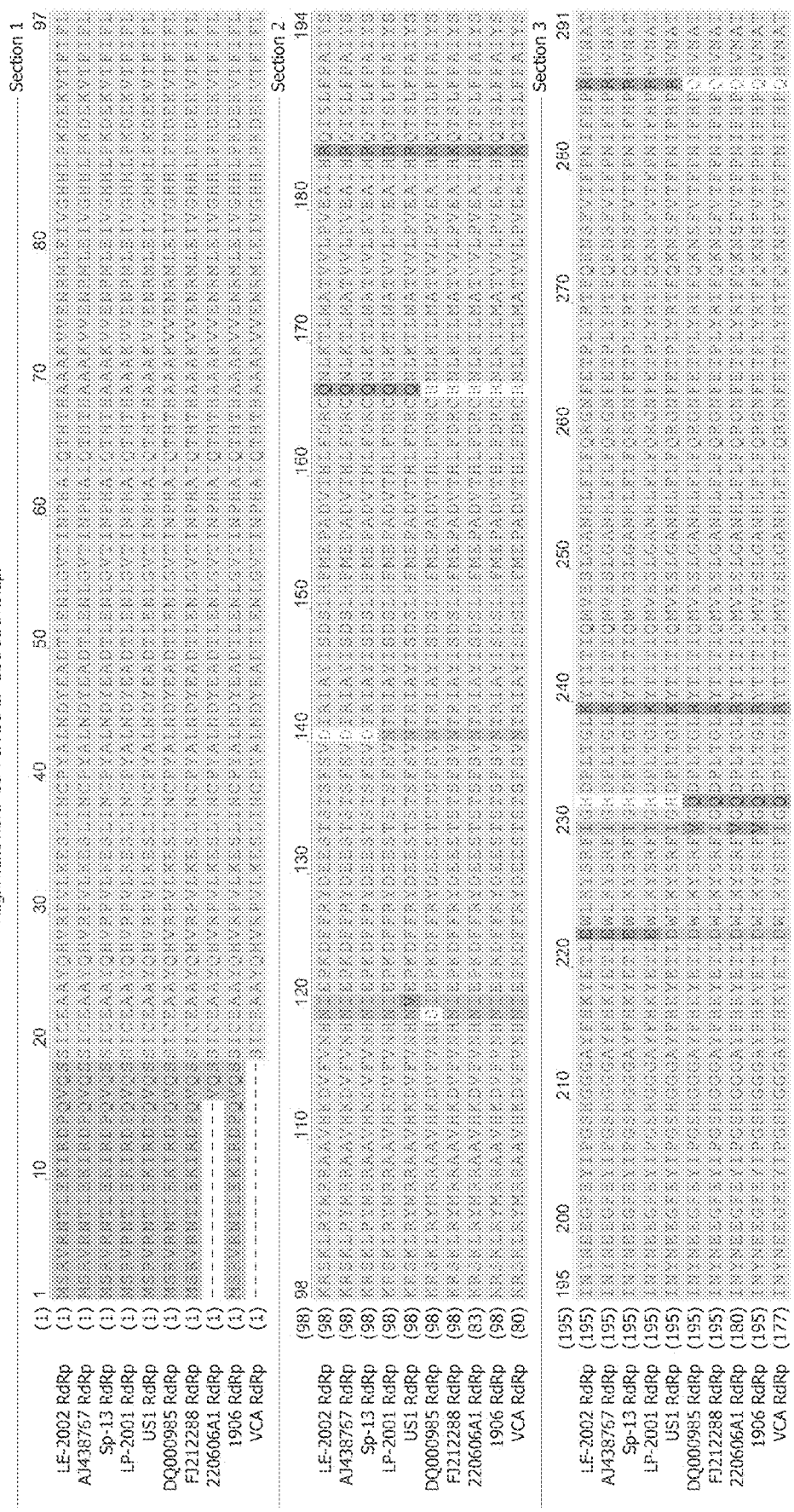
Figures 3, 6A:
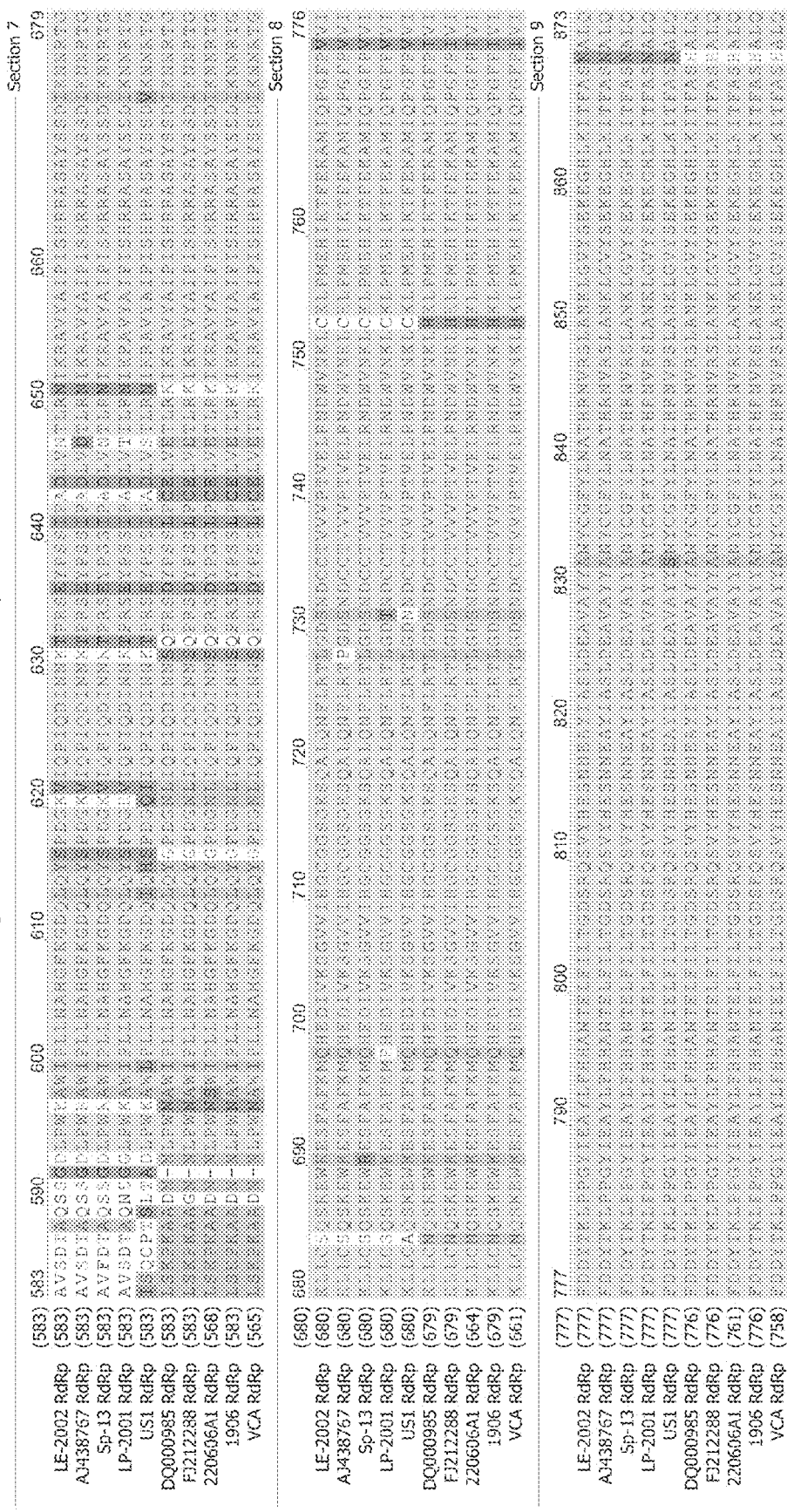

FIGS. 7A-1-7A10. Sequence listing
FIGS. 8A-1-8A-5. Sequence listing

DETAILED DESCRIPTION OF THE DISCLOSED EMBODIMENTS

Cross-protection is the phenomenon of protecting crops against virulent isolates of viruses by pre-treatment with closely related attenuated isolates of the virus. In the 1970s, it was first applied successfully against infection of tomato with *Tobacco mosaic* virus in several countries (Burgyán & Gáborjányi, 1984). Attenuated isolates may be selected among naturally occurring or be developed by the introduction of mutations into such isolates, for example using random mutagenesis. A strategy in which attenuated isolates are applied to plants relies on the identification of an isolate that has as little impact on total yield and fruit quality as possible, and effectively protects against more virulent isolates at the same time.

While not wishing to be bound by theory, cross-protection may be due to RNA silencing activity induced by the protective isolate (Ratcliff et al., 1999; Valkonen et al., 2002). The role of post-transcriptional gene silencing (PTGS) in cross-protection was demonstrated by the observation that two viral constructs derived from different viruses, but sharing a common sequence, could suppress each other when co-inoculated in plants (Ratcliff et al., 1999). PTGS is an antiviral defense mechanism in plants, which targets double stranded RNA (dsRNA) for degradation in a sequence-specific manner. In cross-protection, it is thought that the mild strain 'primes' the defense system of the plant so that it operates against subsequent infection by severe strains.

In the study of Schenk et al. (2010), attenuated isolates of PepMV were tested (EU-Att1 and PE-Att1). The attenuated isolates effectively reduced the effects of isolates of PepMV with aggressive symptoms (namely, EU-Ch11 and EU-Nec1). Total virus accumulation, symptom severity and yield losses were significantly reduced in cross-protected plants compared to the single infections by the aggressive isolates. The yields of the cross-protected plants were on a similar level as those of uninfected plants. Although plants cross-protected by the attenuated isolates reduced symptoms, infection by the attenuated isolates alone also produced symptoms (Table 2 of Schenk et al.) The attenuated isolates caused symptoms shortly after inoculation, a pattern which has also been observed in other trials (Spence et al., 2006). Overall, the symptom severity correlated to virus accumulation, but accumulation alone did not explain all differences in symptom severity. In turn, symptom severity was negatively correlated to yield. The two symptoms that had the largest effect on yield i.e. leaf deformation and leaf necrosis, affected the leaf area of the plants, which would explain the observed yield losses. One aspect of the present invention is the provision of an attenuated virus that cross-protects plants from further PepMV infection while causing minimal symptoms from exposure to the attenuated virus alone.

Accordingly, one aspect of the disclosure provides Pepino mosaic viruses, in particular attenuated viruses. As is known to a skilled person, an attenuated virus is a virus that has been modified from a wild-type pathogenic virus. An attenuated virus has reduced pathogenicity as compared to the wild-type virus. In addition, an attenuated virus disclosed herein can be used to cross-protect plants against infection from virulent PepMV isolates.

The disclosure identifies several nucleotide positions in PepMV which play a role in the symptoms induced by PepMV infection. Specifically, the disclosure provides PepMV viruses and nucleic acid molecules, wherein the nucleic acid sequence encodes arginine at the position corresponding to 868 of SEQ ID NO:2 (corresponding to position 886 of SEQ ID NO:9) and/or encodes phenylalanine at the position corresponding to 1052 of SEQ ID NO:2 (corresponding to position 1070 of SEQ ID NO:9).

The disclosure provides that the nucleotides at positions 2605 and 3156 of SEQ ID NO: 1 (corresponding to positions 2675 and 3226 of SEQ ID NO: 8), and consequently the amino acids encoded (in part) by these nucleotides, play a role in the pathogenic symptoms. Specifically, an amino acid change from lysine to arginine at position 868 of SEQ ID NO:2 (corresponding to position 886 of SEQ ID NO:9) and an amino acid change from leucine to phenylalanine at position 1052 of SEQ ID NO: 2 (corresponding to position 1070 of SEQ ID NO:9) results in a PepMV attenuated virus. In the pathogenic viruses depicted in FIG. 6, as well as the attenuated VC1 virus, the amino acids corresponding to 868 and 1052 of SEQ ID NO:2 (and 886 and 1070 of SEQ ID NO:9) are lysine and leucine, respectively. While not wishing to be bound by theory, these amino acid changes are believed to provide attenuated viruses which demonstrate milder symptoms that the VC1 virus (see Examples).

The disclosure also provides that additional nucleotides— and the amino acids which they encode—also play a role in pathogenic symptoms. Accordingly, in some embodiments the viruses and nucleic acid molecules disclosed herein contain one or more of the following: a C at the nucleotide position corresponding to 191 of SEQ ID NO: 1 (position 261 of SEQ ID NO: 8); a C at the nucleotide position corresponding to 2354 of SEQ ID NO: (position 2424 of SEQ ID NO: 8); a T at the nucleotide position corresponding to 2768 of SEQ ID NO: 1(position 2838 of SEQ ID NO: 8); a T at position corresponding to 2868 of SEQ ID NO:1 (position 2938 of SEQ ID NO: 8); a G at the nucleotide position corresponding to 3422 of SEQ ID NO: 1 (position 3492 of SEQ ID NO: 8); and/or have an A at the nucleotide position corresponding to 3975 of SEQ ID NO: 1 (position 4045 of SEQ ID NO: 8). In some embodiments the viruses or nucleic acid molecules disclosed herein contain at least two, at least three, at least four, at least five, or all 6 of the nucleotides listed above. These six nucleotides are unique to both the VCA attenuated virus and the VC1 attenuated virus as compared to the virulent CH2 strains depicted in FIG. 5. Preferably, the viruses and nucleic acid molecules disclosed herein, in addition to encoding arginine at the position corresponding to 868 of SEQ ID NO:2 (and corresponding to position 886 of SEQ ID NO:9) and/or phenylalanine at the position corresponding to 1052 of SEQ ID NO:2 (and corresponding to position 1070 of SEQ ID NO:9), also encode a phenylalanine at the position corresponding to 956 of SEQ ID NO:2 (and corresponding to position 974 of SEQ ID NO:9) and/or an asparagine at the position corresponding to 1325 of SEQ ID NO:2 (and corresponding to position 1343 of SEQ ID NO:9). As depicted in FIG. 6, the wild-type pathogenic viruses encode a leucine and an aspartic acid at these positions. While not wishing to be bound by theory, these amino acids are believed to play a role in reducing the virulence of the viruses. SEQ ID NO: 1 (herein referred to as the 'VCA' virus) was isolated as an attenuated virus of the CH2 strain. The Examples demonstrate the ability of the VCA virus to cross-protect against wild-type PepMV strains and the reduction of symptoms as compared to another attenuated virus VC1. SEQ ID NO: 1 depicts a partial sequence of the RNA-dependent RNA-polymerase of the VCA virus. SEQ ID NO: 8 depicts the nucleotide sequence of the RNA-dependent RNA-polymerase of the VCA virus, including the complete coding sequence.

See FIGS. 7 and 8 for the sequence listing. As known to a skilled person, Y indicates a C or T, R indicates A or G; and S indicates G or C. In some embodiments, R is G. In some embodiments, Y1 is C. In some embodiments, Y2 is C. In some embodiments, Y3 is T. In some embodiments, Y4 is T. In some embodiments, S is C. In some embodiments, Y5 is T. In some embodiments, Y6 is T. Viruses having the nucleic acid sequence of SEQ ID NO:1 or SEQ ID NO:8 include a single homogenous virus (i.e., having one sequence; for example SEQ ID NO:1 or SEQ ID NO:8 wherein R is G; Y1 is C; Y2 is C; Y3 is T; Y4 is T; S is C; Y5 is T; Y6 is T) as well as mixtures of viruses each having SEQ ID NO:1 or SEQ ID NO:8.

The VCA virus was found to have nucleotide substitutions resulting in amino acid changes in the RNA-dependent RNA polymerase gene of the virus. SEQ ID NO:2 depicts the partial amino acid sequence of the RNA-dependent RNA polymerase from VCA. SEQ ID NO:9 depicts the complete amino acid sequence of the RNA-dependent RNA polymerase from VCA VCA (SEQ ID NO:1/SEQ ID NO:8) is an exemplary attenuated virus of the CH2 strain. The disclosure also provides attenuated viruses from other PepMV strains. Four amino acids in SEQ ID NO:2 were found to be unique when compared to wild-type EU, LP, CH2, and US1 isolates. Arginine at position 868 of SEQ ID NO:2 (886 of SEQ ID NO:9) corresponds to position 887 in the alignment shown in FIG. 6. Phenylalanine at position 956 of SEQ ID NO:2 (974 of SEQ ID NO:9) corresponds to position 975 in the alignment shown in FIG. 6. Phenylalanine at position 1052 of SEQ ID NO:2 (1070 of SEQ ID NO:9) corresponds to position 1071 in the alignment shown in FIG. 6. Asparagine at position 1325 of SEQ ID NO:2 (1343 of SEQ ID NO:9) corresponds to position 1344 in the alignment shown in FIG. 6. It is clear to a skilled person that attenuated viruses from any PepMV isolate can be prepared based on these amino acids.

In some embodiments, the virus is an attenuated virus of a EU strain. Exemplary wild-type EU viral sequences are depicted in SEQ ID Nos:3-5. In some embodiments, the virus is an attenuated virus of a US1 strain. An exemplary wild-type US1 viral sequence is depicted in SEQ ID NO:6. In some embodiments, the virus is an attenuated virus of an LP strain. An exemplary wild-type LP viral sequence is depicted in SEQ ID NO:7.

PepMV viruses have, on the average, around 80% nucleic acid sequence identity. Accordingly, in preferred embodiments the PepMV viruses have a nucleic acid sequence at least 80% identical to SEQ ID NO:1, wherein the nucleic acid sequence encodes arginine at the position corresponding to 868 of SEQ ID NO:2 and/or encodes phenylalanine at the position corresponding to 1052 of SEQ ID NO:2 (or rather, encodes arginine at position 887 of FIG. 6 and/or the nucleic acid sequence encodes phenylalanine at position 1071 of FIG. 6). In preferred embodiments, the PepMV viruses have a nucleic acid sequence at least 80% identical to SEQ ID NO:8, wherein the nucleic acid sequence encodes arginine at the position corresponding to 886 of SEQ ID NO:9 and/or encodes phenylalanine at the position corresponding to 1070 of SEQ ID NO:9. In a preferred embodiment, the attenuated viruses disclosed herein have a nucleic acid sequence at least 80%, at least 90%, preferably at least 95%, more preferably at least 98%, and most preferably at least 99% identical to SEQ ID NO:1, SEQ ID NO:8, SEQ ID NO: 3, SEQ ID NO:4, SEQ ID NO:5, SEQ ID NO:6, or SEQ ID NO: 7. The sequences provided herein refer to the bases A, T, C, and G. However, it is clear to a skilled person that when referring to a PepMV virus (an RNA virus), uracil is present instead of thymine.

The disclosure also provides an isolated nucleic acid molecule comprising a nucleic acid sequence at least 80%, at least 90%, preferably at least 95%, more preferably at least 98%, and most preferably at least 99% identical to SEQ ID NO:1, SEQ ID NO:8, SEQ ID NO: 3, SEQ ID NO:4, SEQ ID NO:5, SEQ ID NO:6, or SEQ ID NO: 7, wherein the nucleic acid sequence encodes arginine at the position corresponding to 868 of SEQ ID NO:2 and/or encodes phenylalanine at the position corresponding to 1052 of SEQ ID NO:2 (or rather, encodes arginine at position 887 of FIG. 6 and/or the nucleic acid sequence encodes phenylalanine at position 1071 of FIG. 6; or rather encodes arginine at position 886 of SEQ ID NO:9 and/or the nucleic acid sequence encodes phenylalanine at position 1070 of SEQ ID NO:9).

In some embodiments, the nucleotide at the position corresponding to 2605 of SEQ ID NO:1 (2675 of SEQ ID NO:8) is G; the nucleotide at the position corresponding to 3156 of SEQ ID NO: 1 (3226 of SEQ ID NO:8) is T and/or the nucleotide at the position corresponding to 3422 SEQ ID NO: 1 (3492 of SEQ ID NO:8) is G. In preferred embodiments, the nucleotide at the position corresponding to 2605 of SEQ ID NO:1 (2675 of SEQ ID NO:8) is G and/or the nucleotide at the position corresponding to 3156 of SEQ ID NO: 1 (3226 of SEQ ID NO:8) is T. In preferred embodiments, the nucleic acid molecules comprise one or more of the following: a C at the nucleotide position corresponding to 191 of SEQ ID NO: 1 (position 261 of SEQ ID NO: 8); a C at the nucleotide position corresponding to 2354 of SEQ ID NO: 1 (position 2424 of SEQ ID NO: 8); a T at the nucleotide position corresponding to 2768 of SEQ ID NO: 1 (position 2838 of SEQ ID NO: 8); a T at position corresponding to 2868 of SEQ ID NO:1 (position 2938 of SEQ ID NO: 8); and/or have an A at the nucleotide position corresponding to 3975 of SEQ ID NO: 1 (position 4045 of SEQ ID NO: 8). Such nucleic acid molecules are useful, for example, for producing the viruses disclosed herein.

As used herein, the term "isolated" refers to a protein, peptide or nucleic acid molecule which is substantially separated from other (sub)cellular components. The term includes a nucleic acid molecule or protein which has been removed from its naturally occurring environment, as well as recombinant or cloned DNA isolates and chemically synthesized analogues or analogues biologically synthesized by heterologous systems.

A further aspect of the disclosure provides vectors and expression vectors comprising the nucleic acid molecules and viruses disclosed herein. Expression vectors useful in the present disclosure include vaccinia virus, retroviruses, and baculovirus. The expression vector may comprise the nucleic acid sequences disclosed herein or a fragment thereof that is under control of or operatively linked to a regulatory element, such as a promoter. The segment of DNA referred to as the promoter is responsible for the regulation of the transcription of DNA into mRNA. The expression vector may comprise one or more promoters suitable for the expression of the gene in, e.g., plant cells, fungal cells, bacterial cells, yeast cells, insect cells or other eukaryotic cells.

The viruses and nucleic acid molecules disclosed herein can be made by any method known to one of skill in the art. Methods of generating full length cDNA clones of the RNA genome of PepMV have been described, see, e.g., Hasiow-Jaroszewsk et al. Arch Virol (2009) 154:853-856. In addition, the cloning of both EU and CH2 PepMV clones has also been described in Duff-Farrier et al., Molecular Plant Pathology (2015) 16:308-315. Duff-Farrier et al. describes the construction of cDNA from PepMV EU and CH2 isolates and well as the introduction of chimeric sequences into the cDNA. Infectious RNA was synthesized in vitro, which was used to infect plants. Similar methods can be used to generate the viruses and nucleic acid molecules with sequences described herein.

The viruses and nucleic acid molecules discloses herein are useful for producing plants with increased resistance to PepMV, in particular to disease causing strains of PepMV such as the Peruvian (LP) strain, the European (EU) strain, the CH2 strain, first identified in Chile, and the US1 strain, identified in the United States. Accordingly, the disclosure provides attenuated viruses and nucleic acid molecules for controlling PepMV infection and/or PepMV disease in a plant. As used herein, controlling PepMV infection includes the reduction, prevention, or delay of PepMV accumulation in a plant. As used herein, controlling PepMV disease includes the reduction, prevention, or delay of PepMV symptoms.

The nucleic acid molecules disclosed herein, the polypetides encoded by said nucleic acid molecules, as well as antibodies recognizing said polypeptides are all useful for, e.g., detecting infection by the attenuated virus and thereby detecting plants with increased resistance to PepMV.

The viruses and nucleic acid molecules disclosed herein may be provided in compositions comprising an agriculturally acceptable carrier. Such compositions can be used for the biological control of plant disease. Preferably, the composition comprises and anti-oxidant, a phosphate buffer and/or a sulphite (sulphite can help prevent rotting). Preferably, the compositions have a pH range of 6-8.5, more preferably a pH of 7.7±0.5. Preferably the compositions comprise one or more of the following: mono-basic potassium phosphate, di-basic sodium phosphate dodecahydrate, and/or sodium sulphite. More preferably, the compositions comprises 0.4-1.6 g of mono-basic potassium phosphate per liter, more preferably around 0.8 g/L; 15-60 g of di-basic sodium phosphate dodecahydrate per liter, more preferably around 30 g/L; and 1-4 g sodium sulphite per liter, more preferably around 2 g/L.

The viruses may be propagated in a suitable plant host. The tissue from infected plants is ground and the homogenate (the sap) can be used to prepare the compositions disclosed herein. Alternatively, the nucleic acid molecules disclosed herein may be cloned into a vector for replication in another host.

The host range of PepMV is mainly restricted to plant species of the Solanaceae family Tomato (*Solanum lycopersicum*) is one of the most economically important natural host of PepMV. Pepino plant (*S. muricatum*) is a host in Peru and China (Jones et al., 1980; Soler et al., 2002; Zhang et al., 2003). In surveys in Peru, PepMV has been found to be naturally present in wild *Solanum* species (*S. chilense, S. chmielewskii, S. parviflorum* and *S. peruvianum*).

Infections, symptomless or with mild symptoms have also been observed in weed species which are member of families of Amaranthaceae, Asteraceae, Boraginaceae, Brassicaceae, Chenopodiaceae, Compositae, Convolvulaceae, Malvaceae, Plantaginaceae, Polygonaceae and Solanaceae. (Córdoba et al., 2004; Jordá et al., 2001; Kazinczi et al., 2005, Papayiannis et al., 2012; Salomone & Roggero 2002; Soler et al., 2002; Stobbs et al., 2009). Most of these infections were found in the vicinity of tomato greenhouses. PepMV has also been detected in a few potato cultivars (e.g., *Solanum tuberosum* cv. 'Yungay').

Several species have been found to be experimentally-susceptible to infection by PepMV following artificial inoculation, including eggplant (*Solanum melongena*) which was found to be infected by PepMV by mechanical inoculation (Salomone & Roggero, 2002; Verhoeven et al., 2003). Some cultivars of potato (*S. tuberosum*) can also be experimentally infected by PepMV (Jones et al., 1980). PepMV can infect *Datura metel, D. stramonium, Nicotiana debneyi, N. benthamiana* systemically (Jones et al., 1980; Verhoeven et al., 2003). Some PepMV isolates can infect *N. glutinosa* and *N. tabacum* (LP and some EU isolates; Verhoeven et al., 2003).

Preferably, the term "plant" refers to any plant which is capable of being infected with PepMV. In some embodiments, the plant belongs to the Solanaceae family, in particular the genus *Solanum* or *Lycopersicon*. As is known to the skilled person, the nomenclature for tomato plants has recently changed. For example, *Solanum juglandifolium* is now referred to as *Lycopersicon juglandifolium*. A preferred plant is a tomato plant.

As used herein, the term "plant part" includes, for example, single cells and tissues from pollen, ovules, leaves, embryos, roots, root tips, anthers, flowers, fruits, stems shoots, and seeds; as well as pollen, ovules, leaves, embryos, roots, root tips, anthers, flowers, fruits, stems, shoots, scions, rootstocks, seeds, protoplasts, calli, and the like.

PepMV induces a wide range of symptoms on tomato, such as yellow mosaic, leaf distortion, leaf blistering or bubbling, nettle-like heads, single yellow spots, inter-veinal chlorosis, severe leaf mosaics, leaf or stem necrosis and fruit discolouration (Van der Vlugt et al., 2000; Jorda et al., 2001; Roggero et al., 2001; Spence et al., 2006; Hasiów et al., 2008; Hasiów-Jaroszewska et al., 2009a; Hanssen et al., 2009). Tomato plants display symptoms shortly after infection with PepMV and, in general, symptoms subsequently subside (Van der Vlugt & Stijger, 2008). However, symptoms may return later during the growing season.

Expression of symptoms may depend on environmental conditions, such as temperature and light intensity. Low environmental temperatures and low light intensity result in more severe damage (Jorda et al., 2001; Van der Vlugt & Stijger, 2008). PepMV is sometimes suggested to cause yield losses in tomato, but the highest economic losses are attributed to symptoms that affect the commercial value of tomato fruits, such as flaming, marbling, blotchy ripening and fruit size reduction (Soler et al., 2000; Spence et al., 2006; Hanssen & Thomma, 2010). In addition, the so-called 'tomato collapse', a sudden and progressive wilt of tomato which can lead to plant death is probably caused by PepMV accumulation in the vascular system (Soler-Aleixandre et al., 2005). Striking differences in the severity of symptomatology have been reported (Verhoeven et al., 2003; Hanssen et al., 2008) and not all isolates cause typical PepMV symptoms such as marbled and flamed fruits (Hanssen et al., 2009).

Symptoms in plants can be characterized either qualitatively or quantitatively.

The viruses disclosed herein are also useful for inducing resistance in "tolerant plants", i.e., plants which may become infected with the virus and further its spread but remain symptomless or will have mild symptoms.

Several methods have been developed to detect PepMV. A robust method to detect PepMV in plants is DAS-ELISA (Van der Vlugt et al., 2002). Commercially available polyclonal antibodies can be purchased at Prime Diagnostics (Wageningen, The Netherlands). Different PCR-assays have been described to detect PepMV: a general potexvirus detection method (Van der Vlugt & Berendsen, 2002), a real-time immunocapture RT-PCR (Mansilla et al., 2003; Matínez-Culebras et al., 2002; Ling, 2005; Ling et al., 2007) and sensitive real-time PCR assays (Alfaro-Fernández et al., 2009; Johnson & Walcott, 2012; Gutiérrez-Aguirre et al., 2009). Simultaneous detection of multiple plant viruses including PepMV can be performed by using micro-arrays (Boonham et al., 2007) and deep sequencing (Li et al., 2012). Preferably, the accumulation of PepMV in a plant is determined using a quantitative detection method (e.g. an ELISA method or a quantitative reverse transcriptase-polymerase chain reaction [RT-PCR]).

A further aspect of the disclosure provides isolated polypeptides expressed by the viruses. In some embodiments the polypeptide is a RNA-dependent polymerase (RdRp) or a coat protein (CP). Preferably, the polypeptide is RdRp.

A further aspect of the disclosure provides antibodies specific for the polypeptides disclosed herein, preferably RdRp. In preferred embodiments, the antibody recognizes an antigen specific to VCA, but does not recognize the CH2, the US-1, the EU, or the LP strains. Preferably the antigen comprises the arginine at the position corresponding to 868 of SEQ ID NO:2 and/or the phenylalanine at the position corresponding to 1052 of SEQ ID NO:2 (or rather, the arginine at the position corresponding to 886 of SEQ ID NO:9 and/or the phenylalanine at the position corresponding to 1070 of SEQ ID NO:9).

A further aspect of the disclosure provides a method for producing said antibodies comprising immunizing a host (such as a mouse) with the attenuated virus, or a protein or peptide fragment thereof; harvesting from blood (including serum) or splenocytes of said host antibodies against said virus, protein or peptide fragment. In a preferred embodiment, the method further comprises selecting one antibody-producing splenocyte, fusing said splenocyte to an immortalized hybridoma cell line and allowing said hybridoma fusion to produce monoclonal antibodies. Preferably, the antigen is in part encoded by a nucleic acid sequence wherein the nucleotide at the position corresponding to 2605 of SEQ ID NO:1 (2675 of SEQ ID NO:8) is G; the nucleotide at the position corresponding to 3156 of SEQ ID NO: 1 (3226 of SEQ ID NO:8) is T and/or the nucleotide at the position corresponding to 3422 SEQ ID NO: 1 (3492 of SEQ ID NO:8) is G. More preferably, the antigen is in part encoded by a nucleic acid sequence wherein the nucleotide at the position corresponding to 2605 of SEQ ID NO:1 (2675 of SEQ ID NO:8) is G and/or the nucleotide at the position corresponding to 3156 of SEQ ID NO: 1 (3226 of SEQ ID NO:8) is T.

A further aspect of the disclosure provides a method for detecting the presence of the attenuated virus in a plant sample comprising reacting said sample with an antibody according to the disclosure. Suitable methods for performing immunoassays are well-known to a skilled person and include, e.g., radio-immunoassay (RIA), immunogold labeling, immunosorbent electron microscopy (ISEM), enzyme-linked immunosorbent assay (ELISA), Western blotting and immunoblotting.

A further aspect of the disclosure provides a method for identifying a pepino mosaic virus (PepMV)-resistant plant, comprising a) exposing a plant or plant part to an infective dosage of the attenuated viruses or nucleic acid molecules disclosed herein,
b) exposing the plant or plant part to an infective dosage of PepMV, and
c) identifying said plant as PepMV-resistant plant when, after exposure to PepMV, disease-symptoms in said plant or plant part are reduced or delayed and/or PepMV accumulation in said plant or plant parts is reduced in comparison to a control plant.

It is clear to a skilled person that step a) includes an incubation period of sufficient duration to allow establishment of the attenuated virus. Preferably, such incubation period is at least one week, more preferably at least 5 weeks. In some embodiments, the presence of virus in the plant can be confirmed by one of the methods disclosed herein. It is also clear to a skilled person that step b) includes an incubation period of sufficient duration to allow establishment of the PepMV virus and detectable symptoms in control plants. Preferably, such incubation period is at least one week, more preferably at least 5 weeks.

As used herein, "resistant" refers to a reduction in multiplication of PepMV, a reduction of movement/spread of the virus to other cells, and/or a reduction or delay in the development of disease symptoms after infection with PepMV. Resistance can be determined by comparing a PepMV infected plant with a plant exposed to VCA and PepMV. Preferably, the PepMV referred to above is a CH2, US-1, EU, or LP strains, however, it also includes other disease causing PepMV strains.

Preferably, the accumulation of PepMV in a plant is determined using a quantitative detection method (e.g. an ELISA method or PCR, such as a quantitative reverse transcriptase-polymerase chain reaction [RT-PCR]).

As used herein, an "infective dosage" refers to the dosage of viral particles or viral nucleic acid molecule capable of infecting a plant. As is clear to as skilled person, the dosage may vary between plant species.

Methods of exposing a plant or a plant part to virus are well-known in the art and include dusting, coating, injecting, rubbing, rolling, dipping, spraying, or brushing. Exemplary methods include mechanical innoculation (e.g., rubbing plants or plant parts with infected plant material) and spraying plants with a solution containing virus particles or viral nucleic acid (see Example 1). The attenuated virus may be isolated from infected plants or other sources by any method known to one of the art.

As is known to a skilled person, cross protection may not lead to resistance in 100% of plants of the same species. Typically, cross protection protects more that 50% of the plants, preferably more than 80% of the plants.

A further aspect of the disclosure provides a method for producing a pepino mosaic virus (PepMV)-resistant plant using the attenuated viruses or nucleic acid molecules disclosed herein for cross-protection. Also provided are methods for controlling or preventing plant disease, in particular PepMV causing disease. Also provided are methods for controlling or preventing infection by PepMV. The methods comprise exposing a plant or plant part to an infective dosage of the attenuated virus, the nucleic acid molecules disclosed herein, or the compositions disclosed herein. In some embodiments, the methods further comprise detecting the attenuated virus in said plants or plant parts, such as by a method disclosed herein.

The disclosure also provides for PepMV-resistant plants comprising the attenuated virus or the nucleic acid sequences disclosed herein. Such plants may have been infected by the attenuated virus or are the progeny of a plant infected by the virus. The plants may also have been transformed by the nucleic acid molecules disclosed herein or a vector comprising the nucleic acid molecule. Progeny of said plants are also encompassed by the invention. Such plants are obtainable by the methods described herein.

PepMV is an RNA virus. As such it is preferred that the nucleic acid molecule that is comprised in the virion is RNA. Sequences indicated herein contain a T and as such refer to DNA. Wherein herein reference is made to a virus comprising a nucleic acid molecule with a certain nucleic acid sequence and reference is made to a DNA sequence in the context of a virus, it is of course clear to the person skilled in the art that the corresponding RNA sequence is intended. In other words that the reference is to the SEQ ID wherein the T is replaced by a U. Vectors and other compositions that do not refer to a virus or virus particle can have the referenced DNA, an RNA with the same sequence or a combination thereof.

Definitions

As used herein, "to comprise" and its conjugations is used in its non-limiting sense to mean that items following the word are included, but items not specifically mentioned are not excluded. In addition the verb "to consist" may be replaced by "to consist essentially of" meaning that a compound or adjunct compound as defined herein may comprise additional component(s) than the ones specifically identified, said additional component(s) not altering the unique characteristic of the invention.

The articles "a" and "an" are used herein to refer to one or to more than one (i.e., to at least one) of the grammatical object of the article. By way of example, "an element" means one element or more than one element.

The word "approximately" or "about" when used in association with a numerical value (approximately 10, about 10) preferably means that the value may be the given value of 10 more or less 1% of the value.

REFERENCES

Aguilar J M, Hernández-Gallardo M D, Cenis J L, Lacasa A and Aranda M A (2002) Complete sequence of the Pepino mosaic virus RNA genome. Archives of Virology 147: 2009-2015.

Alfaro-Fernández A, Cebrián MC, Córdoba-Sellés M C, Herrera-Vásquez J A and Jordá C (2008) First report of the US1 strain of Pepino mosaic virus in tomato in the Canary islands, Spain. Plant Disease 92: 1590.

Alfaro-Fernández A, Córdoba-Sellés M C, Herrera-Vásquez J A, Cebrián MC and Jordá C (2010) Transmission of Pepino mosaic virus by the fungal vector *Olpidium virulentus*. Journal of Phytopathology 158: 217-226.

Alfaro-Fernández A, Sanchez-Navarro J, Cebrián M C, Córdoba-Sellés M C, Pallas V and Jordá C C (2009) Simultaneous detection and identification of Pepino mosaic virus (PepMV) isolates by multiplex one-step RT-PCR. European Journal of Plant Pathology 125: 143-158.

Baulcombe D (2004) RNA silencing in plants. Nature 431: 356-363.

Boonham N, Tomlinson J and Mumford R (2007) Microarrays for rapid identification of plant viruses. Annual Review of Phytopathology 45: 307-328.

Burgyán J and Gáborjányi R (1984) Cross-protection and multiplication of mild and severe strains of TMV in tomato plants. Journal of Phytopathology 110: 156-167.

Candresse T, Marais A, Faure C, Dubrana M P, Gombert J and Bendahmane A (2010) Multiple coat protein mutations abolish recognition of Pepino mosaic potexvirus (PepMV) by the potato Rx resistance gene in transgenic tomatoes. Molecular Plant-Microbe Interactions 23: 376-383.

Carmichael D J, Rey M E C, Naidoo S, Cook G and van Heerden S W (2011) First report of Pepino mosaic virus infecting tomato in South Africa. Plant Disease 95: 767.

Córdoba-Sellés M C, Garcia-Rández A, Alfaro-Fernández A and Jordá-Gutiérrez C (2007) Seed transmission of Pepino mosaic virus and efficacy of tomato seed disinfection treatments. Plant Disease 91: 1250-1254.

Córdoba M C, Martínez-Priego L and Jordá C (2004) New natural hosts of Pepino mosaic virus in Spain. Plant Disease 88: 906.

Costa A S and Muller G W (1980) Tristeza control by cross protection: A US-Brazil cooperative success. Plant Disease 64: 538-541.

Cotillon A C, Girard M and Ducouret S (2002) Complete nucleic acid sequence of the genomic RNA of a French isolate of Pepino mosaic virus (PepMV). Archives of Virology 147: 2231-2238.

Davino S, Bellardi M G, Agosteo G E, Iacono G and Davino M (2006) Characterization of a strain of Pepino mosaic virus found in Sicily. Journal of Plant Pathology 88, S31-S63.

Davino S, Davino M, Bellardi M G, Agosteo G E (2008) Pepino mosaic virus and *Tomato chlorosis* virus causing mixed infection in protected tomato crops in Sicily. Phytopathologia Mediterranea 47: 35-41.

Desbiez C and Lecoq H (1997) *Zucchini yellow mosaic virus*. Plant Pathology 46: 809-829.

Ding S W and Voinnet O (2007) Antiviral immunity directed by small RNAs. Cell 130: 413-426

Duff-Farrier C, Boonham N and Foster G R (2011) The generation of Pepino mosaic virus infectious clones; investigating the link between genotype and phenotype. Phytopathology 101: S46.

Drake J W, Charlesworth B, Charlesworth D and Crow J F (1998) Rates of spontaneous mutation. Genetics 148: 1667-1686.

Efthimiou K E, Gatsios A P, Aretakis K C, Papayiannis L C and Katis N I (2011) First report of Pepino mosaic virus infecting greenhouse cherry tomatoes in Greece. Plant Disease 95: 78.

EPPO (European and Mediterranean Plant Protection Organization) (2000) Pepino mosaic potexvirus found in Spain. EPPO Reporting Service, No. 9, 2000/132.EPPO (2009) EPPO alert list-viruses. Pepino mosaic potexvirus—a new virus of tomato introduced into Europe. www.eppo.org/QUARANTINE/Alert_List/alert_list.htm.

EPPO (2010). Pepino mosaic virus. www.eppo.org/QUARANTINE/Alert_List/viruses/PEPMV0.htm.

Fakhro A, Von Bargen S, Bandte M and Büttner C (2010) Pepino mosaic virus, a first report of a virus infecting tomato in Syria. Phytopathologia Mediterranea 49: 99-101.

Fletcher J (2000) Pepino mosaic, a new disease of tomatoes. Horticultural Development council. Factsheet 12/00. 8pp. http://www.hdc.org.uk/assets/pdf/33201200/4977.pdf.

Forray A, Tüske M and Gáborjányi R (2004) First report on the occurrence of Pepino mosaic virus in Hungary. Növényvédelem 40: 471-473.

Fulton R W (1986) Practices and precautions in the use of cross protection for plant virus disease control. Annual Review of Phytopathology 24: 67-81.

French C J, Bouthillier M, Bernardy M, Ferguson G, Sabourin M, Johnson R C, Masters C, Godkin S and Mumford R (2001) First report of Pepino mosaic virus in Canada and the United States. Plant Disease 85: 1121.

French C J, Bunckle A, Ferguson G, Dubeau C, Bouthillier M and Bernardy M G (2006) Complete sequencing and phylogenetic analysis of isolates of Pepino mosaic virus from Canada. Canadian Journal of Plant Pathology—Revue Canadienne de Phytopathologie 28: 349.

French C, Bunckle A, Ferguson G and Bernardy M (2005) Complete sequencing and phylogenetic analysis of tomato isolates of Pepino mosaic virus from Canada and other geographic regions. Phytopathology 95: S31.

French C J, Dubeau C, Bunckle A, Ferguson G, Haesevoets R, Bouthillier M and Bernardy M G (2008) Overview of Pepino mosaic virus research. Canadian Journal of Plant Pathology—Revue Canadienne de Phytopathologie 30: 373-374.

Gal-On A and Shiboleth Y M (2006) Cross protection. In: Natural Resistance Mechanisms of Plants to Viruses (Loebenstein G and Carr J P, eds), pp. 261-268. Dordrecht: Kluwer Academic Publishers.

Gómez P, Sempere R N, Aranda M A and Elena S F (2012) Phylodynamics of Pepino mosaic virus in Spain. European Journal of Plant Pathology 134: 445-449.

Gómez P, Sempere R N, Amari K, Gomez-Aix C and Aranda M A (2010) Epidemics of *Tomato torrado* virus, Pepino mosaic virus and *Tomato chlorosis* virus in tomato crops: do mixed infections contribute to torrado disease epidemiology? Annals of Applied Biology 156: 401-410.

Gómez P, Sempere R N, Elena S F and Aranda M A (2009) Mixed infections of Pepino mosaic virus strains modulate the evolutionary dynamics of this emergent virus. Journal of Virology 83: 12378-12387.

Gutierrez-Aguirre I, Mehle N, Delic D, Gruden K, Mumford R and Ravnikar M (2009) Real-time quantitative PCR based sensitive detection and genotype discrimination of Pepino mosaic virus Journal of Virological Methods 162: 46-55.

Hanssen I M and Thomma B (2010c). Pepino mosaic virus: A successful pathogen that rapidly evolved from emerging to endemic in tomato crops. Molecular Plant Pathology 11: 179-189.

Hanssen I M, Gutierrez-Aguirre I, Paeleman A, Goen K, Wittemans L, Lievens B, Vanachter A C R C, Ravnikar M and Thomma B P H J (2010a) Cross-protection or enhanced symptom display in greenhouse tomato co-infected with different Pepino mosaic virus isolates. Plant Pathology 59: 13-21.

Hanssen I M, Mumford R, Blystad D R, Cortez I, Hasiów-Jaroszewska B, Hristova D, Pagán I, Pereira A M, Peters J, Pospieszny H, Ravnikar M, Stijger I, Tomassoli L, Varveri C, van der Vlugt R and Nielsen SL (2010b) Seed transmission of Pepino mosaic virus in tomato. European Journal of Plant Pathology 126: 145-152.

Hanssen I M, Paeleman A, Vandewoestijne E, Van Bergen L, Bragard C, Lievens B, Vanachter A C R C and Thomma B P H J (2009) Pepino mosaic virus isolates and differential symptomatology in tomato. Plant Pathology 58: 450-460.

Hanssen I M, Paeleman A, Wittemans L, Goen K, Lievens B, Bragard C, Vanachter A C R C and Thomma B P H J (2008) Genetic characterization of Pepino mosaic virus isolates from Belgian greenhouse tomatoes reveals genetic recombination. European Journal of Plant Pathology: 121: 131-146.

Hanssen I M, Van Esse H P, Ballester A R, Hogewoning S W, Parra N O, Paeleman A, Lievens B, Bovy A G and Thomma B P H J (2011) Differential tomato transcriptomic responses induced by pepino mosaic virus isolates with differential aggressiveness. Plant Physiology 156: 301-318.

Hasiów-Jaroszewska B and Borodynko N (2012) Characterization of the necrosis determinant of the European genotype of pepino mosaic virus by site-specific mutagenesis of an infectious cDNA clone. Archives of Virology 157: 337-341.

Hasiów-Jaroszewska B, Borodynko N, Jackowiak P, Figlerowicz M and Pospieszny H (2010) Pepino mosaic virus—a pathogen of tomato crops in Poland: Biology, evolution and diagnostics. Journal of Plant Protection Research 50: 470-476.

Hasiów-Jaroszewska B, Borodynko N, Jackowiak P, Figlerowicz M and Pospieszny H (2011) A single mutation in TGB3 converts mild pathotype of Pepino mosaic virus into necrotic one. Virus Research 159: 57-61.

Hasiów B, Borodynko N and Pospieszny H (2008) Complete genomic RNA sequence of the Polish Pepino mosaic virus isolate belonging to the US2 strain. Virus Genes 36: 1-8.

Hasiów-Jaroszewska B, Borodynko N and Pospieszny H (2009b) Infectious RNA transcripts derived from cloned cDNA of a Pepino mosaic virus isolate. Archives of Virology 154: 853-856.

Hasiów-Jaroszewska B, Borodynko N and Pospieszny H (2011) Genetic and biological variability of Pepino mosaic virus isolates infecting tomato plants. Phytopathology 101: S70.

Hasiów-Jaroszewska B, Czerwoniec A, Pospieszny H and Elena S (2011) Tridimensional model structure and patterns of molecular evolution of Pepino mosaic virus TGBp3 protein. Virology Journal 8: DOI: 10.1186/1743-422X-8-318.

Hasiów-Jaroszewska B, Jackowiak P, Borodynko N, Figlerowicz M and Pospieszny H (2010) Quasispecies nature of Pepino mosaic virus and its evolutionary dynamics. Virus Genes 41: 260-267.

Hasiów-Jaroszewska B, Kuzniar A, Peters S A, Leunissen J A M and Pospieszny H (2010) Evidence for RNA recombination between distinct isolates of Pepino mosaic virus. Acta Biochimica Polonica 57: 385-388.

Hasiów-Jaroszewska B, Pospieszny H and Borodynko N (2009a) New necrotic isolates of Pepino mosaic virus representing Ch2 genotype. Journal of Phytopathol 157: 494-496

Johnson K and Walcott R (2005) A real-time PCR assay for the simultaneous detection of Pepino mosaic virus and *Clavibacter michiganensis* subsp *michiganensis* (2005) Phytopathology 95: S50.

Johnson K L and Walcott R R (2012) Progress towards a real-time PCR Assay for the simultaneous detection of *Clavibacter michiganensis* subsp *michiganensis* and Pepino mosaic virus in tomato seed. Journal Of Phytopathology 160: 353-363.

Jones R A C, Koenig R and Lesemann D E (1980) Pepino mosaic virus, a new potexvirus from *pepino* (*Solanum muricatum*). Annals of Applied Biology 94: 61-68.

Jorda C, Lázaro Pérez A, Matínez-Culebras P, Abad P, Lacasa A and Guerrero M M (2001) First Report of Pepino mosaic virus on Tomato in Spain. Plant Disease 85: 1292.

Karyeija R F, Kreuze J F, Gibson R W and Valkonen J P T (2000) Synergistic interactions of a Potyvirus and a phloem-limited Crinivirus in sweet potato plants. Virology 269: 26-36.

Kazinczi G, Takacs A P, Horvath J, Gaborjanyi R and Beres I (2005) Susceptibility of some weed species to Pepino mosaic virus (PepMV). Communications in agricultural and applied biological sciences 70: 489-491.

Kondo T, Kasai K, Yamashita K and Ishitani M (2007) Selection and discrimination of an attenuated strain of *Chinese yam necrotic mosaic* virus for cross-protection. Journal of General Plant Pathology 73: 152-155.

Kosaka Y and Fukunishi T (1997) Multiple inoculation with three attenuated viruses for the control of cucumber virus disease. Plant Disease 81: 733-738.

Krinkels, M (2001). Pepino mosaic virus causes sticky problem. Prophyta: The Annual, May 2001, 30-33.

Kulek B (2009) An increasing the resistance of field tomato to Pepino mosaic virus. Communications in agricultural and applied biological sciences 74: 867-877.

Lacasa A, Guerrero M M, Hita I, Martinez M A, Jordá C, Bielza P, Contreras J, Alcazar A and Cano A (2003) Implication of bumble bees (*Bombus* spp.) on Pepino mosaic virus (PepMV) spread on tomato crops. Plagas 29, 393-403

Li R, Gao S, Hernandez A G, Wechter W P, Fei Z and Ling K S (2012) Deep Sequencing of small RNAs in tomato for virus and viroid identification and strain differentiation. PLoS ONE 7: e37127, DOI: 10.1371/journal.pone.0037127.

Ling K (2005) Realtime immunocapture RT-PCR detection of Pepino mosaic virus on tomato seed and plant tissues in a single tube. Phytopathology 95: S61-S62.

Ling K (2006) Two variants of Pepino mosaic virus isolated from imported tomato seed from Chile share high levels of sequence identity with the US isolates. Phytopathology 96: S69.

Ling K S (2007a) Molecular characterization of two Pepino mosaic virus variants from imported tomato seed reveals high levels of sequence identity between Chilean and US isolates. Virus Genes 34: 1-8.

Ling K (2007b) The population genetics of Pepino mosaic virus in North America greenhouse tomatoes. Phytopathology 97: S65.

Ling K S (2008) Pepino mosaic virus on tomato seed: virus location and mechanical transmission. Plant Disease 92: 1701-1705.

Ling K S (2010) Effectiveness of chemo- and thermotherapeutic treatments on Pepino mosaic virus in tomato seed. Plant Disease 94: 325-328.

Ling K S and Scott J W (2007) Sources of resistance to Pepino mosaic virus in tomato accessions. Plant Disease 91: 749-753.

Ling K S and Zhang W (2011) First report of Pepino mosaic virus infecting tomato in Mexico. Plant Disease 95: 1035-1036.

Ling K S, Wechter W P and Jordan R (2007) Development of a one-step immunocapture real-time TaqMan RT-PCR assay for the broad spectrum detection of Pepino mosaic virus. Journal of Virological Methods 144: 65-72.

Ling K S, Wintermantel W M and Bledsoe M (2008) Genetic composition of Pepino mosaic virus population in North American greenhouse tomatoes. Plant Disease 92: 1683-1688.

López C, Soler S and Nuez F (2005) Comparison of the complete sequences of three different isolates of Pepino mosaic virus: size variability of the TGBp3 protein between tomato and *L. peruvianum* isolates. Archives of Virology 150: 619-627.

Malpica J M, Fraile A, Moreno I, Obies C I, Drake J W and Garcia-Arenal F (2002) The rate and character of spontaneous mutation in an RNA virus. Genetics 162: 1505-1511.

Mansilla C, Sánchez F and Ponz F (2003) The diagnosis of the tomato variant of pepino mosaic virus: an IC-RT-PCR approach. European Journal of Plant Pathology 109: 139-146.

Maroon-Lango C, Guaragna M A, Jordan R L, Bandia M and Marquardt S (2003) Detection and characterization of a US isolate of Pepino mosaic virus. Phytopathology 93: S57.

Maroon-Lango C J, Guaragna M A, Jordan R L, Hammond J, Bandla M and Marquardt S K (2005) Two unique US isolates of Pepino mosaic virus from a limited source of pooled tomato tissue are distinct from a third (European-like) US isolate. Archives of Virology 150: 1187-1201.

Matínez-Culebras PV, Lázaro A, Campos P A and Jorda C (2002) A RT-PCR assay combined with RFLP analysis for detection and differentiation of isolates of Pepino mosaic virus (PepMV) from tomato. European Journal of Plant Pathology 108: 887-892.

Mathioudakis M M, Veiga R, Ghita M, Tsikou D, Medina V, Canto T, Makris A M and Livieratos I C (2012) Pepino mosaic virus capsid protein interacts with a tomato heat shock protein cognate 70. Virus Research 163: 28-39.

Mumford R A and Metcalfe E J (2001) The partial sequencing of the genomic RNA of a UK isolate of Pepino mosaic virus and the comparison of the coat protein sequence with other isolates from Europe and Peru. Archives of Virology 146: 2455-2460.

Özdemir S (2010) First report of Pepino mosaic virus in tomato in Turkey. Journal of Plant Pathology 92, 54.107.

Pagán I, Cordoba-Selles M D C, Martinez-Priego L, Fraile A, Malpica J M, Jordá C and Garcia-Arenal F (2006) Genetic structure of the population of Pepino mosaic virus infecting tomato crops in Spain. Phytopathology 96: 274-279.

Papayiannis L C, Kokkinos C D and Alfaro-Fernández A (2012) Detection, characterization and host range studies of Pepino mosaic virus in Cyprus. *European Journal of Plant Pathology* 132: 1-7.

Pennazio S, Roggero P and Conti M (2001) A history of plant virology. Cross protection. New Microbiologica 24: 99-114.

Pepeira final report (2010) EU Pest Risk Analysis Pepino mosaic virus. www.pepeira.wur.nl/UK.

Pospieszny, H., Borodynko, N. and Palczewska, M. (2002). Occurrence of Pepino mosaic virus in Poland. Phytopathologia Polonica 26: 91-94.

Pospieszny H and Borodynko N (2006) New Polish isolate of Pepino mosaic virus highly distinct from European tomato, Peruvian, and US2 strains. Plant Disease 90: 1106.

Pospieszny H, Hasiow B and Borodynko N (2008) Characterization of two distinct Polish isolates of Pepino mosaic virus. European Journal of Plant Pathology 122: 443-445.

Pruss G, Ge X, Shi X M, Carrington J C and Vance V B (1997) Plant viral synergism: The potyviral genome encodes a broad-range pathogenicity enhancer that transactivates replication of heterologous viruses. Plant Cell 9: 859-868.

Ratcliff F G, MacFarlane S A and Baulcombe D C (1999) Gene silencing without DNA: RNA-mediated cross-protection between viruses. Plant Cell 11: 1207-1215.

Roggero P, Masenga V, Lenzi R, Coghe F, Ena S and Winter S (2001) First report of Pepino mosaic virus in tomato in Italy. Plant Pathology (New Disease Reports) 50: 798.

Salomone A and Roggero P (2002) Host range, seed transmission and detection by ELISA and lateral flow of an Italian isolate of Pepino mosaic virus. Journal of Plant Pathology 84: 65-68.

Schenk M F, Hamelink R, Van der Vlugt R A A, Vermunt A M W, Kaarsemaker R C and Stijger C C M M (2010) The use of attenuated isolates of Pepino mosaic virus cross-protection. European Journal of Plant Pathology 127: 249-261.

Schwarz D, Beuch U, Bandte M, Fakhro A, Buettner C and Obermeier C (2010) Spread and interaction of Pepino mosaic virus (PepMV) and *Pythium aphanidermatum* in a closed nutrient solution recirculation system: effects on tomato growth and yield. Plant Pathology 59: 443-452.

Sempere R N, Gomez P, Truniger V and Aranda M A (2011) Development of expression vectors based on pepino mosaic virus. Plant Methods 7: DOI: 10.1186/1746-4811-7-6.

Shipp J L, Buitenhuis R, Stobbs L, Wang K, Kim W S and Ferguson G (2008) Vectoring of Pepino mosaic virus by bumble-bees in tomato greenhouses. Annals of Applied Biology 153: 149-155.

Soler-Aleixandre S, López C, Cebolla-Cornejo J and Nuez F (2007) Sources of resistance to Pepino mosaic virus (PepMV) in tomato. HortScience 42: 40-45.

Soler-Aleixandre S, López C, Diez M J, Perez De Castro A and Nuez F (2005a) Association of Pepino mosaic virus with tomato collapse. Journal of Phytopathology 153: 464-469.

Soler S, López C and Nuez F (2005b). Natural occurrence of viruses in *Lycopersicon* spp. in Ecuador. Plant Disease 89: 1244.

Soler S, Prohens J, López C, Aramburu J, Galipienso L and Nuez F (2010) Viruses infecting tomato in Valencia, Spain: Occurrence, distribution and effect of seed origin. Journal of Phytopathology 158: 797-805.

Soler S, López C, Prohens J and Nuez F (2011) New sources of resistance to PepMV in tomato. Journal of Plant Diseases and Protection 118: 149-155.

Soler-Aleixandre S, López C, Cebolia-Cornejo J and Nuez F (2007) Sources of resistance to Pepino mosaic virus (PepMV) in tomato. HortScience 42: 40-45.

Soler S, Prohens J, Diez M J and Nuez F (2002). Natural occurrence of Pepino mosaic virus in *Lycopersicon* species in Central and Southern Peru. Journal of Phytopathology 150: 49-53

Spence N J, Basham J, Mumford R A, Hayman G, Edmondson R and Jones D R (2006) Effect of Pepino mosaic virus on the yield and quality of glasshouse-grown tomatoes in the UK. Plant Pathology 55: 595-606.

Steinhauer D A, Domingo E and Holland J J (1992) Lack of evidence for proofreading mechanisms associated with an RNA virus polymerase. Gene 122: 281-288.

Stobbs L W, Greig N, Weaver S, Shipp L and Ferguson G (2009) The potential role of native weed species and bumble bees (*Bombus impatiens*) on the epidemiology of Pepino mosaic virus. Canadian Journal of Plant Pathology—Revue Canadienne de Phytopathologie 31: 254-261.

Tiberini A, Davino S, Davino M and Tomassoli L (2011) Complete sequence, genotyping and comparative analysis of pepino mosaic virus isolates from Italy. Journal Of Plant Pathology 93: 437-442.

Tromas N and Elena S F (2010). The rate and spectrum of spontaneous mutations in a plant RNA virus. Genetics 185: 983-989.

Valkonen J P T, Rajamaki M L and Kekarainen T (2002) Mapping of viral genomic regions important in cross-protection between strains of a potyvirus. Molecular Plant-Microbe Interactions 15: 683-692.

Van der Vlugt R A A and Berendsen M (2002) Development of a general potexvirus detection method. European Journal of Plant Pathology 108: 367-371.

Van der Vlugt R A A, Cuperus C, Vink J, Stijger C C M M, Lesemann D-E, Verhoeven J Th J and Roenhorst J W (2002) Identification and characterisation of Pepino mosaic potex virus in tomato. Bulletin OEPP/EPPO Bulletin 32: 503-508.

Van der Vlugt R A A and Stijger C C M M (2008) Pepino mosaic virus. In: Mahy B and Van Regenmortel M H V (eds.) Encyclopedia of Virology Third Edition. Vol. (pp. 103-108) Elsevier Publishers.

Van der Vlugt R A A, Stijger C C M M, Verhoeven J T J and Lesemann D E (2000) First report of Pepino mosaic virus on tomato. Plant Disease 84: 103.

Verhoeven J T J, Van Der Vlugt R A A and Roenhorst J W (2003) High similarity between tomato isolates of Pepino mosaic virus suggests a common origin. European Journal of Plant Pathology 109: 419-425.

Yeh S D and Gonsalves D (1984) Evaluation of induced mutants of *Papaya ringspot* virus for control by cross protection. Phytopathology 74: 1086-1091.

Yeh S D, Gonsalves D, Wang H L, Namba R and Chiu R J (1988) Control of papaya ringspot virus by cross protection. Plant Disease 72: 375-380.

Yoon J Y, Ahn H I, Kim M, Tsuda S and Ryu K H (2006) Pepper mild mottle virus pathogenicity determinants and cross protection effect of attenuated mutants in pepper. Virus Research 118: 23-30.

Wang, H. L., Gonsalves, D., Provvidenti, R. and Lecoq, H. L. (1991) Effectiveness of cross protection by a mild strain of zucchini yellow mosaic virus in cucumber, melon, and squash. Plant Disease 75: 203-207.

Zhang Y L, Shen Z J, Zhong J, Lu X L, Chjeng G and Li R D (2003) Preliminary characterization of Pepino mosaic virus Shanghai isolate (PepMV-Sh) and its detection by ELISA. Acta Agriculturae Shanghai 19: 90-92.

The invention is further explained in the following examples. These examples do not limit the scope of the invention, but merely serve to clarify the invention.

EXAMPLES

Example 1: Cross-Protection Experiments with New Mild Isolates of the CH2 Strain of PepMV VC1 is a mild isolate of the CH2 strain of pepino mosaic virus (PepMV). During wintertime, VC1 infection can produce unwanted symptoms in inoculated plants, namely, nettle-heads and growth retardation. New variants of the CH2 strain were produced in order to identify viruses that would offer cross-protection but with reduced unwanted symptoms. In this trial, the new mild isolate VCA is compared with VC1 for symptoms and their cross-protection effectivity. The RNA-dependent RNA-polymerase (RdRp) of VCA was sequenced and was found to comprise a mixture of closely related viruses having the sequence of SEQ ID NO:1. Additional sequencing was performed to determine the complete coding sequence of the RdRp which is depicted in SEQ ID NO:8. The overlapping sequences of SEQ ID NO:1 and 8 are identical with the exception of position 6290 of SEQ ID NO:8. A"C" is present at this position in SEQ ID NO:8 instead of a "T" in the SEQ ID NO:1. This may reflect a mutation, but does not lead to an amino acid change.

A sequence alignment of VCA with known PepMV viruses is depicted in FIG. 5. Three of the nucleotides in SEQ ID NO:1 (corresponding to positions 2605, 3156 and 3422 of SEQ ID NO:1) are unique to VCA in comparison to not only the known PepMV viruses, but also to the attenuated strain VC1. While not wishing to be bound by theory, it is believed that these two nucleotide changes alter the amino acid sequence, which in turn results in milder symptoms.

Set-Up:

Tomato plants of the cultivar Merlice (on rootstock) were used. Each row of 12 plants was a different treatment. The plants were grown in two greenhouse compartments. The set temperatures were 20° C. at daytime and 18° C. at nighttime. The trial lasted 3 months. Inoculations were carried out by the rubbing protocol (see below).

Plants were innoculated first with mild isolates (VC1 or VCA) and tested with ELISA to determine infection. The results of the ELISA are shown below.

| | |
|---|---|
| VC1 | 4/4+ |
| VCA | 4/4+ |
| Negative control | 0/4+ |

Approximately six weeks (39 days) after the first inoculation the plants were innoculated with the virulent isolate (CHD).

Results

Infection with the mild isolates VCA and VC1 resulted in very mild symptoms, namely, light bubbling on the young leaves and minor nettle-heads (FIG. 2). Infection with the virulent CH2 isolate CHD alone showed strong necrosis of the leaves and stems, from 3 weeks after inoculation of CHD (FIG. 1A). Treatment with VCA or VC1 protected plants from necrosis (see, e.g., FIG. 1B)

Conclusions

VCA is as mild as VC1 and maybe even milder.

Both VCA and VC1 prevented symptoms of the virulent CH2 isolate CHD.

Example 2: Symptoms Observed from Treatment with PepMV Variants

VC1 infection can produce unwanted symptoms in inoculated plants, namely, nettle-heads and growth retardation. In this trial, the new mild isolate VCA is compared with VC1 for the induction of symptoms in treated plants.

Tomato plants of the cultivar Komeett were used. Inoculations were carried out by the rubbing protocol (see below). Plants were innoculated with mild isolates (VC1 or VCA) and tested two weeks later with ELISA to determine infection. It was found on average 95% of the virus inoculated plants had been infected. The virus-free plants remained free until the end of the test. Treatment with either VCA or VC1 resulted in the development of light symptoms, such as leaf misformation. However, plants treated with VCA (FIG. 3B) had more leaf volume and grew better than those treated with VC1 (FIG. 3C).

Example 3: Comparison of Symptoms in Plants Grown Under Optimal Conditions Versus Sub-Optimal Conditions FIG. 4 depicts plants grown under optimal conditions versus sub-optimal conditions. In optimal growing conditions, plants treated with VC1 and VCA show a comparable level of very mild symptoms. However, in sub-optimal growing conditions, VC1 treated plants show much more severe symptoms than VCA treated plants. While not wishing to be bound by theory, it is believed that the nucleotide differences at position 2605, and 3156 of SEQ ID NO:1 result in an amino acid alteration as compared to VC1 and that one or both of these amino acid alterations is responsible for the milder symptoms.

Material and Methods:

Rubbing Protocol:

Knead frozen or fresh infected plant material. Take 7.5-10 ml of extracted plant sap or 7.5-10 ml virus suspension of virus product.

Put the 7.5-10 ml in a plastic tray

Dilute virus suspension 10-times with PBS

Add 1-2% (w/v) carborundum

Mix suspension well.

Put disposable gloves on your hands.

Stir with your fingers and thumb in the suspension.

Inoculate two leaves on each plant in upper half on a leaflet by rubbing 5-times leaflet between thumb and index finger. Leaves should be damaged a little bit. (light discolouration, without holes).

Dip for each plant your finger and inoculate the plant

After inoculation, collect all residual material and put this in a garbage bin or waste container. The residual material should be disinfected by 100-200 ppm hypochlorite and after that it can be processed as regular waste.

Test after 14 (±2) days the percentage of infected plants. This can be determined by the method ELISA.

High pressure spraying protocol:

Usage of spraying liquid: 0.5 L/m.

Measure the needed amount of cold tap water and put this in the tank of the spraying cart.

Prepare virus solution

Add carborundum 800 gram/100 L to spraying liquid.

Mix carborundum well in spray cart, by hand, cover your fore-arm in a disposable overboot, circulate to contents of the tank Pressure on nozzles in spraying arm: 12-15 bar Spraying width: 1.20 m, 6 nozzles Spraying height: 10-15 cm above the plants.

Check the nozzles for blockages and evenness of spray.

After inoculation, collect all residual material and put this in a garbage bin or waste container. The residual material should be disinfected by 100-200 ppm hypochlorite and after that it can be processed as regular waste.

Test after 14 (±2) days the percentage of infected plants. This can be determined by the ELISA method.

ELISA for Measuring PepMV in Sample

Reagents for performing DAS-ELISA were obtained from PRIME Diagnostics, Wageningen, The Netherlands. The ELISAs were carried out according to the manufacturer's instructions.

The invention claimed is:

1. A Pepino mosaic virus comprising a nucleic acid molecule with a nucleic acid sequence that encodes phenylalanine at the position corresponding to 1052 of SEQ ID NO:2.

2. The virus of claim 1, wherein the nucleic acid sequence further encodes arginine at the position corresponding to 868 of SEQ ID NO:2.

3. A Pepino mosaic virus comprising a nucleic acid molecule with a nucleic acid sequence that encodes arginine at the position corresponding to 868 of SEQ ID NO:2.

4. The virus according to claim 1, wherein the nucleic acid sequence is at least 80% identical to SEQ ID NO:1.

5. The virus according to claim 1, wherein the nucleic acid sequence is at least 80% identical to SEQ ID NO:8.

6. A composition for biological control of plant disease comprising the virus of claim 1 and an agriculturally acceptable carrier.

7. A method for producing a pepino mosaic virus (PepMV)-resistant plant, comprising exposing a plant or plant part to the virus of claim 1.

8. A PepMV-resistant plant comprising a virus according to claim 1.

* * * * *

SEQUENCE LISTING

```
<160> NUMBER OF SEQ ID NOS: 26

<210> SEQ ID NO 1
<211> LENGTH: 6231
<212> TYPE: DNA
<213> ORGANISM: Pepino mosaic virus

<400> SEQUENCE: 1
ctagcatttg tgaagccgct taccaacatg ttagacctgt gctcaaggaa tccctaatca      60
actgtcctta tgcgcttaat gactatgaag cagacaccct tgagaattta ggtgtcacaa     120
taaaccccca tgcaatccaa acacatactc atgcggcagc taaagttgtg gaaaatagaa     180
tgctcgaaat cgttggacac cacttgccca aggacgagaa agttaccttc attttcctca     240
aaagaagcaa actgagatac atgcgaagag ctgctgtaca taaagatgtt tttgttaatc     300
acaatataga acccaaggat ttcttcaggt atgatgagga atctacatct actagtttct     360
ccgtgaacac caggatcgct tacatctccg attctctaca tttcatggaa ccagctgatg     420
tgacccacct ctttgaccgt tgccacaatc ttaaaacact gatggcaact gtcgttttac     480
ctgttgaagc catccacaaa caaacatctt tatttccagc gatatactcc attaattaca     540
atgaagaagg ttttgagtat atccctggtt ctcatggtgg aggggcatac tttcataagt     600
atgaaacatt agactggctc aaatactcta gattcattgg ccaggacccc ttaactggac     660
tccgatacac cataaccatt caaatggtag agagtttagg agccaaccat cttttcctct     720
tccaaagagg aaattttgaa acacctttat acaggacgtt tcaaaaaaat agctttgtga     780
cctttcctaa catcttccat ccccaacatg ttaatgccac aaagcccatg ccaagatcca     840
gggcaattca gctgtattta tatgtcaaat ctgtcaataa ggtgacacaa agagatatct     900
ttgcgaaagt aaggcaactt atatctacag ctgaacttga attgtatgac cctgatgaac     960
ttacacatat tgtcaattat ttcgcatatg tctcagaact aagctcaatc aacgactatg    1020
acaatatgct caaatcaagt tttttcaaaa aacttgttgc acccatgcaa catgactgga    1080
ggtgcatgat tgaattcttt cggggaaaaa gtgatttcaa tcaactttta actgctcttc    1140
aatggaaaga cttctcttac accattaaaa ctgaagagtt agttgttgct acacacactg    1200
aaattggcca ggcaatctgt gaagctgcga ccacatacaa agaaagaaga caattgacca    1260
atttagtcaa acaaggcgca gtaacattag ctgatttcaa agaagcggac cagcatgtgg    1320
agtacactca ctttgatcct gagtttaaat ccactgttga cccccaccgg agctatgaaa    1380
atgccatcaa caatcttggc attgagatta atgaggatgt acctgaaagt tccggcacta    1440
```

```
atraaacatt gcttaacaat gaaatatctt tagcaatgtc ayctgctgaa catgtgcaag    1500
ccgttcaaga aattgagtct ttactctcta accccgaagc ggcaccaata ttgcccctg     1560 cacatgttaa acatgggct agccttgcat ctgacayttc cagcactaaa aaccgtgaaa     1620
tcgaagatat agtggctaag ctggaaatac aaagaaatga agctagttgc agctaccttc    1680
aaccaaataa ggaattgtca aaacccaagg ctgctgataa caatctcccc tggaatgctt    1740
ggatcccatt gcttaatgca cacggcttca aaggagatca attacaatac ggcccagatg    1800
gtaacttgat acagcccatc caagacatta acaattcaca gcctagatct gactatccgt    1860
cttctctgcc atgtgaactt gtggaaactt tgaggaaaat taagcgtgct gtctatgcca    1920
tcccaataag ccacaggaga gctagtgctt acagttctga catcaaaaat aacagaactg    1980
gcaaacttct ctgcaaccaa agcaaagaat ggaaagaaag ctttgctttc aaaatgcaac    2040
atgaagacat cgtcaaatca ggtgttgtca tacatggttg cggaggttct ggcaaatccc    2100
aggcattaca aaacttcttg agaacattgg gtgattcaaa tgattgctgt actgttgtag    2160
tacccactgt tgaacttaga aatgactggg taaacaaact ccataaattg cccatggagc    2220
atatcaaaac attttgagaaa gcaatgattc aacctggctt tccaattgtt atatttgatg    2280
attacaccaa gttgccacct ggctacattg aagcatacct atttcaccat gccaacactg    2340
agcttttcat actcactggt gattctaggc aaagcgtgta ccatgaatct aacaatgaag    2400
cgtacattgc ctcattagat gaagctgttg catactacgc taattactgc ggttttttatt   2460 taaatgctac tcatagaaat gtccgtagtt tagccaacaa acttggtgtt tacagtgaga    2520
aagaaggaca cttgaaaatc acttttgctt cacatgcctt acaaaagtgc aaagtgccaa    2580
ttttagttcc ttctcaaatg aaaaggagtg ctatgtyaga cattggacat aaatccatga    2640
cctatgctgg ttgccaaggt ttaacagcac ccaaggtaca aattctcctt gataaccaca    2700
cgcaacattg ctctgacaga gttctgtaca cctgtctgtc tcgtgcagtt gattccatcc    2760
acttcattaa tactggtccc aacaattcag aattttggga taagcttgaa gcaacaccat    2820
atctcaaagc cttcattgat gtctatagag atgaaaaaac tgaaatgttc aattctaagc    2880
ctgctgatga cagtccaact gagcctgaag cacctgttac acatttccca atagcaaatg    2940
gaaataactt agagaaatta gcttctgctt tgcctgaaaa atttgctagg agagatttatg   3000 acaagcatca tggccactcc aacacaatcc aaactgagaa ccctgtggtc caacttttcc    3060
aacatcaaca agcgaaagac gagacactct ttgggctac aattgaagct agattgtcca     3120
taacaactcc tgaagcaaac ctcagagaat ttttgtttaa gaaagatgtt ggagacattc    3180
tcttcttcaa ttaccataat gcgatgtgct tgcctgccga ccctgttgac tttgaagaaa    3240
agacctggga gatctgtgct gctgaagtga aaaacactta tcttgccaaa cccatggcca    3300
atcttatcaa tgcggcaagt agacaatcac ccgactttga ctctaataag atctcattat    3360
tcctaaagtc tcaatgggtg aaaaaagtgg aaaaacttgg agctatcaaa tcaaaacctg    3420
ggcagaccat agctgctttt atgcaacaaa cagtcatgtt gtatggtact atggccaggt    3480
acttaaggaa aatgcggcaa agattccagc caaaacacat attcatcaat tgtgaaacca    3540
caactgatga tctcaataaa tttgtcaaag ayggctggaa ctttaacaga accgcccaaa    3600
caaatgactt cactgctttt gatcagtcac aagatggagc aatgcttcaa tttgaagtca    3660
tgaaagcaaa attttttaac attccagctg atgtcattga aggctacatc aacatcaagc    3720
tgaatgctaa aattttcctt ggaacactct caataatgag actttctggt gaaggtccca    3780
catttgacgc taacactgag tgttcgattg catacactgc cacaagattc catattgaca    3840
```

```
atactgttaa gcaagtgtat gccggtgacg acatggcatt agatggagtt gtgagtgaaa    3900
agaaatcatt caggaagtta caaaatctac taaaactcac ttcaaaaacg ctgtacccaa    3960
aacaggttaa agggaattac gctgaatttt gtggttggac tttcacacca gggggtataa    4020
ttaaaaatcc acttaaaatg catgcctcaa ttatgctgca agaagccatt ggcaatctgc    4080
acacagcagc cagatcttat gcaattgaca tgaagcattc ataccaaatg ggtgaccaac    4140
tgcatgacta cctaaccccc gatgaagctg aacaacattt cctagctgtg agaaagcttc    4200
acaaactcca tcaaggcgag gccatgcgtc ttggggagaa aagtccacca agatcaaccc    4260
attaaggggt taagttttcc ccagtttgaa atggaaagat caactttgat caatttactt    4320
ctgttacaca aatttgaaca caagattaac actgaaggaa tcattgttgt gcacggaatt    4380
gctggaactg ggaaaaccac attgcttagg actttatttt ctgcataccc tagcttagtt    4440
ataggttcac ctaggccttg ttacttagat aaagctaata aaatttcaca agtttgcctt    4500
tcttgttttc caaatacctt gtgtgacatt gttgacgagt atcatctctt agaaagtttt    4560
cctgaaccaa aactagccat ttttggtgac ccctgtcagt gcacttacat tgaaaggttg    4620
agaacaccca actacacatc cttcagaaca caccgatttg gcaaatccac tgctgctcta    4680
ctaaaccagt tatttgatct taacattgag tcagtcaaag cacaagacga cacagtagaa    4740
tactttgatc ctttcgcagt ggaccctct gaacacattt ctgcttcaga aaagaagtt     4800
ttggaatttg taggtgatca agttgagact acaagctctg aagaactagc tggtctcgag    4860
tttagtgaag ttactttcta ctgtaccaca cttgctggtg ctgttcaaga aaatcctgct    4920
aaaaccttca tttcactcac tagacacact tcaaagctca caattggtga actaaatgcc    4980
aggtctgact cctagagctg atcttactga cacgtataaa atcattgcta tagcctttct    5040
actgtcagct tgcatttact tccaaaacag tcattatcaa ccagttgcag gtgataattt    5100
gcacagacta ccctttggtg gtcagtatca agacggaact aagaagattt cttactttcc    5160
gcagcaacaa tcctactttc actcaggaaa caagcttaat gtcctcatac ttatcttcat    5220
tcttacactg ggtattgtcc tcaccaataa atttagtttt agcattagcc gtaatactca    5280
ccagcatcat tgctacaaca cacattctgc aacccaaaca ggtcaatcag tgccaggtca    5340
tcattgacgg tgcagccata gttataacaa attgtccaaa cacacccgaa gttcttaaag    5400
caatcaactt ctcccctttgg aacgggttaa gttttcctca attgtgaaat tatatttgtt    5460
atctagttaa attcaaacaa tttaactcaa ctatggaaaa ccaacctaca gcttctaacc    5520
catcagatgc accaccaact gctgctcaag ctggtgccca gagcccagcs gacttctcaa    5580
atcctaatac agctccttcc ctaagtgatt tgaagaagat caaatacgtg tcaactgtca    5640
cttcagttgc cacgcctgct gaaattgagg cccttggcaa gatctttact gccatgggtt    5700
tagcagccaa tgagaccgga cctgccatgt gggacctcgc tcgtgcttat gctgatgtgc    5760
aaagttcaaa atctgcacaa cttayaggtg ccacaccatc caaccctgct ttgtctagac    5820
gtgcacttgc tgcacagttt gatcgtatca atatcacacc cagacaattc tgcatgtatt    5880
ttgcaaaaat tgtttggaac atactgttag acagcaatgt gccacctgcc aactgggcaa    5940
aattgggcta tcaggaagat accaagtttg ctgcttttga cttctttgat ggagtcacaa    6000
atccagctag tctacagccy gcagatggcc taatcaggca gcccaatgaa aaagagcttg    6060
ctgctcactc ggttgctaaa tatggtgccc ttgcccgcca gaaaatatcc actggtaact    6120
acatcaccac ccttggtgaa gttacacgtg gtcacatggg cggcgccaac actatgtacg    6180
caattgatgc acctcctgaa ctttaaacac tcgaaactta atcagagtgg g              6231
```

<210> SEQ ID NO 2
<211> LENGTH: 1420
<212> TYPE: PRT
<213> ORGANISM: Pepino mosaic virus
<220> FEATURE:
<221> NAME/KEY: misc_feature
<222> LOCATION: (481)..(481)
<223> OTHER INFORMATION: Xaa can be any naturally occurring amino acid
<220> FEATURE:
<221> NAME/KEY: misc_feature
<222> LOCATION: (494)..(494)
<223> OTHER INFORMATION: Xaa can be any naturally occurring amino acid
<220> FEATURE:
<221> NAME/KEY: misc_feature
<222> LOCATION: (532)..(532)
<223> OTHER INFORMATION: Xaa can be any naturally occurring amino acid
<220> FEATURE:
<221> NAME/KEY: misc_feature
<222> LOCATION: (872)..(872)
<223> OTHER INFORMATION: Xaa can be any naturally occurring amino acid

<400> SEQUENCE: 2

```
Ser Ile Cys Glu Ala Ala Tyr Gln His Val Arg Pro Val Leu Lys Glu
1               5                   10                  15

Ser Leu Ile Asn Cys Pro Tyr Ala Leu Asn Asp Tyr Glu Ala Asp Thr
            20                  25                  30

Leu Glu Asn Leu Gly Val Thr Ile Asn Pro His Ala Ile Gln Thr His
        35                  40                  45

Thr His Ala Ala Ala Lys Val Val Glu Asn Arg Met Leu Glu Ile Val
    50                  55                  60

Gly His His Leu Pro Lys Asp Glu Lys Val Thr Phe Ile Phe Leu Lys
65                  70                  75                  80

Arg Ser Lys Leu Arg Tyr Met Arg Arg Ala Ala Val His Lys Asp Val
                85                  90                  95

Phe Val Asn His Asn Ile Glu Pro Lys Asp Phe Phe Arg Tyr Asp Glu
            100                 105                 110

Glu Ser Thr Ser Thr Ser Phe Ser Val Asn Thr Arg Ile Ala Tyr Ile
        115                 120                 125

Ser Asp Ser Leu His Phe Met Glu Pro Ala Asp Val Thr His Leu Phe
    130                 135                 140

Asp Arg Cys His Asn Leu Lys Thr Leu Met Ala Thr Val Val Leu Pro
145                 150                 155                 160

Val Glu Ala Ile His Lys Gln Thr Ser Leu Phe Pro Ala Ile Tyr Ser
                165                 170                 175

Ile Asn Tyr Asn Glu Glu Gly Phe Glu Tyr Ile Pro Gly Ser His Gly
            180                 185                 190

Gly Gly Ala Tyr Phe His Lys Tyr Glu Thr Leu Asp Trp Leu Lys Tyr
        195                 200                 205

Ser Arg Phe Ile Gly Gln Asp Pro Leu Thr Gly Leu Arg Tyr Thr Ile
    210                 215                 220

Thr Ile Gln Met Val Glu Ser Leu Gly Ala Asn His Leu Phe Leu Phe
225                 230                 235                 240

Gln Arg Gly Asn Phe Glu Thr Pro Leu Tyr Arg Thr Phe Gln Lys Asn
                245                 250                 255

Ser Phe Val Thr Phe Pro Asn Ile Phe His Pro Gln His Val Asn Ala
            260                 265                 270

Thr Lys Pro Met Pro Arg Ser Arg Ala Ile Gln Leu Tyr Leu Tyr Val
        275                 280                 285

Lys Ser Val Asn Lys Val Thr Gln Arg Asp Ile Phe Ala Lys Val Arg
    290                 295                 300
```

```
Gln Leu Ile Ser Thr Ala Glu Leu Glu Leu Tyr Asp Pro Asp Glu Leu
305                 310                 315                 320

Thr His Ile Val Asn Tyr Phe Ala Tyr Val Ser Glu Leu Ser Ser Ile
            325                 330                 335

Asn Asp Tyr Asp Asn Met Leu Lys Ser Ser Phe Phe Lys Lys Leu Val
                340                 345                 350

Ala Pro Met Gln His Asp Trp Arg Cys Met Ile Glu Phe Phe Arg Gly
            355                 360                 365

Lys Ser Asp Phe Asn Gln Leu Leu Thr Ala Leu Gln Trp Lys Asp Phe
            370                 375                 380

Ser Tyr Thr Ile Lys Thr Glu Glu Leu Val Val Ala Thr His Thr Glu
385                 390                 395                 400

Ile Gly Gln Ala Ile Cys Glu Ala Ala Thr Thr Tyr Lys Glu Arg Arg
                405                 410                 415

Gln Leu Thr Asn Leu Val Lys Gln Gly Ala Val Thr Leu Ala Asp Phe
            420                 425                 430

Lys Glu Ala Asp Gln His Val Glu Tyr Thr His Phe Asp Pro Glu Phe
            435                 440                 445

Lys Ser Thr Val Asp Pro His Arg Ser Tyr Glu Asn Ala Ile Asn Asn
450                 455                 460

Leu Gly Ile Glu Ile Asn Glu Asp Val Pro Glu Ser Ser Gly Thr Asn
465                 470                 475                 480

Xaa Thr Leu Leu Asn Asn Glu Ile Ser Leu Ala Met Ser Xaa Ala Glu
                485                 490                 495

His Val Gln Ala Val Gln Glu Ile Glu Ser Leu Leu Ser Asn Pro Glu
            500                 505                 510

Ala Ala Pro Ile Leu Pro Pro Ala His Val Lys Thr Trp Ala Ser Leu
            515                 520                 525

Ala Ser Asp Xaa Ser Ser Thr Lys Asn Arg Glu Ile Glu Asp Ile Val
530                 535                 540

Ala Lys Leu Glu Ile Gln Arg Asn Glu Ala Ser Cys Ser Tyr Leu Gln
545                 550                 555                 560

Pro Asn Lys Glu Leu Ser Lys Pro Lys Ala Ala Asp Asn Asn Leu Pro
            565                 570                 575

Trp Asn Ala Trp Ile Pro Leu Leu Asn Ala His Gly Phe Lys Gly Asp
            580                 585                 590

Gln Leu Gln Tyr Gly Pro Asp Gly Asn Leu Ile Gln Pro Ile Gln Asp
            595                 600                 605

Ile Asn Asn Ser Gln Pro Arg Ser Asp Tyr Pro Ser Ser Leu Pro Cys
            610                 615                 620

Glu Leu Val Glu Thr Leu Arg Lys Ile Lys Arg Ala Val Tyr Ala Ile
625                 630                 635                 640

Pro Ile Ser His Arg Arg Ala Ser Ala Tyr Ser Ser Asp Ile Lys Asn
                645                 650                 655

Asn Arg Thr Gly Lys Leu Leu Cys Asn Gln Ser Lys Glu Trp Lys Glu
            660                 665                 670

Ser Phe Ala Phe Lys Met Gln His Glu Asp Ile Val Lys Ser Gly Val
            675                 680                 685

Val Ile His Gly Cys Gly Gly Ser Gly Lys Ser Gln Ala Leu Gln Asn
            690                 695                 700

Phe Leu Arg Thr Leu Gly Asp Ser Asn Asp Cys Cys Thr Val Val Val
705                 710                 715                 720
```

-continued

Pro Thr Val Glu Leu Arg Asn Asp Trp Val Asn Lys Leu His Lys Leu
            725                 730                 735

Pro Met Glu His Ile Lys Thr Phe Glu Lys Ala Met Ile Gln Pro Gly
            740                 745                 750

Phe Pro Ile Val Ile Phe Asp Asp Tyr Thr Lys Leu Pro Pro Gly Tyr
            755                 760                 765

Ile Glu Ala Tyr Leu Phe His His Ala Asn Thr Glu Leu Phe Ile Leu
            770                 775                 780

Thr Gly Asp Ser Arg Gln Ser Val Tyr His Glu Ser Asn Asn Glu Ala
785                 790                 795                 800

Tyr Ile Ala Ser Leu Asp Glu Ala Val Ala Tyr Tyr Ala Asn Tyr Cys
                805                 810                 815

Gly Phe Tyr Leu Asn Ala Thr His Arg Asn Val Arg Ser Leu Ala Asn
            820                 825                 830

Lys Leu Gly Val Tyr Ser Glu Lys Glu Gly His Leu Lys Ile Thr Phe
            835                 840                 845

Ala Ser His Ala Leu Gln Lys Cys Lys Val Pro Ile Leu Val Pro Ser
            850                 855                 860

Gln Met Lys Arg Ser Ala Met Xaa Asp Ile Gly His Lys Ser Met Thr
865                 870                 875                 880

Tyr Ala Gly Cys Gln Gly Leu Thr Ala Pro Lys Val Gln Ile Leu Leu
                885                 890                 895

Asp Asn His Thr Gln His Cys Ser Asp Arg Val Leu Tyr Thr Cys Leu
            900                 905                 910

Ser Arg Ala Val Asp Ser Ile His Phe Ile Asn Thr Gly Pro Asn Asn
            915                 920                 925

Ser Glu Phe Trp Asp Lys Leu Glu Ala Thr Pro Tyr Leu Lys Ala Phe
            930                 935                 940

Ile Asp Val Tyr Arg Asp Glu Lys Thr Glu Met Phe Asn Ser Lys Pro
945                 950                 955                 960

Ala Asp Asp Ser Pro Thr Glu Pro Glu Ala Pro Val Thr His Phe Pro
                965                 970                 975

Ile Ala Asn Gly Asn Asn Leu Gly Lys Leu Ala Ser Ala Leu Pro Glu
            980                 985                 990

Lys Phe Ala Arg Glu Ile Tyr Asp Lys His His Gly His Ser Asn Thr
            995                 1000                1005

Ile Gln Thr Glu Asn Pro Val Val Gln Leu Phe Gln His Gln Gln
            1010                1015                1020

Ala Lys Asp Glu Thr Leu Phe Trp Ala Thr Ile Glu Ala Arg Leu
            1025                1030                1035

Ser Ile Thr Thr Pro Glu Ala Asn Leu Arg Glu Phe Leu Phe Lys
            1040                1045                1050

Lys Asp Val Gly Asp Ile Leu Phe Phe Asn Tyr His Asn Ala Met
            1055                1060                1065

Cys Leu Pro Ala Asp Pro Val Asp Phe Glu Glu Lys Thr Trp Glu
            1070                1075                1080

Ile Cys Ala Ala Glu Val Lys Asn Thr Tyr Leu Ala Lys Pro Met
            1085                1090                1095

Ala Asn Leu Ile Asn Ala Ala Ser Arg Gln Ser Pro Asp Phe Asp
            1100                1105                1110

Ser Asn Lys Ile Ser Leu Phe Leu Lys Ser Gln Trp Val Lys Lys
            1115                1120                1125

| Val | Glu | Lys | Leu | Gly | Ala | Ile | Lys | Ser | Lys | Pro | Gly | Gln | Thr | Ile |
| --- | --- | --- | --- | --- | --- | --- | --- | --- | --- | --- | --- | --- | --- | --- |
| 1130 | | | | | 1135 | | | | | 1140 | | | | |
| Ala | Ala | Phe | Met | Gln | Gln | Thr | Val | Met | Leu | Tyr | Gly | Thr | Met | Ala |
| 1145 | | | | | 1150 | | | | | 1155 | | | | |
| Arg | Tyr | Leu | Arg | Lys | Met | Arg | Gln | Arg | Phe | Gln | Pro | Lys | His | Ile |
| 1160 | | | | | 1165 | | | | | 1170 | | | | |
| Phe | Ile | Asn | Cys | Glu | Thr | Thr | Asp | Asp | Leu | Asn | Lys | Phe | Val | |
| 1175 | | | | | 1180 | | | | | 1185 | | | | |
| Lys | Asp | Gly | Trp | Asn | Phe | Asn | Arg | Thr | Ala | Gln | Thr | Asn | Asp | Phe |
| 1190 | | | | | 1195 | | | | | 1200 | | | | |
| Thr | Ala | Phe | Asp | Gln | Ser | Gln | Asp | Gly | Ala | Met | Leu | Gln | Phe | Glu |
| 1205 | | | | | 1210 | | | | | 1215 | | | | |
| Val | Met | Lys | Ala | Lys | Phe | Phe | Asn | Ile | Pro | Ala | Asp | Val | Ile | Glu |
| 1220 | | | | | 1225 | | | | | 1230 | | | | |
| Gly | Tyr | Ile | Asn | Ile | Lys | Leu | Asn | Ala | Lys | Ile | Phe | Leu | Gly | Thr |
| 1235 | | | | | 1240 | | | | | 1245 | | | | |
| Leu | Ser | Ile | Met | Arg | Leu | Ser | Gly | Glu | Gly | Pro | Thr | Phe | Asp | Ala |
| 1250 | | | | | 1255 | | | | | 1260 | | | | |
| Asn | Thr | Glu | Cys | Ser | Ile | Ala | Tyr | Thr | Ala | Thr | Arg | Phe | His | Ile |
| 1265 | | | | | 1270 | | | | | 1275 | | | | |
| Asp | Asn | Thr | Val | Lys | Gln | Val | Tyr | Ala | Gly | Asp | Asp | Met | Ala | Leu |
| 1280 | | | | | 1285 | | | | | 1290 | | | | |
| Asp | Gly | Val | Val | Ser | Glu | Lys | Lys | Ser | Phe | Arg | Lys | Leu | Gln | Asn |
| 1295 | | | | | 1300 | | | | | 1305 | | | | |
| Leu | Leu | Lys | Leu | Thr | Ser | Lys | Thr | Leu | Tyr | Pro | Lys | Gln | Val | Lys |
| 1310 | | | | | 1315 | | | | | 1320 | | | | |
| Gly | Asn | Tyr | Ala | Glu | Phe | Cys | Gly | Trp | Thr | Phe | Thr | Pro | Gly | Gly |
| 1325 | | | | | 1330 | | | | | 1335 | | | | |
| Ile | Ile | Lys | Asn | Pro | Leu | Lys | Met | His | Ala | Ser | Ile | Met | Leu | Gln |
| 1340 | | | | | 1345 | | | | | 1350 | | | | |
| Glu | Ala | Ile | Gly | Asn | Leu | His | Thr | Ala | Ala | Arg | Ser | Tyr | Ala | Ile |
| 1355 | | | | | 1360 | | | | | 1365 | | | | |
| Asp | Met | Lys | His | Ser | Tyr | Gln | Met | Gly | Asp | Gln | Leu | His | Asp | Tyr |
| 1370 | | | | | 1375 | | | | | 1380 | | | | |
| Leu | Thr | Pro | Asp | Glu | Ala | Glu | Gln | His | Phe | Leu | Ala | Val | Arg | Lys |
| 1385 | | | | | 1390 | | | | | 1395 | | | | |
| Leu | His | Lys | Leu | His | Gln | Gly | Glu | Ala | Met | Arg | Leu | Gly | Glu | Lys |
| 1400 | | | | | 1405 | | | | | 1410 | | | | |
| Ser | Pro | Pro | Arg | Ser | Thr | His | | | | | | | | |
| 1415 | | | | | 1420 | | | | | | | | | |

<210> SEQ ID NO 3
<211> LENGTH: 6410
<212> TYPE: DNA
<213> ORGANISM: Pepino mosaic virus

<400> SEQUENCE: 3

```
gaaaacaaaa caaataaaca aatatacaaa gttaaactaa cacaacataa ccacgtggaa    60
aaacagcgaa agcactttac cacattatgt ctcgtgtcag aaatactttg gaaaagatca   120
gagacccaca agtacagtcc agcatttgtg aagctgccta tcaacatgtt cgacctgtac   180
ttaaagaatc tctaatcaat tgtccttacg cgcttaatga ttatgaagca gacacccttg   240
agaatcttgg tgtcacaatt aaccccccatg caatccaaac acacacacat gccgcagcca   300
aagtagtcga aaatcgtatg cttgaaattg ttggacatca cttgcctaaa gatgaaaaag   360
```

```
taactttcat cttcctcaaa cgtagcaagc tgcgttacat gagaagagct gctgtgcata        420
aagatgtctt tgtcaatcat aacattgaac caaaagactt cttcaggtat gatgaagagt        480
ctacatcaac cagcttttcc gttgatacga gaatcgcata catttcagat tctctacact        540
ttatggaacc tgctgatgtg actcacttgt ttgaccgttg ccaaaacctt aaaacattga        600
tggcaactgt tgtactacct gtggaagcta tacacagaca gacatctcta ttccctgcga        660
tttactccat taactacaat gaagaaggct ttgagtatat cccaggatca cacggtggtg        720
gggcatattt ccacaaatat gaaaccctag aatggctcaa atactctaga ttcattggac        780
atgatccatt gactggttta aaatacacca ttacgattca aatggtggag agtcttggtg        840
ccaaccacct tttcctcttc caaagaggaa actttgagac gccgctatac aggacgtttc        900
aaaagaatag ttttgtgaca ttcccaaata tattccatcc ccgacacgtc aatgccacaa        960
aacctatgcc tagatcaagg gccatacagc tgtacttata tgtgaaatca gtaaataaag       1020
ttacgcaaag agatatattt gccaaggtta gacaactgat ttccactgct gagctagaat       1080
tgtatgaccc tgatgaactc acgcatgttg taaattattt cacatatgtg tcacaactgt       1140
catctatcaa tgattatgac aacatgctca aatccagttt cttcaaaaaa ctggttgcac       1200
ccatgcaaca cgactggagg tgcatgattg aattcttccg gggaaagagt gacttcaatc       1260
aactgctcac agctcttcaa tggaaagatt tttcctatac tattaagact gaagagcttg       1320
taattactac acacactgct ataggacaag caataagcaa tgcagctgcc acatataaag       1380
aaagaaagca gctgactcaa ttggtcaaaa aaggtacaat atccttagca gattttgaac       1440
agagagagcc tgaaataact tacactgagt ttgagcctga aactaggccc caagtggact       1500
gcgttactaa ttataataat gcagttaaaa atttaggtct ttctgcactt gatgaacagc       1560
cccaatgttc atcttctaac agtcatctac cctgcaatga aatatcctta gcaatgactg       1620
atgacgacaa tgctgcggcc attcatgaaa ttgaatctct attgtctgaa ccgataatag       1680
ctcctcaact cccagcattg ccacacaaga catgggccag ttatgcttca gacacttcat       1740
ccatgaagaa ccgtgagatt gagaacataa ttgctgagct tgaaatctca cggaaggaaa       1800
ataatgtgca gcaaactact catgattacc atgcagtttc tgacacagct cagagctccg       1860
gagatctccc atggaaagca tggattccac ttctgaatgc acacggcttc aagggagacc       1920
aacttcaata cagtccggat ggcaaagtga ttcagccaat ccaggacatc aacaacaaaa       1980
caccaagatc tgagtaccca tccagcattc ctgcagatct tgtggataca ctgcgaaaca       2040
ttaaaagagc agtgtatgcc attcctatta gccatcgaag ggcaagtgct tacagctctg       2100
atatcaaaaa caataggacc ggcaaattac tctgttccca atcaaaagaa tggaaggaaa       2160
gttttgcttt caaaatgcaa catgaagaca tcgttaaatc tggagtagtc attcatggct       2220
gtggcggctc tggaaaatca caagcattac aaaactttct cagaactcct ggcgactcta       2280
atgactgctg cacagtggtt gtgccaactg ttgaactcag aaatgattgg gtgaacaaat       2340
tgtgtaagct acccatggaa cacattaaaa catttgaaaa agcaatgatt caaccaggat       2400
tcccagttgt tatctttgat gactacacta aattgccacc tggttacatt gaagcctatt       2460
tgttccacca tgccaacact gaacttttca ttcttactgg ggactcgcgg caaagtgtat       2520
atcatgagtc caacaatgaa gcatacattg cctcattaga tgaagccgtc gcttattatg       2580
ctaactactg tggatttttac ctaaatgcta cacacagaaa tgttcgcagt ttggccaata       2640
agctaggtgt ttacagtgag aaagaaggtc acctcaaaat tacctttgcc tcaaatgctc       2700
tacaaaagtg caaagtgcca attttggtgc cctctcaaat gaagaagagt gctatgcaag       2760
```

```
acatagggca caaagccatg acctacgctg ggtgtcaagg gcttactgca ccgagagtcc    2820
aaattttgct tgacaaccac acacaacact gctcagacag ggtgctgtac acttgtctct    2880
ccagagctgt ggattccatc cactttatca atacaggccc aaacaattct gaattttggg    2940
acaagcttga ggcaacacca tacctcaaag catttattga tacttacaga gatgagaaaa    3000
cagaaatgct caattctaag cctgctgatg acagtcccgc tgagcctgaa gctccattga    3060
ctcactttcc agtgtcaaac ggcaataact tggaaaagtt agcttcagcg cttcctgaaa    3120
aatttgcaag agagttatat gataaacacc atggatattc taatacaatc caaactgaaa    3180
atccagtggt gcaacttttc cagcatcaac aagccaaaga tgaaacactt ttctgggcaa    3240
caatagaagc tagactttct attacaactc cggaagccaa cttacgagaa tttgtgctaa    3300
agaaagatgt tggagatatc ttgttttca attaccacaa tgtcatgtgc ttacctgccg    3360
acccagtgga tttcgagcca agaacatggg aaatatgtgc tgctgaagtt aaaaatacat    3420
acttagccaa accaatggct aacttgatca atgctgctag cagacaatct cctgatttcg    3480
acgctaacaa aatttccctg ttcctaaaat ctcaatgggt caagaaagtg gaaaaattag    3540
gtgctgtcaa gtcaaagcct ggccagacca ttgcagcttt catgcaacaa acagtgatgt    3600
tgtatgggac catggccaga tacctcagaa agatgagaca agatttcaa ccaaaacata    3660 ttttcatcaa ttgtgaaaca caactgata atctgaacca atttgttaaa caaggttgga    3720
attttaacag aacagctcag acaaatgatt tcacagcttt tgaccaatca agatggtg     3780 caatgcttca atttgaagtc atgaaggcaa aattcttcaa tatccctgcc gacatcattg    3840
aaggatacat caacatcaaa ttgaacgcca aaattttcct tggcacattg tccattatga    3900
ggttgtctgg tgaaggtcca acttttgatg ccaacacaga atgttcaata gcatatactg    3960
ctacaagata ccatcttgat tctacagtca agcaggttta tgctggagat gatatggcat    4020
tagatggagt tgtccaagaa aaaccctctt ttaaaaaact acagaacaag cttaaactca    4080
cctcaaagac actattttcca aaacaggtta aaggtgatta tgctgaattc tgtggttgga    4140
ctttcactcc tggtggtatc attaaaaacc ctttgaaaat gcatgcttcc attatgttgc    4200
aagaggcaat cggcaattta cacactgctg ccagatcata tgccattgac atgaagcatt    4260
cataccaaat gggtgatgag ctgcacaatt acttaacacc agatgaagct gaacaacact    4320
tccttgctgt tcggaagttg cacaagttac accaaggaga agcaatgaga cttggtgaaa    4380
agagccctcc aaaagcaaca cattgagggg ttaagttttc cccagttcga aatggaaaga    4440
tcaactctga ttaatttact tcaattgcac cacttcgagc caaaactcag tgttgaagga    4500
atcatagttg tgcacggaat tgcaggcact gggaaaacca ctttacttag gactttattt    4560
tctgcttacc ctagcttagt tataggttca cctaggcctt gctatttaga taaacaaaac    4620 aaaattcac aagtttgctt atcttgcttt cccaataccc attgtgatat tgtcgatgag    4680
tatcatttgc tagaaagttt tccagaacca aaattggcta tctttggtga ccctgtcaa    4740 tgcacataca ttgagagact tagagtccca cattacactt ccttcagaac tcatagattt    4800
ggaaagtcaa ctgctgagat tttgaacaaa ctgtttgacc ttaatatagt ctcagttaag    4860
aaagaagacg acatcgttga attctttaac cctttcgaag ttgaccccac tgagcatatc    4920
tctgcctctg aagaagaagt cttggacttt gtttctgacc aagtggtgac cactagctca    4980
gaggaactag caggacttga gtttgcagaa acaactttct actgcacaac attggccgca    5040
gctgttgctg aaaatcctgc taagactttc atctctctga ctagacacac ccacaaactc    5100
accattgggg aactaaatgc caggtctaac tcctagagct gacctcactg acacatacaa    5160
```

```
aatcattgcc attgctttct tgttgtcagc ttgcatttac ttccaaaata gccactacca    5220
acctgttgct ggagacaact tgcaccgttt gccttttggt ggccaatatc aagacggcac    5280
caaaaagata tcttattttc cacaacagca gtcatacttt cattctggaa acaaattaaa    5340
tgtcctcata cttatcttca ttctcacatt gggtattgtc ctcaccaata aatttagttt    5400
tagctttagt cgtactactc accagcattc ttgctataac acacattcag caaccaacaa    5460
tacacaacca ttgtcaggtc atcattgacg gtgctgcaat agtcataaca aattgtgaga    5520
acacaccaga agtgcttaaa gcaatcaact tctccccttg gaacgggtta agttttccta    5580
aatttgaaaa ttaatattga gtgttcacaa aaatcaactt caataaacaa tcatgcctga    5640
cacaacacct gttgctgcca cttcaagtgc accacccaca gccaaagatg ctggtgccaa    5700
agctccttct gacttctcaa atcccaatac agctcctagt ctcagtgatt tgaagaaagt    5760
caagtatgtc tccaccgtga cctccgtggc cacaccagct gaaattgaag ccctaggcaa    5820
aatcttcacc gctatgggcc ttgccgccaa tgagactggt ccggccatgt gggatctagc    5880
tcgtgcatat gctgatgtgc agagttctaa atcggcacag ctgattggag ctacccctcc    5940
caaccctgca ctatcacgcc gagcccttgc tgctcagttt gatcgaatca atataacccc    6000
caggcaattt tgcatgtact ttgccaaagt tgtttggaac atacttctcg acagcaacat    6060
tccaccagca aattgggcca aacttggtta ccaagaagat acaaaatttg ctgcatttga    6120
cttcttcgat ggagtcacca accctgccag cctgcagcct gctgatggtc ttatcaggca    6180
gccaaatgag aaagaactag ctgctcactc cgtagctaag tacggcgcct ggctaggca    6240 aaagatctcc acaggtaatt atattaccac acttggagaa gtcacacgtg gacacatggg    6300
aggagctaac accatgtacg cgatagacgc acccccctgaa cttttaaacac tcgaaactta    6360 atcgagtgg ggttttctac agtttatctt cctaattatt tctttgaaat               6410
```

<210> SEQ ID NO 4
<211> LENGTH: 6450
<212> TYPE: DNA
<213> ORGANISM: Pepino mosaic virus

<400> SEQUENCE: 4

```
gaaaacaaaa taaataaata aatatacaaa gttaaactaa cacaacataa ccacgtggaa     60
aaacagcgaa agcactttac cacattatgt ctcgtgttag aaatactttg gaaaagatca    120
gagacccaca agtacagtcc agcatttgtg aagctgccta tcaacatgtt cgacctgtac    180
ttaaagaatc tctaatcaat tgtccttacg cgcttaatga ttatgaagca gacacccttg    240
agaatcttgg tgtcacaatt aaccccccatg caatccaaac acacacacat gccgcagcca    300
aagtagtcga aaatcgtatg cttgaaattg ttggacatca cttgcctaaa gatgaaaaag    360
taactttcat cttcctcaaa cgtagcaagc tgcgttacat gagaagagct gctgtgcata    420
aagatgtctt tgtcaatcat aacattgaac caaaagactt cttcaggtat gatgaagagt    480
ctacatcaac cagcttttcc gttgatacga gaatcgcata catttcagat tctctacact    540
ttatggaacc tgctgatgtg actcacttgt ttgaccgttg ccaaaacctt aaaacattga    600
tggcaactgt tgtactacct gtggaagcta tacacagaca gacatctcta ttccctgcga    660
tttactccat taactacaat gaagaaggct ttgagtatat cccaggatca cacggtggtg    720
gggcatattt ccacaaatat gaaacccctag aatggctcaa atactctaga ttcattggac    780
atgatccatt gactggttta aaatacacca ttacgattca aatggtggag agtcttggtg    840
ccaaccacct tttcctcttc caaagaggaa actttgagac gccgctatac aggacgtttc    900
```

```
aaaagaatag ttttgtgaca ttcccaaata tattccatcc ccgacacgtc aatgccacaa    960
aacctatgcc tagatcaagg gccatacagc tgtacttata tgtgaaatca gtaaataaag   1020
ttacgcaaag agatatattt gccaaggtta gacaactgat ttccactgct gagctagaat   1080
tgtatgaccc tgatgaactc acgcacgttg taaattattt cacatatgtg tcacaactgt   1140
catctatcaa tgattatgac aacatgctca atccagtttt cttcaaaaaa ctggttgcac   1200
ccatgcaaca cgactggagg tgcatgattg aattcttccg gggaaagagt gacttcaatc   1260
aactgctcac agctcttcaa tggaaagatt tttcctatac tattaagact gaagagcttg   1320
taattactac acacactgct ataggacaag caataagcaa tgcagctacc acatataaag   1380
aaagaaggca gctgactcaa ttggtcaaaa aaggtacaat atccttagca gattttgaac   1440
agagagaacc tgaaataact tacactgagt ttgagcctga aactaggccc caagtggact   1500
gcgttactaa ttataataat gcagtaaaaa atttaggtct ttctgcactt gatgaacagc   1560
ctcaatgttc atcttctagc agtcatatac cctgcaatga aatatcctta gcaatgactg   1620
atgacgacaa tgctgcggcc attcatgaaa ttgaatctct attgtctgaa ccgataaatag   1680 ctcctcaact cccagcattg ccacacaaga catgggccag ttatgcttca gacacttcat   1740
ccatgaagaa ccgtgagatt gagaacataa ttgctgagct tgaaatctca cggaaggaaa   1800
ataatgtgca gcaaactact catgattacc atgcagtttt tgacacagct cagagctccg   1860
gagatctccc atggaaagca tggattccac ttctgaatgc acacggcttc aagggagacc   1920
aacttcaata cagtccggat ggcaaagtga ttcagccaat ccaggacatc aataacaaaa   1980
caccaagatc tgagtaccca tccagcattc ctgcagatct tgtgaataca ctgcgaaaca   2040
ttaaaagagc agtgtatgcc attcctatta gccatcgaag ggcaagtgct tacagctctg   2100
atatcaaaaa caataggacc ggcaaattac tctgttccca atcaaaagaa tggagggaaa   2160
gttttgcttt caaaatgcaa catgaagaca tcgttaaatc tggagtagtc attcatggct   2220
gtggcggctc tggaaaatca caagcattac aaaactttct cagaactctt ggcgactcta   2280
atgactgctg cacagtggtt gtgccaactg ttgaactcag aaatgattgg gtgaacaaat   2340
tgtgtaagct acccatggaa cacattaaaa catttgaaaa agcaatgatt caaccaggat   2400
tcccagttgt tatctttgat gactacacta aattgccacc tggttacatt gaagcctatt   2460
tgttccacca tgccaacact gaacttttca ttcttactgg agactcgcgg caaagtgtat   2520
atcatgagtc caacaatgaa gcatacattg cctcattaga tgaagccgtc gcttattatg   2580
ctaactactg tggattttac ctaaatgcta cacacagaaa tgttcgcagt ttggccaata   2640
agctaggtgt ttacagtgag aaagaaggtc acctcaaaat tacctttgcc tcaaatgctc   2700
tacaaaagtg caaagtgcca attttggtgc cctctcaaat gaagaagagt gctatgcaag   2760
acatagggca caaagccatg acctacgctg ggtgtcaagg gcttactgca ccgagagtcc   2820
aaattttgct tgacaaccac acacaacact gctcagacag ggtgctgtac acttgtctct   2880
ccagagctgt ggattccatc cactttatca atacaggccc aaacaattct gaattttggg   2940
acaagcttga ggcaacacca tacctcaaag catttattga tacttacaga gatgagaaaa   3000
cagaaatgct caattctaag cctgctgatg acagtcccgc tgagcctgaa gctccattga   3060
ctcactttcc agtgtcaaac ggcaataact tggaaaagtt agcttcagcg cttcctgaaa   3120
aatttgcaag agagttatat gataaacacc atggatattc taatacaatc caaactgaaa   3180
atccagtggt gcaactttcc cagcatcaac aagccaaaga tgaaacactt ttctgggcaa   3240
caatagaagc tagactttct attacaactc cggaagccaa cttacgagaa tttgtgctaa   3300
```

```
agaaagatgt tggagatatc ttgttttttca attaccacaa tgtcatgtgc ttacctgccg    3360
acccagtgga tttcgagcca agaacatggg aaatatgtgc tgctgaagtt aaaaatacat    3420
acttagccaa accaatggct aacttgatca atgctgctag cagacaatct cctgatttcg    3480
acgctaacaa aatttccctg ttcctaaaat ctcaatgggt caagaaagtg aaaaattag     3540
gtgctgtcaa gtcaaagcct ggccagacca ttgcagcttt catgcaacaa acagtgatgt    3600
tgtatgggac catggccaga tacctcagaa agatgagaca aagatttcaa ccaaaacata    3660
ttttcatcaa ttgtgaaaca caactgata atctgaacca atttgttaaa caaggttgga     3720
actttaacag aacagctcag acaaatgatt tcacagcttt tgaccaatca agatggtg      3780
caatgcttca atttgaagtc atgaaggcaa aattcttcaa tatccctgcc gacatcattg    3840
aaggatacat caacatcaaa ttgaacgcca aaattttct tggcacattg tccattatga     3900
ggttgtctgg tgaaggtcca acttttgatg ccaacacaga atgttcaata gcatatactg    3960
ctacaagata ccatcttgat tctacagtca agcaggttta tgctggagat gatatggcat    4020
tagatggagt tgtccaagaa aaaccctctt ttaaaaaact acagaacaag cttaaactca    4080
cctcaaagac actatttcca aaacaggtta aaggtgatta tgctgaattc tgtggttgga    4140
ctttcactcc tggtggtatc attaaaaaacc ctttgaaaat gcatgcttcc attatgttgc   4200
aagaggcaat cggcaattta cacactgctg ccagatcata tgccattgac atgaaacatt    4260
cataccaaat gggtgatgag ctgcacaatt acttaacacc agatgaagct gaacaacact    4320
tccttgctgt tcggaagttg cacaagttac accaaggaga agcaatgaga cttggtgaaa    4380
agagccctcc aaaagcaaca cattgagggg ttaagtttc cccagttcga atggaaaga     4440
tcaactctga ttaatttact tcaattgcac cacttcgagc caaaactcag tgttgaagga    4500
accatagttg tgcacggaat tgcaggcact gggaaaacca ctttacttag gactttattt    4560
tctgcttacc ctagcttagt tataggttca cctaggcctt gctatttaga taaacaaaac    4620
aaaatttcac aagtttgctt atcttgcttt cccaataccc attgtgatat tgtcgatgag    4680
tatcatttgc tagaaagttt tctagaacca aaattggcta tctttggtga ccctgtcaa    4740
tgcacataca ttgagagact tagagtccca cattacactt ccttcagaac tcatagattt    4800
ggaaagtcaa ctgctgagat tttgaacaaa ctgtttgacc ttaatatagt ctcagttaag    4860
aaagaagacg acatcgttga attctttaac ccttttgaag ttgaccccac tgagcatatc    4920
tctgcctctg aagaagaagt cttggacttt gtttctgacc aagtggtgac cactagctca    4980
gaggaactag caggacttga gtttgcagaa acaactttct actgcacaac attggccgca    5040
gctgttgctg aaaatcctgc taagactttc atctctctga ctagacacac ccacaaactc    5100
accattgggg aactaaatgc caggtctaac tcctagagct gacctcactg acacatacaa    5160
aatcattgcc attgctttct tgttgtcagc ttgcatttac ttccaaaata gccactacca    5220
acctgttgct ggagacaact tgcaccgttt gccttttggt ggccaatatc aagacggcac    5280
caaaagagata tcctatttc cacaacagca gtcatacttt cattctggaa acaaattaaa    5340
tgtcctcata cttatcttca ttctcacgtt gggtattgtc ctcaccaata aatttagttt    5400
tagctttagt cgtactactc accagcattc ttgctataac acacattcag caaccaacaa    5460
tacacaacca ttgtcaggcc atcattgaca gtgctgcaat agtcataaca aattgtgaga    5520
acacaccaga agtgcttaaa gcaataaact tctcccctg gaacgggtta agttttccta    5580
aatttgaaaa ttagtattga gtgttcacaa aaatcaactt caataaacaa tcatgcctga    5640
cacaacacct gttgctgcca cttcaagtgc accacccaca gccaaagatg ctggtgccaa    5700
```

```
agctccttct gacttctcaa atcccaatac agctcctagt ctcagtgatt tgaagaaagt   5760
caagtatgtc tccaccgtga cctccgtggc cacaccagct gaaattgaag ccctaggcaa   5820
aatcttcacc gctatgggcc ttgccgccaa tgagactggt ccggccatgt gggatctagc   5880
tcgtgcatat gctgatgtgc agagttctaa atcggcacag ctgattggag ctaccccttc   5940
caaccctgca ctatcacgcc gagcccttgc tgctcagttt gatcgaatca atataacccc   6000
caggcaattt tgcatgtact ttgccaaagt tgtttggaac atacttctcg acagcaacat   6060
tccaccagca aattgggcca aacttggtta ccaagaagat acaaaatttg ctgcatttga   6120
cttcttcgat ggagtcacca accctgccag cctgcagcct gctgatggtc ttatcaggca   6180
gccaaatgaa aaagaactag ctgctcactc cgtagctaag tacggcgcct tggctaggca   6240
aaagatctcc acaggtaatt atattaccac acttggagaa gtcacacgtg gacacatggg   6300
aggagctaac accatgtacg cgatagacgc acccccctgaa ctttaaacac tcgaaactta   6360
atcagagtgg ggttttctac agtttatttt cctaattatt tctttgaaat aaaaaaaaaa   6420
aaaaaaaaaa aaaaaaaaaa aaaaaaaaaa                                    6450
```

<210> SEQ ID NO 5
<211> LENGTH: 6449
<212> TYPE: DNA
<213> ORGANISM: Pepino mosaic virus

<400> SEQUENCE: 5

```
gaaaacaaaa taaataaaca attatacaaa gttaaactaa cacaacataa ccacgtggaa     60
aaacagcgaa agcactttac cgcattatgt ctcgtgtcag aaatactttg gaaaagatca    120
gagacccaca agtacagtcc agcatttgtg aagctgccta tcaacatgtt cgacctgtac    180
ttaaagaatc tctaatcaat tgtccttacg cgcttaatga ttatgaagca gacacccttg    240
agaatcttgg tgtcacaatt aacccccatg caatccaaac acacacacat gccgcagcca    300
aagtagtcga aaatcgtatg cttgaaattg ttggacatca cttgcctaaa gatgaaaaag    360
taactttcat cttcctcaaa cgtagcaagc tgcgttacat gagaagagct gctgtgcata    420
aagatgtctt tgtcaatcat aacattgaac caaaagactt cttcaggtat gatgaagagt    480
ccacatcaac cagcttttcc gttgatacga gaatcgcata catttcagat tctctacact    540
ttatggaacc tgctgatgtg actcacttgt ttgaccgttg ccaaaacctt aaaacattga    600
tggcaactgt tgtactacct gtggaagcta tacacagaca gacatctcta ttccctgcga    660
tttactccat taactacaat gaagaaggct ttgagtatat cccaggatca cacggtggtg    720
gggcatattt ccacaaatat gaaactctag aatggctcaa atactctaga ttcattggac    780
atgatccatt gactggttta aaatacacca ttacgattca aatggtggag agtcttggtg    840
ccaaccacct tttcctcttc caaagaggaa actttgagac gccgctatac aggacgtttc    900
aaaagaatag ttttgtgaca ttcccaaata tattccatcc ccgacacgtc aatgccacaa    960
aacctatgcc tagatcaagg gccatacagc tgtacttata tgtgaaatca gtaaataaag   1020
ttacgcaaag agatatattt gccaaggtta gacaactgat ttccactgct gagctagaat   1080
tgtatgaccc tgatgaactc acgcatgttg taaattattt cacatatgtg tcacaactgt   1140
catctatcaa tgattatgac aacatgctca aatccagttt cttcaaaaaa ctggttgcac   1200
ccatgcaaca cgactggagg tgcatgattg aattcttccg gggaaagagt gacttcaatc   1260
aactgctcac agctcttcaa tggaaagatt tttcctatac tattaagact gaagagcttg   1320
taattactac acacactgct ataggacaag caataagcaa tgcagctacc acatataaag   1380
```

```
aaagaaagca gctgactcaa ttggtcaaaa aaggtacaat atccttagca gattttgaac    1440
agagagaacc tgaaataact tacactgagt ttgagcctga aactaggccc caagtggact    1500
gcgttactaa ttataataat gcagttaaaa atttaggtct ttctgcactt gatgaacagc    1560
ctcaatgttc atcttctagc agtcatctac cctgcaatga atatccttta gcaatgactg    1620
atgacgacaa tgctgcggcc attcatgaaa ttgaatctct attgtctgaa ccgataatag    1680
ctcctcaact tccagcattg ccacacaaga catgggccag ttatgcttca gacacttcat    1740
ccatgaagaa ccgtgagatt gagaacataa ttgctgagct tgaaatctca cggaaggaaa    1800
ataatgtgca gcaaactact catgattacc atgcagtttc tgacacagct cagagctccg    1860
gagatctccc atggaaagca tggattccac ttctgaatgc acacggcttc aagggagacc    1920
aacttcaata cagtccggat ggcaaagtga ttcagccaat ccaggacatc aacaacaaaa    1980
caccaagatc tgagtaccca tccagcattc ctgcagatct tgtgaataca ctgcgaaaca    2040
ttaaaagagc agtgtatgcc attcctatta gccatcgaag ggcaagtgct tacagctctg    2100
atatcaaaaa caataggacc ggcaaattac tctgttccca atcaaaagaa tggaaggaaa    2160
gttttgcttt caaaatgcaa catgaagaca tcgttaaatc tggagtagtc attcacggct    2220
gtggcggctc tggaaaatca caagcattac aaaactttct cagaactctt ggcgactcta    2280
atgactgctg cacagtggtt gtgccaactg ttgaactcag aaatgattgg gtgaacaaat    2340
tgtgtaagct acccatggaa cacattaaaa catttgaaaa agctatgatt caaccaggat    2400
tcccagttgt tatatttgat gactacacta aattgccacc tggttacatt gaagcctatt    2460
tgttccacca tgccaacact gaacttttca ttccttactgg agactcgcgg caaagtgtat    2520
atcatgagtc caacaatgaa gcatacattg cctcattaga tgaagccgtc gcttattatg    2580
ctaactactg tggattttac ctaaatgcta cacacagaaa tgttcgcagt ttggccaata    2640
agctaggtgt ttacagtgag aaagaaggtc acctcaaaat tacctttgcc tcaaatgctc    2700
tacaaaagtg caaagtgcca attttggtgc cctctcaaat gaagaagagt gctatgcaag    2760
acatagggca caaagccatg acctacgctg ggtgtcaagg gcttactgca ccgagagtcc    2820
aaattttgct tgacaaccac acacaacact gctcagacag ggtgctgtac acttgtctct    2880
ccagagctgt ggattccatc cactttatca atacaggccc aaacaattct gaattttggg    2940
acaagcttga ggcaacacca tacctcaaag catttattga tacttacaga gatgagaaaa    3000
cagaaatgct caattctaag cctgctgatg acagtcccgc tgagcctgaa gctccattga    3060
ctcactttcc agtgtcaaac ggcaataact tggaaaagtt agcttcagcg cttcctgaaa    3120
aatttgcaag agagttatat gataaacacc atggatattc taatacaatc caaactgaaa    3180
atccagtggt gcaacttttc cagcatcaac aagccaaaga tgaaacactt ttctgggcaa    3240
caatagaagc tagactttct attacaactc cggaagccaa cttacgagaa tttgttctaa    3300
agaaagatgt tggagatatc ttgttttttca attaccacaa tgtcatgtgc ttacctgccg    3360
acccagtgga tttcgagcca agaacatggg aaatatgtgc tgctgaagtt aaaaatacat    3420
acttagccaa accaatggct aacttgatca atgctgctag cagacaatct cctgatttcg    3480
acgctaacaa aatttccctg ttcctaaaat ctcaatgggt caagaaagtg aaaaattag    3540 gtgctgtcaa gtcaaagcct ggccaaacca ttgcagcttt catgcaacaa acagtgatgt    3600
tgtatgggac catggccaga tacctcagaa agatgagaca agatttcaa ccaaaacata    3660 tttttcatcaa ttgtgaaaca acaactgata atctgaacca atttgttaaa caaggttgga    3720
actttaacag aacagctcag acaaatgatt tcacagcttt tgaccaatca caagatggtg    3780
```

```
caatgcttca atttgaagtc atgaaggcaa aattcttcaa tatccctgcc gacatcattg    3840
aaggatacat caacatcaaa ttgaacgcca aaattttttct tggcacattg tccattatga   3900
ggttgtctgg tgaaggtcca acttttgatg ccaacacaga atgttcaata gcatataccg    3960
ctacaagata ccatcttgat tctacagtca agcaggttta tgctggagat gatatggcat    4020
tagatggagt tgtccaagaa aaaccctctt ttaaaaaact acagaacaag cttaaactca    4080
cctcaaagac actatttcca aaacaggtta aggtgatta tgctgaattc tgtggttgga     4140 cttttcactcc tggtggtatc attaaaaacc ctttgaaaat gcatgcttcc attatgttgc   4200
aagaggcaat cggcaattta cacactgctg ccagatcata tgccattgac atgaagcatt    4260
cataccaaat gggtgatgag ctgcacaatt acttaacacc agatgaagct gaacaacact    4320
tccttgctgt tcggaagttg cacaagttac accaaggaga agcaatgaga cttggtgaaa    4380
agagccctcc aaaagcaaca cattgagggg ttaagttttc cccagttcga aatggaaaga    4440
tcaactctga ttaatttact tcaattgcac cacttcgagc caaaactcag tgttgaagga    4500
atcatagttg tgcacggaat tgcaggcact gggaaaacca ctttacttag gactttattt    4560
tctgcttacc ctagcttagt tataggttca cctaggcctt gctatttaga taaacaaaac    4620
aaaatttcac aagtttgctt atcttgcttt cccaataccc attgtgatat tgtcgatgag    4680
tatcatttgc tagaaagttt tctagaacca aaattggcta tctttggtga ccctgtcaa    4740 tgcacataca ttgagagact tagagtccca cattacactt ccttcagaac tcatagattt    4800
ggaaagtcaa ctgctgagat tttgaacaaa ctgtttgacc tcaatatagt ctcagtcaag    4860
aaagaagacg acatcgttga attctttaac cctttttgaag ttgaccccac tgagcatatc   4920
tctgcctctg aagaagaagt cttgggcttt gtttctgacc aagtggtgac cactagctca    4980
gaggaactag caggacttga gtttgcagaa acaactttct actgcacaac attggccgca    5040
gctgttgcta aaaatcctgc taagactttc atctctctga ctagacacac ccacaaactc    5100
accattgggg aactaaatgc caggtctaac tcctagagct gacctcactg acacatacaa    5160
aatcattgcc attgctttct tgttgtcagc ttgcatttac ttccaaaata gccactacca    5220
acctgttgct ggagacaact tgcaccgttt gccttttggt ggccaatatc aagacggcac    5280
caaaaagata tcttattttc cacaacagca gtcatacttt cactctggaa acaaattaaa    5340
tgtcctcata cttatcttca ttctcacatt gggtattgtc ctcaccaata aatttagttt    5400
tagctttagt cgtactactc accagcattc ttgctataac acacattcag caaccaacaa    5460
tacacaacca ttgtcaggtc atcattgacg gtgctgcaat agtcataaca aattgtgaga    5520
acacaccaga agtgcttaaa gcaatcaact tctccccttg gaacgggtta agttttccta    5580
aatttgaaaa ttaatattga gtgttcacaa aatcaacttc aataaacaat catgcctgac    5640
acaacacctg ttgctgccac ttcaagtgca ccacccacag ccaagatgc tggtgccaaa     5700 gctccttctg acttctcaaa tcccaataca gctcctagtc tcagtgattt gaagaaagtc    5760
aagtatgtct ccaccgtgac ctccgtggcc acaccagctg aaattgaagc cctaggcaaa    5820
atcttcaccg ctatgggcct tgccgccaat gagactggtc cggccatgtg ggatctagct    5880
cgtgcatatg ctgatgtgca gagttctaaa tcggcacagc tgattggagc tacccccttcc   5940 aaccctgcac tatcacgccg agcccttgct gctcagtttg atcgaatcaa tataaccccc    6000
aggcaatttt gcatgtactt tgccaaagtt gtttggaaca tacttctcga cagcaacatt    6060
ccaccagcaa attgggccaa acttggctac caagaagata caaaatttgc tgcatttgac    6120
ttcttcgatg gagtcaccaa ccctgccagc ctgcagcctg ctgatggtct tatcaggcag    6180
```

-continued

```
ccaaatgaga aagaactagc tgctcactcc gtagctaagt acggcgcctt ggctaggcaa      6240
aagatctcca caggtaatta tattaccaca cttggagaag tcacacgtgg acacatggga      6300
ggagctaaca ccatgtacgc gatagacgcg ccccctgaac tttaaacact cgaaacttaa      6360
tcagagtggg gttttctaca gtttatttc ctaattattt ctttgaaaca aaaaaaaaaa      6420
aaaaaaaaaa aaaaaaaaaa aaaaaaaa                                        6449
```

<210> SEQ ID NO 6
<211> LENGTH: 6413
<212> TYPE: DNA
<213> ORGANISM: Pepino mosaic virus

<400> SEQUENCE: 6

```
gaaaacaaaa cataacacat aatatcaaaa gtgaccaaac acaacataac cacgtggaaa        60
aacagcgaaa gcactttacc acattatgtc tcgtgttaga aacactttag aaaagatcag       120
ggacccacaa gtacagtcaa gcatatgcga agcagcatac caacatgttc gaccagtttt       180
gaaggaatct ctaatcaatt gtccctatgc gctcaatgat tatgaagccg acaccccttga      240 gaatttaggt gtcacaatta accctcatgc aattcaaacc catacacacg cagcagctaa       300
agtggttgaa aaccgaatgc tagagattgt tggtcaccat ctaccaaaag atgagaaggt       360
taccttcatt ttcctaaaac gtagtaaatt gcgttacatg agaagagctg ctgttcataa       420
agatgttttt gtcaaccata acgtagagcc caaagatttt tttaggtatg acgaggagtc       480
cacatcaaca agcttctccg tgaatactag aatcgcatac atttcagact ccttacattt       540
catggagcca gctgatgtta cacacccttt cgaccgttgc caaaatctta aacattaat        600 ggcaaccgtt gtcctacctg ttgaagcaat tcatagacaa acatctttat ttcctgcgat       660
atactccatt aactcaatg aagaaggctt tgagtatatc cctggttccc atggtggtgg       720
ggcatacttt cacaagtatg agaccttaga ctggcttaaa tattccagat tcataggaca       780
tgatccattg actggcctca aatataccat tacaattcaa atggttgaaa gtctaggcgc       840
caaccacctt ttcctttttcc aaagaggaaa ttttgaaacg cccttatata ggacctttca       900
aaaaaatagt tttgtgacat tccctaatat atttcatccc cgacatgtca atgccacaaa       960
acctatgcca cgctccaggg caattcaatt gtacttatat gttaagtctg tcaacaaagt      1020
cacacaaaga gacatctttg caaaagttag acagcttata tccacagctg agctggaact      1080
gtatgaccct gatgagctta ctcatgttgt caattacttt tcatatgttt cacaattgtc      1140
atctataaat gattatgaca acatgctaaa atccagtttc ttcaagaaat tggttgcacc      1200
catgcaacaa gactggaggt gcatgattga aytcttccgg ggaaagagtg atttcaatca      1260
acttctcacc gctcttcaat ggaaagattt ttcctatact atcaaaactg aagagctaat      1320
aattactaca cacactgcca ttgggcaagc tataagtgga gcagctaata cttataagga      1380
aagaaggcaa ttgacacaac tggtcaagca aggagtgatt tcactcgctg attttcaatc      1440
tgaagagccc aaaatagaat acaccgaatt cgagcgagaa acaaaaccac cagttgattg      1500
tgtgactaat tacaacaatg ctgttaagaa ccttggcctg tctgaaccag tggatctgcc      1560
agaatgctca tacgctagaa actctgttcc taacaatgag atatctatgg ctatgactga      1620
tgctgacaac ttcgctgtta taaatgaaat tgaatctctc ttgtctgaag aaatcgcagc      1680
accaacactt ccagcattga aaataaaac atgggctagt tatgcatctg acacttcatc      1740
aaagaagaat gaagaaattg aaaatataat tgctgagcta gaagcttcac gtaaggtctc      1800
caatgtccag caaacacagc acaactacca tatctcacaa tgccccactt ccttaactgc      1860
```

```
tgatcttcca tggaaagcct ggctcccact tctcaatgcc catggtttca aaggagatca   1920
gatccaacat agtcccgacg gccaaataat ccaaccaatt caggacatca acaataaaac   1980
accaagatct gaatacccat ctagcatccc tgcagatctt gtttcaacct tgcgcaatat   2040
taaaagagca gtttatgcta ttcctatcag ccacagaagg gccagcgctt atagctcaga   2100
tgttaaaaat aacagaactg gaaaactgct ctgtgctcaa tccaaagaat ggaaagagag   2160
ttttgctttc aaaatgcaac atgaagacat agtcaaatct ggtgttgtca tacatggttg   2220
tggcggctcc ggaaaatcac aagcattgca aaacttcctt agaactttgg gtgacaataa   2280
tgactgctgt acagttgttg tccccacagt agagctcagg aatgactggg ttaacaaatt   2340
gtgcaagttg cctatggaac acatcaaaac atttgaaaaa gcaatgattc aaccaggctt   2400
tcctgttgtc attttttgacg actatactaa gctgccaccc ggttacattg aagcttatct   2460
gttccatcat gccaacactg aactcttcat cctcactggt gactctagac aaagtgtata   2520
tcatgagtcc aacaatgaag cttacattgc ctctcttgat gaagctgttg cctactattc   2580
caactactgt ggtttctatt tgaacgctac gcacagaaat gtacgtagtt tagctaacaa   2640
gttgggagtg tacagtgaaa agaaggaca cctcaaaatt acttttgcat ccaatgctct   2700
acaaaaatgc aaagtaccca tcttggtgcc ctctcagatg aagaaaaatg caatgcaaga   2760
cattggccat aaaagcaatga cttatgcagg atgtcaagga cttactgctc aagagttca   2820
aattttgctt gacaaccaca cacagcattg ctcggacaga gttctttaca catgtctttc   2880
acgagctgtg gattctatcc attttatcaa tactggcccc aacaattccg aattttggga   2940
taagcttgaa gctacaccat acctcaaagc ctttattgat acataccggg atgaaaagac   3000
tgagatgttg aattcaaaac ctgcagatga cagccctgtg gaacctagag ctcctgctac   3060
tcatttcccc gtctctaacg gcaacaactt agagaaatta gcttcaacac tacctgaaaa   3120
gtttgctcgg gagatctatg ataaacatca tggttattcc aacaccatac aaacagagaa   3180
ccccatagta caacttttcc aacatcagca ggcaaaagat gaaactctct tttgggcaac   3240
aattgaggca agactttcta taaccacacc agatgctaac ctcagagaat ttactttgaa   3300
gaaagacgtt ggagatattc tgttctttaa ctatcactca gcaatgtgtc tgccagctga   3360
ccctgtcgac ttcgagccaa gaacttggga aatatgtgca gctgaagtca agaatacata   3420
cctagcaaaa ccaatggcta atttgataaa tgccgctagt cgacaatctc ctgacttcga   3480
gcctaacaag atctcactgt ttttgaagtc acaatgggtt aagaaagtag agaaattggg   3540
agcaatcaaa tcaaagcctg gcaaacaat tgcggctttt atgcagcaaa ccgtcatgct   3600
gtacggaact atggctagat acttaagaaa aatgagacaa agattctcaac caaaacacat   3660
tttcatcaat tgtgaaacta caactgatga tctgaataat tttgttctca atggttggaa   3720
ctttaatcga actgctcaga ctaatgattt cactgcattt gatcaatccc aagatggagc   3780
tatgttacaa tttgaagtca tgaaggctaa attcttcaac attcctgcag acgtgattga   3840
agggtatatc aacattaagc ttaacgctaa aattttccta ggtacccttt caattatgag   3900
gttatcaggt gaaggtccca catttgatgc aaacactgaa tgctctattg cttacacagc   3960
aacaagatac catctcaagt tcagcagtgaa acaagtttac gctggtgatg acatggctct   4020
tgacggagtg gtcatggaaa accctccctt aagaaactta cagagcaagc ttaaattgac   4080
atcaaaaaca ttgttccaa aacaagttaa gggtgattat gccgaatttt gtgggtggac   4140
tttaccccca ggtgggatta ttaaaaatcc tttgaaaatg catgcatcca tcatgttaca   4200
agaagcaata ggtaacctcc acactgctgc taggtcgtat gcaatagaca tgaagcattc   4260
```

```
ataccaaatg ggagataaat tgcatgaata ccttactcct gatgaagctg agcaacattt    4320
cttggctgtt cgcaaattgc acaaactcca ccaaggtgaa gccatgagac ttggggagaa    4380
gagcccccca aaagcaacac attgacgggt aagtttccc ctgttcgaaa tggaaagatc     4440
cactctaata aatttacttc aactgcacca ctttgaacct aaactcagcg ttgaaggagt    4500
tattgttgta cacggaatcg ctggaacagg gaaaactacc ctacttagaa ctttatttc    4560 cgcttacccg aacttagtta taggatcacc taggccttgt tatttagata aagctaataa    4620
aatttcacaa gtttgtttat cttgctttcc aaacacccctt tgtgatattg tcgatgagta   4680
ccatcttcta gaaagttacc aagaacctac tttggctttg tttggagacc cttgtcagtg    4740
tactttcatt gaaagactta gaattccaca ctacacttcc ttcagaacac atagatttgg    4800
caagtctact gcagagcttt taaacaagtt gtttcaactt caaattgtat ctgtaaaaca    4860
agaagacgac atagttgaat tcttcgaccc atttcaagta gacccaactg aaaatatttc    4920
agcatctgag gaagaagttt tggaatttgt ctctgatcaa gtagtgacaa ccagctctga    4980
agaattagca ggattggagt tcactgaaac cactttctac tgcactacac tagctgcagc    5040
agtcactgaa aatcctgcca gaactttcat ctccttaacc agacacactc agagactcac    5100
cattggcgaa ctaaatgcca ggattgactc ctagagctga cctcactgac acctacaaga    5160
taattgctat tgcttttttg ttgtcagctt gcatttactt ccaaaacagc cattaccaac    5220
ctgttgctgg agataatctg catagattgc catttggtgg ccagtatcaa gacggcacca    5280
agaagatatc atattttcct cagcaacaat catactttca ctctggtaac aaattaaatg    5340
tcctcatact catcttcatt cttacattgg gtatcgtcct caccaataaa tttagtttta    5400
gcgttagccg tactactcac cagcattctt gctacaatac acattctgca gccaacacaa    5460
caccaccatt gtcaggtcat cattgacgga gctgccatag ttgttactaa ttgtgaaaac    5520
acgcctgaag ttctaaaagc aatcaacttc tccccttgga acgggttaag ttttcctagt    5580
gtttgaaaat taactttgag cacttcacaa ttaagctaac aattcactaa tcatggctga    5640 caataccca gttgctgcta cttctggttc ccctccaact gctcaagatg ctggtgccaa     5700
agcccctgct gacttttcaa atcctaatac agctcctagc ctcagtgatt tgaagaaagt    5760
caagtatgtg tccacagtca cttcagtggc aacaccaact gaaatagaag cccttggaaa    5820
gatcttcacc gccatgggac tggctgctaa tgaaactgga cccgctatgt gggatctagc    5880
gcgtgcttat gctgatgtcc aaagttcaaa atccgcacaa ctcataggtg ccaccccttc    5940
aaatccagca ctctcacgcc gcgcacttgc tgcccaattt gatcgtatta acatcacacc    6000
caggcagttc tgcatgtatt ttgctaaagt tgtctggaac attctgctag acagcaatat    6060
cccaccagca aactgggcca agcttggtta ccaagaagac acaaaatttg ctgctttcga    6120
tttcttcgat ggagtcacca atccagcaag tttgcaacca gctgacggcc tcatccgaca    6180
acccaatgaa aaggagcttg ctgctcactc agttgctaag tatggtgcac tagccaggca    6240
gaaaatttcc actggcaact acataaccac acttggagag gtcacacgtg gacacatggg    6300
tggagctaac accatgtacg caattgatgc acccccagaa ctttaaaaca ctcgaaactt    6360
aattagagtg gggttttcta tagtttattt tcccaataaa ttgcttttgt aat           6413
```

<210> SEQ ID NO 7
<211> LENGTH: 6448
<212> TYPE: DNA
<213> ORGANISM: Pepino mosaic virus -continued

<400> SEQUENCE: 7

```
gaaaacaaaa tataaacaaa tatacaaagt taaactaaca caacataacc acgtggaaaa      60
acagcgaaag cactttacca cattatgtct cgtgtcagga atactttgga aaagatcaga     120
gacccacaag tacagtccag catttgcgaa gccgcatatc aacatgttcg acccgtactt     180
aaagaatctc taatcaattg tccttatgcg cttaatgatt atgaagcaga caccettgag     240
aatcttggtg tcacaattaa tccccacgca atccaaacac acacacatgc cgcagctaaa     300
gtagttgaaa atcgtatgct tgaaatcgtt ggacatcact tgccaaaaga tgaaaaggta     360
acttttatct tcctcaaacg tagcaagctg cgttacatga aagagctgc tgtgcataaa      420
gatgtctttg tcaatcataa cattgaacca aaagacttct tcaggtatga tgaagagtct     480
acatcaacta gcttttccgt taatacgaga atcgcataca tttcagattc tctacacttt     540
atggaacctg ctgatgtgac tcacttgttt gaccgttgcc aaaaccttaa acattaatg      600
gcaactgttg tactacctgt tgaagctata cacagacaga catccctatt ccctgccatt     660
tactccatta actacaatga agaaggcttt gagtacatcc caggatcaca cggtggtggg     720
gcatatttcc acaaatatga aaccctagaa tggctcaaat actctagatt cattggacat     780
gatccattga ctggttttaaa atacaccatt acaattcaaa tggtagagag tcttggtgcc    840
aaccacctt tccttttcca aagaggaaac tttgagacgc cgttataccg gacgtttcaa      900
aagaatagtt ttgtgacatt cccaaatata tttcatcccc gacatgtcaa tgccacaaaa     960
cctatgccta gatcaagggc catacagctg tacctatatg tgaaatcagt aaataaagtt    1020
acgcaaagag acatatttgc taaacttaga caactgattt ccactgctga actagaattg    1080
tatgaccctg atgaactcac gcatgttgta aattatttca catatgtgtc acaactgtca    1140
tctatcaatt attatgacaa catgctcaaa tccagtttct ttaaaaaact ggtggcaccc    1200
atgcaacacg actggaggtg catgattgaa ttcttccggg aaagagtga cttcaatcaa     1260
ctgctaacag ctcttcaatg gaaagatttt tcatacacta ttaagactga tgagcttgta    1320
atcactacac acactgctat aggacaagca atatgcaatg cagctgctac atataaagaa    1380
agaaggcagc tgactcaatt ggtcaaaaat ggtacaatat ccttagcaga ttttgaacag    1440
aaagaacctg aaataaccta cactgaattt gagcctgaaa ctaggcccca ggtggactgc    1500
gttactaatt acaataatgc agtcagaaat ttaggtcttt ctgcactcga tgaacagcct    1560
caatgttcat cttctaacag tcatataccc tgcaatgaaa tatctctagc aatgactgat    1620
gatgataatg ctgcggccat tcatgaaatt gaatctctat tgtctgaacc gataatagct    1680
cctcaactcc cagcattgcc acacaagaca tgggctagtt atgcttccga cacatcatct    1740
atgaagaacc gtgaaattga aacataatt gctgagcttg aaatctcacg gaaggaaaac     1800
aatgtgcagc aaactactca tgattaccat gctgtttctg atactgctca aaactctgga    1860
ggtctcccat ggaaagcatg gattccactt ctgaatgcac acggctttaa gggagaccaa    1920
cttcaataca gtcctgatgg caaagtgatt cagccaattc aggacatcaa taacaaaaca    1980
ccaagatctg agtacccatc cagtattcct gcagatcttg taactacact gcgaaacatt    2040
aaaagagcag tgtatgccat tcctattagc catcgaaggg caagtgctta cagctctgat    2100
atcaagaaca ataggactgg caaattgctt tgctcccaat caaaagaatg gaaggaaagt    2160
tttgctttca aaatgcgaca tgaagacatc gttaaatctg gagtggtcat tcatggctgt    2220
ggtggctctg gaaaatcaca agcattacaa aactttctca gaactcttgg cgacaccaac    2280
gactgttgca cagtggtggt gccaactgtt gagctcagaa atgattgggt gaacaaattg    2340
```

```
tgcaaactac ccatggaaca cattaaaaca tttgaaaaag caatgattca accaggattc    2400
ccagtcgtta tctttgatga ctacaccaaa ttgccacctg gttacattga agcctatttg    2460
ttccaccatg ccaacaccga acttttcatt ctcactggag actcgcggca aagtgtatat    2520
catgagtcca acaatgaagc atacattgcc tccttagatg aagccgttgc ttactatgct    2580
aactactgcg gattttacct aaatgctaca catagaaatg ttcgcagttt agccaataag    2640
ctaggtgttt acagtgagaa agaaggccac ctcaaaatta cctttgcctc aaatgctcta    2700
caaaagtgca aagtgccaat tttagtgcct tctaaaatga gaaaggtgc catgcaagac     2760 ataggggcaca aagccatgac ctacgctggt tgtcaagggc ttactgctcc aagagtccaa   2820 atttttgcttg acaaccacac acaacactgc tcagacaggg tgctgtacac atgtctctct   2880
agagctgttg attccatcca ttttatcaat acaggtccaa acaattctga atttttgggac  2940 aagctcgagg caacaccata cctcaaagca tttattgata cttacagaga tgagaaaaca   3000
gaaatgctca attctaaacc tgctgacgac agtcctactg agcctgaagc tccattgact   3060
cactttccag tgtccaacgg caacaacttg gaaaagttag cttcagcact tcctgaaaaa   3120
tttgcaaggg agttgtatga caaacaccat gggtattcta acacaatcca aactgaaaat   3180
ccagtggtac aacttttcca gcatcaacaa gccaaagatg aaacgctttt ctgggcaaca   3240
atagaagcta gactttctat tacaactccg gaagccaatt tacgagaatt tgtgctgaag   3300
aaagatgttg gagacatctt gtttttcaac taccacaatg cgatgtgctt acccgctgat   3360
ccagtggact ttgagccaag aacatgggaa atatgtgctg ctgaagttaa aaatacttac   3420
ttagccaaac caatggctaa cctgatcaat gctgctagca gacaatctcc tgattttgat   3480
actaataaaa tttccctgtt cttaaaatct caatgggtca aaaaagtgga aaaattaggt   3540
gctgtcaaat caaagcctgg ccagaccatc gcagctttca tgcaacaaac agtgatgttg   3600
tatgggacca tggccagata cctcagaaag atgagacaaa gattccaacc aaagcatatt   3660
ttcattaatt gtgagacaac aacggatgat ctgaaccaat tgttaaaaca aggttggaac   3720
tttaacagaa ctgctcagac aaatgatttc acagcttttg accaatcaca agatggtgca   3780
atgcttcaat ttgaagtcat gaaggcaaaa ttcttcaata tccctgctga cattattgaa   3840
ggatacatca atatcaaatt gaacgccaaa attttccttg gtacattgtc cattatgagg   3900
ttgtctggtg aagtccaac ttttgatgct aacacagaat gttcaatagc atatactgct    3960
acaagatacc atctcgattc cacagtcaag caggtttatg ctggagatga catggcatta   4020
gatggagttg tccaagaaaa accctctttc aaaaatttac agaacaagct taaactcacc   4080
tcaaagacac tatttccaaa gcaggtcaaa ggtgattacg ctgaattctg tggttggact   4140
ttcactcctg gtggcatcat taaaaaccct ttgaaaatgc atgcttcaat catgttgcaa   4200
gaggcaattg gcaatttgca cactgctgcc agatcatatg ccattgacat gaagcattca   4260
taccaaatgg gtgatgagct gcatgattac ttaacaccag atgaagctga caacatttc   4320 cttgctgttc ggaaattgca caagctacac caaggagaag caatgagact tggtgaaaag   4380
agccctccaa aatcaacaca ttgaggggtt aagttttttcc cagtttgaaa tggaaagatc   4440
aactctgatt aatttacttc aattgcacca cttcgagcca aaactcagtg ttgaaggaat   4500
catagttgtg cacggaattg caggaactgg gaaaaccact ttacttagga ctttattttc   4560
tgcttaccct agcttagtta taggttcacc taggccttgt tatttagaca aacaaaataa   4620
aatttcacaa gtttgcttat cttgcttttcc caatacccat tgtgacattg ttgatgagta   4680
tcatttgcta gaaagttttcc cagaaccaaa attggctatc tttggtgacc cctgtcaatg   4740
```

```
cacatacgtt gaaagactta gagtcccaca ttacacttcc ttcagaactc atagatttgg   4800
aaagtcaact gctgagattt tgaacaaact gtttgatctt aatataatct cagttaagaa   4860
agaagacgac attgttgaat tctttaaccc tttcgaagtt gaccccactg aacatatctc   4920
agcctctgaa gaagaagtct tagactttgt ttctgaccaa gtggtgacca ccagctcaga   4980
agaactagca ggacttgaat ttgctgaaac aactttctac tgcaccacac tggcagcagc   5040
cgttgctgaa aatcctgcta agactttcat ctctctgacc agacacactc acaaactcac   5100
cattggggaa ctaaatgcca ggtctaactc ctagagctga cctcactgac acatacaaaa   5160
tcattgccat tgccttcttg ttgtcagcct gcatttactt ccaaaatagc cactaccaac   5220
ctgttgctgg agacaatttg caccgtttgc cttttggtgg ccaatatcaa gacggcacta   5280
aaaggatttc ttattttcca caacagcagt catactttca ttctggaaac aaattaaatg   5340
tcctcatact tatcttcatt ctcacattgg gtattgtcct caccaataaa tttagtttta   5400
gctttagtcg tactactcac cagcattctt gctataacac acattcagca accaacaaca   5460
cacaaccatt gtcaggtcat cattgacggt gctgcaatag tcataacaaa ttgtgagaac   5520
acaccagaag tacttaaggc aatcaacttc tccccctgga acgggttaag ttttcctaag   5580
tttgaaaatc aatattgagt gttcacaaca atcaacttca acaaacaatc atgcctgaca   5640
caacacctgt tgctgccact tcaagtgcac cacctacagc caaagatgct ggtgccaaag   5700
ctccttctga cttctcaaat cccaatacag ctcctagtct cagtgatttg aagaaagtca   5760
agtatgtctc cacagtgact tccgtggcca caccagctga aattgaagcc ctaggcaaaa   5820
tcttcaccgc tatgggcctt gccgccaatg agactggtcc ggcgatgtgg gatctagctc   5880
gtgcgtatgc tgatgtgcag agctctaaat ccgcacagct gattggtgct acccccttcca   5940 accctgcatt atcacgccga gcccttgctg ctcagtttga tcgaatcaat ataacaccca   6000
ggcaattttg catgtacttt gctaaagttg tttggaacat ccttctcgac agcaatattc   6060
caccagcaaa ttgggctaaa cttggttacc aagaagatac aaaatttgct gcatttgact   6120
tcttcgatgg agtcaccaac cctgccagcc tgcagcctgc tgatggtctc atcaggcaac   6180
caaatgagaa agaactagct gctcactcag tagctaaata tggcgccttg gctaggcaaa   6240
agatctccac aggtaattat attaccacac ttggagaagt cacacgtgga cacatgggtg   6300
gagctaacac catgtacgcg atcgacgcac cccctgaact ttaaacactc gaaacttaat   6360
cagagtgggg ttttctacag tttattttcc taattatttc tttgaaacaa aaaaaaaaaa   6420
aaaaaaaaaa aaaaaaaaaa aaaaaaaa                                      6448
```

<210> SEQ ID NO 8
<211> LENGTH: 6326
<212> TYPE: DNA
<213> ORGANISM: Pepino mosaic virus

<400> SEQUENCE: 8

```
aaagcacttt accacattat gtctcgtgtt agaaacactt tagaaaagat cagggaccca     60
caagtacaat ctagcatttg tgaagccgct taccaacatg ttagacctgt gctcaaggaa    120
tccctaatca actgtcctta tgcgcttaat gactatgaag cagacaccct tgagaattta    180
ggtgtcacaa taaacccccca tgcaatccaa acacatactc atgcggcagc taaagttgtg    240
gaaaatagaa tgctcgaaat cgttggacac cacttgccca aggacgagaa agttaccttc    300
attttcctca aaagaagcaa actgagatac atgcgaagag ctgctgtaca taaagatgtt    360
tttgttaatc acaatataga acccaaggat ttcttcaggt atgatgagga atctacatct    420
```

```
actagtttct ccgtgaacac caggatcgct tacatctccg attctctaca tttcatggaa      480
ccagctgatg tgacccacct cttttgaccgt tgccacaatc ttaaaacact gatggcaact     540
gtcgttttac ctgttgaagc catccacaaa caaacatctt tatttccagc gatatactcc     600
attaattaca atgaagaagg ttttgagtat atccctggtt ctcatggtgg aggggcatac     660
tttcataagt atgaaacatt agactggctc aaatactcta gattcattgg ccaggacccc     720
ttaactggac tccgatacac cataaccatt caaatggtag agagtttagg agccaaccat     780
cttttcctct tccaaagagg aaattttgaa acacctttat acaggacgtt tcaaaaaaat     840
agctttgtga cctttcctaa catcttccat ccccaacatg ttaatgccac aaagcccatg     900
ccaagatcca gggcaattca gctgtattta tatgtcaaat ctgtcaataa ggtgacacaa     960
agagatatct ttgcgaaagt aaggcaactt atatctacag ctgaacttga attgtatgac    1020
cctgatgaac ttacacatat tgtcaattat ttcgcatatg tctcagaact aagctcaatc    1080
aacgactatg acaatatgct caaatcaagt ttttcaaaa aacttgttgc acccatgcaa     1140
catgactgga ggtgcatgat tgaattcttt cggggaaaaa gtgatttcaa tcaactttta    1200
actgctcttc aatggaaaga cttctcttac accattaaaa ctgaagagtt agttgttgct    1260
acacacactg aaattggcca ggcaatctgt gaagctgcga ccacatacaa agaaagaaga    1320
caattgacca atttagtcaa acaaggcgca gtaacattag ctgatttcaa agaagcggac    1380
cagcatgtgg agtacactca ctttgatcct gagtttaaat ccactgttga cccccaccgg    1440
agctatgaaa atgccatcaa caatcttggc attgagatta atgaggatgt acctgaaagt    1500
tccggcacta atraaacatt gcttaacaat gaaatatctt tagcaatgtc ayctgctgaa    1560
catgtgcaag ccgttcaaga aattgagtct ttactctcta accccgaagc ggcaccaata    1620 ttgcccctg cacatgttaa aacatgggct agccttgcat ctgacayttc cagcactaaa    1680
aaccgtgaaa tcgaagatat agtggctaag ctggaaatac aaagaaatga agctagttgc    1740
agctaccttc aaccaaataa ggaattgtca aaacccaagg ctgctgataa caatctcccc    1800
tggaatgctt ggatcccatt gcttaatgca cacggcttca aaggagatca attacaatac    1860
ggcccagatg gtaacttgat acagcccatc caagacatta caattcaca gcctagatct     1920 gactatccgt cttctctgcc atgtgaactt gtggaaactt tgaggaaaat taagcgtgct    1980
gtctatgcca tcccaataag ccacaggaga gctagtgctt acagttctga catcaaaaat    2040
aacagaactg gcaaacttct ctgcaaccaa agcaaagaat ggaaagaaag ctttgctttc    2100
aaaatgcaac atgaagacat cgtcaaatca ggtgttgtca tacatggttg cggaggttct    2160
ggcaaatccc aggcattaca aaacttcttg agaacattgg gtgattcaaa tgattgctgt    2220
actgttgtag tacccactgt tgaacttaga aatgactggg taaacaaact ccataaattg    2280
cccatggagc atatcaaaac atttgagaaa gcaatgattc aacctggctt tccaattgtt    2340
atatttgatg attacaccaa gttgccacct ggctacattg aagcatacct atttcaccat    2400
gccaacactg agcttttcat actcactggt gattctaggc aaagcgtgta ccatgaatct    2460
aacaatgaag cgtacattgc ctcattagat gaagctgttg catactacgc taattactgc    2520 ggttttatt taaatgctac tcatagaaat gtccgtagtt tagccaacaa acttggtgtt    2580
tacagtgaga agaaggaca cttgaaaatc acttttgctt cacatgcctt acaaaagtgc    2640
aaagtgccaa ttttagttcc ttctcaaatg aaaaggagtg ctatgtyaga cattggacat    2700
aaatccatga cctatgctgg ttgccaaggt ttaacagcac ccaaggtaca aattctcctt    2760
gataaccaca cgcaacattg ctctgacaga gttctgtaca cctgtctgtc tcgtgcagtt    2820
```

```
gattccatcc acttcattaa tactggtccc aacaattcag aattttggga taagcttgaa    2880
gcaacaccat atctcaaagc cttcattgat gtctatagag atgaaaaaac tgaaatgttc    2940
aattctaagc ctgctgatga cagtccaact gagcctgaag cacctgttac acatttccca    3000
atagcaaatg gaaataactt agagaaatta gcttctgctt tgcctgaaaa atttgctagg    3060
gagatttatg acaagcatca tggccactcc aacacaatcc aaactgagaa ccctgtggtc    3120
caacttttcc aacatcaaca agcgaaagac gagacactct tttgggctac aattgaagct    3180
agattgtcca taacaactcc tgaagcaaac ctcagagaat ttttgtttaa gaaagatgtt    3240
ggagacattc tcttcttcaa ttaccataat gcgatgtgct tgcctgccga ccctgttgac    3300
tttgaagaaa agacctggga gatctgtgct gctgaagtga aaaacactta tcttgccaaa    3360
cccatggcca atcttatcaa tgcggcaagt agacaatcac ccgactttga ctctaataag    3420
atctcattat tcctaaagtc tcaatgggtg aaaaagtgg aaaaacttgg agctatcaaa    3480
tcaaaacctg gcagaccat agctgctttt atgcaacaaa cagtcatgtt gtatggtact    3540
atggccaggt acttaaggaa aatgcggcaa agattccagc caaacacat attcatcaat    3600
tgtgaaacca caactgatga tctcaataaa tttgtcaaag ayggctggaa ctttaacaga    3660
accgcccaaa caaatgactt cactgctttt gatcagtcac aagatggagc aatgcttcaa    3720
tttgaagtca tgaaagcaaa attttttaac attccagctg atgtcattga aggctacatc    3780
aacatcaagc tgaatgctaa aattttcctt ggaacactct caataatgag actttctggt    3840
gaaggtccca catttgacgc taacactgag tgttcgattg catacactgc cacaagattc    3900
catattgaca atactgttaa gcaagtgtat gccggtgacg acatggcatt agatggagtt    3960
gtgagtgaaa agaaatcatt caggaagtta caaaatctac taaaactcac ttcaaaaacg    4020
ctgtacccaa aacaggttaa agggaattac gctgaatttt gtggttggac tttcacacca    4080
gggggtataa ttaaaaatcc acttaaaatg catgcctcaa ttatgctgca agaagccatt    4140
ggcaatctgc acacagcagc cagatcttat gcaattgaca tgaagcattc ataccaaatg    4200
ggtgaccaac tgcatgacta cctaaccccc gatgaagctg aacaacattt cctagctgtg    4260
agaaagcttc acaaactcca tcaaggcgag gccatgcgtc ttggggagaa aagtccacca    4320
agatcaaccc attaaggggt taagttttcc ccagtttgaa atggaaagat caactttgat    4380
caatttactt ctgttacaca aatttgaaca caagattaac actgaaggaa tcattgttgt    4440
gcacggaatt gctggaactg ggaaaaccac attgcttagg actttatttt ctgcataccc    4500
tagcttagtt ataggttcac ctaggccttg ttacttagat aaagctaata aaatttcaca    4560
agtttgcctt tcttgttttc caaataccctt gtgtgacatt gttgacgagt atcatctctt    4620
agaaagtttt cctgaaccaa aactagccat ttttggtgac ccctgtcagt gcacttacat    4680
tgaaaggttg agaacaccca actacacatc cttcagaaca caccgatttg gcaaatccac    4740
tgctgctcta ctaaaccagt tatttgatct taacattgag tcagtcaaag cacaagacga    4800
cacagtagaa tactttgatc ctttcgcagt ggacccctct gaacacattt ctgcttcaga    4860
aaaagaagtt ttggaatttg taggtgatca agttgagact acaagctctg aagaactagc    4920
tggtctcgag tttagtgaag ttactttcta ctgtaccaca cttgctggtg ctgttcaaga    4980
aaatcctgct aaaaccttca tttcactcac tagacacact tcaaagctca caattggtga    5040
actaaatgcc aggtctgact cctagagctg atcttactga cacgtataaa atcattgcta    5100
tagcctttct actgtcagct tgcatttact tccaaaacag tcattatcaa ccagttgcag    5160
gtgataattt gcacagacta ccccttggtg gtcagtatca agacggaact aagaagattt    5220
```

-continued

```
cttactttcc gcagcaacaa tcctactttc actcaggaaa caagcttaat gtcctcatac    5280
ttatcttcat tcttacactg ggtattgtcc tcaccaataa atttagtttt agcattagcc    5340
gtaatactca ccagcatcat tgctacaaca cacattctgc aacccaaaca ggtcaatcag    5400
tgccaggtca tcattgacgg tgcagccata gttataacaa attgtccaaa cacacccgaa    5460
gttcttaaag caatcaactt ctccccttgg aacgggttaa gttttcctca attgtgaaat    5520
tatatttgtt atctagttaa attcaaacaa tttaactcaa ctatggaaaa ccaacctaca    5580
gcttctaacc catcagatgc accaccaact gctgctcaag ctggtgccca gagcccagcs    5640
gacttctcaa atcctaatac agctccttcc ctaagtgatt tgaagaagat caaatacgtg    5700
tcaactgtca cttcagttgc cacgcctgct gaaattgagg cccttggcaa gatctttact    5760
gccatgggtt tagcagccaa tgagaccgga cctgccatgt gggacctcgc tcgtgcttat    5820
gctgatgtgc aaagttcaaa atctgcacaa cttayaggtg ccacaccatc caaccctgct    5880
ttgtctagac gtgcacttgc tgcacagttt gatcgtatca atatcacacc cagacaattc    5940
tgcatgtatt ttgcaaaaat tgtttggaac atactgttag acagcaatgt gccacctgcc    6000
aactgggcaa aattgggcta tcaggaagat accaagtttg ctgcttttga cttctttgat    6060
ggagtcacaa atccagctag tctacagccy gcagatggcc taatcaggca gcccaatgaa    6120
aaagagcttg ctgctcactc ggttgctaaa tatggtgccc ttgcccgcca gaaaatatcc    6180
actggtaact acatcaccac ccttggtgaa gttacacgtg gtcacatggg cggcgccaac    6240
actatgtacg caattgatgc acctcctgaa ctttaaacac tcgaaactta accagagtgg    6300
ggttttctat agtttatttt ccctta                                         6326
```

```
<210> SEQ ID NO 9
<211> LENGTH: 1438
<212> TYPE: PRT
<213> ORGANISM: pepino mosaic virus
<220> FEATURE:
<221> NAME/KEY: misc_feature
<222> LOCATION: (499)..(499)
<223> OTHER INFORMATION: X -continued Thr His Thr His Ala Ala Ala Lys Val Val Glu Asn Arg Met Leu Glu
65                  70                  75                  80

Ile Val Gly His His Leu Pro Lys Asp Glu Lys Val Thr Phe Ile Phe
                85                  90                  95

Leu Lys Arg Ser Lys Leu Arg Tyr Met Arg Arg Ala Ala Val His Lys
            100                 105                 110

Asp Val Phe Val Asn His Asn Ile Glu Pro Lys Asp Phe Phe Arg Tyr
        115                 120                 125

Asp Glu Glu Ser Thr Ser Thr Ser Phe Ser Val Asn Thr Arg Ile Ala
    130                 135                 140

Tyr Ile Ser Asp Ser Leu His Phe Met Glu Pro Ala Asp Val Thr His
145                 150                 155                 160

Leu Phe Asp Arg Cys His Asn Leu Lys Thr Leu Met Ala Thr Val Val
                165                 170                 175

Leu Pro Val Glu Ala Ile His Lys Gln Thr Ser Leu Phe Pro Ala Ile
            180                 185                 190

Tyr Ser Ile Asn Tyr Asn Glu Glu Gly Phe Glu Tyr Ile Pro Gly Ser
        195                 200                 205

His Gly Gly Gly Ala Tyr Phe His Lys Tyr Glu Thr Leu Asp Trp Leu
    210                 215                 220

Lys Tyr Ser Arg Phe Ile Gly Gln Asp Pro Leu Thr Gly Leu Arg Tyr
225                 230                 235                 240

Thr Ile Thr Ile Gln Met Val Glu Ser Leu Gly Ala Asn His Leu Phe
                245                 250                 255

Leu Phe Gln Arg Gly Asn Phe Glu Thr Pro Leu Tyr Arg Thr Phe Gln
            260                 265                 270

Lys Asn Ser Phe Val Thr Phe Pro Asn Ile Phe His Pro Gln His Val
        275                 280                 285

Asn Ala Thr Lys Pro Met Pro Arg Ser Arg Ala Ile Gln Leu Tyr Leu
    290                 295                 300

Tyr Val Lys Ser Val Asn Lys Val Thr Gln Arg Asp Ile Phe Ala Lys
305                 310                 315                 320

Val Arg Gln Leu Ile Ser Thr Ala Glu Leu Glu Leu Tyr Asp Pro Asp
                325                 330                 335

Glu Leu Thr His Ile Val Asn Tyr Phe Ala Tyr Val Ser Glu Leu Ser
            340                 345                 350

Ser Ile Asn Asp Tyr Asp Asn Met Leu Lys Ser Ser Phe Phe Lys Lys
        355                 360                 365

Leu Val Ala Pro Met Gln His Asp Trp Arg Cys Met Ile Glu Phe Phe
    370                 375                 380

Arg Gly Lys Ser Asp Phe Asn Gln Leu Leu Thr Ala Leu Gln Trp Lys
385                 390                 395                 400

Asp Phe Ser Tyr Thr Ile Lys Thr Glu Glu Leu Val Val Ala Thr His
                405                 410                 415

Thr Glu Ile Gly Gln Ala Ile Cys Glu Ala Ala Thr Thr Tyr Lys Glu
            420                 425                 430

Arg Arg Gln Leu Thr Asn Leu Val Lys Gln Gly Ala Val Thr Leu Ala
        435                 440                 445

Asp Phe Lys Glu Ala Asp Gln His Val Glu Tyr Thr His Phe Asp Pro
    450                 455                 460

Glu Phe Lys Ser Thr Val Asp Pro His Arg Ser Tyr Glu Asn Ala Ile
465                 470                 475                 480

-continued

Asn Asn Leu Gly Ile Glu Ile Asn Glu Asp Val Pro Glu Ser Ser Gly
            485                 490                 495

Thr Asn Xaa Thr Leu Leu Asn Asn Glu Ile Ser Leu Ala Met Ser Xaa
        500                 505                 510

Ala Glu His Val Gln Ala Val Gln Glu Ile Glu Ser Leu Leu Ser Asn
        515                 520                 525

Pro Glu Ala Ala Pro Ile Leu Pro Pro Ala His Val Lys Thr Trp Ala
        530                 535                 540

Ser Leu Ala Ser Asp Xaa Ser Ser Thr Lys Asn Arg Glu Ile Glu Asp
545                 550                 555                 560

Ile Val Ala Lys Leu Glu Ile Gln Arg Asn Glu Ala Ser Cys Ser Tyr
                565                 570                 575

Leu Gln Pro Asn Lys Glu Leu Ser Lys Pro Lys Ala Ala Asp Asn Asn
            580                 585                 590

Leu Pro Trp Asn Ala Trp Ile Pro Leu Leu Asn Ala His Gly Phe Lys
        595                 600                 605

Gly Asp Gln Leu Gln Tyr Gly Pro Asp Gly Asn Leu Ile Gln Pro Ile
        610                 615                 620

Gln Asp Ile Asn Asn Ser Gln Pro Arg Ser Asp Tyr Pro Ser Ser Leu
625                 630                 635                 640

Pro Cys Glu Leu Val Glu Thr Leu Arg Lys Ile Lys Arg Ala Val Tyr
                645                 650                 655

Ala Ile Pro Ile Ser His Arg Arg Ala Ser Ala Tyr Ser Ser Asp Ile
                660                 665                 670

Lys Asn Asn Arg Thr Gly Lys Leu Leu Cys Asn Gln Ser Lys Glu Trp
            675                 680                 685

Lys Glu Ser Phe Ala Phe Lys Met Gln His Glu Asp Ile Val Lys Ser
        690                 695                 700

Gly Val Val Ile His Gly Cys Gly Gly Ser Gly Lys Ser Gln Ala Leu
705                 710                 715                 720

Gln Asn Phe Leu Arg Thr Leu Gly Asp Ser Asn Asp Cys Cys Thr Val
                725                 730                 735

Val Val Pro Thr Val Glu Leu Arg Asn Asp Trp Val Asn Lys Leu His
            740                 745                 750

Lys Leu Pro Met Glu His Ile Lys Thr Phe Glu Lys Ala Met Ile Gln
        755                 760                 765

Pro Gly Phe Pro Ile Val Ile Phe Asp Asp Tyr Thr Lys Leu Pro Pro
        770                 775                 780

Gly Tyr Ile Glu Ala Tyr Leu Phe His His Ala Asn Thr Glu Leu Phe
785                 790                 795                 800

Ile Leu Thr Gly Asp Ser Arg Gln Ser Val Tyr His Glu Ser Asn Asn
                805                 810                 815

Glu Ala Tyr Ile Ala Ser Leu Asp Glu Ala Val Ala Tyr Tyr Ala Asn
                820                 825                 830

Tyr Cys Gly Phe Tyr Leu Asn Ala Thr His Arg Asn Val Arg Ser Leu
        835                 840                 845

Ala Asn Lys Leu Gly Val Tyr Ser Glu Lys Glu Gly His Leu Lys Ile
        850                 855                 860

Thr Phe Ala Ser His Ala Leu Gln Lys Cys Lys Val Pro Ile Leu Val
865                 870                 875                 880

Pro Ser Gln Met Lys Arg Ser Ala Met Xaa Asp Ile Gly His Lys Ser
                885                 890                 895

```
Met Thr Tyr Ala Gly Cys Gln Gly Leu Thr Ala Pro Lys Val Gln Ile
                900                 905                 910

Leu Leu Asp Asn His Thr Gln His Cys Ser Asp Arg Val Leu Tyr Thr
            915                 920                 925

Cys Leu Ser Arg Ala Val Asp Ser Ile His Phe Ile Asn Thr Gly Pro
        930                 935                 940

Asn Asn Ser Glu Phe Trp Asp Lys Leu Glu Ala Thr Pro Tyr Leu Lys
945                 950                 955                 960

Ala Phe Ile Asp Val Tyr Arg Asp Glu Lys Thr Glu Met Phe Asn Ser
                965                 970                 975

Lys Pro Ala Asp Asp Ser Pro Thr Glu Pro Glu Ala Pro Val Thr His
            980                 985                 990

Phe Pro Ile Ala Asn Gly Asn Asn Leu Glu Lys Leu Ala Ser Ala Leu
        995                 1000                1005

Pro Glu Lys Phe Ala Arg Glu Ile Tyr Asp Lys His His Gly His
   1010                1015               1020

Ser Asn Thr Ile Gln Thr Glu Asn Pro Val Val Gln Leu Phe Gln
   1025                1030               1035

His Gln Gln Ala Lys Asp Glu Thr Leu Phe Trp Ala Thr Ile Glu
   1040                1045               1050

Ala Arg Leu Ser Ile Thr Thr Pro Glu Ala Asn Leu Arg Glu Phe
   1055                1060               1065

Leu Phe Lys Lys Asp Val Gly Asp Ile Leu Phe Phe Asn Tyr His
   1070                1075               1080

Asn Ala Met Cys Leu Pro Ala Asp Pro Val Asp Phe Glu Glu Lys
   1085                1090               1095

Thr Trp Glu Ile Cys Ala Ala Glu Val Lys Asn Thr Tyr Leu Ala
   1100                1105               1110

Lys Pro Met Ala Asn Leu Ile Asn Ala Ala Ser Arg Gln Ser Pro
   1115                1120               1125

Asp Phe Asp Ser Asn Lys Ile Ser Leu Phe Leu Lys Ser Gln Trp
   1130                1135               1140

Val Lys Lys Val Glu Lys Leu Gly Ala Ile Lys Ser Lys Pro Gly
   1145                1150               1155

Gln Thr Ile Ala Ala Phe Met Gln Gln Thr Val Met Leu Tyr Gly
   1160                1165               1170

Thr Met Ala Arg Tyr Leu Arg Lys Met Arg Gln Arg Phe Gln Pro
   1175                1180               1185

Lys His Ile Phe Ile Asn Cys Glu Thr Thr Thr Asp Asp Leu Asn
   1190                1195               1200

Lys Phe Val Lys Xaa Gly Trp Asn Phe Asn Arg Thr Ala Gln Thr
   1205                1210               1215

Asn Asp Phe Thr Ala Phe Asp Gln Ser Gln Asp Gly Ala Met Leu
   1220                1225               1230

Gln Phe Glu Val Met Lys Ala Lys Phe Asn Ile Pro Ala Asp
   1235                1240               1245

Val Ile Glu Gly Tyr Ile Asn Ile Lys Leu Asn Ala Lys Ile Phe
   1250                1255               1260

Leu Gly Thr Leu Ser Ile Met Arg Leu Ser Gly Glu Gly Pro Thr
   1265                1270               1275

Phe Asp Ala Asn Thr Glu Cys Ser Ile Ala Tyr Thr Ala Thr Arg
   1280                1285               1290
```

```
Phe His Ile Asp Asn Thr Val Lys Gln Val Tyr Ala Gly Asp Asp
    1295                1300                1305

Met Ala Leu Asp Gly Val Val Ser Glu Lys Lys Ser Phe Arg Lys
    1310                1315                1320

Leu Gln Asn Leu Leu Lys Leu Thr Ser Lys Thr Leu Tyr Pro Lys
    1325                1330                1335

Gln Val Lys Gly Asn Tyr Ala Glu Phe Cys Gly Trp Thr Phe Thr
    1340                1345                1350

Pro Gly Gly Ile Ile Lys Asn Pro Leu Lys Met His Ala Ser Ile
    1355                1360                1365

Met Leu Gln Glu Ala Ile Gly Asn Leu His Thr Ala Ala Arg Ser
    1370                1375                1380

Tyr Ala Ile Asp Met Lys His Ser Tyr Gln Met Gly Asp Gln Leu
    1385                1390                1395

His Asp Tyr Leu Thr Pro Asp Glu Ala Glu Gln His Phe Leu Ala
    1400                1405                1410

Val Arg Lys Leu His Lys Leu His Gln Gly Glu Ala Met Arg Leu
    1415                1420                1425

Gly Glu Lys Ser Pro Pro Arg Ser Thr His
    1430                1435
```

<210> SEQ ID NO 10
<211> LENGTH: 998
<212> TYPE: DNA
<213> ORGANISM: Serratia marcescens

<400> SEQUENCE: 10

```
tacacgaaca aacttacagc cacggtgagc cgcaggcgcc gctgaacgtg gtgggcgaaa      60
ccgagcagac cggcaccatg gtgcgtttct ggccgagcca ccagaccttc accaatgtaa     120
ccgaattcga atacgacatt ctggccaagc gtctgcgcga gctgtccttc ctcaactccg     180
gcgtgtctat ccgcctgaag gacaagcgta ccgaccgtga agaccacttc cattacgaag     240
gcggtatcaa ggcgtttgtc gagtacctga acaagaacaa accccgatc cacccgaacg      300 tgttctactt ctcgaccgtg aaagacgata tcggcgtgga agtggcgctg cagtggaacg     360
acggtttcca ggaaaacatc tactgcttca ccaacaacat tccgcagcgc gacggcggca     420
cgcacctggt cggtttccgt accgcgatga cccgtacgct gaacagctac atggagaagg     480
aaggctacag caagaaggcc aaggtcagcg ccaccggcga tgacgcgcgt gaaggcctga     540
ttgccgtagt gtcggtgaag gtgccggatc cgaagttctc ttctcagact aaagacaagc     600
tggtctcttc cgaggtgaaa actgcggttg aaacgctgat gaacgagaaa ctggtggatt     660
acctgatgga gaatccaagc gacgcgaaaa ttgtggtcgg caaaatcatc gacgcggcgc     720
gcgcgcgcga agcggcgcgt aaagcacgtg agatgacccg tcgcaaaggc gcactggatc     780
tggccggcct gccgggcaag ctggcggact gccaggaacg cgacccggcg ctgtccgaac     840
tgtatctggt ggaaggggac tccgcgggcg gctctgccaa gcaggggcgc aaccgcaaga     900
atcaggctat cttgccgctg aaggggaaaa tcctcaacgt cgagaaagcg cgtttcgaca     960
aaatgctctc ctcgcaggaa gtggcgacgc tgatcacc                             998
```

<210> SEQ ID NO 11
<211> LENGTH: 6291
<212> TYPE: DNA
<213> ORGANISM: Pepino mosaic virus

<400> SEQUENCE: 11

```
atgtctcgtg ttagaaacac tttagaaaag atcagggacc cacaagtaca atctagcatt      60
tgtgaagccg cttaccaaca tgttagacct gtgctcaagg aatccctaat caactgtcct     120
tatgcgctta atgactatga agcagacacc cttgagaatt taggtgtcac aataaacccc     180
catgcaatcc aaacacatac tcatgcggca gctaaagttg tggaaaatag aatgctcgaa     240
attgttggac accacttgcc caaggacgag aaagttacct tcattttcct caaaagaagc     300
aaactgagat acatgcgaag agctgctgta cataaagatg ttttttgttaa tcacaatata     360
gaacccaagg atttcttcag gtatgatgag gaatctacat ctactagttt ctccgtgaac     420
accaggatcg cttacatctc cgattctcta catttcatgg aaccagctga tgtgacccac     480
ctctttgacc gttgccacaa tcttaaaaca ctgatggcaa ctgtcgtttt acctgttgaa     540
gccatccaca aacaaacatc tttatttcca gcgatatact ccattaatta caatgaagaa     600
ggttttgagt atatccctgg ttctcatggt ggagggcat actttcataa gtatgaaaca     660
ttagactggc tcaaatactc tagatttgtt ggccaggacc ccttaactgg actccgatac     720
accataacca ttcaaatggt agagagttta ggagccaacc atcttttcct cttccaaaga     780
ggaaattttg aaacaccttt atacaggacg tttcaaaaaa atagctttgt gacctttcct     840
aacatcttcc atccccaaca tgttaatgcc acaaagccca tgccaagatc cagggcaatt     900
cagctgtatt tatatgtcaa atctgtcaat aaggtgacac aaagagatat ctttgcgaaa     960
gtaaggcaac ttatatctac agctgaactt gaattgtatg accctgatga acttacacat    1020
attgtcaatt atttcgcata tgtctcagaa ctaagctcaa tcaacgacta tgacaatatg    1080
ctcaaatcaa gttttttcaa aaaacttgtt gcacccatgc aacatgactg gaggtgcatg    1140
attgaattct ttcggggaaa aagtgattc aatcaacttt taactgctct tcaatggaaa    1200
gacttctctt acaccattaa aactgaagag ttagttattg ctacacacac tgaaattggc    1260
caggcaatct gtaaagctgc gaccacatac aaagaaagaa gacaattgac caatttagtc    1320
aaacaaggcg cagtaacatt agctgatttc aaagaagcgg accagcatgt ggagtacact    1380
cactttgacc ctgagtttaa atccactgtt gaccccacc ggagctatga aaatgccatc    1440
aacaatcttg gcattgagat taatgaggat gtacctgaaa gttccggcac taatgaaaca    1500
ttgcttaaca atgaaatatc tttagcaatg tcatctgccg aacatgtgca agctgttcaa    1560
gaaattgagt ctttactctc taaccccgaa gcggcaccaa tattgccccc tgcacatgtt    1620
aaaacatggg ctagccttgc atctgacact tccagcacta aaaaccgtga atcgaagat    1680
atagtggcta agctggaaat acaaagaaat gaagctagtt gcagctacct tcaaccaaat    1740
aaggaattgt caaacccaa ggctgctgat aacaatctcc cctggaatgc ttggatccca    1800
ttgcttaatg cacacggctt caaaggagat caattacaat acggcccaga tggtaacttg    1860
atacagccca tccaagacat taacaattca cagcctagat ctgactatcc gtcttctctg    1920
ccatgtgaac ttgtggaaac tttgaggaaa attaagcgtg ctgtctatgc catcccaata    1980
agccacagga gagctagtgc ttacagttct gacatcaaaa ataacagaac tggcaaactt    2040
ctctgcaacc aaagcaaaga atggaaagaa agctttgctt tcaaaatgca acatgaagac    2100
atcgtcaaat caggtgttgt catacatggt tgcggaggtt ctggcaaatc ccaggcatta    2160
caaaacttct tgagaacatt gggtgattca aatgattgct gtactgttgt agtacccact    2220
gttgaactta gaaatgactg ggtaaacaaa cttcataaat tgcccatgga gcatatcaaa    2280
acatttgaga aagcaatgat tcaacctggc tttccaattg ttatatttga tgattacacc    2340
```

```
aagttgccac ctggctacat tgaagcatac ctatttcacc atgccaacac tgagcttttc      2400
atacttactg gtgattctag gcaaagcgtg taccatgaat ctaacaatga agcgtacatt      2460
gcctcattag atgaagctgt tgcatactac gctaattact gcggttttta tttaaatgct      2520
actcatagaa atgtccgtag tttagccaac aaacttggtg tttacagtga aaagaagga      2580 cacttgaaaa tcacttttgc ttcacatgcc ttacaaaagt gcaaagtgcc aattttagtt      2640
ccttctcaaa tgaaaagag tgctatgtta gacattggac ataaatccat gacctatgct      2700
ggttgccaag gtttaacagc acccaaggta caaattctcc ttgataacca cacgcaacat      2760
tgctctgaca gagttctgta cacctgtctg tctcgtgcag ttgattccat ccacttcatc      2820
aatactggtc ccaacaattc agaattttgg gataagcttg aagcaacacc atatctcaaa      2880
gccttcattg atgtctatag agatgaaaaa actgaaatgc tcaattctaa gcctgctgat      2940
gacagtccaa ctgagcctga agcacctgtt acacatttcc cagtagcaaa tggaaataac      3000
ttagagaaat tagcttctgc tttgcctgaa aaatttgcta gggagattta tgacaagcat      3060 catgccact ccaacacaat ccaaactgag aaccctgtgg tccaactttt ccaacatcaa      3120
caagcgaaag acgagacact cttttgggct acaattgaag ctagattgtc cataacaact      3180
cctgaagcaa acctcagaga attttgtctt aagaaagatg ttggagacat tctcttcttc      3240
aattaccata tgctatgtg cttgcctgcc gatcctgttg actttgaaga aaagacctgg      3300
gagatctgtg ctgctgaagt gaaaaacact tatcttgcca aacccatggc caatcttatc      3360
aatgcggcaa gtagacaatc acccgacttc gactctaata agatctcatt attcctaaag      3420
tctcaatggg tgaaaaagt ggaaaaactt ggagctatca aatcaaaacc tggtcagacc      3480
atagctgctt ttatgcaaca aacagtcatg ttgtatggta ctatggccag gtacttaagg      3540
aaaatgcggc aaagattcca gccaaaacac atattcatca attgtgaaac cacaactgat      3600
gatctcaata aatttgtcaa agatggctgg aactttaaca gaaccgccca acaaatgac      3660 ttcactgctt tgatcagtc acaagatgga gcaatgcttc aatttgaagt catgaaagca      3720
aaatttttta acattccagc tgatgtcatt gaaggctaca tcaacatcaa gctgaatgct      3780 aaaatttttcc ttggaacact ctcaataatg agactttctg gtgaaggtcc cacatttgac      3840
gctaacactg agtgttcaat tgcatacact gccacaagat tccatattga caatactgtt      3900
aagcaagtgt atgccggtga cgacatggca ttagatggag ttgtgagtga aaagaaatca      3960
ttcaggaagt tacaaaatct actaaaactc acttcaaaaa cgctgtaccc aaaacaggtt      4020
aaaggggatt acgctgaatt ttgtggttgg actttcacac caggggtat aattaaaaat      4080 ccacttaaaa tgcatgcctc aattatgctg caagaagcca ttggcaatct gcacacagca      4140
gccagatctt atgcaattga catgaagcat tcataccaaa tgggtgacca actgcatgac      4200
tacctaaccc ccgatgaagc tgaacaacat ttcctagctg tgagaaagct tcacaaactc      4260
catcaaggcg aggccatgcg tcttggggag aaaagtccac caagatcaac ccattaaggg      4320
gttaagtttt ccccagtttg aaatggaaag atcaactttg atcaatttac ttctgttaca      4380
caaatttgaa cacaagatta acactgaagg aatcattgtt gtgcacggaa ttgctggaac      4440
tgggaaaacc acattgctta ggactttatt ttctgcatac cctagcttag ttataggttc      4500
acctaggcct tgttacttag ataaagctaa taaaatttca caagtttgcc tttcttgttt      4560
tccaaatacc ttgtgtgaca ttgttgacga gtaccatctc ttagaaagtt ttcctgaacc      4620
aaaactagcc atttttggtg accctgtca gtgcacttac attgaaaggt tgagaacacc      4680
caactacaca tccttcagaa cacaccgatt tggcaaatcc actgctgctc tactaaacaa      4740
```

-continued

```
gttatttgat cttaacattg agtcagtcaa agtacaagac gacacagtag aatactttga   4800
tcctttcgca gtggacccct ctgaacacat ttctgcttca gaaaaagaag ttttggaatt   4860
tgtaggtgat caagttgaga ctacaagctc tgaagaacta gctggtctcg agtttagtga   4920
agttactttc tactgtacca cacttgctgg tgctgttcaa gaaaatcctg ccaaaacctt   4980
catttcactc actagacaca cttcaaagct cacaattggt gaactaaatg ccaggtctga   5040
ctcctagagc tgatcttact gacacgtata aaatcattgc tatagccttt ctactgtcag   5100
cttgcattta cttccaaaac agtcattatc aaccagttgc aggtgataat ttgcacagac   5160
taccctttgg tggtcagtat caagacggaa ctaagaagat ttcttacttt ccgcagcaac   5220
aatcctactt tcactcagga aacaagctta atgtcctcat acttatcttc attcttacac   5280
tgggtattgt cctcaccaat aaatttagtt ttagcattag ccgtaatact caccagcatc   5340
attgctacaa cacacattct gcaacccaaa caggtcaatc agtgccaggt catcattgac   5400
ggtgcagcca tagttataac aaattgtcca aacacacccg aagttcttaa agcaatcaac   5460
ttctcccctt ggaacgggtt aagttttcct caattgtgaa attatatttg ttatctagtt   5520
aaattcaaac aatttaactc aactatggaa aaccaaccta cagcttctaa cccatcagat   5580
gtaccaccaa ctgctgctca agctggtgcc cagagcccag ccgacttctc aaatcctaat   5640
acagctcctt ccctaagtga tttgaagaag atcaaatacg tgtcaactgt cacttcagtt   5700
gccacgcctg ctgaaattga ggcccttggc aagatcttta ctgccatggg tttagcagcc   5760
aatgagaccg gacctgccat gtgggacctc gctcgtgctt atgctgatgt gcaaagttca   5820
aaatctgcac aacttatagg tgccacacca tccaaccctg ctttgtctag acgtgcactt   5880
gctgcacagt ttgatcgtat caatatcaca cccagacaat tctgcatgta ttttgcaaaa   5940
attgtttgga acatactgtt agacagcaat gtgccacctg ccaactgggc aaaattgggc   6000
tatcaggaag ataccaagtt tgctgctttt gacttctttg atggagtcac aaatccagct   6060
agtctacagc ctgcagatgg cctaatcagg cagcccaatg aaaaagagct tgctgctcac   6120
tcggttgcta aatatggcgc ccttgcccgc cagaaaatat ccactggtaa ctacatcacc   6180
acccttggtg aagttacacg tggtcacatg ggcggcgcca acactatgta cgcaattgat   6240
gcacctcctg aactttaaac actcgaaact taatcagagt ggggttttct a            6291
```

<210> SEQ ID NO 12
<211> LENGTH: 6412
<212> TYPE: DNA
<213> ORGANISM: Pepino mosaic virus

<400> SEQUENCE: 12

```
gaaaacaaaa cataacacat aatatcaaaa gtgaccaaac acaacataac cacgtggaaa     60
aacagcgaaa gcactttacc acattatgtc tcgtgttaga aacactttag aaaagatcag    120
ggacccacaa gtacaatcta gcatttgtga agccgcttac caacatgtta gacctgtgct    180
caaggaatcc ctaatcaact gtccttatgc gctcaatgac tatgaagcag acacccttga    240
gaatttaggt gtcacaataa atccccatgc aatccaaaca catactcatg cagcagctaa    300
agttgtggaa aatagaatgc tcgaaattgt tggacaccac ttgcccaagg acgagaaagt    360
taccttcatt ttcctcaaaa gaagcaaact gagatacatg cgaagagctg ctgtacataa    420
agatgttttt gttaatcaca gtatagaacc caaggatttc ttcaggtatg acgaggaatc    480
tacatctact agcttctccg tgaacactag gatcgcttac atctcagatt ctctacattt    540
catggaacca gctgatgtga cccacctctt cgaccgttgc cacaatctta aaacactgat    600
```

```
ggcaactgtt gttttacctg ttgaagccat ccacaaacaa acatctttat ttccagcgat    660
atactccatt aactacaatg aagaaggttt tgagtatatc cctggttctc atggtggagg    720
ggcatacttt cataagtatg aaacattaga ctggctcaaa tactctagat tcgttggcca    780 ggaccccta  actggactcc gatacaccat aaccattcaa atggtggaga gtttaggagc    840
caaccacctt ttcctcttcc aaagaggaaa ctttgaaacg cctttatata ggacgtttca    900
aaaaaatagc tttgtgacct ttcctaacat cttccatccc caacatgtta atgccacaaa    960
gcccatgcca agatccaggg caattcagct gtatttatat gtcaaatctg tcaataaggt   1020
gacacaaaga gatatctttg cgaaagtaag gcaacttata tctacagctg aacttgaatt   1080
gtatgaccct gatgaactta cacatattgt caattatttc gcatatgtct cagaactaag   1140
ctcaatcaac gactatgaca atatgctcaa atcaagtttt ttcaaaaaac ttgttgcacc   1200
catgcaacat gactggaggt gcatgattga attctttcgg ggaaaaagtg atttcaatca   1260
acttttaact gctcttcaat ggaaagactt ctcttacact attaaaactg aagagttagt   1320
tgtttctaca cacactgaaa ttggccaggc aatctgtaaa gctgcgacca tatacaaaga   1380
aagaagacaa ttgaccaatt tagtcaaaca aggcgtagta acattagctg atttcaaaga   1440
agcggaccag caagtggagt acactcactt tgatcctgag tttaaatcca ctgttgaacc   1500
ccaccggagc tatgaaaatg ccatcaacaa tcttggcatt gaaattaatg aggatgtacc   1560
tgaaagttcc ggcactaatg aaacattgct taacaatgaa atatctttag caatgtcatc   1620
tgctgaacat gtgcaagccg ttcaagaaat tgagtcttta ctctctaacc ccgaagcggc   1680
gccaatattg cccctgcgc  atgttaaaac atgggctagc cttgcatctg acacttccag   1740
cactaaaaac cgtgaaattg aagatatagt ggctaagctg gaaatacaaa gaatgaagc    1800 tagttgcagc taccttcaac caaataagga attgtcaaaa cccaaggctg ctgataacaa   1860
tctcccctgg aatgcttgga tcccattgct taatgcacac ggcttcaaag gagatcaatt   1920
acaatacggc ccagatggca acttgataca gcccatccaa gacattaaca attcacagcc   1980
tagatctgac tatccgtctt ctctgccatg tgaacttgtg gaaactttga ggaaaattaa   2040
gcgtgctgtc tatgccatcc aataagcca  caggagggct agtgcttaca gttctgacat   2100
caaaaataac agaactggca aacttctctg caaccaaagc aaagaatgga agaaagctt    2160 tgctttcaaa atgcaacacg aagacatcgt caaatcaggt gttgtcatac atggttgcgg   2220
aggttctggc aaatcccagg cattacaaaa cttcttgaga acattgggtg attcaaatga   2280
ttgctgtact gttgtagtac ccactgttga acttagaaat gactgggtaa acaaactcca   2340
taaattgccc atggagcaca tcaaaacatt tgagaaagca atgattcaac ctggctttcc   2400
aattgttata tttgatgatt acaccaagtt acctcctggc tacattgaag cctacctatt   2460
tcaccatgcc aacactgagc ttttcatact tactggtgat tctaggcaaa gcgtgtatca   2520
tgaatctaac aatgaagcgt acattgcctc attagatgaa gctgttgcat actacgctaa   2580
ttactgcggt ttttacttaa atgctactca tagaaatgtc cgtagtttag ccaataaact   2640
tggtgtttac agtgagaaag aaggacactt gaaaatcact ttcgcttcac atgccttaca   2700
aaagtgcaaa gtgccaattc tagttccttc tcaaatgaaa aagagtgcta tgttagacat   2760
tggacataaa tccatgacct atgctggttg ccaaggttta acagcaccca agtacaaat    2820 tctccttgat aatcacacgc aacattgctc tgacagagtt ctgtacacct gtttgtctcg   2880
tgcagttgat tccatccact tcatcaatac tggtcccaac aattcagaat ttgggataa    2940 gcttgaagca acaccatatc tcaaagcctt cattgatgtc tatagagatg aaaaaactga   3000
```

```
aatgctcaat tctaagcctg ctgatgatag tccaactgag cctgaagcac ctgttacaca    3060
tttcccaata gcaaatggaa ataacttaga gaaattagct tctgctttgc ctgaaaaatt    3120
tgctagggag atttatgaca agcatcatgg ctactccaac acaatccaaa ctgagaaccc    3180
tgtggtccaa cttttccaac atcaacaagc gaaagacgag acactcttct gggctacaat    3240
tgaagctaga ttgtccataa caactcctga agcaaacctc agagaatttt tgcttaagaa    3300
agatgttggg gacattctct tcttcaatta ccacaatgcg atgtgcttgc ctgccgaccc    3360
tgttgacttt gaagaaaaga cctgggagat tgtgctgct gaagtgaaaa acacttatct    3420
tgccaaaccc atggccaatc ttattaatgc ggcaagtaga caatcacccg actttgactc    3480
caataagatc tcattattcc taaagtctca atgggtgaaa aaagtggaaa aacttggagc    3540
tatcaaatca aaacctggtc agaccatagc tgcttttatg caacaaacag tcatgttgta    3600
tggtactatg gccaggtact taaggaaaat gcggcaaaga ttccagccaa aacacatatt    3660
catcaattgt gaaaccacaa ctgatgatct caataaattt gtcaaagacg gctggaactt    3720
taacagaacc gcccaaacaa atgacttcac tgcttttgac cagtcacaag atggagcaat    3780
gcttcaattt gaagtcatga agcaaaaatt ttttaacatt ccagctgatg tcattgaagg    3840
ctacatcaac atcaagctga atgctaaaat tttccttgga acactctcaa taatgagact    3900
ttctggtgaa ggtcccacat ttgacgctaa cactgagtgt tcgattgcat acactgccac    3960
aagattccat attgacaata ctgttaagca agtgtatgcc ggtgacgaca tggcgttaga    4020
tggagttgtg agtgaaaaga aatcattcag gaagttgcaa aatctactaa aactcacttc    4080
aaaaacgctg tacccaaaac aggttaaagg ggattacgct gaattttgcg gttggacatt    4140
cacaccaggg ggtataatta aaaatccact taaaatgcat gcctcaatta tgctgcaaga    4200
agccattggc aatctgcaca cagcagccag atcttatgca atcgacatga agcattcata    4260
ccaaatgggt gaccaactgc acgactacct aaccctcgat gaagctgaac aacatttcct    4320
agctgtgaga aagcttcaca aactccatca aggcgaggcc atgcgtcttg gggagaaaag    4380
tccaccaaga tcaacccatt aaggggttaa gttttcccca gtttgaaatg aaagatcaa    4440
ctttgatcaa tttacttctg ttacacaaat ttgaacacaa gattaacact gaaggaatca    4500
tgttgtgca cggaattgct ggaactggga aaccacatt gcttaggact ttattttctg    4560
catacctag cttagttata ggttcaccta ggccttgtta cttagataaa gctaataaaa    4620
tttcacaggt ttgcctttct tgttttccaa ataccttgtg tgacattgtt gacgagtacc    4680
atctcttaga aagttttctt gaaccaaaac tagccatttt tggtgacccc tgtcagtgca    4740
cttacattga aaggttgaga atacccaact atacatcctt cagaacacac cgatttggca    4800
aatccactgc tgctctacta aacaagttat ttgatcttaa cattgagtca gtcaaagtac    4860
aaggcgacac agtagaatac tttgatcctt tcgcagtgga cccctctgaa cacatttctg    4920
cttcagaaaa agaagttttg gaatttgtag gtgatcaagt tgagactaca agctctgaag    4980
aactagctgg tttcgagttt agtgaagtta ctttctactg taccacactt gctggtgctg    5040
ttcaagaaaa tcctgccaaa accttcattt cacccactag acacacttca aagctcagaa    5100
ttggtgaact aaatgccagg tctgactcct agagctgatc ttactgacac gtacaaaatc    5160
attgctatag cctttctact gtcagcttgc atttacttcc aaaacagtca ttatcaacca    5220
gttgcaggtg ataatttgca cagactaccc ttcggtggtc agtatcaaga cggaactaag    5280
aagatttctt actttccgca gcaacaatct tactttcact caggaaacaa gcttaatgtc    5340
ctcatactta tcttcattct tacactgggt attgtcctca ccaatcaatt tagttttagc    5400
```

```
attagccgta atattcacca gcatcattgc tacaacacac attctgcaac ccaaacaggt   5460
caatcagtgc caggtcatca ttgacggtgc agccatagtt ataacaaatt gtccaaacac   5520
acccgaagtt cttaaagcaa tcaacttctc cccttggaac gggttaagtt ttcctcaatt   5580
gtgaaatcat attcattatc tagttaaatt taaacaattt aactcaacta tggaaaacca   5640
acctacagct tctaacccat cagatgcacc accaactgct gctcaagctg gtgcccagag   5700
cccagccgac ttctcaaatc ctaatacagc tccttcccta agtgatttga agaagatcaa   5760
atacgtgtca actgtcactt cagttgccac gcctgctgaa attgaagccc ttggcaagat   5820
ctttactgcc atgggtttag cagccaatga gaccggacct gccatgtggg acctcgctcg   5880
tgcttatgct gatgtgcaaa gttcaaaatc tgcacaactt ataggtgcca caccatccaa   5940
ccctgctttg tctagacgtg cacttgctgc acagtttgat cgtatcaata tcacacccag   6000
acaattctgc atgtattttg caaaaattgt ttggaacata ctgttagaca gcaatgtgcc   6060
acctgccaac tgggcaaaat tgggctatca ggaagatacc aagtttgctg cttttgactt   6120
ctttgatgga gtcacaaacc cagctagtct acagcctgca gatggcctaa ttaggcagcc   6180
caatgaaaaa gagcttgctg ctcactcggt tgctaaatat ggtgcccttg cccgccagaa   6240
aatatccact ggtaactaca tcaccaccct tggtgaagtt acacgtggtc acatgggcgg   6300
cgccaacact atgtacgcaa ttgatgcacc tcctgaactt taaacactcg aaacttaatc   6360
agagtggggt tttctatagt ttattttccc ttagtatcta aatctactaa at           6412
```

```
<210> SEQ ID NO 13
<211> LENGTH: 6439
<212> TYPE: DNA
<213> ORGANISM: Pepino mosaic virus

<400> SEQUENCE: 13
aaacaaaaca taacacataa tatcaaaagt gactaaacac aacataacca cgtggaaaaa     60
cagcgaaagc actttaccac attatgtctc gtgttagaaa cactttagaa aagatcaggg    120
acccacaagt acaatctagc atttgtgaag ccgcttacca acatgttaga cctgtgctca    180
aagaatccct aatcaactgt ccttatgcgc ttaatgacta tgaagcagac actcttgaga    240
atttaggtgt cacaataaac ccccatgcaa tccaaacaca tactcatgcg gcagctaaag    300
ttgtggaaaa tagaatgctc gaaattgttg gacaccactt gcccaaggac gagaaagtta    360
ctttcatttt cctcaaaaga agcaaactga gatacatgcg aagagctgct gtacataaag    420
atgtttttgt taatcacaat atagaaccca aggatttctt caggtatgat gaggaatcta    480
catctactag tttctctgtg aacaccagga tcgcttacat ctccgattct ctacatttca    540
tggaaccagc tgatgtgacc cacctctttg accgttgcca caatcttaaa acactgatgg    600
caactgtcgt tttacctgtt gaagccatcc acaaacaaac atctttattt ccagcgatat    660
actccattaa ttacaatgaa gaaggttttg agtatatccc tggttctcat ggtggagggg    720
catactttca taagtatgaa acattagact ggctcaaata ctctagattc attggccagg    780
accccttaac tggactccga tacaccataa ccattcaaat ggtggagagt ttaggagcca    840
accatctttt cctcttccaa cgaggaaatt ttgaaacacc tttatacagg acgtttcaaa    900
aaaatagctt tgtgaccttt cctaacatct tccatcccca acatgttaat gccacaaagc    960
ccatgccaag atccagggca attcagctgt atttatatgt caaatctgtc aataaggtga   1020
cacaaagaga tatctttgcg aaagtaaggc aacttatatc cacagctgaa cttgaattgt   1080
```

```
atgaccctga tgaacttaca catattgtca attattttgc atatgtctca gaactaagct   1140
caatcaacga ctatgacaat atgctcaaat caagtttttt caaaaaactt gttgcaccca   1200
tgcaacatga ctggaggtgc atgattgaat tctttcgggg aaaaagtgat ttcaatcaac   1260
ttttaactgc tcttcaatgg aaagacttct cttacaccat taaaactgaa gagttagtta   1320
ttgctacaca cactgaaatt ggccaggcaa tctgtaaagc tgcgaccaca tacaaagaaa   1380
gaagacaatt gaccaattta gtcaaacaag gcgcagtaac attagctgat ttcaaagaag   1440
cggaccagca tgtggagtac actcactttg atcctgagtt taaatccact gttgaacccc   1500
accggagcta tgaaaatgcc atcaacaatc ttggcattga gattaatgag gatgtacctg   1560
aaagttccgg cactaatgaa acattgctta acaatgaaat atctttagca atgtcatctg   1620
ctgaacatgt gcaagctgtt caagaaattg agtctttact ctctaaccac gaagcggcac   1680
caatattgcc ccctgcacat gttaaaacat gggctagcct tgcatctgac acttccagta   1740 ctaaaaccg tgaaatcgaa gatatagtgg ctaagctgga aatacaaaga atgaagcta   1800 gttgcagcta ccttcaacca aataaggaat tgtcaaaacc caaagctgct ggtaacaatc   1860 tccctggaa tgcttggatc ccattgctta atgcacacgg cttcaaagga gatcaattac   1920
aatacggccc agatggtaac ttgatacagc ccatccaaga cattaacaat tcacagccta   1980
gatctgacta tccgtcttct ctgccatgtg aacttgtgga aactttgagg aaaattaagc   2040
gtgctgtcta tgccatccca ataagccaca ggagggctag tcttacagt tctgacatca   2100 aaaataacag aactggcaaa cttctctgca accaaagcaa agaatggaaa gaaagctttg   2160 cttttcaaaat gcaacatgaa gacatcgtca atcaggtgt tgtcatacat ggttgcggag   2220
gttctggcaa atcccaggca ttacaaaact tcttgagaac attgggtgat tcaaatgatt   2280
gctgtactgt tgtagtaccc actgttgaac ttagaaatga ctgggtaaac aaactccata   2340
aattgcccat ggagcatatc aaaacgtttg agaaagcaat gattcaacct ggctttccaa   2400
ttgttatatt tgatgattac accaagttgc cacctggtta cattgaagca tacctatttc   2460
accatgccaa cactgagctt tttatactta ctggcgattc taggcaaagc gtgtaccacg   2520
aatctaacaa tgaagcgtac attgcctcat tagatgaagc tgttgcatac tacgctaatt   2580
actgcggttt ttatttaaat gctactcata gaaatgtccg tagtttagcc aacaaacttg   2640
gtgtttacag tgagaaagaa ggacacctga aaatcacttt tgcttcacat gcattacaaa   2700
agtgcaaagt gccaattta gttccttctc aaatgaaaaa gagtgctatg ttagacattg   2760
gacataaatc catgacctat gctggttgcc aaggtttaac agcacccaag gtacaaattc   2820
tccttgataa ccacacgcaa cattgctctg acagagttct gtacacctgt ctgtctcgtg   2880
cagttgattc catccacttc atcaatactg gccccaacaa ttcagaattt tgggataagc   2940
ttgaagcaac accatatctc aaagccttca ttgatgtcta tagagatgaa aaaactgaaa   3000
tgctcaattc taagcctgct gacgacagtc caactgagcc tgaagcacct gttacacatt   3060
tcccaatagc aaatggaaat aacttagaga aattagcttc tgctttgcct gaaaaatttg   3120
ctagggaaat ttatgacaag catcatggcc actccaacac aatccaaact gagaatcctg   3180
tggtccaact tttccaacat caacaagcga agacgagac actcttttgg ctacaattg   3240 aagctagatt gtccataaca actcctgaag caaacctcag agaattttg cttaagaaag   3300 atgttggaga cattctcttc ttcaattacc ataatgcgat gtgcttgcct gctgatcctg   3360
ttgactttga agaaagacc tgggagatct gtgctgctga agtgaaaaac acttatcttg   3420
ccaaacccat ggccaatctt atcaatgctg caagtagaca atcacccgac tttgactcta   3480
```

```
ataagatctc attattccta aagtctcaat gggtgaaaaa agtggaaaaa cttggagcta    3540
tcaaatcaaa acctggtcag accatagctg cttttatgca acaaacagtc atgttgtatg    3600
gtactatggc caggtactta aggaaaatgc ggcaaagatt ccagccaaaa cacatattca    3660
tcaattgtga aaccacaact gatgatctca ataaatttgt caaagatggc tggaacttta    3720
acagaaccgc ccaaacaaat gacttcactg cttttgatca gtcacaagat ggagcaatgc    3780
ttcaatttga agtcatgaaa gcaaaatttt ttaacattcc agctgatgtc attgaaggct    3840
acatcaacat caagctgaat gctaaaattt tccttggaac actctcaata atgagacttt    3900
ctggtgaagg tcccacattt gacgctaaca ctgagtgttc gattgcatac actgccacaa    3960
gattccatat tgacaatact gttaagcaag tgtatgccgg tgacgacatg gcattagatg    4020
gagttgtgag tgaaaagaag tcgttcagga agttacaaaa tctactaaaa ctcacttcaa    4080
aaacgctgta cccaaaacag gttaaagggg attacgctga attttgtggt tggactttca    4140
caccaggggg tataattaaa aatccactta aaatgcatgc ctcaattatg ctgcaagaag    4200
ccattggcaa tctgcacaca gcagccagat cttatgcaat tgacatgaag cattcatacc    4260
aaatgggtga ccaactgcat gactacctaa ccccgatga agctgaacaa catttcctag    4320
ctgtgagaaa gcttcacaaa ctccatcaag gcgaggccat gcgtcttggg gagaaaagtc    4380
caccaagatc aacccattaa ggggttaagt tttccccagt ttgaaatgga aagatcaact    4440
ttgatcaatt tacttctgtt acacaaattt gaacacaaga ttaacactga aggaatcatt    4500
gttgtgcacg gaattgctgg aactgggaaa accacattgc ttaggacttt attttctgca    4560
taccctagct tagttatagg ttcacctagg ccttgttact tagataaagc taataaaatt    4620
tcacaagttt gccttttcttg ttttccaaat accttgtgtg acattgttga cgagtaccat    4680
ctcttagaaa gttttcctga accaaaacta gccatttttg gtgaccctg tcagtgcact    4740 tacattgaaa ggttgagaac acccaactac acatccttca gaacacaccg atttggcaaa    4800
tccactgctg ctctactaaa caagttattt gatcttaaca ttgagtcagt caaagcacaa    4860
gacgacacag tagaatactt tgatcctttc gcagtggacc cctctgaaca catttctgct    4920
tcagaaaaag aagttttgga atttgtaggt gatcaagttg agactacaag ctctgaagaa    4980
ctagctggtc tagagtttag tgaagttact ttctactgta ccacacttgc tggtgctgtc    5040
caagaaaatc ctgccaaaac cttcatttca ctcactagac acacttcaaa gctcacaatt    5100
ggtgaactaa atgccaggtc tgactcctag agctgatctt actgacacgt acaaaatcat    5160
tgctatagcc tttctactgt cagcttgcat ttacttccaa aacagtcatt atcaaccagt    5220
tgcaggtgat aatttgcaca gactacccctt tggtggtcag tatcaagacg gaactaagaa    5280
gatttcttac tttccgcagc aacaatccta ctttcactca ggaaacaagc ttaatgtcct    5340
catacttatc ttcattctta cactgggtat tgtcctcacc aataaattta gttttagtat    5400
tagccgtaat actcaccagc atcattgcta caacacacat tctgcaaccc aaacaggtca    5460
atcagtgcca ggtcatcatt gacggtgcag ccatagttat aacaaattgt ccaaacacac    5520
ccgaagttct taaagcaatc aacttctccc cttggaacgg gttaagtttt cctcaattgt    5580
gaaatcatat ttgttatcta gttaaattca acaatttaa ctcaactatg gaaaccaac    5640 ctacagcttc taactcatca gatgcaccac caactgctgc tcaagctggt gcccagagcc    5700
cagccgactt ctcaaatcct aatacagctc cttccctaag tgatttgaag aagatcaaat    5760
acgtgtcaac tgtcacttca gttgccacgc ctgctgaaat tgaggccctt ggcaagatct    5820
ttactgccat gggtttagca gccaatgaga ccggacctgc catgtgggac ctcgctcgtg    5880
```

| | |
|---|---:|
| cttatgctga tgtgcaaagt tcaaaatctg cacaacttat aggtgccaca ccatccaacc | 5940 |
| ctgctttgtc tagacgtgca cttgctgcac agtttgatcg tatcaatatc acacccagac | 6000 |
| aattctgcat gtattttgca aaaattgttt ggaacatact gttagacagc aatgtgccac | 6060 |
| ctgccaactg gcaaaattg ggctatcagg aagataccaa gtttgctgct ttcgacttct | 6120 |
| ttgatggagt cacaaatcca gctagtctac agcctgcaga tggcctaatc aggcagccca | 6180 |
| atgaaaaga gcttgctgct cactcggttg ctaaatatgg tgcccttgcc cgccagaaaa | 6240 |
| tatccactgg taactacatc accacccttg gtgaagttac acgtggtcac atgggcggcg | 6300 |
| ccaacactat gtacgcaatt gatgcacctc ctgaacttta aacactcgaa acttaatcag | 6360 |
| agtgggtttt tctatagttt attttccctt agtataaaaa aaaaaaaaaa aaaaaaaaaa | 6420 |
| aaaaaaaaaa aaaaaaaa | 6439 |

<210> SEQ ID NO 14
<211> LENGTH: 6412
<212> TYPE: DNA
<213> ORGANISM: Pepino mosaic virus

<400> SEQUENCE: 14

| | |
|---|---:|
| gaaaacaaaa cataacacat aatatcaaaa gtgacctaac acaacataac cacgtggaaa | 60 |
| aacagcgaaa gcactttacc acattatgtc tcgtgttaga aacactttag aaaagatcag | 120 |
| ggacccacaa gtacaatcta gcatttgcga agccgcttac caacatgtta gacctgtgct | 180 |
| caaggaatcc ctaatcaact gtccttatgc gcttaatgac tatgaagcag acacccttga | 240 |
| gaatttaggt gtcacaataa accccatgc aatccaaaca catactcatg cagcagctaa | 300 |
| agttgtggaa atagaatgc tcgaaattgt tggacaccac ttgcccaagg acgagaaagt | 360 |
| taccttcatt ttcctcaaaa gaagcaaact gagatacatg cgaagagctg ctgtacataa | 420 |
| agatgttttt gttaatcaca atatagaacc caaagatttc ttcaggtatg atgaggaatc | 480 |
| tacatctact agtttctccg tgaacaccag gatcgcttac atctccgatt ctctacattt | 540 |
| catggaacca gctgatgtga cccacctctt tgaccgttgc cacaatctta aacactgat | 600 |
| ggcaactgtc gtttttacctg ttgaagccat ccacaaacaa acatctttat tccagcgat | 660 |
| atactccatt aattacaatg aagaaggttt tgagtatatc cctggttctc atggtggagg | 720 |
| ggcatacttt cataagtatg aaacattaga ctggctcaaa tactctagat tctttggcca | 780 |
| ggacccctta actggactcc gatacaccat aaccattcaa atggtggaga gtttaggagc | 840 |
| caaccatctt tcctcttcc aaagaggaaa ttttgaaaca cctttataca ggacgtttca | 900 |
| aaaaaatagc tttgtgacct ttcctaacat cttccatccc caacatgtta atgccacaaa | 960 |
| gcccatgcca agatccaggg caattcagct gtatttatat gtcaaatctg tcaataaggt | 1020 |
| gacacaaaga gatatctttg cgaaagtaag gcaacttata tctacagctg aacttgaatt | 1080 |
| gtatgacccct gatgaactta cacatattgt caattatttc gcatatgtct cagaattaag | 1140 |
| ctcaatcaac gactatgaca atatgcttaa atcaagtttt ttcaaaaaac ttgttgcacc | 1200 |
| catgcaacat gactggaggt gcatgattga attctttcgg ggaaaaagtg atttcaatca | 1260 |
| acttttaact gctcttcaat ggaaagactt ctccttacacc attaaaactg aagagttagt | 1320 |
| tatttctaca cacactgaaa ttggccaggc aatctgtaaa gctgcgacca catacaaaga | 1380 |
| aagaagacaa ttgaccaatt tagtcaaaca aggcgcagta acattagctg atttcaaaga | 1440 |
| agcggaccag catgtggagt acactcactt tgatcctgag tttaaatcca ctgttgaccc | 1500 |
| ccaccggagc tatgaaaatg ccatcaacaa tcttggcatt gagattaatg aggatgtacc | 1560 |

```
tgaaagttcc ggcactaatg aaacattgct taacaatgaa atatctttag caatgtcatc    1620
tgctgaacat gtgcaagctg ttcaagaaat tgagtcttta ctctctaacc ccgaagcggc    1680
accaatattg cccctgcac acgttaaaac atgggctagc cttgcatctg acacttccag    1740
cactaaaaac cgtgaaatcg aagatatagt ggctaagctg gaaatacaaa gaaatgaagc    1800
tagttgcagc taccttcaac caaataagga attgtcaaaa cccaaggctg ctgataacaa    1860
tctcccctgg aatgcttgga tcccattgct taatgcacac ggcttcaaag gagatcaatt    1920
acaatacggc ccagatggta acttgataca gcccatccaa gacattaaca attcacagcc    1980
tagatctgac tatccgtctt ctctgccatg tgaacttgtg gaaactttga ggaaaattaa    2040
gcgtgctgtc tatgccatcc caataagcca caggagggct agtgcttaca gttctgacat    2100
caaaaataac agaactggca aacttctctg caaccaaagc aaagaatgga agaaagctt    2160 tgctttcaaa atgcaacatg aagacatcgt caaatcaggt ggtgtcatac atggttgcgg    2220
agggtctggc aaatcccagg cattacaaaa cttcttgaga acattgggtg attcaaatga    2280
ttgctgtact gttgtagtac ccactgttga acttagaaat gactgggtaa acaaactcca    2340
taaattgccc atggagcata tcaaaacatt tgagaaagca atgattcaac ctggctttcc    2400
agttgttata tttgatgatt acaccaagtt gccacctggc tacattgaag catacctact    2460
tcaccatgcc aacactgagc ttttcatact tactggtgat ctaggcaaaa gcgtgtacca    2520 tgaatcaac aatgaagcgt acattgcctc attagatgaa gctgttgcat actacgctaa    2580
ttactgcggg ttttatttaa atgctactca tagaaatgtc cgtagtttag ccaacaaact    2640
tggtgtttac agtgagaaag aaggacactt gaaaatcact tttgcttcac atgccttaca    2700
aaagtgcaaa gtgccaattt tagttccttc tcaaatgaaa aagagtgcta tgttagacat    2760
tggacataaa tccatgacct atgctggttg ccaaggttta acagcaccca aggtacaaat    2820
tctccttgat aaccacacgc aacattgctc tgacagagtt ctgtacacct gtctgtctcg    2880
tgcagttgat tctatccact tcatcaatac tggtcccaac aattcagaat tttgggataa    2940
gcttgaggca acaccatacc tcaaagcctt cattgatgtc tatagagatg aaaaaactga    3000
aatgctcaat tctaagcctg ctgatgacag tccaactgag cctgaagcac tgttacaca    3060 tttcccaata gcaaatggaa ataacttaga gaaattagct tctgctttgc ctgaaaaatt    3120
tgctagggag atttatgtca agcatcatgg ccactccaac acaatccaaa ctgagaaccc    3180
tgtggtccaa cttttccaac atcaacaagc gaaagacgag acactctttt gggccacaat    3240
tgaagctaga ttgtccataa caactcctga agcaaacctc agagaatttt tgcttaagaa    3300
agatgttgga gacattctct tcttcaatta ccataatgcg atgtgcttgc ctgccgatcc    3360
tgttgacttt gaagaaaaga cctgggagat ctgtgctgct gaagtgaaaa acacttatct    3420
tgccaaaccc atggccaatc ttatcaatgc cgcaagtaga caatcacccg actttgactc    3480
taataagatc tcattattcc taaagtctca atggggttaaa aaagtggaaa acttggagc    3540 tatcaaatcg aaacctggtc agtccatagc tgctttatg caacaaacag tcatgttgta    3600
tggtactatg gccaggtatt taaggaaaat gcggcaaaga ttccagccaa aacacatatt    3660
catcaattgt gaaaccacaa ccgatgatct caataaattt gtcaaagatg gcgggaactt    3720
taacagaacc gcccaaacaa atgacttcac tgcttttgat cagtcgcaag atggagcaat    3780
ggttcaattt gaagtcatga aagcaaaatt ttttaacatt ccagctgatg tcattgaagg    3840
ctacatcaac atcaagttga atgctaaaat tttccttgga acactctcaa taatgagact    3900
ttctggtgaa ggtcccacat ttgatgataa cactgagtgt tcgattgcat acagtgccac    3960
```

```
aagattccat attgacaaca ctgttaagca agtgtatgcc ggtgacgaca tggcattaga    4020
tggagttgtg agtgaaaaga aatcattcag gaagttacaa aatctactaa aactcacttc    4080
aaaaacgctg tacccaaaac aggttaaagg ggattacgct gaattttgtg gttggacttt    4140
cacaccaggg ggtataatta aaaatccact taaaatgcat gcctcaatta tgctgcaaga    4200
agccattggc aatctgcaca cagcagccag atcttatgca attgacatga agcattcata    4260
ccaaatgggt gaccaactgc atgactacct aaccccgat gaagctgaac aacatttcct     4320
agctgtgaga aagcttcaca aactccatca aggcgaggcc atgcgtcttg gggagaaaag    4380
tccaccaaga tcaacccatt aaggggttaa gttttcccca gtttgaaatg gaaagatcaa    4440
ctttgatcaa tttacttctg ttacacaaat ttgaacacaa gattaacact gaaggaatca    4500
ttgttgtgca cggaattgct ggaactggga aaaccacatt gcttaggact ttattttctg    4560 catacccta g cttagttata ggttcaccta ggccttgtta cttagataaa gctaataaaa    4620
tttcacaagt ttgcctttct tgttttccaa ataccttgtg tgacattgtt gacgagtacc    4680
atctcttaga aagttttcct gaaccaaaac tagccatttt tggtgacccc tgtcagtgca    4740
cttacattga taggttgaga acacccaact acacatcctt cagaacacac cgatttggca    4800
aatccactgc tgctctacta aacaagttat ttgatcttaa cattgagtca gtcaaagcac    4860
aagacgacac agtagaatac tttgatcctt tcgcagtgga cccctccgaa cacatttctg    4920
cttcagaaaa agaagttttg gaatttgtag gtgatcaagt tgagactaca agctctgaag    4980
aactagctgg tctcgagttt agtgaagtta cttttctactg taccacactt gctggtgctg    5040
ttcaagaaaa tcctgccaaa accttcattt cactcactag acacacttca aagctcacaa    5100
ttggtgaact aaatgccagg tctgactcct agagctgatc ttactgacac gtataaaatc    5160
attgctatag cctttctact gtcagcttgc atttacttcc aaaacagtca ttatcaacca    5220
gttgcaggtg ataatttgca cagactaccc tttggtggtc agtatcaaga cggaactaag    5280
aagatttctt actttccgca caacaatcc tactttcact caggaaacaa gcttaatgtc     5340
ctcatactta tcttcattct tacactgggt attgtcctca ccaataaatt tagttttagc    5400
attagccgta atactcacca gcatcattgc tacaacacac attctgcaac ccaaacaggt    5460
caatcagtgc caggtcatca ttgacggtgc agccatagtt ataacaaatt gtccaaacac    5520
acccgaagtt cttgaagcaa tcaacttctc cccttggaac gggttaagtt ttcctcaatt    5580
gtgaaattat atttgttatc tagttaaatt caaacaattt aactcaacta tggaaaacca    5640
acctacagct tctaacccat cagatgcacc accaactgct gctcaagctg gtgcccagag    5700
cccagccgac ttctcaaatc ctaatacagc tccttcccta agtgatttga agaagatcaa    5760
atacgtgtca actgtcactt cagttgccac gcctgctgaa attgaggccc ttggcaagat    5820
ctttactgcc atgggtttag cagccaatga gaccggacct gccatgtggg acctcgctcg    5880
tgcttatgct gatgtgcaaa gttcaaaatc tgcacaactt ataggtgcca caccatccaa    5940
ccctgctttg tctagacgtg cacttgctgc acagtttgat cgtatcaata tcacacccag    6000
acaattctgc atgtattttg caaaaattgt ttggaacata ctgttagaca gcaatgtgcc    6060
acctgccaac tgggcaaaat tgggctatca ggaagatacc aagtttgctg cttttgactt    6120
ctttgatgga gtcacaaatc cagctagtct acagcctgca gatggcctaa tcaggcagcc    6180
caatgaaaaa gagcttgctg ctcactcggt tgctaaatat ggcgcccttg cccgccagaa    6240
aatatccact ggtaactaca tcaccaccct tggtgaagtt acacgtggtc acatgggcgg    6300
```

```
cgccaacact atgtacgcaa ttgatgcacc tcctgaactt taaacactcg aaacttaacc    6360
agagtggggt tttctatagt ttattttccc ttagtatcta aatctactaa at            6412

<210> SEQ ID NO 15
<211> LENGTH: 6412
<212> TYPE: DNA
<213> ORGANISM: Pepino mosaic virus

<400> SEQUENCE: 15
gaaaacaaaa cataacacat aatatcaaaa gtgacctaac acaacataac cacgtggaaa      60
aacagcgaaa gcactttacc acattatgtc tcgtgttaga aacactttag aaaagatcag     120
ggacccacaa gtacaatcta gcatttgtga agccgcttac caacatgtca gacctgtgct     180
caaggaatcc ctaatcaact gtccttatgc gcttaatgac tatgaagcag acacccttga     240
gaatttaggt gtcacaataa accccatgc  aatccaaaca catactcatg cggcagctaa     300
agttgtggaa aatagaatgc tcgaaattgt tggacaccac ttgcccaagg acgagaaagt     360
taccttcatt ttcctcaaaa gaagcaaact gagatacatg cgaagagctg ctgtacataa     420
agatgttttt gttaatcaca atatagaacc caaggatttc ttcaggtatg atgaggaatc     480
tacatctact agtttctccg tgaacaccag gatcgcttac atctccgatt ctctacattt     540
catggaacca gctgatgtga cccacctctt tgaccgttgc cacaatctta aaacactgat     600
ggcaactgtc gttttacctg ttgaagccat ccacaaacaa acatctttat ttccagcgat     660
atactccatt aattacaatg aagaaggttt tgagtatatc cctggttctc atggtggagg     720
ggcatacttt cataagtatg aaacattaga ctggctcaaa tactctagat tgttggcca     780 ggaccccttta actggactcc gatacaccat aaccattcaa atggtagaga gtttaggagc     840
caaccatctt ttcctcttcc aaagaggaaa ttttgaaaca cctttataca ggacgtttca     900
aaaaaatagc tttgtgacct ttcctaacat cttccatccc caacatgtta atgccacaaa     960
gcccatgcca agatccaggg caattcagct gtatttatat gtcaaatctg tcaataaggt    1020
gacacaaaga gatatctttg cgaaagtaag gcaacttata tctacagctg aacttgaatt    1080
gtatgaccct gatgaactta cacatattgt caattatttc gcatatgtct cagaactaag    1140
ctcaatcaac gactatgaca atatgctcaa atcaagtttt tcaaaaaaac ttgttgcacc    1200
catgcaacat gactggaggt gcatgattga attctttcgg ggaaaaagtg atttcaatca    1260
acttttaact gctcttcaat ggaaagactt ctcttacacc attaaaactg aagagttagt    1320
tgttgctaca cacactgaaa ttggccaggc aatctgtgaa gctgcgacca catacaaaga    1380
aagaagacaa ttgaccaatt tagtcaaaca aggcgcagta acattagctg atttcaaaga    1440
agcggaccag catgtggagt acactcactt tgatcctgag tttaaatcca ctgttgaccc    1500
ccaccagagc tatgaaaatg ccatcaacaa tcttggcatt gaaattaatg aggatgtacc    1560
tgaaagttcc ggcactaata aaacattgct taacaatgaa atatctttag caatgtcatc    1620
tgctgaacat gtgcaagctg ttcaagaaat tgagtctttta ctctctaacc ccgaagcggc    1680
accaatattg ccccctgcac atgttaaaac atgggctagc cttgcatctg acacttccag    1740
cactaaaaac cgtgaaatcg aagatatagt ggctaagctg gaaatacaaa gaatgaagc     1800 tagttgcagc taccttcaac caaataagga attgtcaaaa cccaaggctg ctgataacaa    1860
tctcccctgg aatgcttgga tcccattgct taatgcacac ggcttcaaag gggatcaatt    1920
acaatacggc ccagatggta acttgataca gcccatccaa gacattaaca attcacagcc    1980
tagatctgac tatccgtctt ctctgccatg tgaacttgtg gaaactttga ggaaaattaa    2040
```

```
gcgtgctgtc tatgccatcc caataagcca caggagagct agtgcttaca gttctgacat    2100
caaaaataac agaactggca aacttctctg caaccaaagc aaagaatgga aagaaagctt    2160 tgcttcaaa atgcaacatg aagacatcgt caaatcaggt gttgtcatac atggttgcgg    2220
aggttctggc aaatcccagg cattacaaaa cttcttgaga acattgggtg attcaaatga    2280
ttgctgtact gttgtagtac ccactgttga acttagaaat gactgggtaa acaaactcca    2340
taaattgccc atgagcata tcaaaacatt tgagaaagca atgattcaac ctagcttcc     2400 aattgttata tttgatgatt acaccaagtt gccacctggc tacattgaag catacttatt    2460
tcaccatgcc aacactgagc ttttcatact tactggtgat tctaggcaaa gcgtgtacca    2520
tgaatctaac aatgaagcgt acattgcctc attagatgaa gctgttgcat actacgctaa    2580
ttactgcggt ttttatttaa atgctactca tagaaatgtc cgtagtttgg ccaacaaact    2640
tggtgtttac agtgagaaag aaggacactt gaaaatcact tttgcttcac atgccttaca    2700
aaagtgcaaa gtgccaattt tagttccttc tcaaatgaaa aagagtgcta tgttagacat    2760
tggacataaa tccatgacct atgctggttg ccaaggttta acagcaccca gggtacaaat    2820
tctccttgat aaccacacgc aacattgctc tgacagagtt ctgtacacct gtctgtctcg    2880
tgcagttgat tccatccatt tcatcaatac tggtccaac aattcagaat ttgggataa     2940 gcttgaagca acaccatatc tcaaagcctt cattgatgtc tatagagatg aaaaaactga    3000
aatgctcaat tctaagcctg ctgatgacag tccaactgag cctgaagcac tgttacaca    3060 tttcccaata gcaaatggaa ataacttaga gaaattagct tctgctttgc ctgaaaaatt    3120
tgctagggag atttatgacc agcatcatgg ccactccaac acaatccaaa ctgagaaccc    3180
tgtggtccaa cttttccaac atcaacaagc gaaagacgag acactctttt gggctacaat    3240
tgaagctaga ttgtccataa caactcctga agcaaacctc agagaatttt tgcttaagaa    3300
agatgttgga gacattctct tcttcaatta ccataatgcg atgtgcttgc ctgccgatcc    3360 tgtggactt gaagaaaaga cctgggagat ctgtgctgct gaagtgaaaa acacttatct    3420
tgccaaaccc atggccaatc ttatcaatgc ggcaagtaga caatcacccg actttgactc    3480
taataagatc tcattattcc taaagtctca atgggtgaaa aaagtggaaa acttggagc    3540 tatcaaatca aaacctggtc agaccatagc tgcttttatg caacaaacag tcatgttgta    3600
tggtactatg gccaggtact taaggaaaat gcggcaaaga ttccagccaa acacatatt    3660 catcaattgt gaaaccacaa ctgatgatct caataaattt gtcaaagatg gctggaactt    3720
taacagaacc gcccaaacaa atgacttcac tgcttttgat cagtcacaag atggagcaat    3780
gcttcaattt gaagtcatga agcaaaaatt ttttaacatt ccagctgatg tcattgaagg    3840
ctacatcaac atcaagctga atgctaaaat tttccttgga acactctcaa taatgagact    3900
ttctggtgaa ggtcccacat tgacgctaa cactgagtgt tcgattgcat acactgccac    3960
aagattccat attgacaata ctgttaagca agtgtatgcc ggtgacgaca tggcattaga    4020
tggagttgtg agtgaaaaga atcattcag gaagttacaa atctactaa aactcacttc     4080 aaaaacgctg tacccaaaac aggttaaagg ggattacgct gaattttgtg gttggacttt    4140
cacaccaggg ggtataatta aaaatccact taaaatgcat gcctcaatta tgctgcaaga    4200
agccattggc aatctgcaca cagcagccag atcttatgca attgacatga agcattcata    4260
ccaaatgggt gaccaactgc atgactacct aaccccgat gaagctgaac aacatttcct    4320
agctgtgaga aagcttcaca aactccatca aggcgaggcc atgcgtcttg gggagaaaag    4380
tccaccaaga tcaacccatt aaggggttaa gttttccca gtttgaaatg gaaagatcaa     4440
```

```
ctttgatcaa tttacttctg ttacacaaat ttgaacacaa gattaacact gaaggaatca      4500
ttgttgtgca cggaattgct ggaactggga aaaccacatt gcttaggact ttatttccg       4560 catacccctag cttagttata ggttcaccta ggccttgtta cttagataaa gctaataaaa    4620
tttcacaagt ttgcctttct tgttttccaa ataccttgtg tgacattgtt gacgagtatc     4680
atctcttaga aagttttcct gaaccaaaac tagccatttt tggtgacccc tgtcagtgca     4740
cttacattga aaggttgaga acacccaact acacatcctt cagaacacac cgatttggca    4800
aatccactgc tgctctacta aaccagttat ttgatcttaa cattgagtca gtcaaagcac    4860
aagacgacac agtagaatac tttgatcctt cgcagtggaa cccctctgaa cacatctctg    4920
cttcagaaaa agaagttttg gaattcgtag gtgatcaagt tgagactaca agctctgaag   4980
aactagctgg tctcgagttt agtgaagtta ctttctactg taccacactt ggcggtgctg   5040
ttcaagaaaa tcctgccaaa accttcattt cactcactag acacacttca aagctcacaa   5100
ttggtgaact aaatgccagg tctgactcct agagctgatc ttactgacac gtataaaatc   5160
attgctatag cctttctact gtcagcttgc atttacttcc aaaacagtca ttatcaacca   5220
gttgcaggtg ataatttgca cagactaccc tttggtggtc agtatcaaga cggaactaag   5280
aagatttctt actttccgca gcaacaatcc tactttcact caggaaacaa gcttaatgtc   5340
ctcatactta tcttcattct tacactgggt attgtcctca ccaataaatt tagttttagc   5400
attagccgta atactcacca gcatcattgc tacaacacac attctgcaac ccaaacaggt   5460
caatcagtgc caggtcatca ttgacggtgc agccatagtt ataacaaatt gtccaaacac   5520
accagaagtg cttaaagcaa tcaacttctc cccttggaac gggttaagtt ttcctcaatt   5580
gtgaaattat atttgttatc tagttaaatt caaacaattt aactcaacta tggaaaacca   5640
acctacagct tctaacccat cagatgcacc accaactgct gctcaagctg gtgcccagag   5700
cccagccgac ttctcaaatc ctaatacagc tccttcccta agtgatttga agaagatcaa   5760
atacgtgtca actgtcactt cagttgccac gcctgctgaa attgaggccc ttggcaagat   5820
ctttactgcc atgggtttag cagccaatga gaccggacct gccatgtggg acctcgctcg   5880
tgcttatgct gacgtgcaaa gttcaaaatc tgcacaactt ataggtgcca caccatccaa   5940
ccctgctttg tctagacgtg cacttgctgc acagtttgat cgtatcaata tcacacccag   6000
acaattctgc atgtatttg caaaaattgt ttggaacata ctgttagaca gcaatgtgcc   6060
acctgccaac tgggcaaaat tgggctatca ggaagatacc aagtttgctg ctcttgactt   6120
ctttgatgga gtcacaaatc cagctagtct acagcctgca gatggcctaa tcaggcagcc   6180
caatgaaaaa gagcttgccg ctcactcggt tgctaaatat ggtgcccttg cccgccagaa   6240
aatatccact ggcaactaca tcaccaccct tggtgaagtt acacgtggtc acatgggcgg   6300
cgccaacact atgtacgcaa ttgatgcacc tcctgaactt taaacactcg aaacttaacc   6360
agagtggggt tttctatagt ttattttccc ttagtatcta aatctactaa at            6412
```

<210> SEQ ID NO 16
<211> LENGTH: 6231
<212> TYPE: DNA
<213> ORGANISM: Pepino mosaic virus

<400> SEQUENCE: 16

```
ctagcatttg tgaagccgct taccaacatg ttagacctgt gctcaaggaa tccctaatca      60
actgtcctta tgcgcttaat gactatgaag cagacaccct tgagaattta ggtgtcacaa     120
taaaccccca tgcaatccaa acacatactc atgcggcagc taaagttgtg gaaaatagaa     180
```

```
tgctcgaaat cgttggacac cacttgccca aggacgagaa agttaccttc attttcctca    240
aaagaagcaa actgagatac atgcgaagag ctgctgtaca taaagatgtt tttgttaatc    300
acaatataga acccaaggat tcttcaggt  atgatgagga atctacatct actagtttct    360
ccgtgaacac caggatcgct tacatctccg attctctaca tttcatggaa ccagctgatg    420
tgacccacct ctttgaccgt tgccacaatc ttaaaacact gatggcaact gtcgttttac    480
ctgttgaagc catccacaaa caaacatctt tatttccagc gatatactcc attaattaca    540
atgaagaagg ttttgagtat atccctggtt ctcatggtgg aggggcatac tttcataagt    600
atgaaacatt agactggctc aaatactcta gattcattgg ccaggacccc ttaactggac    660
tccgatacac cataaccatt caaatggtag agagtttagg agccaaccat cttttcctct    720
tccaaagagg aaattttgaa acacctttat acaggacgtt tcaaaaaaat agctttgtga    780
cctttcctaa catcttccat ccccaacatg ttaatgccac aaagcccatg ccaagatcca    840
gggcaattca gctgtattta tatgtcaaat ctgtcaataa ggtgacacaa agagatatct    900
ttgcgaaagt aaggcaactt atatctacag ctgaacttga attgtatgac cctgatgaac    960
ttacacatat tgtcaattat ttcgcatatg tctcagaact aagctcaatc aacgactatg   1020
acaatatgct caaatcaagt tttttcaaaa aacttgttgc acccatgcaa catgactgga   1080
ggtgcatgat tgaattcttt cggggaaaaa gtgatttcaa tcaactttta actgctcttc   1140
aatgaaaga cttctcttac accattaaaa ctgaagagtt agttgttgct acacacactg   1200
aaattggcca ggcaatctgt gaagctgcga ccacatacaa agaaagaaga caattgacca   1260
atttagtcaa acaaggcgca gtaacattag ctgatttcaa agaagcggac cagcatgtgg   1320
agtacactca ctttgatcct gagtttaaat ccactgttga ccccaccgg  agctatgaaa   1380
atgccatcaa caatcttggc attgagatta atgaggatgt acctgaaagt tccggcacta   1440
atraaacatt gcttaacaat gaaatatctt tagcaatgtc ayctgctgaa catgtgcaag   1500
ccgttcaaga aattgagtct ttactctcta accccgaagc ggcaccaata ttgcccctg    1560
cacatgttaa acatgggct  agccttgcat ctgacayttc cagcactaaa aaccgtgaaa   1620
tcgaagatat agtggctaag ctggaaatac aaagaaatga agctagttgc agctaccttc   1680
aaccaaataa ggaattgtca aaacccaagg ctgctgataa caatctcccc tggaatgctt   1740
ggatcccatt gcttaatgca cacggcttca aaggagatca attacaatac ggcccagatg   1800
gtaacttgat acagcccatc caagacatta caattcaca  gcctagatct gactatccgt   1860
cttctctgcc atgtgaactt gtggaaactt tgaggaaaat taagcgtgct gtctatgcca   1920
tcccaataag ccacaggaga gctagtgctt acagttctga catcaaaaat aacagaactg   1980
gcaaacttct ctgcaaccaa agcaaagaat ggaaagaaag ctttgctttc aaaatgcaac   2040
atgaagacat cgtcaaatca ggtgttgtca tacatggttg cggaggttct ggcaaatccc   2100
aggcattaca aaacttcttg agaacattgg gtgattcaaa tgattgctgt actgttgtag   2160
tacccactgt tgaacttaga aatgactggg taaacaaact ccataaattg cccatggagc   2220
atatcaaaac atttgagaaa gcaatgattc aacctggctt tccaattgtt atatttgatg   2280
attacaccaa gttgccacct ggctacattg aagcatacct atttcaccat gccaacactg   2340
agcttttcat actcactggt gattctaggc aaagcgtgta ccatgaatct aacaatgaag   2400
cgtacattgc ctcattagat gaagctgttg catactacgc taattactgc ggttttttatt  2460
taaatgctac tcatagaaat gtccgtagtt tagccaacaa acttggtgtt tacagtgaga   2520
aagaaggaca cttgaaaatc acttttgctt cacatgcctt acaaaagtgc aaagtgccaa   2580
```

```
ttttagttcc ttctcaaatg aaaaggagtg ctatgtyaga cattggacat aaatccatga   2640
cctatgctgg ttgccaaggt ttaacagcac ccaaggtaca aattctcctt gataaccaca   2700
cgcaacattg ctctgacaga gttctgtaca cctgtctgtc tcgtgcagtt gattccatcc   2760
acttcattaa tactggtccc aacaattcag aattttggga taagcttgaa gcaacaccat   2820
atctcaaagc cttcattgat gtctatagag atgaaaaaac tgaaatgttc aattctaagc   2880
ctgctgatga cagtccaact gagcctgaag cacctgttac acatttccca atagcaaatg   2940
gaaataactt agagaaatta gcttctgctt tgcctgaaaa atttgctagg gagatttatg   3000
acaagcatca tggccactcc aacacaatcc aaactgagaa ccctgtggtc caacttttcc   3060
aacatcaaca agcgaaagac gagacactct tttgggctac aattgaagct agattgtcca   3120
taacaactcc tgaagcaaac ctcagagaat ttttgtttaa gaaagatgtt ggagacattc   3180
tcttcttcaa ttaccataat gcgatgtgct tgcctgccga ccctgttgac tttgaagaaa   3240
agacctggga gatctgtgct gctgaagtga aaaacactta tcttgccaaa cccatggcca   3300
atcttatcaa tgcggcaagt agacaatcac ccgactttga ctctaataag atctcattat   3360
tcctaaagtc tcaatgggtg aaaaagtgg aaaaacttgg agctatcaaa tcaaaacctg   3420
ggcagaccat agctgctttt atgcaacaaa cagtcatgtt gtatggtact atggccaggt   3480
acttaaggaa aatgcggcaa agattccagc caaaacacat attcatcaat tgtgaaacca   3540
caactgatga tctcaataaa tttgtcaaag ayggctggaa ctttaacaga accgcccaaa   3600
caaatgactt cactgctttt gatcagtcac aagatggagc aatgcttcaa tttgaagtca   3660
tgaaagcaaa attttttaac attccagctg atgtcattga aggctacatc aacatcaagc   3720
tgaatgctaa aattttcctt ggaacactct caataatgag actttctggt gaaggtccca   3780
catttgacgc taacactgag tgttcgattg catacactgc cacaagattc catattgaca   3840
atactgttaa gcaagtgtat gccggtgacg acatggcatt agatggagtt gtgagtgaaa   3900
agaaatcatt caggaagtta caaaatctac taaaactcac ttcaaaaacg ctgtacccaa   3960
aacaggttaa agggaattac gctgaatttt gtggttggac tttcacacca gggggtataa   4020
ttaaaaatcc acttaaaatg catgcctcaa ttatgctgca agaagccatt ggcaatctgc   4080
acacagcagc cagatcttat gcaattgaca tgaagcattc ataccaaatg ggtgaccaac   4140
tgcatgacta cctaaccccc gatgaagctg aacaacattt cctagctgtg agaaagcttc   4200
acaaactcca tcaaggcgag gccatgcgtc ttggggagaa aagtccacca agatcaaccc   4260
attaaggggt taagttttcc ccagtttgaa atggaaagat caacttttgat caatttactt   4320 ctgttacaca aatttgaaca caagattaac actgaaggaa tcattgttgt gcacggaatt   4380
gctggaactg ggaaaaccac attgcttagg acttttatttt ctgcataccc tagcttagtt   4440
ataggttcac ctaggccttg ttacttagat aaagctaata aaatttcaca agtttgcctt   4500
tcttgttttc caaatacctt gtgtgacatt gttgacgagt atcatctctt agaaagtttt   4560
cctgaaccaa aactagccat ttttggtgac ccctgtcagt gcacttacat tgaaaggttg   4620
agaacaccca actacacatc cttcagaaca caccgatttg gcaaatccac tgctgctcta   4680 ctaaccagt tatttgatct taacattgag tcagtcaaag cacaagacga cacagtagaa   4740
tactttgatc cttttcgcagt ggacccctct gaacacattt ctgcttcaga aaagaagtt   4800 ttggaatttg taggtgatca agttgagact acaagctctg aagaactagc tggtctcgag   4860
tttagtgaag ttacttttcta ctgtaccaca cttgctggtg ctgttcaaga aaatcctgct   4920
aaaaccttca tttcactcac tagacacact tcaaagctca caattggtga actaaatgcc   4980
```

```
aggtctgact cctagagctg atcttactga cacgtataaa atcattgcta tagcctttct    5040
actgtcagct tgcatttact tccaaaacag tcattatcaa ccagttgcag gtgataattt    5100
gcacagacta ccctttggtg gtcagtatca agacggaact aagaagattt cttactttcc    5160
gcagcaacaa tcctactttc actcaggaaa caagcttaat gtcctcatac ttatcttcat    5220
tcttacactg ggtattgtcc tcaccaataa atttagtttt agcattagcc gtaatactca    5280
ccagcatcat tgctacaaca cacattctgc aacccaaaca ggtcaatcag tgccaggtca    5340
tcattgacgg tgcagccata gttataacaa attgtccaaa cacacccgaa gttcttaaag    5400
caatcaactt ctccccttgg aacgggttaa gttttcctca attgtgaaat tatatttgtt    5460
atctagttaa attcaaacaa tttaactcaa ctatggaaaa ccaacctaca gcttctaacc    5520
catcagatgc accaccaact gctgctcaag ctggtgccca gagcccagcs gacttctcaa    5580
atcctaatac agctccttcc ctaagtgatt tgaagaagat caaatacgtg tcaactgtca    5640
cttcagttgc cacgcctgct gaaattgagg cccttggcaa gatctttact gccatgggtt    5700
tagcagccaa tgagaccgga cctgccatgt gggacctcgc tcgtgcttat gctgatgtgc    5760
aaagttcaaa atctgcacaa cttayaggtg ccacaccatc caaccctgct ttgtctagac    5820
gtgcacttgc tgcacagttt gatcgtatca atatcacacc cagacaattc tgcatgtatt    5880
ttgcaaaaat tgtttggaac atactgttag acagcaatgt gccacctgcc aactgggcaa    5940
aattgggcta tcaggaagat accaagtttg ctgcttttga cttctttgat ggagtcacaa    6000
atccagctag tctacagccy gcagatggcc taatcaggca gcccaatgaa aaagagcttg    6060
ctgctcactc ggttgctaaa tatggtgccc ttgcccgcca gaaaatatcc actggtaact    6120
acatcaccac ccttggtgaa gttacacgtg gtcacatggg cggcgccaac actatgtacg    6180
caattgatgc acctcctgaa ctttaaacac tcgaaactta atcagagtgg g             6231
```

<210> SEQ ID NO 17
<211> LENGTH: 1439
<212> TYPE: PRT
<213> ORGANISM: Pepino mosaic virus

<400> SEQUENCE: 17

```
Met Ser Arg Val Arg Asn Thr Leu Glu Lys Ile Arg Asp Pro Gln Val
1               5                   10                  15

Gln Ser Ser Ile Cys Glu Ala Ala Tyr Gln His Val Arg Pro Val Leu
            20                  25                  30

Lys Glu Ser Leu Ile Asn Cys Pro Tyr Ala Leu Asn Asp Tyr Glu Ala
        35                  40                  45

Asp Thr Leu Glu Asn Leu Gly Val Thr Ile Asn Pro His Ala Ile Gln
    50                  55                  60

Thr His Thr His Ala Ala Lys Val Val Glu Asn Arg Met Leu Glu
65                  70                  75                  80

Ile Val Gly His His Leu Pro Lys Asp Glu Lys Val Thr Phe Ile Phe
                85                  90                  95

Leu Lys Arg Ser Lys Leu Arg Tyr Met Arg Arg Ala Ala Val His Lys
            100                 105                 110

Asp Val Phe Val Asn His Asn Ile Glu Pro Lys Asp Phe Phe Arg Tyr
        115                 120                 125

Asp Glu Glu Ser Thr Ser Thr Ser Phe Ser Val Asp Thr Arg Ile Ala
    130                 135                 140

Tyr Ile Ser Asp Ser Leu His Phe Met Glu Pro Ala Asp Val Thr His
145                 150                 155                 160
```

-continued

```
Leu Phe Asp Arg Cys Gln Asn Leu Lys Thr Leu Met Ala Thr Val Val
                165                 170                 175
Leu Pro Val Glu Ala Ile His Arg Gln Thr Ser Leu Phe Pro Ala Ile
            180                 185                 190
Tyr Ser Ile Asn Tyr Asn Glu Glu Gly Phe Glu Tyr Ile Pro Gly Ser
        195                 200                 205
His Gly Gly Gly Ala Tyr Phe His Lys Tyr Glu Thr Leu Glu Trp Leu
    210                 215                 220
Lys Tyr Ser Arg Phe Ile Gly His Asp Pro Leu Thr Gly Leu Lys Tyr
225                 230                 235                 240
Thr Ile Thr Ile Gln Met Val Glu Ser Leu Gly Ala Asn His Leu Phe
                245                 250                 255
Leu Phe Gln Arg Gly Asn Phe Glu Thr Pro Leu Tyr Arg Thr Phe Gln
            260                 265                 270
Lys Asn Ser Phe Val Thr Phe Pro Asn Ile Phe His Pro Arg His Val
        275                 280                 285
Asn Ala Thr Lys Pro Met Pro Arg Ser Arg Ala Ile Gln Leu Tyr Leu
    290                 295                 300
Tyr Val Lys Ser Val Asn Lys Val Thr Gln Arg Asp Ile Phe Ala Lys
305                 310                 315                 320
Val Arg Gln Leu Ile Ser Thr Ala Glu Leu Glu Leu Tyr Asp Pro Asp
                325                 330                 335
Glu Leu Thr His Val Val Asn Tyr Phe Thr Tyr Val Ser Gln Leu Ser
            340                 345                 350
Ser Ile Asn Asp Tyr Asp Asn Met Leu Lys Ser Ser Phe Phe Lys Lys
        355                 360                 365
Leu Val Ala Pro Met Gln His Asp Trp Arg Cys Met Ile Glu Phe Phe
    370                 375                 380
Arg Gly Lys Ser Asp Phe Asn Gln Leu Leu Thr Ala Leu Gln Trp Lys
385                 390                 395                 400
Asp Phe Ser Tyr Thr Ile Lys Thr Glu Glu Leu Val Ile Thr Thr His
                405                 410                 415
Thr Ala Ile Gly Gln Ala Ile Ser Asn Ala Ala Thr Thr Tyr Lys Glu
            420                 425                 430
Arg Lys Gln Leu Thr Gln Leu Val Lys Lys Gly Thr Ile Ser Leu Ala
        435                 440                 445
Asp Phe Glu Gln Arg Glu Pro Glu Ile Thr Tyr Thr Glu Phe Glu Pro
    450                 455                 460
Glu Thr Arg Pro Gln Val Asp Cys Val Thr Asn Tyr Asn Asn Ala Val
465                 470                 475                 480
Lys Asn Leu Gly Leu Ser Ala Leu Asp Glu Gln Pro Gln Cys Ser Ser
                485                 490                 495
Ser Ser Ser His Leu Pro Cys Asn Glu Ile Ser Leu Ala Met Thr Asp
            500                 505                 510
Asp Asp Asn Ala Ala Ile His Glu Ile Glu Ser Leu Leu Ser Glu
        515                 520                 525
Pro Ile Ile Ala Pro Gln Leu Pro Ala Leu Pro His Lys Thr Trp Ala
    530                 535                 540
Ser Tyr Ala Ser Asp Thr Ser Ser Met Lys Asn Arg Glu Ile Glu Asn
545                 550                 555                 560
Ile Ile Ala Glu Leu Glu Ile Ser Arg Lys Glu Asn Asn Val Gln Gln
                565                 570                 575
```

-continued

```
Thr Thr His Asp Tyr His Ala Val Ser Asp Thr Ala Gln Ser Ser Gly
            580                 585                 590

Asp Leu Pro Trp Lys Ala Trp Ile Pro Leu Leu Asn Ala His Gly Phe
        595                 600                 605

Lys Gly Asp Gln Leu Gln Tyr Ser Pro Asp Gly Lys Val Ile Gln Pro
    610                 615                 620

Ile Gln Asp Ile Asn Asn Lys Thr Pro Arg Ser Glu Tyr Pro Ser Ser
625                 630                 635                 640

Ile Pro Ala Asp Leu Val Asn Thr Leu Arg Asn Ile Lys Arg Ala Val
                645                 650                 655

Tyr Ala Ile Pro Ile Ser His Arg Arg Ala Ser Ala Tyr Ser Ser Asp
            660                 665                 670

Ile Lys Asn Asn Arg Thr Gly Lys Leu Leu Cys Ser Gln Ser Lys Glu
        675                 680                 685

Trp Lys Glu Ser Phe Ala Phe Lys Met Gln His Glu Asp Ile Val Lys
    690                 695                 700

Ser Gly Val Val Ile His Gly Cys Gly Gly Ser Gly Lys Ser Gln Ala
705                 710                 715                 720

Leu Gln Asn Phe Leu Arg Thr Leu Gly Asp Ser Asn Asp Cys Cys Thr
                725                 730                 735

Val Val Val Pro Thr Val Glu Leu Arg Asn Asp Trp Val Asn Lys Leu
            740                 745                 750

Cys Lys Leu Pro Met Glu His Ile Lys Thr Phe Glu Lys Ala Met Ile
        755                 760                 765

Gln Pro Gly Phe Pro Val Val Ile Phe Asp Asp Tyr Thr Lys Leu Pro
    770                 775                 780

Pro Gly Tyr Ile Glu Ala Tyr Leu Phe His His Ala Asn Thr Glu Leu
785                 790                 795                 800

Phe Ile Leu Thr Gly Asp Ser Arg Gln Ser Val Tyr His Glu Ser Asn
                805                 810                 815

Asn Glu Ala Tyr Ile Ala Ser Leu Asp Glu Ala Val Ala Tyr Tyr Ala
            820                 825                 830

Asn Tyr Cys Gly Phe Tyr Leu Asn Ala Thr His Arg Asn Val Arg Ser
        835                 840                 845

Leu Ala Asn Lys Leu Gly Val Tyr Ser Glu Lys Glu Gly His Leu Lys
    850                 855                 860

Ile Thr Phe Ala Ser Asn Ala Leu Gln Lys Cys Lys Val Pro Ile Leu
865                 870                 875                 880

Val Pro Ser Gln Met Lys Lys Ser Ala Met Gln Asp Ile Gly His Lys
                885                 890                 895

Ala Met Thr Tyr Ala Gly Cys Gln Gly Leu Thr Ala Pro Arg Val Gln
            900                 905                 910

Ile Leu Leu Asp Asn His Thr Gln His Cys Ser Asp Arg Val Leu Tyr
        915                 920                 925

Thr Cys Leu Ser Arg Ala Val Asp Ser Ile His Phe Ile Asn Thr Gly
    930                 935                 940

Pro Asn Asn Ser Glu Phe Trp Asp Lys Leu Glu Ala Thr Pro Tyr Leu
945                 950                 955                 960

Lys Ala Phe Ile Asp Thr Tyr Arg Asp Glu Lys Thr Glu Met Leu Asn
                965                 970                 975

Ser Lys Pro Ala Asp Asp Ser Pro Ala Glu Pro Glu Ala Pro Leu Thr
            980                 985                 990
```

```
His Phe Pro Val Ser Asn Gly Asn  Asn Leu Glu Lys Leu  Ala Ser Ala
            995              1000                1005

Leu Pro Glu Lys Phe Ala Arg  Glu Leu Tyr Asp Lys  His His Gly
    1010             1015                 1020

Tyr Ser Asn Thr Ile Gln Thr  Glu Asn Pro Val Gln  Leu Phe
    1025             1030                 1035

Gln His Gln Gln Ala Lys Asp  Glu Thr Leu Phe Trp  Ala Thr Ile
    1040             1045                 1050

Glu Ala Arg Leu Ser Ile Thr  Thr Pro Glu Ala Asn  Leu Arg Glu
    1055             1060                 1065

Phe Val Leu Lys Lys Asp Val  Gly Asp Ile Leu Phe  Phe Asn Tyr
    1070             1075                 1080

His Asn Val Met Cys Leu Pro  Ala Asp Pro Val Asp  Phe Glu Pro
    1085             1090                 1095

Arg Thr Trp Glu Ile Cys Ala  Ala Glu Val Lys Asn  Thr Tyr Leu
    1100             1105                 1110

Ala Lys Pro Met Ala Asn Leu  Ile Asn Ala Ala Ser  Arg Gln Ser
    1115             1120                 1125

Pro Asp Phe Asp Ala Asn Lys  Ile Ser Leu Phe Leu  Lys Ser Gln
    1130             1135                 1140

Trp Val Lys Lys Val Glu Lys  Leu Gly Ala Val Lys  Ser Lys Pro
    1145             1150                 1155

Gly Gln Thr Ile Ala Ala Phe  Met Gln Gln Thr Val  Met Leu Tyr
    1160             1165                 1170

Gly Thr Met Ala Arg Tyr Leu  Arg Lys Met Arg Gln  Arg Phe Gln
    1175             1180                 1185

Pro Lys His Ile Phe Ile Asn  Cys Glu Thr Thr Thr  Asp Asn Leu
    1190             1195                 1200

Asn Gln Phe Val Lys Gln Gly  Trp Asn Phe Asn Arg  Thr Ala Gln
    1205             1210                 1215

Thr Asn Asp Phe Thr Ala Phe  Asp Gln Ser Gln Asp  Gly Ala Met
    1220             1225                 1230

Leu Gln Phe Glu Val Met Lys  Ala Lys Phe Phe Asn  Ile Pro Ala
    1235             1240                 1245

Asp Ile Ile Glu Gly Tyr Ile  Asn Ile Lys Leu Asn  Ala Lys Ile
    1250             1255                 1260

Phe Leu Gly Thr Leu Ser Ile  Met Arg Leu Ser Gly  Glu Gly Pro
    1265             1270                 1275

Thr Phe Asp Ala Asn Thr Glu  Cys Ser Ile Ala Tyr  Thr Ala Thr
    1280             1285                 1290

Arg Tyr His Leu Asp Ser Thr  Val Lys Gln Val Tyr  Ala Gly Asp
    1295             1300                 1305

Asp Met Ala Leu Asp Gly Val  Val Gln Glu Lys Pro  Ser Phe Lys
    1310             1315                 1320

Lys Leu Gln Asn Lys Leu Lys  Leu Thr Ser Lys Thr  Leu Phe Pro
    1325             1330                 1335

Lys Gln Val Lys Gly Asp Tyr  Ala Glu Phe Cys Gly  Trp Thr Phe
    1340             1345                 1350

Thr Pro Gly Gly Ile Ile Lys  Asn Pro Leu Lys Met  His Ala Ser
    1355             1360                 1365

Ile Met Leu Gln Glu Ala Ile  Gly Asn Leu His Thr  Ala Ala Arg
    1370             1375                 1380
```

```
Ser Tyr  Ala Ile Asp Met Lys  His Ser Tyr Gln Met  Gly Asp Glu
    1385                 1390                 1395

Leu His  Asn Tyr Leu Thr Pro  Asp Glu Ala Glu Gln  His Phe Leu
    1400                 1405                 1410

Ala Val  Arg Lys Leu His Lys  Leu His Gln Gly Glu  Ala Met Arg
    1415                 1420                 1425

Leu Gly  Glu Lys Ser Pro Pro  Lys Ala Thr His
    1430                 1435

<210> SEQ ID NO 18
<211> LENGTH: 1439
<212> TYPE: PRT
<213> ORGANISM: Pepino mosaic virus

<400> SEQUENCE: 18

Met Ser Arg Val Arg Asn Thr Leu Glu Lys Ile Arg Asp Pro Gln Val
1               5                   10                  15

Gln Ser Ser Ile Cys Glu Ala Ala Tyr Gln His Val Arg Pro Val Leu
            20                  25                  30

Lys Glu Ser Leu Ile Asn Cys Pro Tyr Ala Leu Asn Asp Tyr Glu Ala
        35                  40                  45

Asp Thr Leu Glu Asn Leu Gly Val Thr Ile Asn Pro His Ala Ile Gln
    50                  55                  60

Thr His Thr His Ala Ala Ala Lys Val Val Glu Asn Arg Met Leu Glu
65                  70                  75                  80

Ile Val Gly His His Leu Pro Lys Asp Glu Lys Val Thr Phe Ile Phe
                85                  90                  95

Leu Lys Arg Ser Lys Leu Arg Tyr Met Arg Arg Ala Ala Val His Lys
            100                 105                 110

Asp Val Phe Val Asn His Asn Ile Glu Pro Lys Asp Phe Phe Arg Tyr
        115                 120                 125

Asp Glu Glu Ser Thr Ser Thr Ser Phe Ser Val Asp Thr Arg Ile Ala
    130                 135                 140

Tyr Ile Ser Asp Ser Leu His Phe Met Glu Pro Ala Asp Val Thr His
145                 150                 155                 160

Leu Phe Asp Arg Cys Gln Asn Leu Lys Thr Leu Met Ala Thr Val Val
                165                 170                 175

Leu Pro Val Glu Ala Ile His Arg Gln Thr Ser Leu Phe Pro Ala Ile
            180                 185                 190

Tyr Ser Ile Asn Tyr Asn Glu Glu Gly Phe Glu Tyr Ile Pro Gly Ser
        195                 200                 205

His Gly Gly Gly Ala Tyr Phe His Lys Tyr Glu Thr Leu Glu Trp Leu
    210                 215                 220

Lys Tyr Ser Arg Phe Ile Gly His Asp Pro Leu Thr Gly Leu Lys Tyr
225                 230                 235                 240

Thr Ile Thr Ile Gln Met Val Glu Ser Leu Gly Ala Asn His Leu Phe
                245                 250                 255

Leu Phe Gln Arg Gly Asn Phe Glu Thr Pro Leu Tyr Arg Thr Phe Gln
            260                 265                 270

Lys Asn Ser Phe Val Thr Phe Pro Asn Ile Phe His Pro Arg His Val
        275                 280                 285

Asn Ala Thr Lys Pro Met Pro Arg Ser Arg Ala Ile Gln Leu Tyr Leu
    290                 295                 300

Tyr Val Lys Ser Val Asn Lys Val Thr Gln Arg Asp Ile Phe Ala Lys
305                 310                 315                 320
```

-continued

```
Val Arg Gln Leu Ile Ser Thr Ala Glu Leu Glu Tyr Asp Pro Asp
            325                 330                 335

Glu Leu Thr His Val Val Asn Tyr Phe Thr Tyr Val Ser Gln Leu Ser
        340                 345                 350

Ser Ile Asn Asp Tyr Asp Asn Met Leu Lys Ser Ser Phe Phe Lys Lys
        355                 360                 365

Leu Val Ala Pro Met Gln His Asp Trp Arg Cys Met Ile Glu Phe Phe
370                 375                 380

Arg Gly Lys Ser Asp Phe Asn Gln Leu Leu Thr Ala Leu Gln Trp Lys
385                 390                 395                 400

Asp Phe Ser Tyr Thr Ile Lys Thr Glu Glu Leu Val Ile Thr Thr His
                405                 410                 415

Thr Ala Ile Gly Gln Ala Ile Ser Asn Ala Ala Ala Thr Tyr Lys Glu
            420                 425                 430

Arg Lys Gln Leu Thr Gln Leu Val Lys Lys Gly Thr Ile Ser Leu Ala
        435                 440                 445

Asp Phe Glu Gln Arg Glu Pro Glu Ile Thr Tyr Thr Glu Phe Glu Pro
        450                 455                 460

Glu Thr Arg Pro Gln Val Asp Cys Val Thr Asn Tyr Asn Asn Ala Val
465                 470                 475                 480

Lys Asn Leu Gly Leu Ser Ala Leu Asp Glu Gln Pro Gln Cys Ser Ser
                485                 490                 495

Ser Asn Ser His Leu Pro Cys Asn Glu Ile Ser Leu Ala Met Thr Asp
            500                 505                 510

Asp Asp Asn Ala Ala Ala Ile His Glu Ile Glu Ser Leu Leu Ser Glu
        515                 520                 525

Pro Ile Ile Ala Pro Gln Leu Pro Ala Leu Pro His Lys Thr Trp Ala
        530                 535                 540

Ser Tyr Ala Ser Asp Thr Ser Ser Met Lys Asn Arg Glu Ile Glu Asn
545                 550                 555                 560

Ile Ile Ala Glu Leu Glu Ile Ser Arg Lys Glu Asn Asn Val Gln Gln
                565                 570                 575

Thr Thr His Asp Tyr His Ala Val Ser Asp Thr Ala Gln Ser Ser Gly
            580                 585                 590

Asp Leu Pro Trp Lys Ala Trp Ile Pro Leu Leu Asn Ala His Gly Phe
        595                 600                 605

Lys Gly Asp Gln Leu Gln Tyr Ser Pro Asp Gly Lys Val Ile Gln Pro
        610                 615                 620

Ile Gln Asp Ile Asn Asn Lys Thr Pro Arg Ser Glu Tyr Pro Ser Ser
625                 630                 635                 640

Ile Pro Ala Asp Leu Val Asp Thr Leu Arg Asn Ile Lys Arg Ala Val
                645                 650                 655

Tyr Ala Ile Pro Ile Ser His Arg Arg Ala Ser Ala Tyr Ser Ser Asp
            660                 665                 670

Ile Lys Asn Asn Arg Thr Gly Lys Leu Leu Cys Ser Gln Ser Lys Glu
        675                 680                 685

Trp Lys Glu Ser Phe Ala Phe Lys Met Gln His Glu Asp Ile Val Lys
        690                 695                 700

Ser Gly Val Val Ile His Gly Cys Gly Gly Ser Gly Lys Ser Gln Ala
705                 710                 715                 720

Leu Gln Asn Phe Leu Arg Thr Pro Gly Asp Ser Asn Asp Cys Cys Thr
                725                 730                 735
```

```
Val Val Val Pro Thr Val Glu Leu Arg Asn Asp Trp Val Asn Lys Leu
            740                 745                 750

Cys Lys Leu Pro Met Glu His Ile Lys Thr Phe Glu Lys Ala Met Ile
            755                 760                 765

Gln Pro Gly Phe Pro Val Val Ile Phe Asp Asp Tyr Thr Lys Leu Pro
            770                 775                 780

Pro Gly Tyr Ile Glu Ala Tyr Leu Phe His His Ala Asn Thr Glu Leu
785                 790                 795                 800

Phe Ile Leu Thr Gly Asp Ser Arg Gln Ser Val Tyr His Glu Ser Asn
            805                 810                 815

Asn Glu Ala Tyr Ile Ala Ser Leu Asp Glu Ala Val Ala Tyr Tyr Ala
            820                 825                 830

Asn Tyr Cys Gly Phe Tyr Leu Asn Ala Thr His Arg Asn Val Arg Ser
            835                 840                 845

Leu Ala Asn Lys Leu Gly Val Tyr Ser Glu Lys Glu Gly His Leu Lys
            850                 855                 860

Ile Thr Phe Ala Ser Asn Ala Leu Gln Lys Cys Lys Val Pro Ile Leu
865                 870                 875                 880

Val Pro Ser Gln Met Lys Lys Ser Ala Met Gln Asp Ile Gly His Lys
            885                 890                 895

Ala Met Thr Tyr Ala Gly Cys Gln Gly Leu Thr Ala Pro Arg Val Gln
            900                 905                 910

Ile Leu Leu Asp Asn His Thr Gln His Cys Ser Asp Arg Val Leu Tyr
            915                 920                 925

Thr Cys Leu Ser Arg Ala Val Asp Ser Ile His Phe Ile Asn Thr Gly
            930                 935                 940

Pro Asn Asn Ser Glu Phe Trp Asp Lys Leu Glu Ala Thr Pro Tyr Leu
945                 950                 955                 960

Lys Ala Phe Ile Asp Thr Tyr Arg Asp Glu Lys Thr Glu Met Leu Asn
            965                 970                 975

Ser Lys Pro Ala Asp Asp Ser Pro Ala Glu Pro Glu Ala Pro Leu Thr
            980                 985                 990

His Phe Pro Val Ser Asn Gly Asn  Asn Leu Glu Lys Leu  Ala Ser Ala
            995                 1000                1005

Leu Pro  Glu Lys Phe Ala Arg  Glu Leu Tyr Asp Lys  His His Gly
    1010                1015                1020

Tyr Ser  Asn Thr Ile Gln Thr  Glu Asn Pro Val Val  Gln Leu Phe
    1025                1030                1035

Gln His  Gln Gln Ala Lys Asp  Glu Thr Leu Phe Trp  Ala Thr Ile
    1040                1045                1050

Glu Ala  Arg Leu Ser Ile Thr  Thr Pro Glu Ala Asn  Leu Arg Glu
    1055                1060                1065

Phe Val  Leu Lys Lys Asp Val  Gly Asp Ile Leu Phe  Phe Asn Tyr
    1070                1075                1080

His Asn  Val Met Cys Leu Pro  Ala Asp Pro Val Asp  Phe Glu Pro
    1085                1090                1095

Arg Thr  Trp Glu Ile Cys Ala  Ala Glu Val Lys Asn  Thr Tyr Leu
    1100                1105                1110

Ala Lys  Pro Met Ala Asn Leu  Ile Asn Ala Ala Ser  Arg Gln Ser
    1115                1120                1125

Pro Asp  Phe Asp Ala Asn Lys  Ile Ser Leu Phe Leu  Lys Ser Gln
    1130                1135                1140
```

Trp Val Lys Lys Val Glu Lys Leu Gly Ala Val Lys Ser Lys Pro
    1145            1150                1155

Gly Gln Thr Ile Ala Ala Phe Met Gln Gln Thr Val Met Leu Tyr
    1160            1165                1170

Gly Thr Met Ala Arg Tyr Leu Arg Lys Met Arg Gln Arg Phe Gln
    1175            1180                1185

Pro Lys His Ile Phe Ile Asn Cys Glu Thr Thr Thr Asp Asn Leu
    1190            1195                1200

Asn Gln Phe Val Lys Gln Gly Trp Asn Phe Asn Arg Thr Ala Gln
    1205            1210                1215

Thr Asn Asp Phe Thr Ala Phe Asp Gln Ser Gln Asp Gly Ala Met
    1220            1225                1230

Leu Gln Phe Glu Val Met Lys Ala Lys Phe Phe Asn Ile Pro Ala
    1235            1240                1245

Asp Ile Ile Glu Gly Tyr Ile Asn Ile Lys Leu Asn Ala Lys Ile
    1250            1255                1260

Phe Leu Gly Thr Leu Ser Ile Met Arg Leu Ser Gly Glu Gly Pro
    1265            1270                1275

Thr Phe Asp Ala Asn Thr Glu Cys Ser Ile Ala Tyr Thr Ala Thr
    1280            1285                1290

Arg Tyr His Leu Asp Ser Thr Val Lys Gln Val Tyr Ala Gly Asp
    1295            1300                1305

Asp Met Ala Leu Asp Gly Val Val Gln Glu Lys Pro Ser Phe Lys
    1310            1315                1320

Lys Leu Gln Asn Lys Leu Lys Leu Thr Ser Lys Thr Leu Phe Pro
    1325            1330                1335

Lys Gln Val Lys Gly Asp Tyr Ala Glu Phe Cys Gly Trp Thr Phe
    1340            1345                1350

Thr Pro Gly Gly Ile Ile Lys Asn Pro Leu Lys Met His Ala Ser
    1355            1360                1365

Ile Met Leu Gln Glu Ala Ile Gly Asn Leu His Thr Ala Ala Arg
    1370            1375                1380

Ser Tyr Ala Ile Asp Met Lys His Ser Tyr Gln Met Gly Asp Glu
    1385            1390                1395

Leu His Asn Tyr Leu Thr Pro Asp Glu Ala Glu Gln His Phe Leu
    1400            1405                1410

Ala Val Arg Lys Leu His Lys Leu His Gln Gly Glu Ala Met Arg
    1415            1420                1425

Leu Gly Glu Lys Ser Pro Pro Lys Ala Thr His
    1430            1435

<210> SEQ ID NO 19
<211> LENGTH: 1439
<212> TYPE: PRT
<213> ORGANISM: Pepino mosaic virus

<400> SEQUENCE: 19

Met Ser Arg Val Arg Asn Thr Leu Glu Lys Ile Arg Asp Pro Gln Val
1               5                   10                  15

Gln Ser Ser Ile Cys Glu Ala Ala Tyr Gln His Val Arg Pro Val Leu
            20                  25                  30

Lys Glu Ser Leu Ile Asn Cys Pro Tyr Ala Leu Asn Asp Tyr Glu Ala
        35                  40                  45

Asp Thr Leu Glu Asn Leu Gly Val Thr Ile Asn Pro His Ala Ile Gln
    50                  55                  60

```
Thr His Thr His Ala Ala Lys Val Val Glu Asn Arg Met Leu Glu
 65                  70                  75                  80

Ile Val Gly His His Leu Pro Lys Asp Glu Lys Val Thr Phe Ile Phe
                 85                  90                  95

Leu Lys Arg Ser Lys Leu Arg Tyr Met Arg Arg Ala Ala Val His Lys
            100                 105                 110

Asp Val Phe Val Asn His Asn Ile Glu Pro Lys Asp Phe Phe Arg Tyr
        115                 120                 125

Asp Glu Glu Ser Thr Ser Thr Ser Phe Ser Val Asp Thr Arg Ile Ala
    130                 135                 140

Tyr Ile Ser Asp Ser Leu His Phe Met Glu Pro Ala Asp Val Thr His
145                 150                 155                 160

Leu Phe Asp Arg Cys Gln Asn Leu Lys Thr Leu Met Ala Thr Val Val
                165                 170                 175

Leu Pro Val Glu Ala Ile His Arg Gln Thr Ser Leu Phe Pro Ala Ile
            180                 185                 190

Tyr Ser Ile Asn Tyr Asn Glu Glu Gly Phe Glu Tyr Ile Pro Gly Ser
        195                 200                 205

His Gly Gly Gly Ala Tyr Phe His Lys Tyr Glu Thr Leu Glu Trp Leu
    210                 215                 220

Lys Tyr Ser Arg Phe Ile Gly His Asp Pro Leu Thr Gly Leu Lys Tyr
225                 230                 235                 240

Thr Ile Thr Ile Gln Met Val Glu Ser Leu Gly Ala Asn His Leu Phe
                245                 250                 255

Leu Phe Gln Arg Gly Asn Phe Glu Thr Pro Leu Tyr Arg Thr Phe Gln
            260                 265                 270

Lys Asn Ser Phe Val Thr Phe Pro Asn Ile Phe His Pro Arg His Val
        275                 280                 285

Asn Ala Thr Lys Pro Met Pro Arg Ser Arg Ala Ile Gln Leu Tyr Leu
    290                 295                 300

Tyr Val Lys Ser Val Asn Lys Val Thr Gln Arg Asp Ile Phe Ala Lys
305                 310                 315                 320

Val Arg Gln Leu Ile Ser Thr Ala Glu Leu Glu Leu Tyr Asp Pro Asp
                325                 330                 335

Glu Leu Thr His Val Val Asn Tyr Phe Thr Tyr Val Ser Gln Leu Ser
            340                 345                 350

Ser Ile Asn Asp Tyr Asp Asn Met Leu Lys Ser Ser Phe Phe Lys Lys
        355                 360                 365

Leu Val Ala Pro Met Gln His Asp Trp Arg Cys Met Ile Glu Phe Phe
    370                 375                 380

Arg Gly Lys Ser Asp Phe Asn Gln Leu Leu Thr Ala Leu Gln Trp Lys
385                 390                 395                 400

Asp Phe Ser Tyr Thr Ile Lys Thr Glu Glu Leu Val Ile Thr Thr His
                405                 410                 415

Thr Ala Ile Gly Gln Ala Ile Ser Asn Ala Ala Thr Thr Tyr Lys Glu
            420                 425                 430

Arg Arg Gln Leu Thr Gln Leu Val Lys Lys Gly Thr Ile Ser Leu Ala
        435                 440                 445

Asp Phe Glu Gln Arg Glu Pro Glu Ile Thr Tyr Thr Glu Phe Glu Pro
    450                 455                 460

Glu Thr Arg Pro Gln Val Asp Cys Val Thr Asn Tyr Asn Asn Ala Val
465                 470                 475                 480
```

-continued

```
Lys Asn Leu Gly Leu Ser Ala Leu Asp Glu Gln Pro Gln Cys Ser Ser
                485                 490                 495
Ser Ser Ser His Ile Pro Cys Asn Glu Ile Ser Leu Ala Met Thr Asp
            500                 505                 510
Asp Asp Asn Ala Ala Ala Ile His Glu Ile Glu Ser Leu Leu Ser Glu
        515                 520                 525
Pro Ile Ile Ala Pro Gln Leu Pro Ala Leu Pro His Lys Thr Trp Ala
    530                 535                 540
Ser Tyr Ala Ser Asp Thr Ser Ser Met Lys Asn Arg Glu Ile Glu Asn
545                 550                 555                 560
Ile Ile Ala Glu Leu Glu Ile Ser Arg Lys Glu Asn Asn Val Gln Gln
                565                 570                 575
Thr Thr His Asp Tyr His Ala Val Phe Asp Thr Ala Gln Ser Ser Gly
            580                 585                 590
Asp Leu Pro Trp Lys Ala Trp Ile Pro Leu Leu Asn Ala His Gly Phe
        595                 600                 605
Lys Gly Asp Gln Leu Gln Tyr Ser Pro Asp Gly Lys Val Ile Gln Pro
    610                 615                 620
Ile Gln Asp Ile Asn Asn Lys Thr Pro Arg Ser Glu Tyr Pro Ser Ser
625                 630                 635                 640
Ile Pro Ala Asp Leu Val Asn Thr Leu Arg Asn Ile Lys Arg Ala Val
                645                 650                 655
Tyr Ala Ile Pro Ile Ser His Arg Arg Ala Ser Ala Tyr Ser Ser Asp
            660                 665                 670
Ile Lys Asn Asn Arg Thr Gly Lys Leu Leu Cys Ser Gln Ser Lys Glu
        675                 680                 685
Trp Arg Glu Ser Phe Ala Phe Lys Met Gln His Glu Asp Ile Val Lys
    690                 695                 700
Ser Gly Val Val Ile His Gly Cys Gly Gly Ser Gly Lys Ser Gln Ala
705                 710                 715                 720
Leu Gln Asn Phe Leu Arg Thr Leu Gly Asp Ser Asn Asp Cys Cys Thr
                725                 730                 735
Val Val Pro Thr Val Glu Leu Arg Asn Asp Trp Val Asn Lys Leu
            740                 745                 750
Cys Lys Leu Pro Met Glu His Ile Lys Thr Phe Glu Lys Ala Met Ile
        755                 760                 765
Gln Pro Gly Phe Pro Val Val Ile Phe Asp Asp Tyr Thr Lys Leu Pro
    770                 775                 780
Pro Gly Tyr Ile Glu Ala Tyr Leu Phe His His Ala Asn Thr Glu Leu
785                 790                 795                 800
Phe Ile Leu Thr Gly Asp Ser Arg Gln Ser Val Tyr His Glu Ser Asn
                805                 810                 815
Asn Glu Ala Tyr Ile Ala Ser Leu Asp Glu Ala Val Ala Tyr Tyr Ala
            820                 825                 830
Asn Tyr Cys Gly Phe Tyr Leu Asn Ala Thr His Arg Asn Val Arg Ser
        835                 840                 845
Leu Ala Asn Lys Leu Gly Val Tyr Ser Glu Lys Glu Gly His Leu Lys
    850                 855                 860
Ile Thr Phe Ala Ser Asn Ala Leu Gln Lys Cys Lys Val Pro Ile Leu
865                 870                 875                 880
Val Pro Ser Gln Met Lys Lys Ser Ala Met Gln Asp Ile Gly His Lys
                885                 890                 895
```

```
Ala Met Thr Tyr Ala Gly Cys Gln Gly Leu Thr Ala Pro Arg Val Gln
                900             905             910

Ile Leu Leu Asp Asn His Thr Gln His Cys Ser Asp Arg Val Leu Tyr
            915             920             925

Thr Cys Leu Ser Arg Ala Val Asp Ser Ile His Phe Ile Asn Thr Gly
        930             935             940

Pro Asn Asn Ser Glu Phe Trp Asp Lys Leu Glu Ala Thr Pro Tyr Leu
945             950             955             960

Lys Ala Phe Ile Asp Thr Tyr Arg Asp Glu Lys Thr Glu Met Leu Asn
                965             970             975

Ser Lys Pro Ala Asp Asp Ser Pro Ala Glu Pro Glu Ala Pro Leu Thr
            980             985             990

His Phe Pro Val Ser Asn Gly Asn  Asn Leu Glu Lys Leu  Ala Ser Ala
        995             1000                1005

Leu Pro  Glu Lys Phe Ala Arg  Glu Leu Tyr Asp Lys  His His Gly
    1010             1015             1020

Tyr Ser  Asn Thr Ile Gln Thr  Glu Asn Pro Val Val  Gln Leu Phe
    1025             1030             1035

Gln His  Gln Gln Ala Lys Asp  Glu Thr Leu Phe Trp  Ala Thr Ile
    1040             1045             1050

Glu Ala  Arg Leu Ser Ile Thr  Thr Pro Glu Ala Asn  Leu Arg Glu
    1055             1060             1065

Phe Val  Leu Lys Lys Asp Val  Gly Asp Ile Leu Phe  Phe Asn Tyr
    1070             1075             1080

His Asn  Val Met Cys Leu Pro  Ala Asp Pro Val Asp  Phe Glu Pro
    1085             1090             1095

Arg Thr  Trp Glu Ile Cys Ala  Ala Glu Val Lys Asn  Thr Tyr Leu
    1100             1105             1110

Ala Lys  Pro Met Ala Asn Leu  Ile Asn Ala Ala Ser  Arg Gln Ser
    1115             1120             1125

Pro Asp  Phe Asp Ala Asn Lys  Ile Ser Leu Phe Leu  Lys Ser Gln
    1130             1135             1140

Trp Val  Lys Lys Val Glu Lys  Leu Gly Ala Val Lys  Ser Lys Pro
    1145             1150             1155

Gly Gln  Thr Ile Ala Ala Phe  Met Gln Gln Thr Val  Met Leu Tyr
    1160             1165             1170

Gly Thr  Met Ala Arg Tyr Leu  Arg Lys Met Arg Gln  Arg Phe Gln
    1175             1180             1185

Pro Lys  His Ile Phe Ile Asn  Cys Glu Thr Thr Thr  Asp Asn Leu
    1190             1195             1200

Asn Gln  Phe Val Lys Gln Gly  Trp Asn Phe Asn Arg  Thr Ala Gln
    1205             1210             1215

Thr Asn  Asp Phe Thr Ala Phe  Asp Gln Ser Gln Asp  Gly Ala Met
    1220             1225             1230

Leu Gln  Phe Glu Val Met Lys  Ala Lys Phe Phe Asn  Ile Pro Ala
    1235             1240             1245

Asp Ile  Ile Glu Gly Tyr Ile  Asn Ile Lys Leu Asn  Ala Lys Ile
    1250             1255             1260

Phe Leu  Gly Thr Leu Ser Ile  Met Arg Leu Ser Gly  Glu Gly Pro
    1265             1270             1275

Thr Phe  Asp Ala Asn Thr Glu  Cys Ser Ile Ala Tyr  Thr Ala Thr
    1280             1285             1290
```

```
Arg Tyr  His Leu Asp Ser Thr  Val Lys Gln Val Tyr  Ala Gly Asp
    1295                 1300                 1305

Asp Met  Ala Leu Asp Gly Val  Val Gln Glu Lys Pro  Ser Phe Lys
    1310                 1315                 1320

Lys Leu  Gln Asn Lys Leu Lys  Leu Thr Ser Lys Thr  Leu Phe Pro
    1325                 1330                 1335

Lys Gln  Val Lys Gly Asp Tyr  Ala Glu Phe Cys Gly  Trp Thr Phe
    1340                 1345                 1350

Thr Pro  Gly Gly Ile Ile Lys  Asn Pro Leu Lys Met  His Ala Ser
    1355                 1360                 1365

Ile Met  Leu Gln Glu Ala Ile  Gly Asn Leu His Thr  Ala Ala Arg
    1370                 1375                 1380

Ser Tyr  Ala Ile Asp Met Lys  His Ser Tyr Gln Met  Gly Asp Glu
    1385                 1390                 1395

Leu His  Asn Tyr Leu Thr Pro  Asp Glu Ala Glu Gln  His Phe Leu
    1400                 1405                 1410

Ala Val  Arg Lys Leu His Lys  Leu His Gln Gly Glu  Ala Met Arg
    1415                 1420                 1425

Leu Gly  Glu Lys Ser Pro Pro  Lys Ala Thr His
    1430                 1435
```

<210> SEQ ID NO 20
<211> LENGTH: 1439
<212> TYPE: PRT
<213> ORGANISM: Pepino mosaic virus

<400> SEQUENCE: 20

```
Met Ser Arg Val Arg Asn Thr Leu Glu Lys Ile Arg Asp Pro Gln Val
1               5                   10                  15

Gln Ser Ser Ile Cys Glu Ala Ala Tyr Gln His Val Arg Pro Val Leu
            20                  25                  30

Lys Glu Ser Leu Ile Asn Cys Pro Tyr Ala Leu Asn Asp Tyr Glu Ala
        35                  40                  45

Asp Thr Leu Glu Asn Leu Gly Val Thr Ile Asn Pro His Ala Ile Gln
    50                  55                  60

Thr His Thr His Ala Ala Ala Lys Val Val Glu Asn Arg Met Leu Glu
65                  70                  75                  80

Ile Val Gly His His Leu Pro Lys Asp Glu Lys Val Thr Phe Ile Phe
                85                  90                  95

Leu Lys Arg Ser Lys Leu Arg Tyr Met Arg Arg Ala Ala Val His Lys
            100                 105                 110

Asp Val Phe Val Asn His Asn Ile Glu Pro Lys Asp Phe Phe Arg Tyr
        115                 120                 125

Asp Glu Glu Ser Thr Ser Thr Ser Phe Ser Val Asn Thr Arg Ile Ala
    130                 135                 140

Tyr Ile Ser Asp Ser Leu His Phe Met Glu Pro Ala Asp Val Thr His
145                 150                 155                 160

Leu Phe Asp Arg Cys Gln Asn Leu Lys Thr Leu Met Ala Thr Val Val
                165                 170                 175

Leu Pro Val Glu Ala Ile His Arg Gln Thr Ser Leu Phe Pro Ala Ile
            180                 185                 190

Tyr Ser Ile Asn Tyr Asn Glu Glu Gly Phe Glu Tyr Ile Pro Gly Ser
        195                 200                 205

His Gly Gly Gly Ala Tyr Phe His Lys Tyr Glu Thr Leu Glu Trp Leu
    210                 215                 220
```

```
Lys Tyr Ser Arg Phe Ile Gly His Asp Pro Leu Thr Gly Leu Lys Tyr
225                 230                 235                 240

Thr Ile Thr Ile Gln Met Val Glu Ser Leu Gly Ala Asn His Leu Phe
            245                 250                 255

Leu Phe Gln Arg Gly Asn Phe Glu Thr Pro Leu Tyr Arg Thr Phe Gln
        260                 265                 270

Lys Asn Ser Phe Val Thr Phe Pro Asn Ile Phe His Pro Arg His Val
    275                 280                 285

Asn Ala Thr Lys Pro Met Pro Arg Ser Arg Ala Ile Gln Leu Tyr Leu
290                 295                 300

Tyr Val Lys Ser Val Asn Lys Val Thr Gln Arg Asp Ile Phe Ala Lys
305                 310                 315                 320

Leu Arg Gln Leu Ile Ser Thr Ala Glu Leu Glu Leu Tyr Asp Pro Asp
                325                 330                 335

Glu Leu Thr His Val Val Asn Tyr Phe Thr Tyr Val Ser Gln Leu Ser
            340                 345                 350

Ser Ile Asn Asp Tyr Asp Asn Met Leu Lys Ser Ser Phe Phe Lys Lys
        355                 360                 365

Leu Val Ala Pro Met Gln His Asp Trp Arg Cys Met Ile Glu Phe Phe
370                 375                 380

Arg Gly Lys Ser Asp Phe Asn Gln Leu Leu Thr Ala Leu Gln Trp Lys
385                 390                 395                 400

Asp Phe Ser Tyr Thr Ile Lys Thr Asp Glu Leu Val Ile Thr Thr His
                405                 410                 415

Thr Ala Ile Gly Gln Ala Ile Cys Asn Ala Ala Ala Thr Tyr Lys Glu
            420                 425                 430

Arg Arg Gln Leu Thr Gln Leu Val Lys Asn Gly Thr Ile Ser Leu Ala
        435                 440                 445

Asp Phe Glu Gln Lys Glu Pro Glu Ile Thr Tyr Thr Glu Phe Glu Pro
450                 455                 460

Glu Thr Arg Pro Gln Val Asp Cys Val Thr Asn Tyr Asn Asn Ala Val
465                 470                 475                 480

Arg Asn Leu Gly Leu Ser Ala Leu Asp Glu Gln Pro Gln Cys Ser Ser
                485                 490                 495

Ser Asn Ser His Ile Pro Cys Asn Glu Ile Ser Leu Ala Met Thr Asp
            500                 505                 510

Asp Asp Asn Ala Ala Ile His Glu Ile Glu Ser Leu Leu Ser Glu
        515                 520                 525

Pro Ile Ile Ala Pro Gln Leu Pro Ala Leu Pro His Lys Thr Trp Ala
530                 535                 540

Ser Tyr Ala Ser Asp Thr Ser Ser Met Lys Asn Arg Glu Ile Glu Asn
545                 550                 555                 560

Ile Ile Ala Glu Leu Glu Ile Ser Arg Lys Glu Asn Asn Val Gln Gln
                565                 570                 575

Thr Thr His Asp Tyr His Ala Val Ser Asp Thr Ala Gln Asn Ser Gly
            580                 585                 590

Gly Leu Pro Trp Lys Ala Trp Ile Pro Leu Leu Asn Ala His Gly Phe
        595                 600                 605

Lys Gly Asp Gln Leu Gln Tyr Ser Pro Asp Gly Lys Val Ile Gln Pro
610                 615                 620

Ile Gln Asp Ile Asn Asn Lys Thr Pro Arg Ser Glu Tyr Pro Ser Ser
625                 630                 635                 640
```

```
Ile Pro Ala Asp Leu Val Thr Thr Leu Arg Asn Ile Lys Arg Ala Val
            645                 650                 655

Tyr Ala Ile Pro Ile Ser His Arg Arg Ala Ser Ala Tyr Ser Ser Asp
        660                 665                 670

Ile Lys Asn Asn Arg Thr Gly Lys Leu Leu Cys Ser Gln Ser Lys Glu
        675                 680                 685

Trp Lys Glu Ser Phe Ala Phe Lys Met Arg His Glu Asp Ile Val Lys
        690                 695                 700

Ser Gly Val Val Ile His Gly Cys Gly Gly Ser Lys Ser Gln Ala
705                 710                 715                 720

Leu Gln Asn Phe Leu Arg Thr Leu Gly Asp Thr Asn Asp Cys Cys Thr
        725                 730                 735

Val Val Val Pro Thr Val Glu Leu Arg Asn Asp Trp Val Asn Lys Leu
        740                 745                 750

Cys Lys Leu Pro Met Glu His Ile Lys Thr Phe Glu Lys Ala Met Ile
        755                 760                 765

Gln Pro Gly Phe Pro Val Val Ile Phe Asp Asp Tyr Thr Lys Leu Pro
        770                 775                 780

Pro Gly Tyr Ile Glu Ala Tyr Leu Phe His His Ala Asn Thr Glu Leu
785                 790                 795                 800

Phe Ile Leu Thr Gly Asp Ser Arg Gln Ser Val Tyr His Glu Ser Asn
        805                 810                 815

Asn Glu Ala Tyr Ile Ala Ser Leu Asp Glu Ala Val Ala Tyr Tyr Ala
        820                 825                 830

Asn Tyr Cys Gly Phe Tyr Leu Asn Ala Thr His Arg Asn Val Arg Ser
        835                 840                 845

Leu Ala Asn Lys Leu Gly Val Tyr Ser Glu Lys Glu Gly His Leu Lys
        850                 855                 860

Ile Thr Phe Ala Ser Asn Ala Leu Gln Lys Cys Lys Val Pro Ile Leu
865                 870                 875                 880

Val Pro Ser Lys Met Lys Lys Gly Ala Met Gln Asp Ile Gly His Lys
        885                 890                 895

Ala Met Thr Tyr Ala Gly Cys Gln Gly Leu Thr Ala Pro Arg Val Gln
        900                 905                 910

Ile Leu Leu Asp Asn His Thr Gln His Cys Ser Asp Arg Val Leu Tyr
        915                 920                 925

Thr Cys Leu Ser Arg Ala Val Asp Ser Ile His Phe Ile Asn Thr Gly
        930                 935                 940

Pro Asn Asn Ser Glu Phe Trp Asp Lys Leu Glu Ala Thr Pro Tyr Leu
945                 950                 955                 960

Lys Ala Phe Ile Asp Thr Tyr Arg Asp Glu Lys Thr Glu Met Leu Asn
        965                 970                 975

Ser Lys Pro Ala Asp Asp Ser Pro Thr Glu Pro Glu Ala Pro Leu Thr
        980                 985                 990

His Phe Pro Val Ser Asn Gly Asn Asn Leu Glu Lys Leu Ala Ser Ala
        995                 1000                1005

Leu Pro Glu Lys Phe Ala Arg Glu Leu Tyr Asp Lys His His Gly
        1010                1015                1020

Tyr Ser Asn Thr Ile Gln Thr Glu Asn Pro Val Val Gln Leu Phe
        1025                1030                1035

Gln His Gln Gln Ala Lys Asp Glu Thr Leu Phe Trp Ala Thr Ile
        1040                1045                1050
```

```
Glu Ala Arg Leu Ser Ile Thr Thr Pro Glu Ala Asn Leu Arg Glu
1055                1060                1065

Phe Val Leu Lys Lys Asp Val Gly Asp Ile Leu Phe Phe Asn Tyr
1070                1075                1080

His Asn Ala Met Cys Leu Pro Ala Asp Pro Val Asp Phe Glu Pro
1085                1090                1095

Arg Thr Trp Glu Ile Cys Ala Ala Glu Val Lys Asn Thr Tyr Leu
1100                1105                1110

Ala Lys Pro Met Ala Asn Leu Ile Asn Ala Ala Ser Arg Gln Ser
1115                1120                1125

Pro Asp Phe Asp Thr Asn Lys Ile Ser Leu Phe Leu Lys Ser Gln
1130                1135                1140

Trp Val Lys Lys Val Glu Lys Leu Gly Ala Val Lys Ser Lys Pro
1145                1150                1155

Gly Gln Thr Ile Ala Ala Phe Met Gln Gln Thr Val Met Leu Tyr
1160                1165                1170

Gly Thr Met Ala Arg Tyr Leu Arg Lys Met Arg Gln Arg Phe Gln
1175                1180                1185

Pro Lys His Ile Phe Ile Asn Cys Glu Thr Thr Thr Asp Asp Leu
1190                1195                1200

Asn Gln Phe Val Lys Gln Gly Trp Asn Phe Asn Arg Thr Ala Gln
1205                1210                1215

Thr Asn Asp Phe Thr Ala Phe Asp Gln Ser Gln Asp Gly Ala Met
1220                1225                1230

Leu Gln Phe Glu Val Met Lys Ala Lys Phe Phe Asn Ile Pro Ala
1235                1240                1245

Asp Ile Ile Glu Gly Tyr Ile Asn Ile Lys Leu Asn Ala Lys Ile
1250                1255                1260

Phe Leu Gly Thr Leu Ser Ile Met Arg Leu Ser Gly Glu Gly Pro
1265                1270                1275

Thr Phe Asp Ala Asn Thr Glu Cys Ser Ile Ala Tyr Thr Ala Thr
1280                1285                1290

Arg Tyr His Leu Asp Ser Thr Val Lys Gln Val Tyr Ala Gly Asp
1295                1300                1305

Asp Met Ala Leu Asp Gly Val Val Gln Glu Lys Pro Ser Phe Lys
1310                1315                1320

Asn Leu Gln Asn Lys Leu Lys Leu Thr Ser Lys Thr Leu Phe Pro
1325                1330                1335

Lys Gln Val Lys Gly Asp Tyr Ala Glu Phe Cys Gly Trp Thr Phe
1340                1345                1350

Thr Pro Gly Gly Ile Ile Lys Asn Pro Leu Lys Met His Ala Ser
1355                1360                1365

Ile Met Leu Gln Glu Ala Ile Gly Asn Leu His Thr Ala Ala Arg
1370                1375                1380

Ser Tyr Ala Ile Asp Met Lys His Ser Tyr Gln Met Gly Asp Glu
1385                1390                1395

Leu His Asp Tyr Leu Thr Pro Asp Glu Ala Glu Gln His Phe Leu
1400                1405                1410

Ala Val Arg Lys Leu His Lys Leu His Gln Gly Glu Ala Met Arg
1415                1420                1425

Leu Gly Glu Lys Ser Pro Pro Lys Ser Thr His
1430                1435
```

```
<210> SEQ ID NO 21
<211> LENGTH: 1439
<212> TYPE: PRT
<213> ORGANISM: Pepino mosaic virus
<220

```
Leu Val Ala Pro Met Gln Gln Asp Trp Arg Cys Met Ile Glu Xaa Phe
370                 375                 380
Arg Gly Lys Ser Asp Phe Asn Gln Leu Leu Thr Ala Leu Gln Trp Lys
385                 390                 395                 400
Asp Phe Ser Tyr Thr Ile Lys Thr Glu Glu Leu Ile Ile Thr Thr His
                405                 410                 415
Thr Ala Ile Gly Gln Ala Ile Ser Gly Ala Ala Asn Thr Tyr Lys Glu
                420                 425                 430
Arg Arg Gln Leu Thr Gln Leu Val Lys Gln Gly Val Ile Ser Leu Ala
                435                 440                 445
Asp Phe Gln Ser Glu Glu Pro Lys Ile Glu Tyr Thr Glu Phe Glu Arg
450                 455                 460
Glu Thr Lys Pro Pro Val Asp Cys Val Thr Asn Tyr Asn Asn Ala Val
465                 470                 475                 480
Lys Asn Leu Gly Leu Ser Glu Pro Val Asp Leu Pro Glu Cys Ser Tyr
                485                 490                 495
Ala Arg Asn Ser Val Pro Asn Asn Glu Ile Ser Met Ala Met Thr Asp
                500                 505                 510
Ala Asp Asn Phe Ala Val Ile Asn Glu Ile Glu Ser Leu Leu Ser Glu
                515                 520                 525
Glu Ile Ala Ala Pro Thr Leu Pro Ala Leu Lys Asn Lys Thr Trp Ala
530                 535                 540
Ser Tyr Ala Ser Asp Thr Ser Lys Lys Asn Glu Glu Ile Glu Asn
545                 550                 555                 560
Ile Ile Ala Glu Leu Glu Ala Ser Arg Lys Val Ser Asn Val Gln Gln
                565                 570                 575
Thr Gln His Asn Tyr His Ile Ser Gln Cys Pro Thr Ser Leu Thr Ala
                580                 585                 590
Asp Leu Pro Trp Lys Ala Trp Leu Pro Leu Leu Asn Ala His Gly Phe
                595                 600                 605
Lys Gly Asp Gln Ile Gln His Ser Pro Asp Gly Gln Ile Ile Gln Pro
                610                 615                 620
Ile Gln Asp Ile Asn Asn Lys Thr Pro Arg Ser Glu Tyr Pro Ser Ser
625                 630                 635                 640
Ile Pro Ala Asp Leu Val Ser Thr Leu Arg Asn Ile Lys Arg Ala Val
                645                 650                 655
Tyr Ala Ile Pro Ile Ser His Arg Arg Ala Ser Ala Tyr Ser Ser Asp
                660                 665                 670
Val Lys Asn Asn Arg Thr Gly Lys Leu Leu Cys Ala Gln Ser Lys Glu
                675                 680                 685
Trp Lys Glu Ser Phe Ala Phe Lys Met Gln His Glu Asp Ile Val Lys
                690                 695                 700
Ser Gly Val Val Ile His Gly Cys Gly Gly Ser Gly Lys Ser Gln Ala
705                 710                 715                 720
Leu Gln Asn Phe Leu Arg Thr Leu Gly Asp Asn Asn Asp Cys Cys Thr
                725                 730                 735
Val Val Pro Thr Val Glu Leu Arg Asn Asp Trp Val Asn Lys Leu
                740                 745                 750
Cys Lys Leu Pro Met Glu His Ile Lys Thr Phe Glu Lys Ala Met Ile
                755                 760                 765
Gln Pro Gly Phe Pro Val Val Ile Phe Asp Asp Tyr Thr Lys Leu Pro
770                 775                 780
```

```
Pro Gly Tyr Ile Glu Ala Tyr Leu Phe His His Ala Asn Thr Glu Leu
785                 790                 795                 800

Phe Ile Leu Thr Gly Asp Ser Arg Gln Ser Val Tyr His Glu Ser Asn
            805                 810                 815

Asn Glu Ala Tyr Ile Ala Ser Leu Asp Glu Ala Val Ala Tyr Tyr Ser
        820                 825                 830

Asn Tyr Cys Gly Phe Tyr Leu Asn Ala Thr His Arg Asn Val Arg Ser
    835                 840                 845

Leu Ala Asn Lys Leu Gly Val Tyr Ser Glu Lys Gly His Leu Lys
850                 855                 860

Ile Thr Phe Ala Ser Asn Ala Leu Gln Lys Cys Lys Val Pro Ile Leu
865                 870                 875                 880

Val Pro Ser Gln Met Lys Lys Asn Ala Met Gln Asp Ile Gly His Lys
            885                 890                 895

Ala Met Thr Tyr Ala Gly Cys Gln Gly Leu Thr Ala Pro Arg Val Gln
        900                 905                 910

Ile Leu Leu Asp Asn His Thr Gln His Cys Ser Asp Arg Val Leu Tyr
    915                 920                 925

Thr Cys Leu Ser Arg Ala Val Asp Ser Ile His Phe Ile Asn Thr Gly
930                 935                 940

Pro Asn Asn Ser Glu Phe Trp Asp Lys Leu Glu Ala Thr Pro Tyr Leu
945                 950                 955                 960

Lys Ala Phe Ile Asp Thr Tyr Arg Asp Glu Lys Thr Glu Met Leu Asn
            965                 970                 975

Ser Lys Pro Ala Asp Asp Ser Pro Val Glu Pro Arg Ala Pro Ala Thr
        980                 985                 990

His Phe Pro Val Ser Asn Gly Asn  Asn Leu Glu Lys Leu  Ala Ser Thr
        995                 1000                 1005

Leu Pro  Glu Lys Phe Ala Arg  Glu Ile Tyr Asp Lys  His His Gly
   1010                 1015                 1020

Tyr Ser  Asn Thr Ile Gln Thr  Glu Asn Pro Ile Val  Gln Leu Phe
   1025                 1030                 1035

Gln His  Gln Gln Ala Lys Asp  Glu Thr Leu Phe Trp  Ala Thr Ile
   1040                 1045                 1050

Glu Ala  Arg Leu Ser Ile Thr  Thr Pro Asp Ala Asn  Leu Arg Glu
   1055                 1060                 1065

Phe Thr  Leu Lys Lys Asp Val  Gly Asp Ile Leu Phe  Phe Asn Tyr
   1070                 1075                 1080

His Ser  Ala Met Cys Leu Pro  Ala Asp Pro Val Asp  Phe Glu Pro
   1085                 1090                 1095

Arg Thr  Trp Glu Ile Cys Ala  Ala Glu Val Lys Asn  Thr Tyr Leu
   1100                 1105                 1110

Ala Lys  Pro Met Ala Asn Leu  Ile Asn Ala Ala Ser  Arg Gln Ser
   1115                 1120                 1125

Pro Asp  Phe Glu Pro Asn Lys  Ile Ser Leu Phe Leu  Lys Ser Gln
   1130                 1135                 1140

Trp Val  Lys Lys Val Glu Lys  Leu Gly Ala Ile Lys  Ser Lys Pro
   1145                 1150                 1155

Gly Gln  Thr Ile Ala Ala Phe  Met Gln Gln Thr Val  Met Leu Tyr
   1160                 1165                 1170

Gly Thr  Met Ala Arg Tyr Leu  Arg Lys Met Arg Gln  Arg Phe Gln
   1175                 1180                 1185
```

-continued

Pro Lys His Ile Phe Ile Asn Cys Glu Thr Thr Thr Asp Asp Leu
    1190                 1195                 1200

Asn Asn Phe Val Leu Asn Gly Trp Asn Phe Asn Arg Thr Ala Gln
    1205                 1210                 1215

Thr Asn Asp Phe Thr Ala Phe Asp Gln Ser Gln Asp Gly Ala Met
    1220                 1225                 1230

Leu Gln Phe Glu Val Met Lys Ala Lys Phe Phe Asn Ile Pro Ala
    1235                 1240                 1245

Asp Val Ile Glu Gly Tyr Ile Asn Ile Lys Leu Asn Ala Lys Ile
    1250                 1255                 1260

Phe Leu Gly Thr Leu Ser Ile Met Arg Leu Ser Gly Glu Gly Pro
    1265                 1270                 1275

Thr Phe Asp Ala Asn Thr Glu Cys Ser Ile Ala Tyr Thr Ala Thr
    1280                 1285                 1290

Arg Tyr His Leu Ser Ser Ala Val Lys Gln Val Tyr Ala Gly Asp
    1295                 1300                 1305

Asp Met Ala Leu Asp Gly Val Val Met Glu Lys Pro Ser Phe Lys
    1310                 1315                 1320

Lys Leu Gln Ser Lys Leu Lys Leu Thr Ser Lys Thr Leu Phe Pro
    1325                 1330                 1335

Lys Gln Val Lys Gly Asp Tyr Ala Glu Phe Cys Gly Trp Thr Phe
    1340                 1345                 1350

Thr Pro Gly Gly Ile Ile Lys Asn Pro Leu Lys Met His Ala Ser
    1355                 1360                 1365

Ile Met Leu Gln Glu Ala Ile Gly Asn Leu His Thr Ala Ala Arg
    1370                 1375                 1380

Ser Tyr Ala Ile Asp Met Lys His Ser Tyr Gln Met Gly Asp Lys
    1385                 1390                 1395

Leu His Glu Tyr Leu Thr Pro Asp Glu Ala Glu Gln His Phe Leu
    1400                 1405                 1410

Ala Val Arg Lys Leu His Lys Leu His Gln Gly Glu Ala Met Arg
    1415                 1420                 1425

Leu Gly Glu Lys Ser Pro Pro Lys Ala Thr His
    1430                 1435

<210> SEQ ID NO 22
<211> LENGTH: 1438
<212> TYPE: PRT
<213> ORGANISM: Pepino mosaic virus

<400> SEQUENCE: 22

Met Ser Arg Val Arg Asn Thr Leu Glu Lys Ile Arg Asp Pro Gln Val
1               5                   10                  15

Gln Ser Ser Ile Cys Glu Ala Ala Tyr Gln His Val Arg Pro Val Leu
            20                  25                  30

Lys Glu Ser Leu Ile Asn Cys Pro Tyr Ala Leu Asn Asp Tyr Glu Ala
        35                  40                  45

Asp Thr Leu Glu Asn Leu Gly Val Thr Ile Asn Pro His Ala Ile Gln
    50                  55                  60

Thr His Thr His Ala Ala Ala Lys Val Val Glu Asn Arg Met Leu Glu
65                  70                  75                  80

Ile Val Gly His His Leu Pro Lys Asp Glu Lys Val Thr Phe Ile Phe
                85                  90                  95

Leu Lys Arg Ser Lys Leu Arg Tyr Met Arg Arg Ala Ala Val His Lys
            100                 105                 110

```
Asp Val Phe Val Asn His Ser Ile Glu Pro Lys Asp Phe Arg Tyr
            115                 120                 125

Asp Glu Glu Ser Thr Ser Thr Ser Phe Ser Val Asn Thr Arg Ile Ala
    130                 135                 140

Tyr Ile Ser Asp Ser Leu His Phe Met Glu Pro Ala Asp Val Thr His
145                 150                 155                 160

Leu Phe Asp Arg Cys His Asn Leu Lys Thr Leu Met Ala Thr Val Val
                165                 170                 175

Leu Pro Val Glu Ala Ile His Lys Gln Thr Ser Leu Phe Pro Ala Ile
            180                 185                 190

Tyr Ser Ile Asn Tyr Asn Glu Glu Gly Phe Glu Tyr Ile Pro Gly Ser
        195                 200                 205

His Gly Gly Gly Ala Tyr Phe His Lys Tyr Glu Thr Leu Asp Trp Leu
    210                 215                 220

Lys Tyr Ser Arg Phe Val Gly Gln Asp Pro Leu Thr Gly Leu Arg Tyr
225                 230                 235                 240

Thr Ile Thr Ile Gln Met Val Glu Ser Leu Gly Ala Asn His Leu Phe
                245                 250                 255

Leu Phe Gln Arg Gly Asn Phe Glu Thr Pro Leu Tyr Arg Thr Phe Gln
            260                 265                 270

Lys Asn Ser Phe Val Thr Phe Pro Asn Ile Phe His Pro Gln His Val
        275                 280                 285

Asn Ala Thr Lys Pro Met Pro Arg Ser Arg Ala Ile Gln Leu Tyr Leu
    290                 295                 300

Tyr Val Lys Ser Val Asn Lys Val Thr Gln Arg Asp Ile Phe Ala Lys
305                 310                 315                 320

Val Arg Gln Leu Ile Ser Thr Ala Glu Leu Glu Leu Tyr Asp Pro Asp
                325                 330                 335

Glu Leu Thr His Ile Val Asn Tyr Phe Ala Tyr Val Ser Glu Leu Ser
            340                 345                 350

Ser Ile Asn Asp Tyr Asp Asn Met Leu Lys Ser Ser Phe Phe Lys Lys
        355                 360                 365

Leu Val Ala Pro Met Gln His Asp Trp Arg Cys Met Ile Glu Phe Phe
    370                 375                 380

Arg Gly Lys Ser Asp Phe Asn Gln Leu Leu Thr Ala Leu Gln Trp Lys
385                 390                 395                 400

Asp Phe Ser Tyr Thr Ile Lys Thr Glu Glu Leu Val Val Ser Thr His
                405                 410                 415

Thr Glu Ile Gly Gln Ala Ile Cys Lys Ala Ala Thr Ile Tyr Lys Glu
            420                 425                 430

Arg Arg Gln Leu Thr Asn Leu Val Lys Gln Gly Val Val Thr Leu Ala
        435                 440                 445

Asp Phe Lys Glu Ala Asp Gln Gln Val Glu Tyr Thr His Phe Asp Pro
    450                 455                 460

Glu Phe Lys Ser Thr Val Glu Pro His Arg Ser Tyr Glu Asn Ala Ile
465                 470                 475                 480

Asn Asn Leu Gly Ile Glu Ile Asn Glu Asp Val Pro Glu Ser Ser Gly
                485                 490                 495

Thr Asn Glu Thr Leu Leu Asn Asn Glu Ile Ser Leu Ala Met Ser Ser
            500                 505                 510

Ala Glu His Val Gln Ala Val Gln Glu Ile Glu Ser Leu Leu Ser Asn
        515                 520                 525
```

-continued

```
Pro Glu Ala Ala Pro Ile Leu Pro Pro Ala His Val Lys Thr Trp Ala
    530                 535                 540
Ser Leu Ala Ser Asp Thr Ser Thr Lys Asn Arg Glu Ile Glu Asp
545                 550                 555                 560
Ile Val Ala Lys Leu Glu Ile Gln Arg Asn Glu Ala Ser Cys Ser Tyr
                565                 570                 575
Leu Gln Pro Asn Lys Glu Leu Ser Lys Pro Lys Ala Ala Asp Asn Asn
            580                 585                 590
Leu Pro Trp Asn Ala Trp Ile Pro Leu Leu Asn Ala His Gly Phe Lys
            595                 600                 605
Gly Asp Gln Leu Gln Tyr Gly Pro Asp Gly Asn Leu Ile Gln Pro Ile
610                 615                 620
Gln Asp Ile Asn Asn Ser Gln Pro Arg Ser Asp Tyr Pro Ser Ser Leu
625                 630                 635                 640
Pro Cys Glu Leu Val Glu Thr Leu Arg Lys Ile Lys Arg Ala Val Tyr
                645                 650                 655
Ala Ile Pro Ile Ser His Arg Arg Ala Ser Ala Tyr Ser Ser Asp Ile
                660                 665                 670
Lys Asn Asn Arg Thr Gly Lys Leu Leu Cys Asn Gln Ser Lys Glu Trp
            675                 680                 685
Lys Glu Ser Phe Ala Phe Lys Met Gln His Glu Asp Ile Val Lys Ser
            690                 695                 700
Gly Val Val Ile His Gly Cys Gly Gly Ser Gly Lys Ser Gln Ala Leu
705                 710                 715                 720
Gln Asn Phe Leu Arg Thr Leu Gly Asp Ser Asn Asp Cys Cys Thr Val
                725                 730                 735
Val Val Pro Thr Val Glu Leu Arg Asn Asp Trp Val Asn Lys Leu His
            740                 745                 750
Lys Leu Pro Met Glu His Ile Lys Thr Phe Glu Lys Ala Met Ile Gln
            755                 760                 765
Pro Gly Phe Pro Ile Val Ile Phe Asp Asp Tyr Thr Lys Leu Pro Pro
            770                 775                 780
Gly Tyr Ile Glu Ala Tyr Leu Phe His His Ala Asn Thr Glu Leu Phe
785                 790                 795                 800
Ile Leu Thr Gly Asp Ser Arg Gln Ser Val Tyr His Glu Ser Asn Asn
                805                 810                 815
Glu Ala Tyr Ile Ala Ser Leu Asp Glu Ala Val Ala Tyr Tyr Ala Asn
                820                 825                 830
Tyr Cys Gly Phe Tyr Leu Asn Ala Thr His Arg Asn Val Arg Ser Leu
            835                 840                 845
Ala Asn Lys Leu Gly Val Tyr Ser Glu Lys Glu Gly His Leu Lys Ile
            850                 855                 860
Thr Phe Ala Ser His Ala Leu Gln Lys Cys Lys Val Pro Ile Leu Val
865                 870                 875                 880
Pro Ser Gln Met Lys Lys Ser Ala Met Leu Asp Ile Gly His Lys Ser
                885                 890                 895
Met Thr Tyr Ala Gly Cys Gln Gly Leu Thr Ala Pro Lys Val Gln Ile
                900                 905                 910
Leu Leu Asp Asn His Thr Gln His Cys Ser Asp Arg Val Leu Tyr Thr
            915                 920                 925
Cys Leu Ser Arg Ala Val Asp Ser Ile His Phe Ile Asn Thr Gly Pro
930                 935                 940
```

```
Asn Asn Ser Glu Phe Trp Asp Lys Leu Glu Ala Thr Pro Tyr Leu Lys
945                 950                 955                 960

Ala Phe Ile Asp Val Tyr Arg Asp Glu Lys Thr Glu Met Leu Asn Ser
            965                 970                 975

Lys Pro Ala Asp Asp Ser Pro Thr Glu Pro Glu Ala Pro Val Thr His
            980                 985                 990

Phe Pro Ile Ala Asn Gly Asn Asn Leu Glu Lys Leu Ala Ser Ala Leu
            995                 1000                1005

Pro Glu Lys Phe Ala Arg Glu Ile Tyr Asp Lys His His Gly Tyr
    1010                1015                1020

Ser Asn Thr Ile Gln Thr Glu Asn Pro Val Val Gln Leu Phe Gln
    1025                1030                1035

His Gln Gln Ala Lys Asp Glu Thr Leu Phe Trp Ala Thr Ile Glu
    1040                1045                1050

Ala Arg Leu Ser Ile Thr Thr Pro Glu Ala Asn Leu Arg Glu Phe
    1055                1060                1065

Leu Leu Lys Lys Asp Val Gly Asp Ile Leu Phe Phe Asn Tyr His
    1070                1075                1080

Asn Ala Met Cys Leu Pro Ala Asp Pro Val Asp Phe Glu Glu Lys
    1085                1090                1095

Thr Trp Glu Ile Cys Ala Ala Glu Val Lys Asn Thr Tyr Leu Ala
    1100                1105                1110

Lys Pro Met Ala Asn Leu Ile Asn Ala Ala Ser Arg Gln Ser Pro
    1115                1120                1125

Asp Phe Asp Ser Asn Lys Ile Ser Leu Phe Leu Lys Ser Gln Trp
    1130                1135                1140

Val Lys Lys Val Glu Lys Leu Gly Ala Ile Lys Ser Lys Pro Gly
    1145                1150                1155

Gln Thr Ile Ala Ala Phe Met Gln Gln Thr Val Met Leu Tyr Gly
    1160                1165                1170

Thr Met Ala Arg Tyr Leu Arg Lys Met Arg Gln Arg Phe Gln Pro
    1175                1180                1185

Lys His Ile Phe Ile Asn Cys Glu Thr Thr Thr Asp Asp Leu Asn
    1190                1195                1200

Lys Phe Val Lys Asp Gly Trp Asn Phe Asn Arg Thr Ala Gln Thr
    1205                1210                1215

Asn Asp Phe Thr Ala Phe Asp Gln Ser Gln Asp Gly Ala Met Leu
    1220                1225                1230

Gln Phe Glu Val Met Lys Ala Lys Phe Phe Asn Ile Pro Ala Asp
    1235                1240                1245

Val Ile Glu Gly Tyr Ile Asn Ile Lys Leu Asn Ala Lys Ile Phe
    1250                1255                1260

Leu Gly Thr Leu Ser Ile Met Arg Leu Ser Gly Glu Gly Pro Thr
    1265                1270                1275

Phe Asp Ala Asn Thr Glu Cys Ser Ile Ala Tyr Thr Ala Thr Arg
    1280                1285                1290

Phe His Ile Asp Asn Thr Val Lys Gln Val Tyr Ala Gly Asp Asp
    1295                1300                1305

Met Ala Leu Asp Gly Val Val Ser Glu Lys Lys Ser Phe Arg Lys
    1310                1315                1320

Leu Gln Asn Leu Leu Lys Leu Thr Ser Lys Thr Leu Tyr Pro Lys
    1325                1330                1335
```

```
Gln Val  Lys Gly Asp Tyr Ala  Glu Phe Cys Gly Trp  Thr Phe Thr
    1340                1345                1350

Pro Gly  Gly Ile Ile Lys Asn  Pro Leu Lys Met His  Ala Ser Ile
    1355                1360                1365

Met Leu  Gln Glu Ala Ile Gly  Asn Leu His Thr Ala  Ala Arg Ser
    1370                1375                1380

Tyr Ala  Ile Asp Met Lys His  Ser Tyr Gln Met Gly  Asp Gln Leu
    1385                1390                1395

His Asp  Tyr Leu Thr Leu Asp  Glu Ala Glu Gln His  Phe Leu Ala
    1400                1405                1410

Val Arg  Lys Leu His Lys Leu  His Gln Gly Glu Ala  Met Arg Leu
    1415                1420                1425

Gly Glu  Lys Ser Pro Pro Arg  Ser Thr His
    1430                1435
```

<210> SEQ ID NO 23
<211> LENGTH: 1438
<212> TYPE: PRT
<213> ORGANISM: Pepino mosaic virus

<400> SEQUENCE: 23

```
Met Ser Arg Val Arg Asn Thr Leu Glu Lys Ile Arg Asp Pro Gln Val
1               5                   10                  15

Gln Ser Ser Ile Cys Glu Ala Ala Tyr Gln His Val Arg Pro Val Leu
            20                  25                  30

Lys Glu Ser Leu Ile Asn Cys Pro Tyr Ala Leu Asn Asp Tyr Glu Ala
        35                  40                  45

Asp Thr Leu Glu Asn Leu Gly Val Thr Ile Asn Pro His Ala Ile Gln
    50                  55                  60

Thr His Thr His Ala Ala Ala Lys Val Val Glu Asn Arg Met Leu Glu
65                  70                  75                  80

Ile Val Gly His His Leu Pro Lys Asp Glu Lys Val Thr Phe Ile Phe
                85                  90                  95

Leu Lys Arg Ser Lys Leu Arg Tyr Met Arg Arg Ala Ala Val His Lys
            100                 105                 110

Asp Val Phe Val Asn His Asn Ile Glu Pro Lys Asp Phe Phe Arg Tyr
        115                 120                 125

Asp Glu Glu Ser Thr Ser Thr Ser Phe Ser Val Asn Thr Arg Ile Ala
    130                 135                 140

Tyr Ile Ser Asp Ser Leu His Phe Met Glu Pro Ala Asp Val Thr His
145                 150                 155                 160

Leu Phe Asp Arg Cys His Asn Leu Lys Thr Leu Met Ala Thr Val Val
                165                 170                 175

Leu Pro Val Glu Ala Ile His Lys Gln Thr Ser Leu Phe Pro Ala Ile
            180                 185                 190

Tyr Ser Ile Asn Tyr Asn Glu Glu Gly Phe Glu Tyr Ile Pro Gly Ser
        195                 200                 205

His Gly Gly Gly Ala Tyr Phe His Lys Tyr Glu Thr Leu Asp Trp Leu
    210                 215                 220

Lys Tyr Ser Arg Phe Ile Gly Gln Asp Pro Leu Thr Gly Leu Arg Tyr
225                 230                 235                 240

Thr Ile Thr Ile Gln Met Val Glu Ser Leu Gly Ala Asn His Leu Phe
                245                 250                 255

Leu Phe Gln Arg Gly Asn Phe Glu Thr Pro Leu Tyr Arg Thr Phe Gln
            260                 265                 270
```

```
Lys Asn Ser Phe Val Thr Phe Pro Asn Ile Phe His Pro Gln His Val
            275                 280                 285

Asn Ala Thr Lys Pro Met Pro Arg Ser Arg Ala Ile Gln Leu Tyr Leu
        290                 295                 300

Tyr Val Lys Ser Val Asn Lys Val Thr Gln Arg Asp Ile Phe Ala Lys
305                 310                 315                 320

Val Arg Gln Leu Ile Ser Thr Ala Glu Leu Glu Leu Tyr Asp Pro Asp
                325                 330                 335

Glu Leu Thr His Ile Val Asn Tyr Phe Ala Tyr Val Ser Glu Leu Ser
                340                 345                 350

Ser Ile Asn Asp Tyr Asp Asn Met Leu Lys Ser Ser Phe Phe Lys Lys
            355                 360                 365

Leu Val Ala Pro Met Gln His Asp Trp Arg Cys Met Ile Glu Phe Phe
        370                 375                 380

Arg Gly Lys Ser Asp Phe Asn Gln Leu Leu Thr Ala Leu Gln Trp Lys
385                 390                 395                 400

Asp Phe Ser Tyr Thr Ile Lys Thr Glu Glu Leu Val Ile Ala Thr His
                405                 410                 415

Thr Glu Ile Gly Gln Ala Ile Cys Lys Ala Ala Thr Thr Tyr Lys Glu
            420                 425                 430

Arg Arg Gln Leu Thr Asn Leu Val Lys Gln Gly Ala Val Thr Leu Ala
        435                 440                 445

Asp Phe Lys Glu Ala Asp Gln His Val Glu Tyr Thr His Phe Asp Pro
450                 455                 460

Glu Phe Lys Ser Thr Val Glu Pro His Arg Ser Tyr Glu Asn Ala Ile
465                 470                 475                 480

Asn Asn Leu Gly Ile Glu Ile Asn Glu Asp Val Pro Glu Ser Ser Gly
                485                 490                 495

Thr Asn Glu Thr Leu Leu Asn Asn Glu Ile Ser Leu Ala Met Ser Ser
            500                 505                 510

Ala Glu His Val Gln Ala Val Gln Glu Ile Glu Ser Leu Leu Ser Asn
        515                 520                 525

His Glu Ala Ala Pro Ile Leu Pro Pro Ala His Val Lys Thr Trp Ala
        530                 535                 540

Ser Leu Ala Ser Asp Thr Ser Ser Thr Lys Asn Arg Glu Ile Glu Asp
545                 550                 555                 560

Ile Val Ala Lys Leu Glu Ile Gln Arg Asn Glu Ala Ser Cys Ser Tyr
                565                 570                 575

Leu Gln Pro Asn Lys Glu Leu Ser Lys Pro Lys Ala Ala Gly Asn Asn
            580                 585                 590

Leu Pro Trp Asn Ala Trp Ile Pro Leu Leu Asn Ala His Gly Phe Lys
        595                 600                 605

Gly Asp Gln Leu Gln Tyr Gly Pro Asp Gly Asn Leu Ile Gln Pro Ile
        610                 615                 620

Gln Asp Ile Asn Asn Ser Gln Pro Arg Ser Asp Tyr Pro Ser Ser Leu
625                 630                 635                 640

Pro Cys Glu Leu Val Glu Thr Leu Arg Lys Ile Lys Arg Ala Val Tyr
                645                 650                 655

Ala Ile Pro Ile Ser His Arg Arg Ala Ser Ala Tyr Ser Ser Asp Ile
            660                 665                 670

Lys Asn Asn Arg Thr Gly Lys Leu Leu Cys Asn Gln Ser Lys Glu Trp
        675                 680                 685
```

```
Lys Glu Ser Phe Ala Phe Lys Met Gln His Glu Asp Ile Val Lys Ser
690                 695                 700

Gly Val Val Ile His Gly Cys Gly Gly Ser Lys Ser Gln Ala Leu
705                 710                 715                 720

Gln Asn Phe Leu Arg Thr Leu Gly Asp Ser Asn Asp Cys Cys Thr Val
                725                 730                 735

Val Val Pro Thr Val Glu Leu Arg Asn Asp Trp Val Asn Lys Leu His
            740                 745                 750

Lys Leu Pro Met Glu His Ile Lys Thr Phe Glu Lys Ala Met Ile Gln
        755                 760                 765

Pro Gly Phe Pro Ile Val Ile Phe Asp Tyr Thr Lys Leu Pro Pro
770                 775                 780

Gly Tyr Ile Glu Ala Tyr Leu Phe His His Ala Asn Thr Glu Leu Phe
785                 790                 795                 800

Ile Leu Thr Gly Asp Ser Arg Gln Ser Val Tyr His Glu Ser Asn Asn
                805                 810                 815

Glu Ala Tyr Ile Ala Ser Leu Asp Glu Ala Val Ala Tyr Tyr Ala Asn
            820                 825                 830

Tyr Cys Gly Phe Tyr Leu Asn Ala Thr His Arg Asn Val Arg Ser Leu
        835                 840                 845

Ala Asn Lys Leu Gly Val Tyr Ser Glu Lys Glu Gly His Leu Lys Ile
850                 855                 860

Thr Phe Ala Ser His Ala Leu Gln Lys Cys Lys Val Pro Ile Leu Val
865                 870                 875                 880

Pro Ser Gln Met Lys Lys Ser Ala Met Leu Asp Ile Gly His Lys Ser
                885                 890                 895

Met Thr Tyr Ala Gly Cys Gln Gly Leu Thr Ala Pro Lys Val Gln Ile
            900                 905                 910

Leu Leu Asp Asn His Thr Gln His Cys Ser Asp Arg Val Leu Tyr Thr
        915                 920                 925

Cys Leu Ser Arg Ala Val Asp Ser Ile His Phe Ile Asn Thr Gly Pro
930                 935                 940

Asn Asn Ser Glu Phe Trp Asp Lys Leu Glu Ala Thr Pro Tyr Leu Lys
945                 950                 955                 960

Ala Phe Ile Asp Val Tyr Arg Asp Glu Lys Thr Glu Met Leu Asn Ser
                965                 970                 975

Lys Pro Ala Asp Asp Ser Pro Thr Glu Pro Glu Ala Pro Val Thr His
            980                 985                 990

Phe Pro Ile Ala Asn Gly Asn Asn Leu Glu Lys Leu Ala Ser Ala Leu
        995                 1000                1005

Pro Glu Lys Phe Ala Arg Glu Ile Tyr Asp Lys His His Gly His
    1010                1015                1020

Ser Asn Thr Ile Gln Thr Glu Asn Pro Val Val Gln Leu Phe Gln
    1025                1030                1035

His Gln Gln Ala Lys Asp Glu Thr Leu Phe Trp Ala Thr Ile Glu
    1040                1045                1050

Ala Arg Leu Ser Ile Thr Thr Pro Glu Ala Asn Leu Arg Glu Phe
    1055                1060                1065

Leu Leu Lys Lys Asp Val Gly Asp Ile Leu Phe Phe Asn Tyr His
    1070                1075                1080

Asn Ala Met Cys Leu Pro Ala Asp Pro Val Asp Phe Glu Glu Lys
    1085                1090                1095
```

```
Thr Trp Glu Ile Cys Ala Ala Glu Val Lys Asn Thr Tyr Leu Ala
1100                1105                1110

Lys Pro Met Ala Asn Leu Ile Asn Ala Ala Ser Arg Gln Ser Pro
    1115                1120                1125

Asp Phe Asp Ser Asn Lys Ile Ser Leu Phe Leu Lys Ser Gln Trp
        1130                1135                1140

Val Lys Lys Val Glu Lys Leu Gly Ala Ile Lys Ser Lys Pro Gly
1145                1150                1155

Gln Thr Ile Ala Ala Phe Met Gln Gln Thr Val Met Leu Tyr Gly
    1160                1165                1170

Thr Met Ala Arg Tyr Leu Arg Lys Met Arg Gln Arg Phe Gln Pro
        1175                1180                1185

Lys His Ile Phe Ile Asn Cys Glu Thr Thr Thr Asp Asp Leu Asn
1190                1195                1200

Lys Phe Val Lys Asp Gly Trp Asn Phe Asn Arg Thr Ala Gln Thr
    1205                1210                1215

Asn Asp Phe Thr Ala Phe Asp Gln Ser Gln Asp Gly Ala Met Leu
        1220                1225                1230

Gln Phe Glu Val Met Lys Ala Lys Phe Phe Asn Ile Pro Ala Asp
1235                1240                1245

Val Ile Glu Gly Tyr Ile Asn Ile Lys Leu Asn Ala Lys Ile Phe
    1250                1255                1260

Leu Gly Thr Leu Ser Ile Met Arg Leu Ser Gly Glu Gly Pro Thr
        1265                1270                1275

Phe Asp Ala Asn Thr Glu Cys Ser Ile Ala Tyr Thr Ala Thr Arg
1280                1285                1290

Phe His Ile Asp Asn Thr Val Lys Gln Val Tyr Ala Gly Asp Asp
    1295                1300                1305

Met Ala Leu Asp Gly Val Val Ser Glu Lys Lys Ser Phe Arg Lys
        1310                1315                1320

Leu Gln Asn Leu Leu Lys Leu Thr Ser Lys Thr Leu Tyr Pro Lys
1325                1330                1335

Gln Val Lys Gly Asp Tyr Ala Glu Phe Cys Gly Trp Thr Phe Thr
    1340                1345                1350

Pro Gly Gly Ile Ile Lys Asn Pro Leu Lys Met His Ala Ser Ile
        1355                1360                1365

Met Leu Gln Glu Ala Ile Gly Asn Leu His Thr Ala Ala Arg Ser
1370                1375                1380

Tyr Ala Ile Asp Met Lys His Ser Tyr Gln Met Gly Asp Gln Leu
    1385                1390                1395

His Asp Tyr Leu Thr Pro Asp Glu Ala Glu Gln His Phe Leu Ala
        1400                1405                1410

Val Arg Lys Leu His Lys Leu His Gln Gly Glu Ala Met Arg Leu
1415                1420                1425

Gly Glu Lys Ser Pro Pro Arg Ser Thr His
    1430                1435

<210> SEQ ID NO 24
<211> LENGTH: 1423
<212> TYPE: PRT
<213> ORGANISM: Pepino mosaic virus
```

```
<400> SEQUENCE: 24

Val Gln Ser Ser Ile Cys Glu Ala Ala Tyr Gln His Val Arg Pro Val
1               5                   10                  15

Leu Lys Glu Ser Leu Ile Asn Cys Pro Tyr Ala Leu Asn Asp Tyr Glu
            20                  25                  30

Ala Asp Thr Leu Glu Asn Leu Gly Val Thr Ile Asn Pro His Ala Ile
                35                  40                  45

Gln Thr His Thr His Ala Ala Lys Val Val Glu Asn Arg Met Leu
    50                  55                  60

Glu Ile Val Gly His His Leu Pro Lys Asp Glu Lys Val Thr Phe Ile
65              70                  75                  80

Phe Leu Lys Arg Ser Lys Leu Arg Tyr Met Arg Arg Ala Ala Val His
                85                  90                  95

Lys Asp Val Phe Val Asn His Asn Ile Glu Pro Lys Phe Phe Arg
            100                 105                 110

Tyr Asp Glu Glu Ser Thr Ser Thr Ser Phe Ser Val Asn Thr Arg Ile
            115                 120                 125

Ala Tyr Ile Ser Asp Ser Leu His Phe Met Glu Pro Ala Asp Val Thr
        130                 135                 140

His Leu Phe Asp Arg Cys His Asn Leu Lys Thr Leu Met Ala Thr Val
145                 150                 155                 160

Val Leu Pro Val Glu Ala Ile His Lys Gln Thr Ser Leu Phe Pro Ala
                165                 170                 175

Ile Tyr Ser Ile Asn Tyr Asn Glu Glu Gly Phe Glu Tyr Ile Pro Gly
                180                 185                 190

Ser His Gly Gly Gly Ala Tyr Phe His Lys Tyr Glu Thr Leu Asp Trp
        195                 200                 205

Leu Lys Tyr Ser Arg Phe Val Gly Gln Asp Pro Leu Thr Gly Leu Arg
        210                 215                 220

Tyr Thr Ile Thr Ile Gln Met Val Glu Ser Leu Gly Ala Asn His Leu
225                 230                 235                 240

Phe Leu Phe Gln Arg Gly Asn Phe Glu Thr Pro Leu Tyr Arg Thr Phe
                245                 250                 255

Gln Lys Asn Ser Phe Val Thr Phe Pro Asn Ile Phe His Pro Gln His
            260                 265                 270

Val Asn Ala Thr Lys Pro Met Pro Arg Ser Arg Ala Ile Gln Leu Tyr
            275                 280                 285

Leu Tyr Val Lys Ser Val Asn Lys Val Thr Gln Arg Asp Ile Phe Ala
        290                 295                 300

Lys Val Arg Gln Leu Ile Ser Thr Ala Glu Leu Glu Leu Tyr Asp Pro
305                 310                 315                 320

Asp Glu Leu Thr His Ile Val Asn Tyr Phe Ala Tyr Val Ser Glu Leu
                325                 330                 335

Ser Ser Ile Asn Asp Tyr Asp Asn Met Leu Lys Ser Ser Phe Phe Lys
            340                 345                 350

Lys Leu Val Ala Pro Met Gln His Asp Trp Arg Cys Met Ile Glu Phe
        355                 360                 365

Phe Arg Gly Lys Ser Asp Phe Asn Gln Leu Leu Thr Ala Leu Gln Trp
370                 375                 380

Lys Asp Phe Ser Tyr Thr Ile Lys Thr Glu Glu Leu Val Ile Ala Thr
385                 390                 395                 400

His Thr Glu Ile Gly Gln Ala Ile Cys Lys Ala Ala Thr Thr Tyr Lys
                405                 410                 415
```

```
Glu Arg Arg Gln Leu Thr Asn Leu Val Lys Gln Gly Ala Val Thr Leu
            420                 425                 430

Ala Asp Phe Lys Glu Ala Asp Gln His Val Glu Tyr Thr His Phe Asp
        435                 440                 445

Pro Glu Phe Lys Ser Thr Val Asp Pro His Arg Ser Tyr Glu Asn Ala
    450                 455                 460

Ile Asn Asn Leu Gly Ile Glu Ile Asn Glu Asp Val Pro Glu Ser Ser
465                 470                 475                 480

Gly Thr Asn Glu Thr Leu Leu Asn Asn Glu Ile Ser Leu Ala Met Ser
                485                 490                 495

Ser Thr Glu His Val Gln Ala Val Gln Glu Ile Glu Ser Leu Leu Ser
            500                 505                 510

Asn Pro Glu Ala Ala Pro Ile Leu Pro Pro Ala His Val Lys Thr Trp
        515                 520                 525

Ala Ser Leu Ala Ser Asp Thr Ser Ser Thr Lys Asn Arg Glu Ile Glu
    530                 535                 540

Asp Ile Val Ala Lys Leu Glu Ile Gln Arg Asn Lys Ala Ser Cys Ser
545                 550                 555                 560

Tyr Leu Gln Pro Asn Lys Glu Leu Ser Lys Pro Lys Ala Ala Asp Asn
                565                 570                 575

Asn Leu Pro Trp Asn Ser Trp Ile Pro Leu Leu Asn Ala His Gly Phe
            580                 585                 590

Lys Gly Asp Gln Leu Gln Tyr Gly Pro Asp Gly Asn Leu Ile Gln Pro
        595                 600                 605

Ile Gln Asp Ile Asn Asn Ser Gln Pro Arg Ser Asp Tyr Pro Ser Ser
    610                 615                 620

Leu Pro Cys Glu Leu Val Glu Thr Leu Arg Lys Ile Lys Arg Ala Val
625                 630                 635                 640

Tyr Ala Ile Pro Ile Ser His Arg Arg Ala Ser Ala Tyr Ser Ser Asp
                645                 650                 655

Ile Lys Asn Asn Arg Thr Gly Lys Leu Leu Cys Asn Gln Ser Lys Glu
            660                 665                 670

Trp Lys Glu Ser Phe Ala Phe Lys Met Gln His Glu Asp Ile Val Lys
        675                 680                 685

Ser Gly Val Val Ile His Gly Cys Gly Gly Ser Gly Lys Ser Gln Ala
690                 695                 700

Leu Gln Asn Phe Leu Arg Thr Leu Gly Asp Ser Asn Asp Cys Cys Thr
705                 710                 715                 720

Val Val Val Pro Thr Val Glu Leu Arg Asn Asp Trp Val Asn Lys Leu
                725                 730                 735

His Lys Leu Pro Met Glu His Ile Lys Thr Phe Glu Lys Ala Met Ile
            740                 745                 750

Gln Pro Gly Phe Pro Ile Val Ile Phe Asp Asp Tyr Thr Lys Leu Pro
        755                 760                 765

Pro Gly Tyr Ile Glu Ala Tyr Leu Phe His His Ala Asn Thr Glu Leu
    770                 775                 780

Phe Ile Leu Thr Gly Asp Ser Arg Gln Ser Val Tyr His Glu Ser Asn
785                 790                 795                 800

Asn Glu Ala Tyr Ile Ala Ser Leu Asp Glu Ala Val Ala Tyr Tyr Ala
                805                 810                 815

Asn Tyr Cys Gly Phe Tyr Leu Asn Ala Thr His Arg Asn Val Arg Ser
            820                 825                 830
```

```
Leu Ala Asn Lys Leu Gly Val Tyr Ser Glu Lys Glu Gly His Leu Lys
        835                 840                 845

Ile Thr Phe Ala Ser His Ala Leu Gln Lys Cys Lys Val Pro Ile Leu
    850                 855                 860

Val Pro Ser Gln Met Lys Lys Ser Ala Met Leu Asp Ile Gly His Lys
865                 870                 875                 880

Ser Met Thr Tyr Ala Gly Cys Gln Gly Leu Thr Ala Pro Lys Val Gln
                885                 890                 895

Ile Leu Leu Asp Asn His Thr Gln His Cys Ser Asp Arg Val Leu Tyr
                900                 905                 910

Thr Cys Leu Ser Arg Ala Val Asp Ser Ile His Phe Ile Asn Thr Gly
        915                 920                 925

Pro Asn Asn Ser Glu Phe Trp Asp Lys Leu Glu Ala Thr Pro Tyr Leu
    930                 935                 940

Lys Ala Phe Ile Asp Val Tyr Arg Asp Glu Lys Thr Glu Met Leu Asn
945                 950                 955                 960

Ser Lys Pro Ala Asp Asp Ser Pro Thr Glu Pro Glu Ala Pro Val Thr
                965                 970                 975

His Phe Pro Ile Ala Asn Gly Asn Asn Leu Glu Lys Leu Ala Ser Ala
                980                 985                 990

Leu Pro Glu Lys Phe Ala Arg Glu Ile Tyr Asp Lys His His Gly His
        995                 1000                1005

Ser Asn Thr Ile Gln Thr Glu Asn Pro Val Val Gln Leu Phe Gln
    1010                1015                1020

His Gln Gln Ala Lys Asp Glu Thr Leu Phe Trp Ala Thr Ile Glu
    1025                1030                1035

Ala Arg Leu Ser Ile Thr Thr Pro Glu Ala Asn Leu Arg Glu Phe
    1040                1045                1050

Leu Leu Lys Lys Asp Val Gly Asp Ile Leu Phe Phe Asn Tyr His
    1055                1060                1065

Asn Ala Met Cys Leu Pro Ala Asp Pro Val Asp Phe Glu Glu Lys
    1070                1075                1080

Thr Trp Glu Ile Cys Ala Ala Glu Val Lys Asn Thr Tyr Leu Ala
    1085                1090                1095

Lys Pro Met Ala Asn Leu Ile Asn Ala Ala Ser Arg Gln Ser Pro
    1100                1105                1110

Asp Phe Asp Ser Asn Lys Ile Ser Leu Phe Leu Lys Ser Gln Trp
    1115                1120                1125

Val Lys Lys Val Glu Lys Leu Gly Ala Ile Lys Ser Lys Pro Gly
    1130                1135                1140

Gln Thr Ile Ala Ala Phe Met Gln Gln Thr Val Met Leu Tyr Gly
    1145                1150                1155

Thr Met Ala Arg Tyr Leu Arg Lys Met Arg Gln Arg Phe Gln Pro
    1160                1165                1170

Lys His Ile Phe Ile Asn Cys Glu Thr Thr Thr Asp Asp Leu Asn
    1175                1180                1185

Lys Phe Val Lys Asp Gly Trp Asn Phe Asn Arg Thr Ala Gln Thr
    1190                1195                1200

Asn Asp Phe Thr Ala Phe Asp Gln Ser Gln Asp Gly Ala Met Leu
    1205                1210                1215

Gln Phe Glu Val Met Lys Ala Lys Phe Phe Asn Ile Pro Ala Asp
    1220                1225                1230
```

Val Ile Glu Gly Tyr Ile Asn Ile Lys Leu Asn Ala Lys Ile Phe
1235                1240                1245

Leu Gly Thr Leu Ser Ile Met Arg Leu Ser Gly Glu Gly Pro Thr
1250                1255                1260

Phe Asp Ala Asn Thr Glu Cys Ser Ile Ala Tyr Thr Ala Thr Arg
1265                1270                1275

Phe His Ile Asp Asn Thr Val Lys Gln Val Tyr Ala Gly Asp Asp
1280                1285                1290

Met Ala Leu Asp Gly Val Val Ser Glu Lys Lys Ser Phe Arg Lys
1295                1300                1305

Leu Gln Asn Leu Leu Lys Leu Thr Ser Lys Thr Leu Tyr Pro Lys
1310                1315                1320

Gln Val Lys Gly Asp Tyr Ala Glu Phe Cys Gly Trp Thr Phe Thr
1325                1330                1335

Pro Gly Gly Ile Ile Lys Asn Pro Leu Lys Met His Ala Ser Ile
1340                1345                1350

Met Leu Gln Glu Ala Ile Gly Asn Leu His Thr Ala Ala Arg Ser
1355                1360                1365

Tyr Ala Ile Asp Met Lys His Ser Tyr Gln Met Gly Asp Gln Leu
1370                1375                1380

His Asp Tyr Leu Thr Pro Asp Glu Ala Glu Gln His Phe Leu Ala
1385                1390                1395

Val Arg Lys Leu His Lys Leu His Gln Gly Glu Ala Met Arg Leu
1400                1405                1410

Gly Glu Lys Ser Pro Pro Arg Ser Thr His
1415                1420

<210> SEQ ID NO 25
<211> LENGTH: 1438
<212> TYPE: PRT
<213> ORGANISM: Pepino mosaic virus

<400> SEQUENCE: 25

Met Ser Arg Val Arg Asn Thr Leu Glu Lys Ile Arg Asp Pro Gln Val
1               5                   10                  15

Gln Ser Ser Ile Cys Glu Ala Ala Tyr Gln His Val Arg Pro Val Leu
                20                  25                  30

Lys Glu Ser Leu Ile Asn Cys Pro Tyr Ala Leu Asn Asp Tyr Glu Ala
            35                  40                  45

Asp Thr Leu Glu Asn Leu Gly Val Thr Ile Asn Pro His Ala Ile Gln
50                  55                  60

Thr His Thr His Ala Ala Ala Lys Val Val Glu Asn Arg Met Leu Glu
65                  70                  75                  80

Ile Val Gly His His Leu Pro Lys Asp Glu Lys Val Thr Phe Ile Phe
                85                  90                  95

Leu Lys Arg Ser Lys Leu Arg Tyr Met Arg Arg Ala Ala Val His Lys
            100                 105                 110

Asp Val Phe Val Asn His Asn Ile Glu Pro Lys Asp Phe Phe Arg Tyr
        115                 120                 125

Asp Glu Glu Ser Thr Ser Thr Ser Phe Ser Val Asn Thr Arg Ile Ala
    130                 135                 140

Tyr Ile Ser Asp Ser Leu His Phe Met Glu Pro Ala Asp Val Thr His
145                 150                 155                 160

Leu Phe Asp Arg Cys His Asn Leu Lys Thr Leu Met Ala Thr Val Val
                165                 170                 175

```
Leu Pro Val Glu Ala Ile His Lys Gln Thr Ser Leu Phe Pro Ala Ile
            180                 185                 190

Tyr Ser Ile Asn Tyr Asn Glu Glu Gly Phe Glu Tyr Ile Pro Gly Ser
        195                 200                 205

His Gly Gly Gly Ala Tyr Phe His Lys Tyr Glu Thr Leu Asp Trp Leu
    210                 215                 220

Lys Tyr Ser Arg Phe Val Gly Gln Asp Pro Leu Thr Gly Leu Arg Tyr
225                 230                 235                 240

Thr Ile Thr Ile Gln Met Val Glu Ser Leu Gly Ala Asn His Leu Phe
                245                 250                 255

Leu Phe Gln Arg Gly Asn Phe Glu Thr Pro Leu Tyr Arg Thr Phe Gln
            260                 265                 270

Lys Asn Ser Phe Val Thr Phe Pro Asn Ile Phe His Pro Gln His Val
        275                 280                 285

Asn Ala Thr Lys Pro Met Pro Arg Ser Arg Ala Ile Gln Leu Tyr Leu
    290                 295                 300

Tyr Val Lys Ser Val Asn Lys Val Thr Gln Arg Asp Ile Phe Ala Lys
305                 310                 315                 320

Val Arg Gln Leu Ile Ser Thr Ala Glu Leu Glu Leu Tyr Asp Pro Asp
                325                 330                 335

Glu Leu Thr His Ile Val Asn Tyr Phe Ala Tyr Val Ser Glu Leu Ser
            340                 345                 350

Ser Ile Asn Asp Tyr Asp Asn Met Leu Lys Ser Ser Phe Phe Lys Lys
        355                 360                 365

Leu Val Ala Pro Met Gln His Asp Trp Arg Cys Met Ile Glu Phe Phe
    370                 375                 380

Arg Gly Lys Ser Asp Phe Asn Gln Leu Leu Thr Ala Leu Gln Trp Lys
385                 390                 395                 400

Asp Phe Ser Tyr Thr Ile Lys Thr Glu Glu Leu Val Ile Ala Thr His
                405                 410                 415

Thr Glu Ile Gly Gln Ala Ile Cys Lys Ala Ala Thr Thr Tyr Lys Glu
            420                 425                 430

Arg Arg Gln Leu Thr Asn Leu Val Lys Gln Gly Ala Val Thr Leu Ala
        435                 440                 445

Asp Phe Lys Glu Ala Asp Gln His Val Glu Tyr Thr His Phe Asp Pro
    450                 455                 460

Glu Phe Lys Ser Thr Val Asp Pro His Arg Ser Tyr Glu Asn Ala Ile
465                 470                 475                 480

Asn Asn Leu Gly Ile Glu Ile Asn Glu Asp Val Pro Glu Ser Ser Gly
                485                 490                 495

Thr Asn Glu Thr Leu Leu Asn Asn Glu Ile Ser Leu Ala Met Ser Ser
            500                 505                 510

Ala Glu His Val Gln Ala Val Gln Glu Ile Glu Ser Leu Leu Ser Asn
        515                 520                 525

Pro Glu Ala Ala Pro Ile Leu Pro Pro Ala His Val Lys Thr Trp Ala
    530                 535                 540

Ser Leu Ala Ser Asp Thr Ser Thr Lys Asn Arg Glu Ile Glu Asp
545                 550                 555                 560

Ile Val Ala Lys Leu Glu Ile Gln Arg Asn Glu Ala Ser Cys Ser Tyr
                565                 570                 575

Leu Gln Pro Asn Lys Glu Leu Ser Lys Pro Lys Ala Ala Asp Asn Asn
            580                 585                 590
```

```
Leu Pro Trp Asn Ala Trp Ile Pro Leu Leu Asn Ala His Gly Phe Lys
            595                 600                 605

Gly Asp Gln Leu Gln Tyr Gly Pro Asp Gly Asn Leu Ile Gln Pro Ile
        610                 615                 620

Gln Asp Ile Asn Asn Ser Gln Pro Arg Ser Asp Tyr Pro Ser Ser Leu
625                 630                 635                 640

Pro Cys Glu Leu Val Glu Thr Leu Arg Lys Ile Lys Arg Ala Val Tyr
                645                 650                 655

Ala Ile Pro Ile Ser His Arg Arg Ala Ser Ala Tyr Ser Ser Asp Ile
            660                 665                 670

Lys Asn Asn Arg Thr Gly Lys Leu Leu Cys Asn Gln Ser Lys Glu Trp
        675                 680                 685

Lys Glu Ser Phe Ala Phe Lys Met Gln His Glu Asp Ile Val Lys Ser
    690                 695                 700

Gly Val Val Ile His Gly Cys Gly Gly Ser Gly Lys Ser Gln Ala Leu
705                 710                 715                 720

Gln Asn Phe Leu Arg Thr Leu Gly Asp Ser Asn Asp Cys Cys Thr Val
                725                 730                 735

Val Val Pro Thr Val Glu Leu Arg Asn Asp Trp Val Asn Lys Leu His
            740                 745                 750

Lys Leu Pro Met Glu His Ile Lys Thr Phe Glu Lys Ala Met Ile Gln
        755                 760                 765

Pro Gly Phe Pro Ile Val Ile Phe Asp Asp Tyr Thr Lys Leu Pro Pro
    770                 775                 780

Gly Tyr Ile Glu Ala Tyr Leu Phe His His Ala Asn Thr Glu Leu Phe
785                 790                 795                 800

Ile Leu Thr Gly Asp Ser Arg Gln Ser Val Tyr His Glu Ser Asn Asn
                805                 810                 815

Glu Ala Tyr Ile Ala Ser Leu Asp Glu Ala Val Ala Tyr Tyr Ala Asn
            820                 825                 830

Tyr Cys Gly Phe Tyr Leu Asn Ala Thr His Arg Asn Val Arg Ser Leu
        835                 840                 845

Ala Asn Lys Leu Gly Val Tyr Ser Glu Lys Glu Gly His Leu Lys Ile
    850                 855                 860

Thr Phe Ala Ser His Ala Leu Gln Lys Cys Lys Val Pro Ile Leu Val
865                 870                 875                 880

Pro Ser Gln Met Lys Lys Ser Ala Met Leu Asp Ile Gly His Lys Ser
                885                 890                 895

Met Thr Tyr Ala Gly Cys Gln Gly Leu Thr Ala Pro Lys Val Gln Ile
            900                 905                 910

Leu Leu Asp Asn His Thr Gln His Cys Ser Asp Arg Val Leu Tyr Thr
        915                 920                 925

Cys Leu Ser Arg Ala Val Asp Ser Ile His Phe Ile Asn Thr Gly Pro
    930                 935                 940

Asn Asn Ser Glu Phe Trp Asp Lys Leu Glu Ala Thr Pro Tyr Leu Lys
945                 950                 955                 960

Ala Phe Ile Asp Val Tyr Arg Asp Glu Lys Thr Glu Met Leu Asn Ser
                965                 970                 975

Lys Pro Ala Asp Asp Ser Pro Thr Glu Pro Glu Ala Pro Val Thr His
            980                 985                 990

Phe Pro Val Ala Asn Gly Asn Asn  Leu Glu Lys Leu Ala  Ser Ala Leu
        995                 1000                1005
```

-continued

```
Pro Glu Lys Phe Ala Arg Glu Ile Tyr Asp Lys His His Gly His
    1010                1015                1020

Ser Asn Thr Ile Gln Thr Glu Asn Pro Val Val Gln Leu Phe Gln
    1025                1030                1035

His Gln Gln Ala Lys Asp Glu Thr Leu Phe Trp Ala Thr Ile Glu
    1040                1045                1050

Ala Arg Leu Ser Ile Thr Thr Pro Glu Ala Asn Leu Arg Glu Phe
    1055                1060                1065

Leu Leu Lys Lys Asp Val Gly Asp Ile Leu Phe Phe Asn Tyr His
    1070                1075                1080

Asn Ala Met Cys Leu Pro Ala Asp Pro Val Asp Phe Glu Glu Lys
    1085                1090                1095

Thr Trp Glu Ile Cys Ala Ala Glu Val Lys Asn Thr Tyr Leu Ala
    1100                1105                1110

Lys Pro Met Ala Asn Leu Ile Asn Ala Ala Ser Arg Gln Ser Pro
    1115                1120                1125

Asp Phe Asp Ser Asn Lys Ile Ser Leu Phe Leu Lys Ser Gln Trp
    1130                1135                1140

Val Lys Lys Val Glu Lys Leu Gly Ala Ile Lys Ser Lys Pro Gly
    1145                1150                1155

Gln Thr Ile Ala Ala Phe Met Gln Gln Thr Val Met Leu Tyr Gly
    1160                1165                1170

Thr Met Ala Arg Tyr Leu Arg Lys Met Arg Gln Arg Phe Gln Pro
    1175                1180                1185

Lys His Ile Phe Ile Asn Cys Glu Thr Thr Thr Asp Asp Leu Asn
    1190                1195                1200

Lys Phe Val Lys Asp Gly Trp Asn Phe Asn Arg Thr Ala Gln Thr
    1205                1210                1215

Asn Asp Phe Thr Ala Phe Asp Gln Ser Gln Asp Gly Ala Met Leu
    1220                1225                1230

Gln Phe Glu Val Met Lys Ala Lys Phe Phe Asn Ile Pro Ala Asp
    1235                1240                1245

Val Ile Glu Gly Tyr Ile Asn Ile Lys Leu Asn Ala Lys Ile Phe
    1250                1255                1260

Leu Gly Thr Leu Ser Ile Met Arg Leu Ser Gly Glu Gly Pro Thr
    1265                1270                1275

Phe Asp Ala Asn Thr Glu Cys Ser Ile Ala Tyr Thr Ala Thr Arg
    1280                1285                1290

Phe His Ile Asp Asn Thr Val Lys Gln Val Tyr Ala Gly Asp Asp
    1295                1300                1305

Met Ala Leu Asp Gly Val Val Ser Glu Lys Lys Ser Phe Arg Lys
    1310                1315                1320

Leu Gln Asn Leu Leu Lys Leu Thr Ser Lys Thr Leu Tyr Pro Lys
    1325                1330                1335

Gln Val Lys Gly Asp Tyr Ala Glu Phe Cys Gly Trp Thr Phe Thr
    1340                1345                1350

Pro Gly Gly Ile Ile Lys Asn Pro Leu Lys Met His Ala Ser Ile
    1355                1360                1365

Met Leu Gln Glu Ala Ile Gly Asn Leu His Thr Ala Ala Arg Ser
    1370                1375                1380

Tyr Ala Ile Asp Met Lys His Ser Tyr Gln Met Gly Asp Gln Leu
    1385                1390                1395
```

-continued

```
His Asp  Tyr Leu Thr Pro Asp  Glu Ala Glu Gln His  Phe Leu Ala
    1400                 1405                 1410

Val Arg  Lys Leu His Lys Leu  His Gln Gly Glu Ala  Met Arg Leu
    1415                 1420                 1425

Gly Glu  Lys Ser Pro Pro Arg  Ser Thr His
    1430                 1435
```

<210> SEQ ID NO 26
<211> LENGTH: 1420
<212> TYPE: PRT
<213> ORGANISM: Pepino mosaic virus
<220> FEATURE:
<221> NAME/KEY: misc_feature
<222> LOCATION: (481)..(481)
<223> OTHER INFORMATION: Xaa can be any naturally occurring amino acid
<220> FEATURE:
<221> NAME/KEY: misc_feature
<222> LOCATION: (494)..(494)
<223> OTHER INFORMATION: Xaa can be any naturally occurring amino acid
<220> FEATURE:
<221> NAME/KEY: misc_feature
<222> LOCATION: (532)..(532)
<223> OTHER INFORMATION: Xaa can be any naturally occurring amino acid
<220> FEATURE:
<221> NAME/KEY: misc_feature
<222> LOCATION: (872)..(872)
<223> OTHER INFORMATION: Xaa can be any naturally occurring amino acid
<220> FEATURE:
<221> NAME/KEY: misc_feature
<222> LOCATION: (1190)..(1190)
<223> OTHER INFORMATION: Xaa can be any naturally occurring amino acid

<400> SEQUENCE: 26

```
Ser Ile Cys Glu Ala Ala Tyr Gln His Val Arg Pro Val Leu Lys Glu
1               5                   10                  15

Ser Leu Ile Asn Cys Pro Tyr Ala Leu Asn Asp Tyr Glu Ala Asp Thr
            20                  25                  30

Leu Glu Asn Leu Gly Val Thr Ile Asn Pro His Ala Ile Gln Thr His
        35                  40                  45

Thr His Ala Ala Ala Lys Val Val Glu Asn Arg Met Leu Glu Ile Val
    50                  55                  60

Gly His His Leu Pro Lys Asp Glu Lys Val Thr Phe Ile Phe Leu Lys
65                  70                  75                  80

Arg Ser Lys Leu Arg Tyr Met Arg Arg Ala Ala Val His Lys Asp Val
                85                  90                  95

Phe Val Asn His Asn Ile Glu Pro Lys Asp Phe Phe Arg Tyr Asp Glu
            100                 105                 110

Glu Ser Thr Ser Thr Ser Phe Ser Val Asn Thr Arg Ile Ala Tyr Ile
        115                 120                 125

Ser Asp Ser Leu His Phe Met Glu Pro Ala Asp Val Thr His Leu Phe
    130                 135                 140

Asp Arg Cys His Asn Leu Lys Thr Leu Met Ala Thr Val Val Leu Pro
145                 150                 155                 160

Val Glu Ala Ile His Lys Gln Thr Ser Leu Phe Pro Ala Ile Tyr Ser
                165                 170                 175

Ile Asn Tyr Asn Glu Glu Gly Phe Glu Tyr Ile Pro Gly Ser His Gly
            180                 185                 190

Gly Gly Ala Tyr Phe His Lys Tyr Glu Thr Leu Asp Trp Leu Lys Tyr
        195                 200                 205

Ser Arg Phe Ile Gly Gln Asp Pro Leu Thr Gly Leu Arg Tyr Thr Ile
    210                 215                 220
```

-continued

| | | | | | | | | | | | | | | |
|---|---|---|---|---|---|---|---|---|---|---|---|---|---|---|
| Thr | Ile | Gln | Met | Val | Glu | Ser | Leu | Gly | Ala | Asn | His | Leu | Phe | Leu | Phe |
| 225 | | | | | 230 | | | | | 235 | | | | | 240 |

Gln Arg Gly Asn Phe Glu Thr Pro Leu Tyr Arg Thr Phe Gln Lys Asn
                245                 250                 255

Ser Phe Val Thr Phe Pro Asn Ile Phe His Pro Gln His Val Asn Ala
            260                 265                 270

Thr Lys Pro Met Pro Arg Ser Arg Ala Ile Gln Leu Tyr Leu Tyr Val
        275                 280                 285

Lys Ser Val Asn Lys Val Thr Gln Arg Asp Ile Phe Ala Lys Val Arg
    290                 295                 300

Gln Leu Ile Ser Thr Ala Glu Leu Glu Leu Tyr Asp Pro Asp Glu Leu
305                 310                 315                 320

Thr His Ile Val Asn Tyr Phe Ala Tyr Val Ser Glu Leu Ser Ser Ile
                325                 330                 335

Asn Asp Tyr Asp Asn Met Leu Lys Ser Ser Phe Phe Lys Lys Leu Val
            340                 345                 350

Ala Pro Met Gln His Asp Trp Arg Cys Met Ile Glu Phe Phe Arg Gly
        355                 360                 365

Lys Ser Asp Phe Asn Gln Leu Leu Thr Ala Leu Gln Trp Lys Asp Phe
    370                 375                 380

Ser Tyr Thr Ile Lys Thr Glu Glu Leu Val Val Ala Thr His Thr Glu
385                 390                 395                 400

Ile Gly Gln Ala Ile Cys Glu Ala Ala Thr Thr Tyr Lys Glu Arg Arg
                405                 410                 415

Gln Leu Thr Asn Leu Val Lys Gln Gly Ala Val Thr Leu Ala Asp Phe
            420                 425                 430

Lys Glu Ala Asp Gln His Val Glu Tyr Thr His Phe Asp Pro Glu Phe
        435                 440                 445

Lys Ser Thr Val Asp Pro His Arg Ser Tyr Glu Asn Ala Ile Asn Asn
    450                 455                 460

Leu Gly Ile Glu Ile Asn Glu Asp Val Pro Glu Ser Ser Gly Thr Asn
465                 470                 475                 480

Xaa Thr Leu Leu Asn Asn Glu Ile Ser Leu Ala Met Ser Xaa Ala Glu
                485                 490                 495

His Val Gln Ala Val Gln Glu Ile Glu Ser Leu Leu Ser Asn Pro Glu
            500                 505                 510

Ala Ala Pro Ile Leu Pro Pro Ala His Val Lys Thr Trp Ala Ser Leu
        515                 520                 525

Ala Ser Asp Xaa Ser Ser Thr Lys Asn Arg Glu Ile Glu Asp Ile Val
    530                 535                 540

Ala Lys Leu Glu Ile Gln Arg Asn Glu Ala Ser Cys Ser Tyr Leu Gln
545                 550                 555                 560

Pro Asn Lys Glu Leu Ser Lys Pro Lys Ala Ala Asp Asn Asn Leu Pro
                565                 570                 575

Trp Asn Ala Trp Ile Pro Leu Leu Asn Ala His Gly Phe Lys Gly Asp
            580                 585                 590

Gln Leu Gln Tyr Gly Pro Asp Gly Asn Leu Ile Gln Pro Ile Gln Asp
        595                 600                 605

Ile Asn Asn Ser Gln Pro Arg Ser Asp Tyr Pro Ser Ser Leu Pro Cys
    610                 615                 620

Glu Leu Val Glu Thr Leu Arg Lys Ile Lys Arg Ala Val Tyr Ala Ile
625                 630                 635                 640

```
Pro Ile Ser His Arg Arg Ala Ser Ala Tyr Ser Ser Asp Ile Lys Asn
                645                 650                 655

Asn Arg Thr Gly Lys Leu Leu Cys Asn Gln Ser Lys Glu Trp Lys Glu
            660                 665                 670

Ser Phe Ala Phe Lys Met Gln His Glu Asp Ile Val Lys Ser Gly Val
        675                 680                 685

Val Ile His Gly Cys Gly Gly Ser Gly Lys Ser Gln Ala Leu Gln Asn
    690                 695                 700

Phe Leu Arg Thr Leu Gly Asp Ser Asn Asp Cys Cys Thr Val Val Val
705                 710                 715                 720

Pro Thr Val Glu Leu Arg Asn Asp Trp Val Asn Lys Leu His Lys Leu
                725                 730                 735

Pro Met Glu His Ile Lys Thr Phe Glu Lys Ala Met Ile Gln Pro Gly
                740                 745                 750

Phe Pro Ile Val Ile Phe Asp Asp Tyr Thr Lys Leu Pro Pro Gly Tyr
            755                 760                 765

Ile Glu Ala Tyr Leu Phe His His Ala Asn Thr Glu Leu Phe Ile Leu
    770                 775                 780

Thr Gly Asp Ser Arg Gln Ser Val Tyr His Glu Ser Asn Asn Glu Ala
785                 790                 795                 800

Tyr Ile Ala Ser Leu Asp Glu Ala Val Ala Tyr Tyr Ala Asn Tyr Cys
                805                 810                 815

Gly Phe Tyr Leu Asn Ala Thr His Arg Asn Val Arg Ser Leu Ala Asn
                820                 825                 830

Lys Leu Gly Val Tyr Ser Glu Lys Glu Gly His Leu Lys Ile Thr Phe
            835                 840                 845

Ala Ser His Ala Leu Gln Lys Cys Lys Val Pro Ile Leu Val Pro Ser
    850                 855                 860

Gln Met Lys Arg Ser Ala Met Xaa Asp Ile Gly His Lys Ser Met Thr
865                 870                 875                 880

Tyr Ala Gly Cys Gln Gly Leu Thr Ala Pro Lys Val Gln Ile Leu Leu
                885                 890                 895

Asp Asn His Thr Gln His Cys Ser Asp Arg Val Leu Tyr Thr Cys Leu
            900                 905                 910

Ser Arg Ala Val Asp Ser Ile His Phe Ile Asn Thr Gly Pro Asn Asn
        915                 920                 925

Ser Glu Phe Trp Asp Lys Leu Glu Ala Thr Pro Tyr Leu Lys Ala Phe
    930                 935                 940

Ile Asp Val Tyr Arg Asp Glu Lys Thr Glu Met Phe Asn Ser Lys Pro
945                 950                 955                 960

Ala Asp Asp Ser Pro Thr Glu Pro Glu Ala Pro Val Thr His Phe Pro
                965                 970                 975

Ile Ala Asn Gly Asn Asn Leu Gly Lys Leu Ala Ser Ala Leu Pro Glu
            980                 985                 990

Lys Phe Ala Arg Glu Ile Tyr Asp Lys His His Gly His Ser Asn Thr
        995                 1000                1005

Ile Gln Thr Glu Asn Pro Val Val Gln Leu Phe Gln His Gln Gln
    1010                1015                1020

Ala Lys Asp Glu Thr Leu Phe Trp Ala Thr Ile Glu Ala Arg Leu
    1025                1030                1035
```

```
Ser Ile Thr Thr Pro Glu Ala Asn Leu Arg Glu Phe Leu Phe Lys
    1040            1045                1050
Lys Asp Val Gly Asp Ile Leu Phe Phe Asn Tyr His Asn Ala Met
    1055            1060                1065
Cys Leu Pro Ala Asp Pro Val Asp Phe Glu Glu Lys Thr Trp Glu
    1070            1075                1080
Ile Cys Ala Ala Glu Val Lys Asn Thr Tyr Leu Ala Lys Pro Met
    1085            1090                1095
Ala Asn Leu Ile Asn Ala Ala Ser Arg Gln Ser Pro Asp Phe Asp
    1100            1105                1110
Ser Asn Lys Ile Ser Leu Phe Leu Lys Ser Gln Trp Val Lys Lys
    1115            1120                1125
Val Glu Lys Leu Gly Ala Ile Lys Ser Lys Pro Gly Gln Thr Ile
    1130            1135                1140
Ala Ala Phe Met Gln Gln Thr Val Met Leu Tyr Gly Thr Met Ala
    1145            1150                1155
Arg Tyr Leu Arg Lys Met Arg Gln Arg Phe Gln Pro Lys His Ile
    1160            1165                1170
Phe Ile Asn Cys Glu Thr Thr Thr Asp Asp Leu Asn Lys Phe Val
    1175            1180                1185
Lys Xaa Gly Trp Asn Phe Asn Arg Thr Ala Gln Thr Asn Asp Phe
    1190            1195                1200
Thr Ala Phe Asp Gln Ser Gln Asp Gly Ala Met Leu Gln Phe Glu
    1205            1210                1215
Val Met Lys Ala Lys Phe Phe Asn Ile Pro Ala Asp Val Ile Glu
    1220            1225                1230
Gly Tyr Ile Asn Ile Lys Leu Asn Ala Lys Ile Phe Leu Gly Thr
    1235            1240                1245
Leu Ser Ile Met Arg Leu Ser Gly Glu Gly Pro Thr Phe Asp Ala
    1250            1255                1260
Asn Thr Glu Cys Ser Ile Ala Tyr Thr Ala Thr Arg Phe His Ile
    1265            1270                1275
Asp Asn Thr Val Lys Gln Val Tyr Ala Gly Asp Asp Met Ala Leu
    1280            1285                1290
Asp Gly Val Val Ser Glu Lys Lys Ser Phe Arg Lys Leu Gln Asn
    1295            1300                1305
Leu Leu Lys Leu Thr Ser Lys Thr Leu Tyr Pro Lys Gln Val Lys
    1310            1315                1320
Gly Asn Tyr Ala Glu Phe Cys Gly Trp Thr Phe Thr Pro Gly Gly
    1325            1330                1335
Ile Ile Lys Asn Pro Leu Lys Met His Ala Ser Ile Met Leu Gln
    1340            1345                1350
Glu Ala Ile Gly Asn Leu His Thr Ala Ala Arg Ser Tyr Ala Ile
    1355            1360                1365
Asp Met Lys His Ser Tyr Gln Met Gly Asp Gln Leu His Asp Tyr
    1370            1375                1380
Leu Thr Pro Asp Glu Ala Glu Gln His Phe Leu Ala Val Arg Lys
    1385            1390                1395
Leu His Lys Leu His Gln Gly Glu Ala Met Arg Leu Gly Glu Lys
    1400            1405                1410
Ser Pro Pro Arg Ser Thr His
    1415            1420
```